(12) United States Patent
Steffan et al.

(10) Patent No.: US 6,506,901 B2
(45) Date of Patent: Jan. 14, 2003

(54) SUBSTITUTED 2-(S)-HYDROXY-3-(PIPERIDIN-4-YL-METHYLAMINO)-PROPYL ETHERS AND SUBSTITUTED 2-ARYL-2-(R)-HYDROXY-1-(PIPERIDIN-4-YL-METHYL)-ETHYLAMINE β-3 ADRENERGIC RECEPTOR AGONISTS

(75) Inventors: Robert John Steffan, Langhorne, PA (US); Mark Anthony Ashwell, Plainsboro, NJ (US); Jeffrey Claude Pelletier, Lafayette Hill, PA (US); William Ronald Solvibile, East Windsor, NJ (US); Edward Martin Matelan, Yardley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/903,738

(22) Filed: Jul. 12, 2001

(65) Prior Publication Data

US 2002/0037907 A1 Mar. 28, 2002

Related U.S. Application Data

(60) Provisional application No. 60/218,753, filed on Jul. 17, 2000.

(51) Int. Cl.[7] ...................... C07D 211/96; A61K 31/445
(52) U.S. Cl. .......................................... 546/192; 514/327
(58) Field of Search ............................ 546/192; 514/327

(56) References Cited

U.S. PATENT DOCUMENTS

| | | | | |
|---|---|---|---|---|
| 4,813,998 A | * | 3/1989 | Van Lommen et al. | 71/92 |
| 5,561,142 A | | 10/1996 | Fisher et al. | 514/312 |
| 5,578,620 A | | 11/1996 | Fujita et al. | 514/370 |
| 5,614,523 A | | 3/1997 | Audia et al. | 514/252 |
| 5,741,789 A | | 4/1998 | Hibschman | 514/210 |
| 5,786,356 A | | 7/1998 | Bell et al. | 514/248 |
| 5,789,402 A | | 8/1998 | Audia et al. | 514/213 |
| 6,069,176 A | | 5/2000 | Tsuchiya et al. | 514/646 |
| 6,150,378 A | * | 11/2000 | Chatterjee et al. | 514/336 |
| 6,288,231 B1 | * | 9/2001 | Chaterjee et al. | 544/316 |

FOREIGN PATENT DOCUMENTS

| | | |
|---|---|---|
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | 99/65895 | 12/1999 |
| WO | 01/43744 A | 12/2000 |
| WO | 01/17989 A2 | 3/2001 |
| WO | 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sept. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., Il Farmaco, 1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie VanWetswinkel et al., J. Anitbiotics, Sep. 1994, 1041–1051, 47(9).
S. Tamada et al., JP 01061468 A2 (English abstract), 1989.
A.E. Weber et al., Bioorganic & Medicinal Chemistry Letters, May 1 1998, 1101–1106, 8(9).
Robert J. Steffan et al., Abstracts of Papers American Chemical Society, 2001, 1–2, 221.

* cited by examiner

*Primary Examiner*—Alan L. Rotman
*Assistant Examiner*—Rita Desai
(74) *Attorney, Agent, or Firm*—Arnold S. Milowsky

(57) ABSTRACT

This invention provides compounds of Formula I having the structure

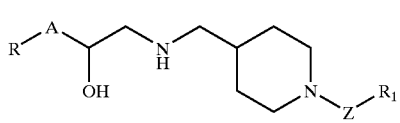

wherein A, B, Z, R and R[1] are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

5 Claims, No Drawings

SUBSTITUTED 2-(S)-HYDROXY-3-(PIPERIDIN-4-YL-METHYLAMINO)-PROPYL ETHERS AND SUBSTITUTED 2-ARYL-2-(R)-HYDROXY-1-(PIPERIDIN-4-YL-METHYL)-ETHYLAMINE β-3 ADRENERGIC RECEPTOR AGONISTS

This application claims the benefit of U.S. Provisional Application No. 60/218,753, filed Jul. 17, 2000.

BACKGROUND OF THE INVENTION

This invention relates to substituted 2-(S)-hydroxy-3-(piperidin-4-yl-methylamino)-propyl ethers and substituted 2-aryl-2-(R)-hydroxy-1-(piperidin-4-yl-methyl)-ethylamine $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and and frequent urination, and are particularly useful in the treatment or inhibition of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agonists, see: 1. A. D. Strosberg, Annu. Rev. Pharmacol. Toxicol. 1997, 37, 421; 2. A. E. Weber, Ann. Rep. Med. Chem. 1998, 33, 193; 3. C. P. Kordik and A. B. Reitz, J. Med. Chem. 1999, 42, 181; 4. C. Weyer, J. F. Gautier and E. Danforth, Diabetes and Metabolism, 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478, 849, 4,999,377, 5,153,210. Although the early developments purport to claim compounds with greater $\beta_3$-AR selectivity over the $\beta^1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5,578,620. These compounds were evaluated in Chinese hamster ovary (CHO) cells test procedures, expressing cloned human $\beta_3$ receptors, which predict the effects that can be expected in humans (Granneman et al., Mol Pharmacol., 1992, 42, 964; Emorine et al., Science, 1989, 245, 1118; Liggett Mol. Pharmacol., 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T Pharmacology 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. Br. J. Pharmacol. 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

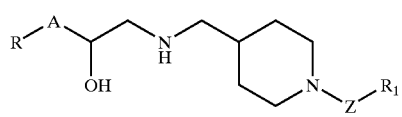

I wherein,

A is —OCH$_2$— or a bond;

R is
(a) aryl optionally substituted with $R^2$, $R^3$, $R^4$, $R^5$, or $R^6$; or
(b) Het optionally substituted with $R^2$, $R^3$, or $R^4$;

$R^1$ is:
 (a) alkyl of 1–6 carbon atoms, alkoxy of 1–6 carbon atoms, alkylamino of 1–6 carbon atoms, cycloalkyl of 1–6 carbon atoms, or cycloalkylamino of 3–8 carbon atoms;
 (b) aryl optionally substituted with $R^9$, $R^{10}$, or $R^{11}$;
 (c) arylamino optionally substituted with $R^9$, $R^{10}$, or $R^{11}$;
 (d) arylalkyl having 1–6 carbon atoms in the alkyl moiety, and which the aryl moiety may be optionally substituted with $R^9$, $R^{10}$, or $R^{11}$;
 (e) Het optionally substituted with $R^9$ or $R^{10}$ $R^2$, $R^3$, $R^4$, $R^5$, and $R^6$ are each, independently, alkyl of 1–6 carbon atoms, hydroxy, alkoxy of 1–6 carbon atoms, arylalkoxy having 1–6 carbon atoms in the alkyl moiety, halogen, —$NHSO_2R^7$, —$CO_2R^8$, or —$CONH_2$;

$R^7$ and $R^8$ are each, independently, hydrogen, alkyl of 1–6 carbon atoms, or arylalkyl having 1–6 carbon atoms in the alkyl moiety;

Z is a bond, —$SO_2$— or —CO—;

Het is
 (a) a 5–6 membered heterocycle having 1–4 heteroatoms selected from O, N, and S;
 (b) a phenyl fused heterocycle having 1–4 heteroatoms selected from O, N, and S;
 (c) a phenyl fused heterocycle having 1–4 heteroatoms selected from O, N, and S, having a second phenyl ring fused to the heterocyclic ring;

$R^9$, $R^{10}$, and $R^{11}$ are each, independently:
 (a) alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, trifluoromethylalkyl of 2–7 carbon atoms, trifluoromethoxy, —$(CH_2)_n$—$NHR^{14}$, —$OCH_2(CH_2)_nCO_2R^7$, —$(CH_2)_n$—$CO_2R^7$, —$COR^7$, —$SO_2R^{13}$, —$(CH_2)_nNHCOR^{14}$, —CN, or $NO_2$;
 (b) Het optionally substituted with $R^{15}$; or

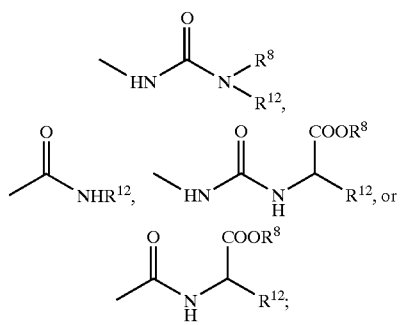

(c)

$R^{12}$ is hydrogen, alkyl of 1–6 carbon atoms, aryl optionally substituted with $R^{15}$, arylalkyl having 1–6 carbon atoms in the alkyl moiety and the aryl moiety optionally substituted with $R^{15}$, Het optionally substituted with $R^{15}$, Hetalkyl having 1–6 carbon atoms in the alkyl moiety and the Het moiety optionally substituted with $R^{15}$, —$(CH_2)_n$—$CO_2R^7$, or —$OCH_2(CH_2)_nCO_2R^7$;

$R^{13}$ is alkyl of 1–6 carbon atoms, aryl optionally substituted by $R^{16}$, or Het optionally substituted with $R^{16}$;

$R^{14}$ is hydrogen, alkyl of 1–6 carbon atoms, aryl optionally substituted by $R^{16}$, or Het optionally substituted with $R^{16}$;

$R^{15}$ is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, —$(CH_2)_n$—$NHR^{14}$, —$OCH_2(CH_2)_nCO_2R^7$, —$(CH_2)_n$—$CO_2R^7$, —$COR^7$, —$SO_2R^{13}$, —$(CH_2)_nNHCOR^{14}$, —CN, or $NO_2$;

$R^{16}$ is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, —$CO_2R^7$, —$COR^7$, —CN, —$NO_2$, or trifluoromethyl;

n=0–6;

with the proviso that when R is aryl, and $R^1$ is Het, Z is not a bond;

or a pharmaceutically acceptable salt thereof, which are selective agonists at human $\beta_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration.

Alkyl and alkenyl include both straight chain as well as branched moieties. Halogen means bromine, chlorine, fluorine, and iodine. Aryl includes monocyclic, bicyclic, or tricyclic aromatic carbocyclic groups such as phenyl, naphthyl, and fluorenyl. As defined in this invention, fluoren-9-one and fluoren-2-oxime are considered to be aryl moieties. Arylalkyl is defined as an aryl group bonded to a alkyl moiety. Benzyl is the preferred arylalkyl moiety. As used herein, a heterocyclic ring is a ring contining 1–4 heteroatoms selected from N, O, and S, indicates a heterocycle which may be saturated, unsaturated, or partially unsaturated. The heterocyclic ring may be attached within structural Formula I by any carbon atom or appropriate heteroatom. As described herein, the term heterocycle includes heterocyclic rings or ring systems in which ring carbon atoms may exist as a carbonyl group, or as an oxime of a carbonyl group. It is understood that the heterocyclic ring does not contain heteroatoms in arrangements which would make them inherently unstable. For example, the term heterocyclic ring does not include ring systems containing O—O bonds in the ring backbone. Preferred heterocycles include pyridyl, piperidinyl, quinolinyl, pyrimidinyl, pyrrolyl, pyrrolidinyl, thienyl, imidazolyl, thiazolyl, benzimidazolyl, thiadiazolyl, benzothiadiazolyl, indolyl, indolinyl, benzodioxolyl, benziodioxanyl, benzothiophenyl, benzofuranyl, benzoxazinyl, dihydrobenzofuranyl, tetrahydroquinolinyl, furopyridinyl, thienopyridinyl, thienyl, furyl, isoindolyl, isoquinolinyl, benzothiazolyl, benzoxazolyl, benzofuranzanyl, carbazolyl, 1,3-dihydro-benzoimidazol-2-one, 1,3-dihydro-indol-2-one, 1,2,3,4-tetrahydroquinolin-2-one, indazolyl, imidazolidin-2-one, and pyrazolyl, oxadiazolyl. More preferred heterocycles include carbazolyl, indolyl, 1,3-dihydro-benzoimidazol-2-one, 1,3-dihydro-indol-2-one, 1,2,3,4-tetrahydroquinolin-2-one, quinolinyl, pyridyl, imidazolyl, thienyl, indazolyl, imidazolidin-2-one, pyrazolyl, oxadiazolyl, piperidyl, pyrrolidinyl, benzothiadiazolyl and pyrimidinyl.

Preferred compounds of Formula I are those in which

R is
  (a) phenyl, naphthyl, fluorenyl, fluoren-2-one, or fluoren-2-oxime optionally substituted with $R^2$, $R^3$, $R^4$, $R^5$, or $R^6$; or
  (b) Het optionally substituted with $R^2$, $R^3$, or $R^4$;

$R^1$ is:
  (a) alkyl of 1–6 carbon atoms, alkoxy of 1–6 carbon atoms, alkylamino of 1–6 carbon atoms, cycloalkyl of 1–6 carbon atoms, or cycloalkylamino of 3–8 carbon atoms;
  (b) phenyl or naphthyl optionally substituted with $R^9$, $R^{10}$, or $R^{11}$;
  (c) phenylamino optionally substituted with $R^9$, $R^{10}$, or $R^{11}$;
  (d) benzyl in which the phenyl ring may be optionally substituted with $R^9$, $R^{10}$, or $R^{11}$;
  (e) Het optionally substituted with $R^9$ or $R^{10}$ Het is carbazolyl, indolyl, 1,3-dihydro-benzoimidazol-2-one, 1,3-dihydro-indol-2-one, 1,2,3,4-tetrahydroquinolin-2-one, quinolinyl, pyridyl, imidazolyl, thienyl, indazolyl, imidazolidin-2-one, pyrazolyl, oxadiazolyl, piperidyl, pyrrolidinyl, benzothiadiazolyl or pyrimidinyl;

with the remaining subsitituent as defined above.

This invention also provides preferred compounds of Formula I, having the structure

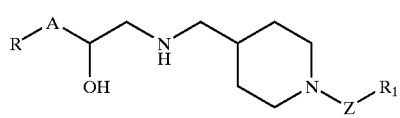

I wherein,
  A is —OCH$_2$— or a bond;
  R is Het optionally substituted with $R^2$, $R^3$, or $R^4$;
  $R^1$ is:
    (a) alkyl of 1–6 carbon atoms, alkoxy of 1–6 carbon atoms, alkylamino of 1–6 carbon atoms, cycloalkyl of 1–6 carbon atoms, or cycloalkylamino of 3–8 carbon atoms;
    (b) aryl optionally substituted with $R^9$, $R^{10}$, or $R^{11}$;
    (c) arylamino optionally substituted with $R^9$, $R^{10}$, or $R^{11}$;
    (d) arylalkyl having 1–6 carbon atoms in the alkyl moiety, and which the aryl moiety may be optionally substituted with $R^9$, $R^{10}$, or $R^{11}$;
    (e) Het optionally substituted with $R^9$ or $R^{10}$ $R^2$, $R^3$, $R^4$, $R^5$, and $R^6$ are each, independently, alkyl of 1–6 carbon atoms, hydroxy, alkoxy of 1–6 carbon atoms, arylalkoxy having 1–6 carbon atoms in the alkyl moiety, halogen, —NHSO$_2$R$^7$, —CO$_2$R$^8$, or —CONH$_2$;

$R^7$ and $R^8$ are each, independently, hydrogen, alkyl of 1–6 carbon atoms, or arylalkyl having 1–6 carbon atoms in the alkyl moiety;

Z is a bond, —SO$_2$— or —CO—;

Het is
    (a) a 5–6 membered heterocycle having 1–4 heteroatoms selected from O, N, and S;
    (b) a phenyl fused heterocycle having 1–4 heteroatoms selected from O, N, and S;
    (c) a phenyl fused heterocycle having 1–4 heteroatoms selected from O, N, and S, having a second phenyl ring fused to the heterocyclic ring;

$R^9$, $R^{10}$, and $R^{11}$ are each, independently:
    (a) alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, trifluoromethylalkyl of 2–7 carbon atoms, trifluoromethoxy, —(CH$_2$)$_n$—NHR$^{14}$, —OCH$_2$(CH$_2$)$_n$CO$_2$R$^7$, —(CH$_2$)$_n$—CO$_2$R$^7$, —COR$^7$, —SO$_2$R$^{13}$, —(CH$_2$)$_n$NHCOR$^{14}$, —CN, or NO$_2$;
    (b) Het optionally substituted with $R^{15}$; or

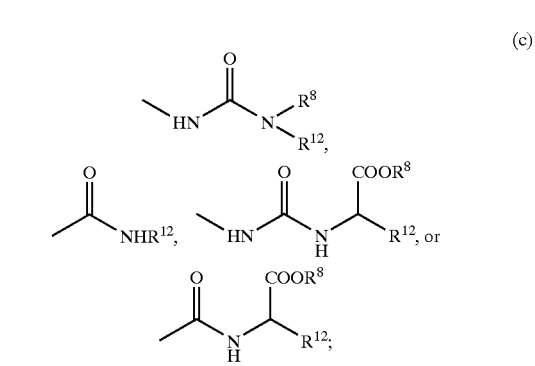

(c)

$R^{12}$ is hydrogen, alkyl of 1–6 carbon atoms, aryl optionally substituted with $R^{15}$, arylalkyl having 1–6 carbon atoms in the alkyl moiety and the aryl moiety optionally substituted with $R^{15}$, Het optionally substituted with $R^{15}$, Hetalkyl having 1–6 carbon atoms in the alkyl moiety and the Het moiety optionally substituted with $R^{15}$, —(CH$_2$)$_n$—CO$_2$R$^7$, or —OCH$_2$(CH$_2$)$_n$CO$_2$R$^7$;

R[13] is alkyl of 1–6 carbon atoms, aryl optionally substituted by R[16], or Het optionally substituted with R[16];

R[14] is hydrogen, alkyl of 1–6 carbon atoms, aryl optionally substituted by R[16], or Het optionally substituted with R[16];

R[15] is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, —$(CH_2)_n$—$NHR^{14}$, —$OCH_2(CH_2)_nCO_2R^7$, —$(CH_2)_n$—$CO_2R^7$, —$COR^7$, —$SO_2R^{13}$, —$(CH_2)_n NHCOR^{14}$, —CN, or $NO_2$;

R[16] is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, —$CO_2R^7$, —$COR^7$, —CN, —$NO_2$, or trifluoromethyl;

n=0–6;

or a pharmaceutically acceptable salt thereof.

This invention also provides preferred compounds of Formula I, having the structure

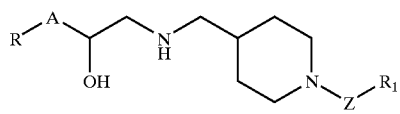

I wherein,

A is —$OCH_2$— or a bond;

R is
(a) aryl optionally substituted with R[2], R[3], R[4], R[5], or R[6]; or
(b) Het optionally substituted with R[2], R[3], or R[4];

R[1] is:
(a) alkyl of 1–6 carbon atoms, alkoxy of 1–6 carbon atoms, alkylamino of 1–6 carbon atoms, cycloalkyl of 1–6 carbon atoms, or cycloalkylamino of 3–8 carbon atoms;
(b) aryl optionally substituted with R[9], R[10], or R[11];
(c) arylamino optionally substituted with R[9], R[10], or R[11];
(d) arylalkyl having 1–6 carbon atoms in the alkyl moiety, and which the aryl moiety may be optionally substituted with R[9], R[10], or R[11];

R[2], R[3], R[4], R[5], and R[6] are each, independently, alkyl of 1–6 carbon atoms, hydroxy, alkoxy of 1–6 carbon atoms, arylalkoxy having 1–6 carbon atoms in the alkyl moiety, halogen, —$NHSO_2R^7$, —$CO_2R^8$, or —$CONH_2$;

R[7] and R[8] are each, independently, hydrogen, alkyl of 1–6 carbon atoms, or arylalkyl having 1–6 carbon atoms in the alkyl moiety;

Z is a bond, —$SO_2$— or —CO—;

Het is
(a) a 5–6 membered heterocycle having 1–4 heteroatoms selected from O, N, and S;
(b) a phenyl fused heterocycle having 1–4 heteroatoms selected from O, N, and S;
(c) a phenyl fused heterocycle having 1–4 heteroatoms selected from O, N, and S, having a second phenyl ring fused to the heterocyclic ring;

R[9], R[10], and R[11] are each, independently:
(a) alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, trifluoromethylalkyl of 2–7 carbon atoms, trifluoromethoxy, —$(CH_2)_n$—$NHR^{14}$, —$OCH_2(CH_2)_nCO_2R^7$, —$(CH_2)_n$—$CO_2R^7$, —$COR^7$, —$SO_2R^{13}$, —$(CH_2)_n NHCOR^{14}$, —CN, or $NO_2$;
(b) Het optionally substituted with R[15]; or

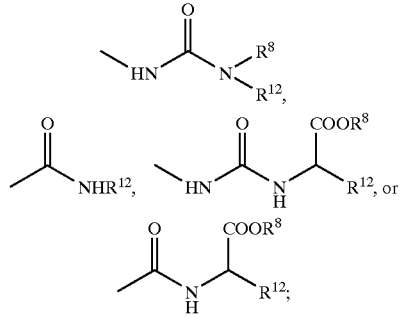

(c)

R[12] is hydrogen, alkyl of 1–6 carbon atoms, aryl optionally substituted with R[15], arylalkyl having 1–6 carbon atoms in the alkyl moiety and the aryl moiety optionally substituted with R[15], Het optionally substituted with R[15], Hetalkyl having 1–6 carbon atoms in the alkyl moiety and the Het moiety optionally substituted with R[15], —$(CH_2)_n$—$CO_2R^7$, or —$OCH_2(CH_2)_nCO_2R^7$;

R[13] is alkyl of 1–6 carbon atoms, aryl optionally substituted by R[16], or Het optionally substituted with R[16];

R[14] is hydrogen, alkyl of 1–6 carbon atoms, aryl optionally substituted by R[16], or Het optionally substituted with R[16];

R[15] is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, —$(CH_2)_n$—$NHR^{14}$, —$OCH_2(CH_2)_nCO_2R^7$, —$(CH_2)_n$—$CO_2R^7$, —$COR^7$, —$SO_2R^{13}$, —$(CH_2)_n NHCOR^{14}$, —CN, or $NO_2$;

R[16] is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, —$CO_2R^7$, —$COR^7$, —CN, —$NO_2$, or trifluoromethyl;

n=0–6;

or a pharmaceutically acceptable salt thereof.

This invention also provides preferred compounds of Formula I, having the structure

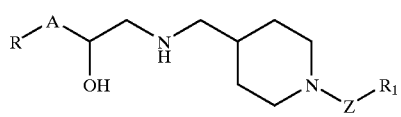

I wherein,

A is —OCH$_2$— or a bond;

R is
- (a) aryl optionally substituted with $R^2$, $R^3$, $R^4$, $R^5$, or $R^6$; or
- (b) Het optionally substituted with $R^2$, $R^3$, or $R^4$;

$R^1$ is:
- (a) alkyl of 1–6 carbon atoms, alkoxy of 1–6 carbon atoms, alkylamino of 1–6 carbon atoms, cycloalkyl of 1–6 carbon atoms, or cycloalkylamino of 3–8 carbon atoms;
- (b) aryl optionally substituted with $R^9$, $R^{10}$, or $R^{11}$;
- (c) arylamino optionally substituted with $R^9$, $R^{10}$, or $R^{11}$;
- (d) arylalkyl having 1–6 carbon atoms in the alkyl moiety, and which the aryl moiety may be optionally substituted with $R^9$, $R^{10}$, or $R^{11}$;
- (e) Het optionally substituted with $R^9$ or $R^{10}$ $R^2$, $R^3$, $R^4$, $R^5$, and $R^6$ are each, independently, alkyl of 1–6 carbon atoms, hydroxy, alkoxy of 1–6 carbon atoms, arylalkoxy having 1–6 carbon atoms in the alkyl moiety, halogen, —NHSO$_2$R$^7$, —CO$_2$R$^8$, or —CONH$_2$;

$R^7$ and $R^8$ are each, independently, hydrogen, alkyl of 1–6 carbon atoms, or arylalkyl having 1–6 carbon atoms in the alkyl moiety;

Z is —SO$_2$— or —CO—;

Het is
- (a) a 5–6 membered heterocycle having 1–4 heteroatoms selected from O, N, and S;
- (b) a phenyl fused heterocycle having 1–4 heteroatoms selected from O, N, and S;
- (c) a phenyl fused heterocycle having 1–4 heteroatoms selected from O, N, and S, having a second phenyl ring fused to the heterocyclic ring;

$R^9$, $R^{10}$, and $R^{11}$ are each, independently:
- (a) alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, trifluoromethylalkyl of 2–7 carbon atoms, trifluoromethoxy, —(CH$_2$)$_n$—NHR$^{14}$, —OCH$_2$(CH$_2$)$_n$CO$_2$R$^7$, —(CH$_2$)$_n$—CO$_2$R$^7$, —COR$^7$, —SO$_2$R$^{13}$, —(CH$_2$)$_n$NHCOR$^{14}$, —CN, or NO$_2$;
- (b) Het optionally substituted with $R^{15}$; or

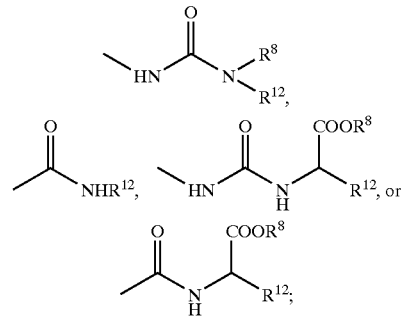

$R^{12}$ is hydrogen, alkyl of 1–6 carbon atoms, aryl optionally substituted with $R^{15}$, arylalkyl having 1–6 carbon atoms in the alkyl moiety and the aryl moiety optionally substituted with $R^{15}$, Het optionally substituted with $R^{15}$, Hetalkyl having 1–6 carbon atoms in the alkyl moiety and the Het moiety optionally substituted with $R^{15}$, —(CH$_2$)$_n$—CO$_2$R$^7$, or —OCH$_2$(CH$_2$)$_n$CO$_2$R$^7$;

$R^{13}$ is alkyl of 1–6 carbon atoms, aryl optionally substituted by $R^{16}$, or Het optionally substituted with $R^{16}$;

$R^{14}$ is hydrogen, alkyl of 1–6 carbon atoms, aryl optionally substituted by $R^{16}$, or Het optionally substituted with $R^{16}$;

$R^{15}$ is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, —(CH$_2$)$_n$—NHR$^{14}$, —OCH$_2$(CH$_2$)$_n$CO$_2$R$^7$, —(CH$_2$)$_n$—CO$_2$R$^7$, —COR$^7$—SO$_2$R$^{13}$, —(CH$_2$)$_n$NHCOR$^{14}$, —CN, or NO$_2$;

$R^{16}$ is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, —CO$_2$R$^7$, —COR$^7$, —CN, —NO$_2$, or trifluoromethyl;

n=0–6;

or a pharmaceutically acceptable salt thereof.

Specifically preferred compounds of this invention are:

| | |
|---|---|
| a) | (2S)-1-(9H-Carbazol-4-yloxy)-3-{[1-(7-trifluoromethyl-quinolin-4-yl)-piperidin-4-ylmethyl]-amino}-propan-2-ol; |
| b) | 2S)-1-(4-Benzyloxy-phenoxy)-3-{[1-(7-trifluoromethyl-quinolin-4-yl)-piperidin-4-ylmethyl]-amino}-propan-2-ol; |
| c) | -((2S)-2-Hydroxy-3-{[1-(7-trifluoromethyl-quinolin-4-yl)-piperidin-4-ylmethyl]-amino}-propoxy)-fluoren-9-one; |
| d) | -((2S)-2-Hydroxy-3-{[1-(7-trifluoromethyl-quinolin-4-yl)-piperidin-4-ylmethyl]-amino}-propoxy)-fluoren-9-one oxime; |

-continued

| | |
|---|---|
| e) | 2S)-1-(9H-Carbazol-4-yloxy)-3-[(4'-trifluoromethyl-3,4,5,6-tetrahydro-2H-[1,2']bipyridinyl-4-ylmethyl)-amino]-propan-2-ol; |
| f) | -{(2S)-2-Hydroxy-3-[(4'-trifluoromethyl-3,4,5,6-tetrahydro-2H-[1,2']bipyridinyl-4-ylmethyl)-amino]-propoxy}-fluoren-9-one; |
| g) | -{(2S)-2-Hydroxy-3-[(4'-trifluoromethyl-3,4,5,6-tetrahydro-2H-[1,2']bipyridinyl-4-ylmethyl)-amino]-propoxy}-fluoren-9-one; |
| h) | 2S)-1-(9H-Carbazol-4-yloxy)-3-[(1-propyl-piperidin-4-ylmethyl)-amino]-propan-2-ol; |
| i) | 2S)-1-(9H-Carbazol-4-yloxy)-3-[(1-isopropyl-piperidin-4-ylmethyl)-amino]-propan-2-ol; |
| j) | (2S)-1-(9H-Carbazol-4-yloxy)-3-{[1-(3,3,3-trifluoro-propyl)-piperidin-4-ylmethyl]-amino}-propan-2-ol; |
| k) | (2S)-1-(4-Benzyloxy-phenoxy)-3-{[1-(3,3,3-trifluoro-propyl)-piperidin-4-ylmethyl]-amino}-propan-2-ol; |
| l) | 4-((2S)-2-Hydroxy-3-{[1-(3,3,3-trifluoro-propyl)-piperidin-4-ylmethyl]-amino}-propoxy)-phenol; |
| m) | 4-(2-Hydroxy-3-{[1-(3,3,3-trifluoro-propyl)-piperidin-4-ylmethyl]-amino}-propoxy)-fluoren-9-one; |
| n) | 4-((2S)-2-Hydroxy-3-{[1-(3,3,3-trifluoro-propyl)-piperidin-4-ylmethyl]-amino}-propoxy)-9H-fluoren-9-ol; |
| o) | 4-((2S)-2-Hydroxy-3-{[1-(3,3,3-trifluoro-propyl)-piperidin-4-ylmethyl]-amino}-propoxy)-9H-carbazol-3-ol; |
| p) | (2S)-1-(1-Bromo-9H-carbazol-4-yloxy)-3-{[1-(3,3,3-trifluoro-propyl)-piperidin-4-ylmethyl]-amino}-propan-2-ol; |
| q) | (2S)-1-(1-Chloro-9H-carbazol-4-yloxy)-3-{[1-(3,3,3-trifluoro-propyl)-piperidin-4-ylmethyl]-amino}-propan-2-ol; |
| r) | (2S)-1-(3-Bromo-9H-carbazol-4-yloxy)-3-{[1-(3,3,3-trifluoro-propyl)-piperidin-4-ylmethyl]-amino}-propan-2-ol; |
| s) | (2S)-1-(3-Chloro-9H-carbazol-4-yloxy)-3-{[1-(3,3,3-trifluoro-propyl)-piperidin-4-ylmethyl]-amino}-propan-2-ol; |
| t) | (2S)-1-(1H-Indol-4-yloxy)-3-{[1-(3,3,3-trifluoro-propyl)-piperidin-4-ylmethyl]-amino}-propan-2-ol; |
| u) | (2S)-1-(1H-Indol-5-yloxy)-3-{[1-(3,3,3-trifluoro-propyl)-piperidin-4-ylmethyl]-amino}-propan-2-ol; |
| v) | 4-((2S)-2-Hydroxy-3-{[1-(3,3,3-trifluoro-propyl)-piperidin-4-ylmethyl]-amino}-propoxy)-1,3-dihydro-benzoimidazol-2-one; |
| w) | (2S)-1-(2-Methyl-1H-indol-4-yloxy)-3-{[1-(3,3,3-trifluoro-propyl)-piperidin-4-ylmethyl]-amino}-propan-2-ol; |
| x) | (2S)-1-(9H-Carbazol-4-yloxy)-3-{[1-(4,4,4-trifluoro-butyl)-piperidin-4-ylmethyl]-amino}-propan-2-ol; |
| y) | (2S)-1-(9H-Carbazol-4-yloxy)-3-[(1-pentyl-piperidin-4-ylmethyl)-amino]-propan-2-ol; |
| z) | (2S)-1-(9H-Carbazol-4-yloxy)-3-[(1-hexyl-piperidin-4-ylmethyl)-amino]-propan-2-ol; |
| aa) | (2S)-1-(9H-Carbazol-4-yloxy)-3-[(1-octyl-piperidin-4-ylmethyl)-amino]-propan-2-ol; |
| bb) | (2S)-1-(9H-Carbazol-4-yloxy)-3-[(1-tridecyl-piperidin-4-ylmethyl)-amino]-propan-2-ol; |
| cc) | (2S)-1-(9H-Carbazol-4-yloxy)-3-[(1-pentadecyl-piperidin-4-ylmethyl)-amino]-propan-2-ol; |
| dd) | 12-(4-{[(2S)-3-(9H-Carbazol-4-yloxy)-2-hydroxy-propylamino]-methyl}-piperidin-1-yl)-dodecan-1-ol; |
| ee) | (2S)-1-(9H-Carbazol-4-yloxy)-3-{[1-(naphthalene-2-sulfonyl)-piperidin-4-ylmethyl]-amino}-propan-2-ol; |
| ff) | (2S)-1-(9H-Carbazol-4-yloxy)-3-{[1-(propane-2-sulfonyl)-piperidin-4-ylmethyl]-amino}-propan-2-ol; |
| gg) | (2S)-1-(9H-Carbazol-4-yloxy)-3-{[1-(4-methoxy-benzenesulfonyl)-piperidin-4-ylmethyl]-amino}-propan-2-ol; |
| hh) | (2S)-1-(3-Bromo-9H-carbazol-4-yloxy)-3-{[1-(4-methoxy-benzenesulfonyl)-piperidin-4-ylmethyl]-amino}-propan-2-ol; |
| ii) | (2S)-1-(3-Chloro-9H-carbazol-4-yloxy)-3-{[1-(4-methoxy-benzenesulfonyl)-piperidin-4-ylmethyl]-amino)-propan-2-ol; |
| jj) | (2S)-1-(1-Bromo-9H-carbazol-4-yloxy)-3-{[1-(4-methoxy-benzenesulfonyl)-piperidin-4-ylmethyl]-amino}-propan-2-ol; |
| kk) | 4-((2S)-2-Hydroxy-3-{[1-(4-methoxy-benzenesulfonyl)-piperidin-4-ylmethyl]-amino}-propoxy)-phenol; |
| ll) | 4-((2S)-2-Hydroxy-3-{[1-(4-methoxy-benzenesulfonyl)-piperidin-4-ylmethyl]-amino}-propoxy)-fluoren-9-one; |
| mm) | 4-((2S)-2-Hydroxy-3-{[1-(4-methoxy-benzenesulfonyl)-piperidin-4-ylmethyl]-amino}-propoxy)-1,3-dihydro-benzoimidazol-2-one; |
| nn) | 4-((2S)-2-Hydroxy-3-{[1-(4-methoxy-benzenesulfonyl)-piperidin-4-ylmethyl]-amino}-propoxy)-2-methyl-1H-indole; |
| oo) | 4-((2S)-3-{[1-(4-Methoxy-benzenesulfonyl)-piperidin-4-ylmethyl]-amino}-2-hydroxy-propoxy)-1,3-dihydro-indol-2-one; |
| pp) | 4-((2S)-2-Hydroxy-3-{[1-(3,4-dimethoxy-benzenesulfonyl)-piperidin-4-ylmethyl]-amino}-propoxy)-1,3-dihydro-benzoimidazol-2-one; |
| qq) | 4-((2S)-2-Hydroxy-3-{[1-(3,4-dimethoxy-benzenesulfonyl)-piperidin-4-ylmethyl]-amino}-propoxy)-phenol; |

-continued

| | |
|---|---|
| rr) | 4-((2S)-3-{[1-(3,4-Dimethoxy-benzenesulfonyl)-piperidin-4-ylmethyl]-amino}-2-hydroxy-propoxy)-1,3-dihydro-indol-2-one; |
| ss) | 4-((2S)-2-Hydroxy-3-{[1-(4-nitro-benzenesulfonyl)-piperidin-4-ylmethyl]-amino}-propoxy)-phenol; |
| tt) | 4-((2S)-2-Hydroxy-3-{[1-(4-trifluoromethoxy-benzenesulfonyl)-piperidin-4-ylmethyl]-amino}-propoxy)-1,3-dihydro-indol-2-one; |
| uu) | 4-((2S)-2-Hydroxy-3-{[1-(4-trifluoromethoxy-benzenesulfonyl)-piperidin-4-ylmethyl]-amino}-propoxy)-phenol; |
| vv) | (1R)-1-(3-Chloro-phenyl)-2-{[1-(4-trifluoromethoxy-benzenesulfonyl)-piperidin-4-ylmethyl]-amino}-ethanol; |
| ww) | 4-((2S)-2-Hydroxy-3-{[1-(1-methyl-1H-imidazole-4-sulfonyl)-piperidin-4-ylmethyl]-amino}-propoxy)-phenol; |
| xx) | 3-[(4-{[(2S)-3-(9H-Carbazol-4-yloxy)-2-hydroxy-propylamino)-methyl}-piperidine-1-carbonyl)-amino]-benzoic acid ethyl ester; |
| yy) | 3-[(4-{[(2S)-3-(9H-Carbazol-4-yloxy)-2-hydroxy-propylamino]-methyl}-piperidine-1-carbonyl)-amino]-benzoic acid; |
| zz) | 3-[(4-{[(2S)-2-Hydroxy-3-(4-hydroxy-phenoxy)-propylamino]-methyl}-piperidine-1-carbonyl)-amino]-benzoic acid ethyl ester; |
| aaa) | 4-[(4-{[(2S)-3-(9H-Carbazol-4-yloxy)-2-hydroxy-propylamino]-methyl}-piperidine-1-carbonyl)-amino]-benzoic acid ethyl ester; |
| bbb) | 4-[(4-{[(2S)-2-Hydroxy-3-(4-hydroxy-phenoxy)-propylamino]-methyl}-piperidine-1-carbonyl)-amino]-benzoic acid ethyl ester; |
| ccc) | 4-{[(2S)-3-(9H-Carbazol-4-yloxy)-2-hydroxy-propylamino]-methyl}-piperidine-1-carboxylic acid hexylamide; |
| ddd) | 4-{[(2S)-3-(9-H-Carbazol-4-yloxy)-2-hydroxy-propylamino]-methyl}-piperidine-1-carboxylic acid cyclohexylamide; |
| eee) | 4-{[(2S)-2-Hydroxy-3-(4-hydroxy-phenoxy)-propylamino]-methyl}-piperidine-1-carboxylic acid cyclohexylamide; |
| fff) | 1-[4-(4-{[(2S)-3-(9H-Carbazol-4-yloxy)-2-hydroxy-propylamino]-methyl}-piperidine-1-sulfonyl)-phenyl]-3-hexyl-urea; |
| ggg) | 1-Hexyl-3-[4-(4-{[(2S)-2-hydroxy-3-(4-hydroxy-phenoxy)-propylamino]-methyl}-piperidine-1-sulfonyl)-phenyl)-urea; |
| hhh) | 1-Hexyl-3-[4-(4-{[(2S)-2-hydroxy-3-(2-oxo-2,3-dihydro-1H-benzoimidazol-4-yloxy)-propylamino]-methyl}-piperidine-1-sulfonyl)-phenyl]-urea; |
| iii) | 1-[4-(4-{[(2S)-2-Hydroxy-3-(2-methyl-1H-indol-7-yloxy)-propylamino]-methyl}-piperidine-1-sulfonyl)-phenyl]-3-phenyl-urea; |
| jjj) | 1-[4-(4-{[2-Hydroxy-3-(2-oxo-2,3-dihydro-1H-benzoimidazol-4-yloxy)-propylamino]-methyl}-piperidine-1-sulfonyl)-phenyl]-3-phenyl-urea; |
| kkk) | 1-[4-(4-{[(2S)-2-Hydroxy-3-(4-hydroxy-phenoxy)-propylamino]-methyl}-piperidine-1-sulfonyl)-phenyl]-3-phenyl-urea; |
| lll) | 1-Cyclohexyl-3-[4-(4-{[(2S)-2-hydroxy-3-(4-hydroxy-phenoxy)-propylamino]-methyl}-piperidine-1-sulfonyl)-phenyl]-urea; |
| mmm) | 1-[4-(4-{[2-Hydroxy-3-(4-hydroxy-phenoxy)-propylamino]-methyl}-piperidine-1-sulfonyl)-phenyl]-3-isobutyl-ureA; |
| nnn) | 1-[4-(4-([(2S)-2-Hydroxy-3-(4-hydroxy-phenoxy)-propylamino)-methyl}-piperidine-1-sulfonyl)-phenyl]-3-pyridin-2-yl-urea; |
| ooo) | N-{2-Hydroxy-5-[(1R)-1-hydroxy-2-({1-[4-(3-pyridin-2-yl-ureido)-benzenesulfonyl]-piperidin-4-ylmethyl}-amino)-ethyl]-phenyl}-methanesulfonamide; |
| ppp) | N-{5-[1-Hydroxy-2-({1-[4-(3-pyridin-2-yl-ureido)-benzenesulfonyl]-piperidin-4-ylmethyl}-amino)-ethyl]-1H-indol-7-yl}-methanesulfonamide; |
| qqq) | 1-[4-(4-{[(2S)-2-Hydroxy-3-(4-hydroxy-phenoxy)-propylamino]-methyl}-piperidine-1-sulfonyl)-phenyl]-3-octyl-urea; |
| rrr) | 1-[4-(4-{[(2S)-2-Hydroxy-3-(2-oxo-2,3-dihydro-1H-indol-4-yloxy)-propylamino]-methyl}-piperidine-1-sulfonyl)-phenyl]-3-octyl-urea; |
| sss) | 4-[2-Hydroxy-3-({1-[4-(3-octyl-ureide)-benzenesulfonyl]-piperidin-4-ylmethyl}-amino)-propoxy]-1H-indole-2-carboxylic acid amide; |
| ttt) | 1-[4-(4-{[(2S)-2-Hydroxy-3-(1H-indol-5-yloxy)-propylamino]-methyl}-piperidine-1-sulfonyl)-phenyl]-3-octyl-urea; |
| uuu) | (R)-N-{2-Hydroxy-5-[1-hydroxy-2-({1-[4-(3-octyl-ureido)-benzenesulfonyl]-piperidine-4-ylmethyl}-amino)-ethyl]-phenyl}-methanesulfonamide; |
| vvv) | 1-[4-(4-{[(2S)-2-Hydroxy-3-(8-hydroxy-2-oxo-1,2,3,4-tetrahydro-quinolin-5-yloxy)-propylamino]-methyl}-piperidine-1-sulfonyl)-phenyl]-3-octyl-urea; |
| www) | 1-[4-(4-{[(2S)-2-Hydroxy-3-(4-hydroxy-phenoxy)-propylamino]-methyl}-piperidine-1-sulfonyl)-phenyl]-3-(3-thiophen-2-yl-propyl)-urea; |
| xxx) | 1-(2,5-Difluoro-benzyl)-3-[4-(4-{[(2S)-2-hydroxy-3-(1H-indol-5-yloxy)-propylamino]-methyl}-piperidine-1-sulfonyl)-phenyl]-urea; |
| yyy) | 1-(2,5-Difluoro-benzyl)-3-[4-(4-{[(2S)-2-hydroxy-3-(4-hydroxy-phenoxy)-propylamino]-methyl}-piperidine-1-sulfonyl)-phenyl]-urea; |
| zzz) | 1-(2,5-Difluoro-benzyl)-3-[4-(4-{[(2S)-3-(3-fluoro-4-hydroxy-phenoxy)-2-hydroxy-propylamino]-methyl}-piperidine-1-sulfonyl)-phenyl]-urea; |
| aaaa) | N-(5-{(2S)-3-[(1-{4-[3-(2,5-Difluoro-benzyl)-ureido]-benzenesulfonyl}-piperidin-4-ylmethyl)-amino]-2-hydroxy-propoxy}-2-hydroxy-phenyl)-methanesulfonamide; |
| bbbb) | 1-[4-(4-{[(2S)-3-(2-Chloro-4-hydroxy-phenoxy)-2-hydroxy-propylamino]-methyl}-piperidine-1-sulfonyl)-phenyl]-3-(2,5-difluoro-benzyl)-urea; |
| cccc) | N-{5-[(1R)-2-(({1-(4-[({[2-(2,5-difluorophenyl)ethyl]amino}carbonyl)amino]-phenyl}sulfonyl)piperidin-4-yl]methyl}amino)-1-hydroxyethyl]-2-hydroxyphenyl}-methanesulfonamide; |

| | -continued |
|---|---|
| dddd) | 1-[2-(2,4-Difluoro-phenyl)-ethyl]-3-[4-(4-{[(2S)-2-hydroxy-3-(4-hydroxy-phenoxy)-propylamino]-methyl}-piperidine-1-sulfonyl)-phenyl)-urea; |
| eeee) | 1-(2,6-Difluoro-phenyl)3-[4-(4-{[(2S)-2-hydroxy-3-(4-hydroxy-phenoxy)-propylamino]-methyl}-piperidine-1-sulfonyl)-phenyl]-urea; |
| ffff) | N-(5-{(1R)-2-[(1-{4-[3-(2,6-Difluoro-benzyl)-3-isopropyl-ureido]-benzenesulfonyl}-piperidin-4-ylmethyl)-amino]-1-hydroxy-ethyl}-2-hydroxy-phenyl)-methane-sulfonamide; |
| gggg) | N-(5-{2-[(1-{4-[3-(2,6-Difluoro-benzyl)-3-methyl-ureido]-benzenesulfonyl}-piperidin-4-ylmethyl)-amino]-1-hydroxy-ethyl}-2-hydroxy-phenyl)-methanesulfonamide; |
| hhhh) | N-(5-{(1R)-2-[(1-{4-[3-(2,5-Difluoro-benzyl)-3-isopropyl-ureido]-benzenesulfonyl}-piperidin-4-ylmethyl)-amino]-1-hydroxy-ethyl}-2-hydroxy-phenyl)-methane-sulfonamide; |
| iiii) | N-[5-[(R)-2-[[[1-[[4-[[[[(2,5-Difluorophenyl)methyl]-methylamino]-carbonyl]amino]-phenyl]sulfonyl]-4-piperidinyl]methyl]amino]-1-hydroxyethyl]-2-hydroxyphenyl]-methanesulfonamide; |
| jjjj) | [3-Fluoro-4-[[[[[4-[[4-[[[(R)-2-hydroxy-2-[4-hydroxy-3-[(methylsulfonyl)amino]-phenyl]ethyl]amino]methyl]-1-piperidinyl]sulfonyl]phenyl]amino]carbonyl]-amino]methyl]phenoxy]acetic acid, methyl ester; |
| kkkk) | [3-Fluoro-4-[[[[[4-[[4-[[[(R)-2-hydroxy-2-[4-hydroxy-3-[(methylsulfonyl)amino]-phenyl]-ethyl]amino]methyl]-1-piperidinyl]sulfonyl)phenyl]amino]carbonyl]-amino]-methyl]phenoxy]acetic acid; |
| llll) | Heptanoic acid [4-(4-{[(2S)-2-hydroxy-3-(4-hydroxy-phenoxy)-propylamino]-methyl}-piperidine-1-sulfonyl)-phenyl]-amide; |
| mmmm) | N-(2,6-Difluoro-benzyl)4-(4-{[(2S)-2-hydroxy-3-(4-hydroxy-phenoxy)-propylamino]-methyl}-piperidine-1-sulfonyl)-benzamide; |
| nnnn) | 1H-Indazole-3-carboxylic acid [4-(4-{[(2S)-2-hydroxy-3-(4-hydroxy-phenoxy)-propylamino]-methyl}-piperidine-1-sulfonyl)-phenyl]-amide; |
| oooo) | 4-(2-Hydroxy-3-{[1-(4-pyrazol-1-yl-benzenesulfonyl)-piperidin-4-ylmethyl]-amino}-propoxy)-phenol; |
| pppp) | 1-[4-(4-{[2-Hydroxy-3-(4-hydroxy-phenoxy)-propylamino]-methyl}-piperidine-1-sulfonyl)-phenyl]-3-methyl-imidazolidin-2-one; |
| qqqq) | 1-[4-(4-{[(2R)-2-Hydroxy-2-(4-hydroxy-3-methanesulfonylamino-phenyl)-ethyl-amino]-methyl}-piperidine-1-sulfonyl)-phenyl]-1H-indole-2-carboxylic acid ethyl ester; |
| rrrr) | {1-[4-(4-[[(2R)-2-Hydroxy-2-(4-hydroxy-3-methanesulfonylamino-phenyl)-ethylamino]-methyl}-piperidine-1-sulfonyl)-phenyl]-1H-indol-3-yl}-acetic acid ethyl ester; |
| ssss) | (1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indol-3-yl}-acetic acid; |
| tttt) | 1-[4-(4-{[(2R)-2-Hydroxy-2-(4-hydroxy-3-methanesulfonylamino-phenyl)-ethyl-amino]-methyl}-piperidine-1-sulfonyl)-phenyl]-1H-indole-4-carboxylic acid methyl ester; |
| uuuu) | 1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indole-4-carboxylic acid; |
| vvvv) | Ethyl 1-{4-[(4-{[(((2R)-2-hydroxy-2-(4-hydroxy-3-[(methylsulfonyl)amino]-phenyl}ethyl)amino]methyl}piperidin-1-yl)sulfonyl]phenyl}-1H-pyrazole-4-carboxylate; |
| wwww) | 1-(4-[(4-([(((2R)-2-Hydroxy-2-{4-hydroxy-3-[(methylsulfonyl)amino]-phenyl}ethyl)amino]methyl}piperidin-1-yl)sulfonyl]phenyl}-1H-pyrazole-4-carboxylic acid; |
| xxxx) | 4-[(2S)-2-Hydroxy-3-({1-[4-(5-octyl-[1,2,4]oxadiazol-3-yl)-benzenesulfonyl]-piperidin-4-ylmethyl}-amino)-propoxy]-phenol; |
| yyyy) | N-{2-Hydroxy-5-[1-hydroxy-2-((1-[4-(5-octyl-[1,2,4]oxadiazol-3-yl)-benzene-sulfonyl]-piperidin-4-ylmethyl}-amino)-ethyl]-phenyl}-methanesulfonamide; |
| zzzz) | 3-{3-[4-(4-{[(2R)-2-Hydroxy-2-(4-hydroxy-3-methanesulfonylamino-phenyl)-ethylamino]-methyl}-piperidine-1-sulfonyl)-phenyl]-[1,2,4]oxadiazol-5-yl]-propionic acid methyl ester; |
| aaaaa) | 3-(3-(4-[(4-([(((2S)-2-Hydroxy-2-{4-hydroxy-3-[(methylsulfonyl)amino]-phenyl}ethyl)amino]methyl}-1-piperidinyl)sulfonyl]phenyl}-1,2,4-oxadiazol-5-yl]propanoic acid; |
| bbbbb) | (R)-N-{2-Hydroxy-5-[1-hydroxy-2-({1-[4-(piperidine-1-sulfonyl)-phenyl]-piperidin-4-ylmethyl}-amino)-ethyl]-phenyl}-methanesulfonamide; |
| ccccc) | Methyl 6-(4-([(((2R)-2-hydroxy-2-(4-hydroxy-3-[(methylsulfonyl)amino]phenyl}-ethyl)amino]methyl}piperidin-1-yl)-nicotinate; |
| ddddd) | (2S)-2-([4-(4-{[((2R)-2-Hydroxy-2-(4-hydroxy-3-[(methylsulfonyl)amino]phenyl}-ethyl)amino]methyl}piperidin-1-yl)benzoyl]amino}butanedioic acid; |
| eeeee) | (2S)-2-([4-(4-([((2R)-2-Hydroxy-2-{4-hydroxy-3-[(methylsulfonyl)amino]phenyl}-ethyl)amino]methyl}piperidin-1-yl)benzoyl]amino}-3-phenylpropanoic acid; |
| fffff) | (2R)-2-{[4-(4-([(((2R)-2-hydroxy-2-{4-hydroxy-3-[(methylsulfonyl)amino]phenyl}-ethyl)amino]methyl}piperidin-1-yl)benzoyl]amino}butanedioic acid; |
| ggggg) | (2S)-1-({4-[(4-{[((2R)-2-Hydroxy-2-{4-hydroxy-3-[(methylsulfonyl)amino]-phenyl}ethyl)amino]methyl}piperidin-1-yl)sulfonyl]anilino}carbonyl)pyrrolidine-2-carboxylic acid methyl ester; |

-continued

| | |
|---|---|
| hhhhh) | (2S)-1-({4-[(4-{[((2R)-2-hydroxy-2-{4-hydroxy-3-[(methylsulfonyl)amino]phenyl}-ethyl)amino]methyl}piperidin-1-yl)sulfonyl]anilino}carbonyl)pyrrolidine-2-carboxylic acid; |
| iiiii) | (2S)-2-[({4-[(4-{[((2R)-2-Hydroxy-2-{4-hydroxy-3-[(methylsulfonyl)amino]-phenyl}ethyl)amino]methyl}piperidin-1-yl)sulfonyl]anilino}carbonyl)amino]-3-phenylpropanoic acid; |
| jjjjj) | (2S)-2-{[4-(4-{[((2R)-2-Hydroxy-2-{4-hydroxy-3-[(methylsulfonyl)amino]phenyl}-ethyl)amino]methyl}piperidin-1-yl)benzoyl]amino}-4-methylpentanoic acid; |
| kkkkk) | (2S)-1-[4-(4-{[((2R)-2-hydroxy-2-{4-hydroxy-3-[(methylsulfonyl)amino]phenyl}-ethyl)amino]methyl}piperidin-1-yl)benzoyl]pyrrolidine-2-carboxylic acid; |
| lllll) | (2S)-1-[4-(benzyloxy)phenoxy]-3-({[1-(phenylsulfonyl)piperidin-4-yl]methyl}amino)propan-2-ol; |
| mmmmm) | 4-{[(2S)-2-hydroxy-3-({[1-(phenylsulfonyl)piperidin-4-yl]methyl}amino)propyl]oxy}phenol; |
| nnnnn) | (2S)-1-(9H-carbazol-4-yloxy)-3-({[1-(phenylsulfonyl)piperidin-4-yl]methyl}amino)propan-2-ol; |
| ooooo) | 4-{[(2S)-2-hydroxy-3-({[1-(phenylsulfonyl)piperidin-4-yl]methyl}amino)propyl]oxy}-1,3-dihydro-2H-benzimidazol-2-one; |
| ppppp) | (2S)-1-[4-(benzyloxy)phenoxy]-3-[({1-[(4-isopropylphenyl)sulfonyl]piperidin-4-yl}methyl)amino]propan-2-ol; |
| qqqqq) | 4-({(2S)-2-hydroxy-3-[({1-[(4-isopropylphenyl)sulfonyl]piperidin-4-yl}methyl)amino]propyl}oxy)phenol; |
| rrrrr) | (2S)-1-(9H-carbazol-4-yloxy)-3-({1-[(4-isopropylphenyl)sulfonyl]piperidin-4-yl}methyl)amino]propan-2-ol; |
| sssss) | 4-({(2S)-2-hydroxy-3-[({1-[(4-isopropylphenyl)sulfonyl]piperidin-4-yl}methyl)amino]propyl}oxy)-1,3-dihydro-2H-benzimidazol-2-one; |
| ttttt) | N-(2-hydroxy-5-{(1R)-1-hydroxy-2-[({1-[(4-isopropylphenyl)-sulfonyl]piperidin-4-yl}methyl)amino]ethyl}phenyl)-methanesulfonamide; |
| uuuuu) | (2S)-1-[4-(benzyloxy)phenoxy]-3-[({1-[(4-ethylphenyl)sulfonyl]piperidin-4-yl}methyl)amino]propan-2-ol; |
| vvvvv) | 4-(((2S)-3-[((1-[(4-ethylphenyl)sulfonyl]piperidin-4-yl}methyl)amino]-2-hydroxypropyl}oxy)phenol; |
| wwwww) | (2S)-1-(9H-carbazol-4-yloxy)-3-[((1-[(4-ethylphenyl)sulfonyl]piperidin-4-yl}methyl)amino]propan-2-ol; |
| xxxxx) | 4-(((2S)-3-[((1-[(4-ethylphenyl)sulfonyl]piperidin-4-yl}methyl)-amino]-2-hydroxypropyl}oxy)-1,3-dihydro-2H-benzimidazol-2-one; |
| yyyyy) | N-(5-((1R)-2-[((1-[(4-ethylphenyl)sulfonyl]piperidin-4-yl}methyl)-amino]-1-hydroxyethyl}-2-hydroxyphenyl)methanesulfonamide; |
| zzzzz) | (2S)-1-[4-(benzyloxy)phenoxy]-3-[(((1-[(4-methoxyphenyl)sulfonyl]piperidin-4-yl}methyl)amino]propan-2-ol; |
| aaaaaa) | 4-((2S)-2-Hydroxy-3-{[1-(4-methoxy-benzenesulfonyl)-piperidin-4-ylmethyl]-amino}-propoxy)-phenol; |
| bbbbbb) | (2S)-1-(9H-Carbazol-4-yloxy)-3-([1-(4-methoxy-benzenesulfonyl)-piperidin-4-ylmethyl]-amino}-propan-2-ol; |
| cccccc) | 4-((2S)-2-Hydroxy-3-([1-(4-methoxy-benzenesulfonyl)-piperidin-4-ylmethyl]-amino}-propoxy)-1,3-dihydro-benzoimidazol-2-one; |
| dddddd) | (2S)-1-[4-(benzyloxy)phenoxy]-3-[((1-[(2,4,6-triisopropylphenyl)sulfonyl]piperidin-4-yl}methyl)amino]propan-2-ol; |
| eeeeee) | 4-(((2S)-2-hydroxy-3-[((1-[(2,4,6-triisopropylphenyl)sulfonyl]-piperidin-4-yl}methyl)amino]propyl}oxy)phenol; |
| ffffff) | (2S)-1-(9H-carbazol-4-yloxy)-3-[({1-[(2,4,6-triisopropylphenyl)sulfonyl]piperidin-4-yl}methyl)amino]propan-2-ol; |
| gggggg) | 4-(((2S)-2-hydroxy-3-[((1-[(2,4,6-triisopropylphenyl)sulfonyl]piperidin-4-yl}methyl)amino]propyl}oxy)-1,3-dihydro-2H-benzimidazol-2-one; |
| hhhhhh) | N-(2-hydroxy-5-((1R)-1-hydroxy-2-[((1-[(2,4,6-triisopropyl-phenyl)sulfonyl]piperidin-4-yl}methyl)amino]ethyl}phenyl)-methanesulfonamide; |
| iiiiii) | (2S)-1-[4-(benzyloxy)phenoxy]-3-[((1-[(2,3,4,5,6-pentamethylphenyl)sulfonyl]piperidin-4-yl}methyl)amino]propan-2-ol; |
| jjjjjj) | 4-(((2S)-2-hydroxy-3-[((1-[(2,3,4,5,6-pentamethylphenyl)-sulfonyl]-piperidin-4-yl}methyl)amino]propyl}oxy)phenol; |
| kkkkkk) | (2S)-1-(9H-carbazol-4-yloxy)-3-[((1-[(2,3,4,5,6-pentamethylphenyl)sulfonyl]piperidin-4-yl}methyl)amino]propan 2 ol; |
| llllll) | 4-(((2S)-2-hydroxy-3-[((1-[(2,3,4,5,6-pentamethylphenyl)sulfonyl]piperidin-4-yl}methyl)amino]propyl}oxy)-1,3-dihydro-2H-benzimidazol-2-one; |
| mmmmmm) | N-(2-hydroxy-5-{(1R)-1-hydroxy-2-[({1-[(2,3,4,5,6-pentamethylphenyl)sulfonyl]piperidin-4-yl}methyl)amino]ethyl}phenyl)methanesulfonamide; |
| nnnnnn) | (2S)-1-[4-(benzyloxy)phenoxy]-3-{[(1-{[4-(tert-pentyl)phenyl]sulfonyl}piperidin-4-yl)methyl]amino}propan-2-ol; |
| oooooo) | 4-[((2S)-2-hydroxy-3-{[(1-{[4-(tert-pentyl)phenyl]sulfonyl}piperidin-4-yl)methyl]amino}propyl)oxy]phenol; |
| pppppp) | (2S)-1-(9H-carbazol-4-yloxy)-3-{[(1-{[4-(tert-pentyl)phenyl]sulfonyl}piperidin-4-yl)methyl]amino}propan-2-ol; |
| qqqqqq) | 4-[((2S)-2-hydroxy-3-{[(1-{[4-(tert-pentyl)phenyl]sulfonyl}piperidin-4-yl)methyl]amino}propyl)oxy]-1,3-dihydro-2H-benzimidazol-2-one; |

| | |
|---|---|
| rrrrrr) | N-[2-hydroxy-5-((1R)-1-hydroxy-2-{[(1-{[4-(tert-pentyl)phenyl]sulfonyl}piperidin-4-yl]methyl]amino}ethyl)phenyl]methanesulfonamide; |
| ssssss) | (2S)-1-[4-(benzyloxy)phenoxy]-3-({[1-(1-naphthylsulfonyl)piperidin-4-yl]methyl}amino)propan-2-ol; |
| tttttt) | 4-{[(2S)-2-hydroxy-3-({[1-(1-naphthylsulfonyl)piperidin-4-yl]methyl}amino)propyl]oxy}phenol; |
| uuuuuu) | (2S)-1-(9H-carbazol-4-yloxy)-3-({[1-(1-naphthylsulfonyl)piperidin-4-yl]methyl}amino)propan-2-ol; |
| vvvvvv) | 4-{[(2S)-2-hydroxy-3-({[1-(1-naphthylsulfonyl)piperidin-4-yl]methyl}amino)propyl]oxy}-1,3-dihydro-2H-benzimidazol-2-one; |
| wwwwww) | N-{2-hydroxy-5-[(1R)-1-hydroxy-2-({[1-(1-naphthylsulfonyl)piperidin-4-yl]methyl}amino)ethyl]phenyl}methanesulfonamide; |
| xxxxxx) | (2S)-1-[4-(benzyloxy)phenoxy]-3-({[1-(2-naphthylsulfonyl)piperidin-4-yl]methyl}amino)propan-2-ol; |
| yyyyyy) | 4-{[(2S)-2-hydroxy-3-({[1-(2-naphthylsulfonyl)piperidin-4-yl]methyl}amino)propyl]oxy}phenol; |
| zzzzzz) | (2S)-1-(9H-Carbazol-4-yloxy)-3-({1-(naphthalene-2-sulfonyl)-piperidin-4-ylmethyl]-amino}-propan-2-ol; |
| aaaaaaa) | 4-{[(2S)-2-hydroxy-3-({[1-(2-naphthylsulfonyl)piperidin-4-yl]methyl}amino)propyl]oxy}-1,3-dihydro-2H-benzimidazol-2-one; |
| bbbbbbb) | N-{2-hydroxy-5-[(1R)-1-hydroxy-2-({[1-(2-naphthylsulfonyl)-piperidin-4-yl]methyl}amino)ethyl]phenyl}methanesulfonamide; |
| ccccccc) | (2S)-1-[4-(benzyloxy)phenoxy]-3-({[(1-{[4-(tert-butyl)phenyl]sulfonyl}piperidin-4-yl)methyl]amino}propan-2-ol; |
| ddddddd) | 4-[((2S)-3-{[(1-{[4-(tert-butyl)phenyl]sulfonyl}piperidin-4-yl)methyl]amino}-2-hydroxypropyl)oxy]phenol; |
| eeeeeee) | (2S)-1-{[(1-{[4-(tert-butyl)phenyl]sulfonyl}piperidin-4-yl)methyl]amino}-3-(9H-carbazol-4-yloxy)propan-2-ol; |
| fffffff) | 4-[((2S)-3-{[(1-{[4-(tert-butyl)phenyl]sulfonyl}piperidin-4-yl)methyl]-amino}-2-hydroxypropyl)oxy]-1,3-dihydro-2H-benzimidazol-2-one; |
| ggggggg) | N-[5-((1R)-2-{[(1-{[4-(tert-butyl)phenyl]sulfonyl}piperidin-4-yl)-methyl]amino}-1-hydroxyethyl)-2-hydroxyphenyl]-methanesulfonamide; |
| hhhhhhh) | (2S)-1-[4-(benzyloxy)phenoxy]-3-[({1-[(4-bromo-2-ethylphenyl)sulfonyl]piperidin-4-yl}methyl)amino]propan-2-ol; |
| iiiiiii) | 4-([(2S)-3-[({1-[(4-bromo-2-ethylphenyl)sulfonyl]piperidin-4-yl}methyl)amino]-2-hydroxypropyl}oxy)phenol; |
| jjjjjjj) | (2S)-1-[({1-[(4-bromo-2-ethylphenyl)sulfonyl]piperidin-4-yl}methyl)amino]-3-(9H-carbazol-4-yloxy)propan-2-ol; |
| kkkkkkk) | 4-({(2S)-3-[({1-[(4-bromo-2-ethylphenyl)sulfonyl]piperidin-4-yl}-methyl)amino]-2-hydroxypropyl}oxy)-1,3-dihydro-2H-benzimidazol-2-one; |
| lllllll) | N-(5-{(1R)-2-[({1-[(4-bromo-2-ethylphenyl)sulfonyl]piperidin-4-yl}-methyl)amino]-1-hydroxyethyl}-2-hydroxyphenyl)-methanesulfonamide; |
| mmmmmmm) | (2S)-1-[4-(benzyloxy)phenoxy]-3-[({1-[(4-bromo-2,5-dichlorothien-3-yl)sulfonyl]piperidin-4-yl}methyl)amino]propan-2-ol; |
| nnnnnnn) | 4-({(2S)-3-[({1-[(4-bromo-2,5-dichlorothien-3-yl)sulfonyl]piperidin-4-yl}methyl)amino]-2-hydroxypropyl}oxy)phenol; |
| ooooooo) | (2S)-1-[({1-[(4-bromo-2,5-dichlorothien-3-yl)sulfonyl]piperidin-4-yl}methyl)amino]-3-(9H-carbazol-4-yloxy)propan-2-ol; |
| ppppppp) | 4-({(2S)-3-[({1-[(4-bromo-2,5-dichlorothien-3-yl)sulfonyl]piperidin-4-yl}methyl)amino]-2-hydroxypropyl}oxy)-1,3-dihydro-2H-benzimidazol-2-one; |
| qqqqqqq) | N-(5-{(1R)-2-[({1-[(4-bromo-2,5-dichlorothien-3-yl)sulfonyl]-piperidin-4-yl}methyl)amino]-1-hydroxyethyl}-2-hydroxyphenyl)-methanesulfonamide; |
| rrrrrrr) | (2S)-1-[4-(benzyloxy)phenoxy]-3-[({1-[(3-bromophenyl)sulfonyl]piperidin-4-yl}methyl)amino]propan-2-ol; |
| sssssss) | 4-({(2S)-3-[({1-[(3-bromophenyl)sulfonyl]piperidin-4-yl}methyl)amino]-2-hydroxypropyl}oxy)phenol; |
| ttttttt) | (2S)-1-[({1-[(3-bromophenyl)sulfonyl]piperidin-4-yl}methyl)amino]-3-(9H-carbazol-4-yloxy)propan-2-ol; |
| uuuuuuu) | 4-({(2S)-3-[({1-[(3-bromophenyl)sulfonyl]piperidin-4-yl}methyl)-amino]-2-hydroxypropyl}oxy)-1,3-dihydro-2H-benzimidazol-2-one; |
| vvvvvvv) | N-(5-{(1R)-2-[({1-[(3-bromophenyl)sulfonyl]piperidin-4-yl}methyl)-amino]-1-hydroxypropyl}oxy)-1,3-dihydro-2H-benzimidazol-2-one; |
| wwwwwww) | N-{[5-({4-[({(2S)-3-[4-(benzyloxy)phenoxy]-2-hydroxypropyl}amino)methyl]piperidin-1-yl}sulfonyl)thien-2-yl]methyl}benzamide; |
| xxxxxxx) | N-[(5-{[4-({[(2S)-2-hydroxy-3-(4-hydroxyphenoxy)propyl]amino}-methyl)piperidin-1-yl]sulfonyl}thien-2-yl)methyl]benzamide; |
| yyyyyyy) | N-[(5-{[4-({[(2S)-3-(9H-carbazol-4-yloxy)-2-hydroxypropyl]amino}-methyl)piperidin-1-yl]sulfonyl}thien-2-yl)methyl]benzamide; |
| zzzzzzz) | N-{[5-({4-[({(2S)-2-hydroxy-3-[(2-oxo-2,3-dihydro-1H-benzimidazol-4-yl)oxy]propyl}amino)methyl]piperidin-1-yl}sulfonyl)thien-2-yl]methyl}benzamide; |
| aaaaaaaa) | N-({5-[4-{[((2R)-2-hydroxy-2-{4-hydroxy-3-[(methylsulfonyl)-amino]-phenyl}ethyl)amino]methyl]piperidin-1-yl)sulfonyl]thien-2-yl}methyl)benzamide; |
| bbbbbbbb) | (2S)-1-[4-(benzyloxy)phenoxy]-3-[({1-[(4-butoxyphenyl)sulfonyl]piperidin-4-yl}methyl)amino]propan-2-ol; |

-continued

| | |
|---|---|
| cccccccc) | (2S)-1-[({1-[(4-butoxyphenyl)sulfonyl]piperidin-4-yl}methyl)amino]-3-(9H-carbazol-4-yloxy)propan-2-ol; |
| dddddddd) | 4-({(2S)-3-[({1-[(4-butoxyphenyl)sulfonyl]piperidin-4-yl}methyl)amino]-2-hydroxypropyl}oxy)-1,3-dihydro-2H-benzimidazol-2-one; |
| eeeeeeee) | N-(5-{(1R)-2-[({1-[(4-butoxyphenyl)sulfonyl]piperidin-4-yl}methyl)-amino]-1-hydroxyethyl}-2-hydroxyphenyl)methanesulfonamide; |
| ffffffff) | (2S)-1-[4-(benzyloxy)phenoxy]-3-[({1-[(4-butylphenyl)sulfonyl]piperidin-4-yl}methyl)amino]propan-2-ol; |
| gggggggg) | 4-({(2S)-3-[({1-[(4-butylphenyl)sulfonyl]piperidin-4-yl}methyl)amino]-2-hydroxypropyl}oxy)phenol; |
| hhhhhhhh) | (2S)-1-[({1-[(4-butylphenyl)sulfonyl]piperidin-4-yl}methyl)amino]-3-(9H-carbazol-4-yloxy)propan-2-ol; |
| iiiiiiii) | 4-({(2S)-3-[({1-[(4-butylphenyl)sulfonyl]piperidin-4-yl}methyl)amino]-2-hydroxypropyl}oxy)-1,3-dihydro-2H-benzimidazol-2-one; |
| jjjjjjjj) | N-(5-{(1R)-2-[({1-[(4-butylphenyl)sulfonyl]piperidin-4-yl}methyl)-amino]-1-hydroxyethyl}-2-hydroxyphenyl)-methanesulfonamide; |
| kkkkkkkk) | N-(4-{[4-({[(2S)-3-(9H-carbazol-4-yloxy)-2-hydroxypropyl]-amino}methyl)piperidin-1-yl]sulfonyl}phenyl)acetamide; |
| llllllll) | N-[4-({4-[({(2S)-2-hydroxy-3-[(2-oxo-2,3-dihydro-1H-benzimidazol-4-yl)oxy]propyl}amino)methyl]piperidin-1-yl}sulfonyl)phenyl]acetamide; |
| mmmmmmmm) | (2S)-1-[4-(benzyloxy)phenoxy]-3-({[1-([1,1'-biphenyl]-4-ylsulfonyl)piperidin-4-yl]methyl}amino)propan-2-ol; |
| nnnnnnnn) | 4-{[(2S)-3-(({1-([1,1'-biphenyl]-4-ylsulfonyl)piperidin-4-yl}methyl}amino)-2-hydroxypropyl]oxy}phenol; |
| oooooooo) | (2S)-1-({[1-([1,1'-biphenyl]-4-ylsulfonyl)piperidin-4-yl]methyl}amino)-3-(9H-carbazol-4-yloxy)propan-2-ol; |
| pppppppp) | 4-{[(2S)-3-({[1-([1,1'-biphenyl]-4-ylsulfonyl)piperidin-4-yl]methyl}amino)-2-hydroxypropyl]oxy}-1,3-dihydro-2H-benzimidazol-2-one; |
| qqqqqqqq) | N-(5-[(1R)-2-({[1-([1,1'-biphenyl]-4-ylsulfonyl)piperidin-4-yl]methyl}amino)-1-hydroxyethyl]-2-hydroxyphenyl}-methanesulfonamide; |
| rrrrrrrr) | (2S)-1-({[1-(2,1,3-benzothiadiazol-4-ylsulfonyl)piperidin-4-yl]methyl}amino)-3-[4-(benzyloxy)phenoxy]propan-2-ol; |
| ssssssss) | 4-({(2S)-3-({[1-(2,1,3-benzothiadiazol-4-ylsulfonyl)piperidin-4-yl]methyl}amino)-2-hydroxypropyl]oxy}phenol; |
| tttttttt) | (2S)-1-({[1-(2,1,3-benzothiadiazol-4-ylsulfonyl)piperidin-4-yl]methyl}amino)-3-(9H-carbazol-4-yloxy)propan-2-ol; |
| uuuuuuuu) | 4-{[(2S)-3-({[1-(2,1,3-benzothiadiazol-4-ylsulfonyl)piperidin-4-yl]methyl}amino)-2-hydroxypropyl]oxy}-1,3-dihydro-2H-benzimidazol-2-one; |
| vvvvvvvv) | N-{5-[(1R)-2-({[1-(2,1,3-benzothiadiazol-4-ylsulfonyl)piperidin-4-yl]methyl}amino)-1-hydroxyethyl]-2-hydroxyphenyl}methanesulfonamide; |
| wwwwwwww) | (2S)-1-[4-(benzyloxy)phenoxy]-3-({[1-(benzylsulfonyl)piperidin-4-yl]methyl}amino)propan-2-ol; |
| xxxxxxxx) | (2S)-1-({[1-(benzylsulfonyl)piperidin-4-yl]methyl}amino)-3-(9H-carbazol-4-yloxy)propan-2-ol; |
| yyyyyyyy) | 4-{[(2S)-3-({[1-(benzylsulfonyl)piperidin-4-yl]methyl}amino)-2-hydroxypropyl]oxy}-1,3-dihydro-2H-benzimidazol-2-one; |
| zzzzzzzz) | (2S)-1-[4-(benzyloxy)phenoxy]-3-([(1-{[4-(methylsulfonyl)phenyl]-sulfonyl}-piperidin-4-yl)methyl]amino)propan-2-ol; |
| aaaaaaaaa) | 4-[((2S)-2-hydroxy-3-{[(1-{[4-(methylsulfonyl)phenyl]-sulfonyl}piperidin-4-yl)methyl]amino}propyl)oxy]phenol; |
| bbbbbbbbb) | (2S)-1-(9H-carbazol-4-yloxy)-3-{[(1-{[4-(methylsulfonyl)-phenyl]sulfonyl}piperidin-4-yl)methyl]amino}propan-2-ol; |
| ccccccccc) | 4-[((2S)-2-hydroxy-3-{[(1-{[4-(methylsulfonyl)phenyl]sulfonyl}piperidin-4-yl)methyl]amino}propyl)oxy]-1,3-dihydro-2H-benzimidazol-2-one; |
| ddddddddd) | (2S)-1-[4-(benzyloxy)phenoxy]-3-{[(1-{[5-(phenylsulfonyl)thien-2-yl]sulfonyl}piperidin-4-yl)methyl]amino}propan-2-ol; |
| eeeeeeeee) | 4-[((2S)-2-hydroxy-3-{[(1-([5-(phenylsulfonyl)thien-2-yl]sulfonyl}piperidin-4-yl)methyl]amino}propyl)oxy]phenol; |
| fffffffff) | (2S)-1-(9H-carbazol-4-yloxy)-3-{[(1-{[5-(phenylsulfonyl)thien-2-yl]sulfonyl}piperidin-4-yl)methyl]amino}propan-2-ol; |
| ggggggggg) | 4-[((2S)-2-hydroxy-3-{[(1-{[5-(phenylsulfonyl)thien-2-yl]sulfonyl}piperidin-4-yl)methyl]amino}propyl)oxy]-1,3-dihydro-2H-benzimidazol-2-one; |
| hhhhhhhhh) | (2S)-1-[4-(benzyloxy)phenoxy]-3-[((1-[(4-methylphenyl)sulfonyl]piperidin-4-yl}methyl)amino]propan-2-ol; |
| iiiiiiiii) | 4-({(2S)-2-hydroxy-3-[({1-[(4-methylphenyl)sulfonyl]piperidin-4-yl}methyl)amino]propyl}oxy)phenol; |
| jjjjjjjjj) | (2S)-1-(9H-carbazol-4-yloxy)-3-[({1-[(4-methylphenyl)sulfonyl]piperidin-4-yl}methyl)amino]propan-2-ol; |
| kkkkkkkkk) | 4-(((2S)-2-hydroxy-3-[({1-[(4-methylphenyl)sulfonyl]piperidin-4-yl}methyl)amino]propyl}oxy)-1,3-dihydro-2H-benzimidazol-2-one; |
| lllllllll) | N-(2-hydroxy-5-{(1R)-1-hydroxy-2-[({1-[(4-methylphenyl)sulfonyl]piperidin-4-yl}methyl)amino]ethyl}phenyl)methanesulfonamide; |
| mmmmmmmmm) | (2S)-1-[4-(benzyloxy)phenoxy]-3-[({1-[(3,4-dimethoxyphenyl)sulfonyl]piperidin-4 yl}methyl)amino]propan-2-ol; |
| nnnnnnnnn) | 4-({(2S)-3-[({1-[(3,4-dimethoxyphenyl)sulfonyl]piperidin-4-yl}methyl)amino]-2-hydroxypropyl}oxy)phenol; |
| ooooooooo) | (2S)-1-(9H-carbazol-4-yloxy)-3-[({1-[(3,4-dimethoxyphenyl)sulfonyl]piperidin-4-yl}methyl)amino]propan-2-ol; |

-continued

| | |
|---|---|
| ppppppppp) | 4-({(2S)-3-[({1-[(3,4-dimethoxyphenyl)sulfonyl]piperidin-4-yl}methyl)amino]-2-hydroxypropyl}oxy)-1,3-dihydro-2H-benzimidazol-2-one; |
| qqqqqqqqq) | N-(5-{(1R)-2-[({1-[(3,4-dimethoxyphenyl)sulfonyl]piperidin-4-yl}methyl)amino]-1-1-hydroxyethyl}-2-hydroxyphenyl)methanesulfonamide; |
| rrrrrrrrr) | 4-({(2S)-2-hydroxy-3-[({1-[(5-{[5-(trifluoromethyl)pyridin-2-yl]sulfonyl}thien-2-yl)sulfonyl]piperidin-4-yl}methyl)amino]propyl}oxy)phenol; |
| sssssssss) | (2S)-1-(9H-carbazol-4-yloxy)-3-[({1-[(5-{[5-(trifluoromethyl)pyridin-2-yl]sulfonyl]thien-2-yl)sulfonyl]piperidin-4-yl}methyl)amino]propan-2-ol; |
| ttttttttt) | 4-({(2S)-2-hydroxy-3-[({1-[(5-{[5-(trifluoromethyl)pyridin-2-yl]sulfonyl}thien-yl)sulfonyl]piperidin-4-yl}methyl)amino]propyl}oxy)-1,3-dihydro-2H-benzimidazol-2-one; |
| uuuuuuuuu) | (2S)-1-[4-(benzyloxy)phenoxy]-3-{[(1-{[5-(dimethylamino)-1-naphthyl]sulfonyl}piperidin-4-yl)methyl]amino}propan-2-ol; |
| vvvvvvvvv) | 4-[((2S)-3-{[(1-{[5-(dimethylamino)-1-naphthyl]sulfonyl}piperidin-4-yl)methyl]amino}-2-hydroxypropyl)oxy]phenol; |
| wwwwwwwww) | (2S)-1-(9H-carbazol-4-yloxy)-3-{[(1-{[5-(dimethylamino)-1-naphthyl]sulfonyl}piperidin-4-yl)methyl]amino}propan-2-ol; |
| xxxxxxxxx) | 4-[((2S)-3-{[(1-{[5-(dimethylamino)-1-naphthyl]sulfonyl}piperidin-4-yl)methyl]amino}-2-hydroxypropyl)oxy]-1,3-dihydro-2H-benzimidazol-2-one; |
| yyyyyyyyy) | (2S)-1-[4-(benzyloxy)phenoxy]-3-[({1-[(5-pyridin-2-ylthien-2-yl)sulfonyl]piperidin-4-yl}methyl)amino]propan-2-ol; |
| zzzzzzzzz) | 4-({(2S)-2-hydroxy-3-[({1-[(5-pyridin-2-ylthien-2-yl)sulfonyl]piperidin-4-yl}methyl)amino]propyl}oxy)phenol; |
| aaaaaaaaaa) | (2S)-1-(9H-carbazol-4-yloxy)-3-[({1-[(5-pyridin-2-ylthien-2-yl)sulfonyl]piperidin-4-yl}methyl)amino]propan-2-ol; |
| bbbbbbbbbb) | 4-({(2S)-2-hydroxy-3-[({1-[(5-pyridin-2-ylthien-2-yl)sulfonyl]piperidin-4-yl}methyl)amino]propyl}oxy)-1,3-dihydro-2H-benzimidazol-2-one; |
| cccccccccc) | (2S)-1-[4-(benzyloxy)phenoxy]-3-({[1-({5-[2-(methylthio)pyrimidin-4-yl]thien-2-yl}sulfonyl)piperidin-4-yl]methyl}amino)propan-2-ol; |
| dddddddddd) | (2S)-1-(9H-carbazol-4-yloxy)-3-({[1-({5-[2-(methylthio)pyrimidin-4-yl]thien-2-yl}sulfonyl)piperidin-4-yl]methyl}amino)propan-2-ol; |
| eeeeeeeeee) | 4-{[(2S)-2-hydroxy-3-({[1-({5-[2-(methylthio)pyrimidin-4-yl]thien-2-yl}sulfonyl)piperidin-4-yl]methyl}amino)propyl]oxy}-1,3-dihydro-2H-benzimidazol-2-one; or |
| ffffffffff) | N-{2-hydroxy-5-[(1R)-1-hydroxy-2-({[1-({5-[2-(methylthio)pyrimidin-4-yl]thien-or a pharmaceutically acceptable salt thereof. |

The compounds of this invention were be prepared according to the following schemes from commercially available starting materials or starting materials which can be prepared using literature procedures. These schemes show the preparation of representative compounds of this invention.

The compounds of formula I of the present invention where Z=OCH$_2$ can be prepared by the regiospecific ring opening of a substituted (2S)-aryloxymethyl-oxirane of formula II

(II)

wherein R is defined in relation to formula I
 with an appropriately 1-substituted-4-(aminomethyl)-piperidine of formula III.

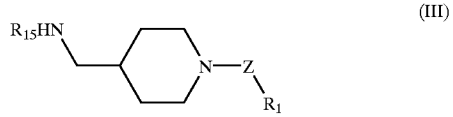
(III)

where R$_1$ is defined in relation to formula I and R$_{15}$=H or trimethylsilyl.

When R$_{15}$=H, ring opening of the chiral epoxide to give the β-amino alcohol was carried out using conditions similar to those described by Klunder et al., *JOC*, (1989), 54, 1295. Thus, a mixture of 1 equivalent of the compounds of formula II and an excess of the compounds of formula III are heated as a solution in methanol at 60° C. for 16–24 hours to provide, the chiral β-amino alcohols of formula I.

For the case when R$_{15}$=trimethylsilyl (TMS), the initially prepared free amine of formula II can be functionalized to the TMS analog as described in R. K. Atkins et al, *Tet Lett*, (1986), 27, 2451. The TMS analog can then be coupled with 1 equivalent of a compound of formula II as described above.

In the case of compounds of formula II where R=4-hydroxyphenyl, a mixture of 4-protected-oxy-phenoxymethyloxirane and an excess of the compounds of formula III are coupled to form intermediates of formula IV using the procedures stated above.

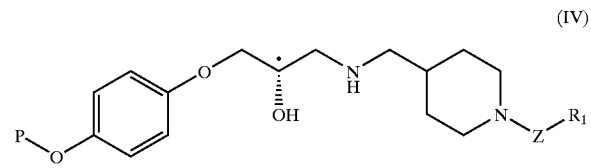
(IV)

wherein
 P=benzyl or t-butyldiphenylsilyl.
When P=benzyl, deprotection to the phenol is accomplished by hydrogenation over 10% palladium on carbon using either hydrogen gas, or catalytic hydride transfer with cyclohexene or ammonium formate.

When P=tert-butyldiphenylsilyl, deprotection to the phenol is accomplished by treatment of the tert-butyidiphenylsilyl intermediates of formula IV with 1M tetrabutylammonium fluoride (TBAF) as described by Corey et al., *JACS* (1970), 94. 6190), in tetrahydrofuran (THF) to give compounds of formula I where R$_4$=OH. The silyl protecting group may also be removed by treatment with hydrochloric acid as a solution in a solvent such as dioxane or by other suitable methods known to those skilled in the art.

Alternatively, compounds of formula I of the present invention can be prepared by reductive amination of substituted (2R)-hydroxyethylamines of formula V by the method of Borch, R F et al, *JACS* (1971), 93, 2897

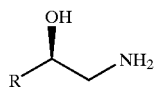
(V)

wherein R is defined in relation to formula I with appropriately (1-substituted-piperidin-4-ylmethyl)-carboxaldehydes of formula VI

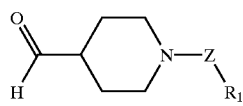
(VI)

Thus, a solution of compounds of formula V and formula VI are stirred in the presence of 1 equivalent of acetic acid in a suitable solvent such as methanol to form the intermediate imine which is reduced to the substituted 2-aryl-2-(R)-hydroxy-1-(piperidin-4-yl-methyl)-ethylamine compounds of the present invention with a hydride source such as sodium cyanoborohydride.

Compounds of formula II can be conveniently prepared as outlined in Scheme 1.

Scheme 1

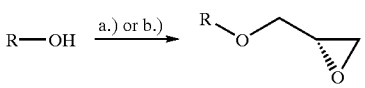

a.) (S)-glycidyl nosylate, K₂CO₃, 2-butanone (MEK) reflux or
b.) (R)-glycidol, diethylazodicarboxylate (DEAD), triphenylphosphine A mixture of a hydroxyaryl compound, either available commercially or is known in the art, or can be prepared by procedures analogous to those in the literature for the known compounds, and (S)-glycidyl nosylate is heated at reflux for at least 18 hours in an appropriate solvent such as 2-butanone (MEK) in the presence of a suitable base such as potassium carbonate to provide compounds of formula II.

Alternatively, compounds of formula II can be prepared from dropwise treatment of a solution of the hydroxyaryl compound, R(+)-glycidol and triphenylphosphine in dry THF with 1.1 eq. of diethylazodicarboxylate as described by O. Mitsinobu., *Bull Soc. Chem Jap.*, (1967), 60, 2380.

Compounds of formula III can be conveniently prepared via Scheme 2.

Scheme 2

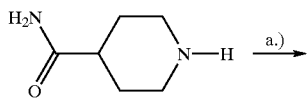

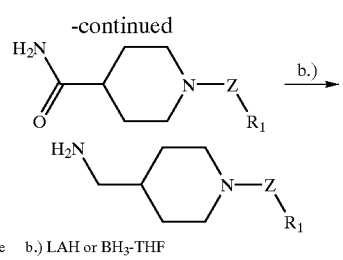

a.) R₁Z-halo, base   b.) LAH or BH₃-THF

Thus, when R₁=alkyl, hydroxyalkyl and Z=bond, reaction of commercially available isonipecotamide with an alkyl iodide (or bromide), either available commercially or is known in the art, or can be prepared by procedures analogous to those in the literature for the known compounds, in an appropriate solvent such as MEK and base such as potassium carbonate provides the intermediate carboxamides. The carbonyl can then be reduced conveniently to the desired 1-substituted-4-aminomethyl-piperidine with lithium aluminum hydride (LAH) in a solvent such as THF to give compounds of formula III.

The above procedure is also used for the case where R₁=heteroaryl and Z=bond from reaction of isonipecotamide in an analogous fashion with chloro or bromo substituted heterocycles, either available commercially or are known in the art, or can be prepared by procedures analogous to those in the literature for the known compounds.

Where R₁ is defined in relation to formula I and Z=SO₂, reaction of isonipecotamide with a substituted sulfonyl chloride, either available commercially or is known in the art, or can be prepared by procedures analogous to those in the literature for the known compounds, in a solvent such as THF, dioxane or methylene chloride with an acid scavenger such as diisopropylethyl amine or other hindered organic base provides the intermediate 4-carboxamido-1-piperidinyl-substituted sulfonamides. Selective reduction of the amide carbonyl to the desired 4-aminomethyl-1-piperidinyl-substituted sulfonamides can be accomplished using a suitable reducing agent such as BH₃-THF complex in THF to give compounds of formula III as described by Green et al., *Tetrahedron* (1995), 51, 2865.

Where R₁ is defined in relation to formula I and Z=(C=O), reaction of isonipecotamide with a substituted isocyanate, either available commercially or is known in the art, or can be prepared by procedures analogous to those in the literature for the known compounds, in a solvent such as THF, dioxane, ethanol, methanol or methylene chloride provides the intermediate 1-(4-carboxamido-piperidin-1-yl)-3-substituted urea. Reduction of the amide carbonyl to the desired 1-(4-aminomethyl-piperidin-1-yl)-3-substituted urea can be accomplished using a suitable reducing agent such as BH₃-THF complex in THF to give compounds of formula III.

Alternatively, the urea formation can be accomplished by first treating isonipecotamide with 0.33 equivalents of triphosgene dropwise over at least 1 hour in the presence of an acid scavenger such as diisopropylethyl amine. The other amine of choice is added in one portion to complete the urea formation.

Compounds of formula III may also be prepared from piperidin-4-ylmethyl-carbamic acid t-butyl ester as outlined in Scheme 3.

Scheme 3

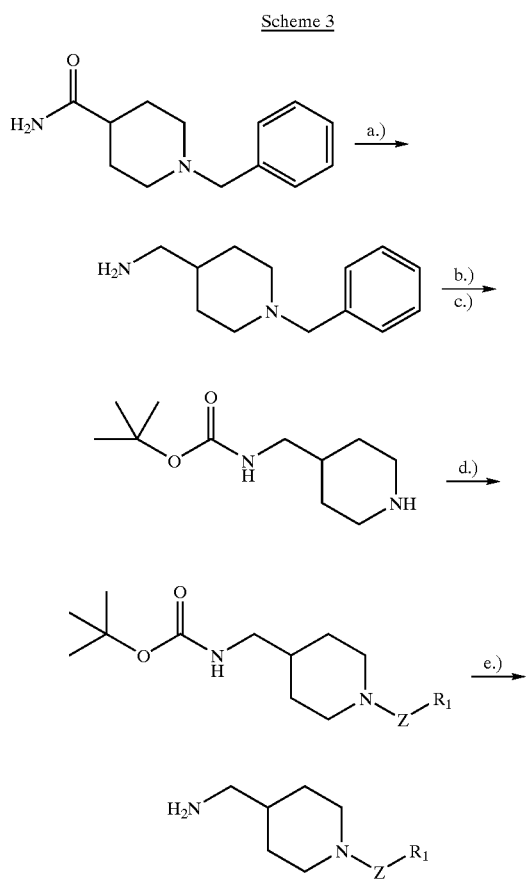

a.) LAH, THF  b.) Boc$_2$O, K$_2$CO$_3$  c.) H$_2$, 10% Pd/C  d.) R$_1$Z-halo, base  e.) formic acid or TFA

Scheme 4

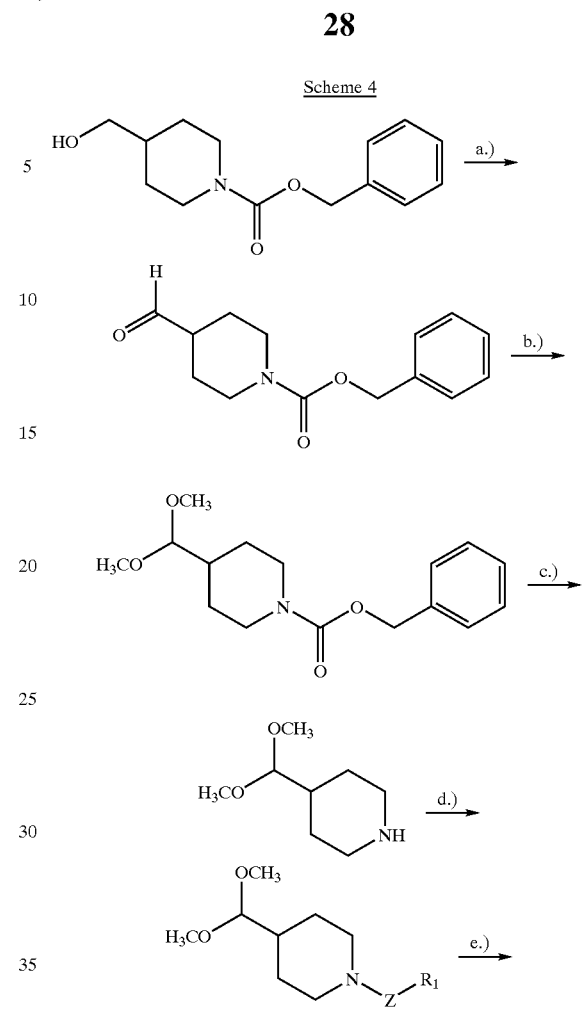

a.) PCC, CH$_2$Cl$_2$  b.) HC(OCH$_3$)$_3$ p-tosH  c.) cyclohexene, 10% Pd/C  d.) R$_1$Z-halo, base  e.) formic acid or TFA Thus, in the case where R$_1$ is defined in relation to formula I and Z=SO$_2$, reaction of piperidin-4-ylmethyl-carbamic acid t-butyl ester with a substituted sulfonyl chloride, either available commercially or is known in the art, or can be prepared by procedures analogous to those in the literature for the known compounds, in a solvent such as THF, dioxane or methylene chloride with an acid scavenger such as diisopropylethyl amine or other organic base. Several methods available for deprotection of the carbamate (Boc) are known (see Greene T., "Protective Groups in Organic Synthesis", Wiley Interscience) to one skilled in the art. The preferred method used was treatment with neat formic acid or neat trifluoroacetic acid (TFA) to give sulfonamides of formula III.

Piperidin-4-ylmethyl-carbamic acid t-butyl ester is prepared as shown in Scheme 3 from reduction of 1-benzyl-isonipecotamide with LAH followed by Boc protection of the primary amine by treatment with di-t-butyidicarbonate in a suitable solvent such as dioxane-water in the presence of potassium carbonate.

Similarly compounds of formula VI where R$_1$ is defined in relation to formula I and Z=SO$_2$, may be prepared from 4-formylpiperidine dimethyl acetal as outlined in Scheme 4:

Thus, reaction of 4-formylpiperidine dimethyl acetal with a substituted sulfonyl chloride, either available commercially or is known in the art, or can be prepared by procedures analogous to those in the literature for the known compounds, in a solvent such as THF, dioxane or methylene chloride with an acid scavenger such as diisopropylethyl amine or other organic base followed by deprotection of the aldehyde with neat formic acid or neat TFA affords sulfonamides of formula VI. Deprotection may also be accomplished by treatment with trichloromethylsilane and sodium iodide in acetonitrile at ambient temperature using a procedure described by G. Olah et al, JOC (1983), 48, 3667.

4-Formylpiperidine dimethyl acetal is prepared as outlined in Scheme 4. Thus, 4-hydroxymethyl-1-piperidinyl carbamic acid benzyl ester is oxidized with pyridinium chlorochromate to the aldehyde which is protected as the dimethyl acetal by reaction with a large excess of trimethyl orthoformate in the presence of a catalytic amount of p-toluenesulfonic acid in a suitable solvent such as methanol.

Compounds of formula III and formula VI where Z=SO$_2$, R$_1$=analogs of the type

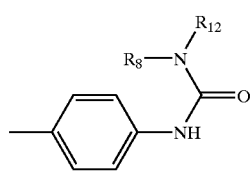

(VII)

and where $R_8$ and $R_{12}$ are defined in relation to formula I, can be conveniently prepared from the intermediates of formula VIII.

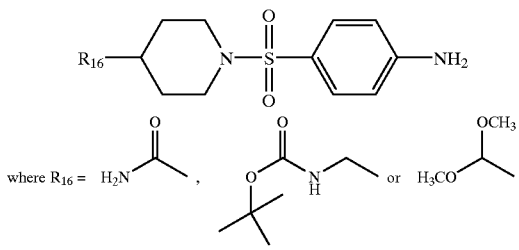

(VIII)

The intermediate of formula VIII, where $R_{16}$ is the carboxamido derivative, can be converted to compounds of formula VII by reaction with reactive substituted isocyanates, either available commercially or are known in the art, or can be prepared by procedures analogous to those in the literature for the known compounds, to provide the urea. The carboxamide can be reduced with borane-THF as described above to the 1-[4-(4-aminomethyl-1-piperidinyl)-benzenesulfonyl]-3-substituted urea of formula VII.

The intermediate of formula VIII, where $R_{16}$ is the Boc-aminomethyl moiety can be converted to ureas of formula VII by reaction of [1-(4-Aminobenzenesulfonyl)-piperidin-4-ylmethyl]-carbamic acid t-butyl ester with 0.33 equivalents of triphosgene in the presence of an acid scavenger such as triethyl amine in an appropriate solvent such as THF or methylene chloride followed by a primary amine, either available commercially or is known in the art, or can be prepared by procedures analogous to those in the literature for the known compounds. Alternatively a secondary amine can be used which is either available commercially, known in the art or can be prepared by procedures analogous to those in the literature for the known compounds. In the present invention these secondary amines are prepared by reaction of carboxylic acids activated by carbonyldiimidazole with primary amines described above in the presence of an organic base such as diisopropylethyl amine. Deprotection of the intermediate [1-(4-substituted ureido-benzenesulfonyl)-piperidin-4-ylmethyl]-carbamic acid t-butyl ester is carried out with formic acid or TFA as described above to give compounds of formula VII.

Alternatively, [1-(4-Aminobenzenesulfonyl)-piperidin-4-ylmethyl]-carbamic acid t-butyl ester can be derivatized to the urea by reaction with an isocyanate derived via Curtius rearrangement of an intermediate acyl azide, prepared by reaction of a carboxylic acid, either available commercially or is known in the art, or can be prepared by procedures analogous to those in the literature for the known compounds, with diphenylphosphoryl azide in the presence of an acid scavenger such as triethyl amine (Shioiri, T. et al., *J. Amer. Chem. Soc.* (1972), 94, 6203–5).

Alternatively, the intermediate of formula VIII, where $R_{16}$ is the 4-formyl-dimethyl acetal moiety can be converted to ureas of formula VII via the urea forming reactions presented above. Deprotection of the of the intermediate [1-(4-substituted ureido-benzenesulfonyl)-piperidin-4-yl]-carboxaldehyde dimethyl acetal is carried out with formic acid or TFA as described above to give compounds of formula VII.

Compounds of formula III and formula VI where Z=SO$_2$ and R$_1$=amide analogs of the type IX

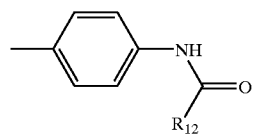

(IX)

where $R_{12}$=alkyl, arylalkyl, heteroaryl, can also be prepared from the reaction of the intermediates of VII with an acid chloride prepared from a carboxylic acid, either available commercially or is known in the art, or can be prepared by procedures analogous to those in the literature for the preparation of activated esters commonly used in peptide synthesis (see M. Bodanszky and A. Bodansky "*The Practice of Peptide Synthesis*", Springer-Verlag Berlin Heidelberg New York Tokyo, 1984)and known to those skilled in the art. Following deprotection or reduction as previously described provides compounds of the formula IX.

Compounds of formula VII can be prepared as outlined in scheme 2, scheme 3 or scheme 4 by reaction of 4-nitrobenzene sulfonyl chloride with either isonipecotamide or (piperidin-4-ylmethyl)-carbamic acid t-butyl ester or 4-formylpiperidine dimethyl acetal in methylene chloride or THF in the presence of a suitable acid scavenger such as diisopropyl amine. The nitro can be reduced to the amine by hydrogenation at atmospheric pressure in ethanol over 10% palladium on carbon or by a variety of other methods known to those skilled in the art.

Alternatively, the compound of formula VII where $R_{16}$=Boc-aminomethyl, can be prepared from 4-aminomethylpiperidine according to the procedure outlined by J. D. Prugh et. al. *Synth Comm*, 22, 2357 (1992). A solution of benzaldehyde and 4-aminomethylpiperidine in toluene is heated at reflux until 1 equivalent of water was collected in a Dean-Stark trap. To the cooled reaction mixture is added 4-nitro-benzenesulfonyl chloride and a suitable acid scavenger such as diisopropylethyl amine. The intermediate coupled imine is decomposed by the addition of mild inorganic acid such as dilute HCl. Protection of the amine can be accomplished by treatment with ditertbutyl-dicarbonate in a suitable solvent system such as THF or dioxane-water.

Compounds of formula III and formula VI where Z=SO$_2$, R$_1$=compounds of the formula

(X)

and $R_9$ is heteroaryl, can be prepared from the intermediates of formula XI

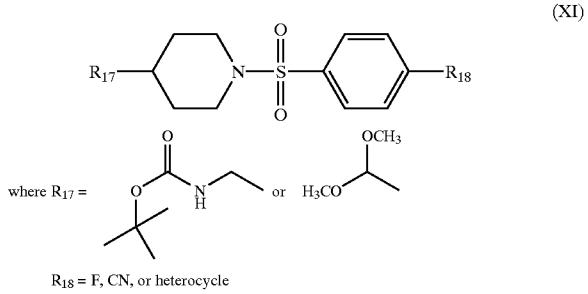

(XI)

where $R_{17}$ =

$R_{18}$ = F, CN, or heterocycle

For compounds of formula XI where $R_{17}$ is the methyl-carbamic acid t-butyl ester moiety or dimethyl acetal and $R_{18}$ is F, an anion of a heterocycle is coupled with an arylfluoro compound as described by Caubere, P. et al., *Bull. Soc. Chim. Fr.* (1969), Issue 8, 2854–63. Thus a solution of [1-(4-fluorobenzenesulfonyl)-piperidin-4-ylmethyl]-carbamic acid t-butyl ester or [1-(4-fluorobenzenesulfonyl)-piperidin-4-yl]-carboxaldehyde dimethyl acetal with an anion derived from potassium hydride of a nitrogen containing heterocycle, either available commercially or is known in the art, or can be prepared by procedures analogous to those in the literature for the known compounds, in a suitable solvent such as DMF is maintained at 80° C. to 100° C. for at least 18 hours, followed by deprotection of the Boc or acetal groups as described above to give compounds of formula X.

For compounds of formula XI where $R_{17}$ is the methyl-carbamic acid t-butyl ester moiety or dimethyl acetal and $R_{18}$ is CN, oxadiazoles of formula X can be prepared by a method descibed by Hussein A. Q., *Heterocycles*, (1987), 26, 163. Thus the cyano is functionalized by reaction with ammonium hydroxide hydrochloride in the presence of potassium carbonate in a suitable solvent such as ethanol to give the intermediate amino(hydroxyimino)methyl compound. The intermediate is coupled with acid chlorides either available commercially or is known in the art, or can be prepared by procedures analogous to those in the literature for the known compounds, in the presence of a suitable base such as pyridine followed by deprotection of the Boc or acetal groups as described above to give compounds of formula X where $R_9$=5-substituted oxadiazoles.

Compounds of formula XI where $R_{17}$ is the methyl-carbamic acid t-butyl ester moiety or dimethyl acetal and $R_{18}$=heterocycles such as imidazol-2-ones can also prepared by the method described by Poindexter et al., *JOC*, (1992), 57, 6257. Thus, heating a mixture of aniline hydrochloride and a 2-substituted oxazolidinone at temperatures of at least 180° C. for a period of at least 2 hours affords the intermediate phenylethylene diamine. The imidazolone is formed by reaction of this intermediate with triphosgene in the presence of a suitable base such as triethyl amine to give the intermediate 1-phenyl-3-substituted-imidazol-2-one. Sulfo-chlorination with chlorosulfonic acid provides the intermediate 4-(3-substituted-2-oxo-imidazolidin-1-yl)-benzenesulfonyl chloride which can be converted to compounds of formula XI by reaction with either piperidin-4-ylmethyl-carbamic acid t-butyl ester or 4-formylpiperidine dimethyl acetal using methodology described previously.

The intermediates of formula XI are prepared by coupling 4-fluorobenzensultonyl chloride with (piperidin-4-ylmethyl)-carbamic acid t-butyl ester or 4-formylpiperidine dimethyl acetal in DMF in the presence of a suitable acid scavenger such as such as potassium carbonate at 100° C. for a period of at least 18 hours.

Compounds of formula III and formula VI where Z=bond, $R_1$=compounds of the following type

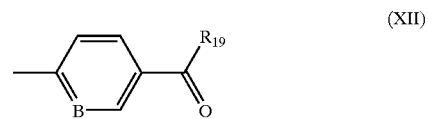

(XII)

wherein B=CH or N and $R_{19}$=NHR$_{12}$, NHCH(COOR$_8$)R$_{12}$ or NHCH(COOH)R$_{12}$ can be prepared via intermediate XIII:

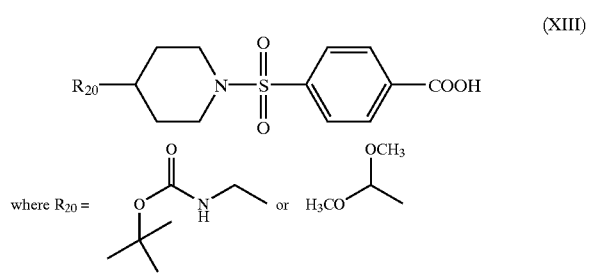

(XIII)

where $R_{20}$ = by standard peptide coupling reactions such as coupling an amine or amino acid ester, either available commercially or is known in the art, or can be prepared by procedures analogous to those in the literature for the known compounds, with an activated ester of VII prepared from benzyltriazol-1-yloxytris(dimethylamino)-phosphonium hexafluorophosphate and an organic base like triethyl amine in a solvent such as DMF. Alternatively an activated ester of XIII may be prepared with 1-(3-dimethylamino-propyl)-3-ethylcarbodiimide HCl and 1-hydroxybenzotriazole in the presence of an organic base such as N-ethyl morpholine in a solvent such as THF.

Compounds of formula V can be prepared via mono-chlorination of intermediates of the formula XIV

(XIV)

wherein R is defined as in formula I by a procedure outlined by Kajigaeshi et al, *Synthesis* (1988), 546. Thus the appropriate acetyl compound, either available commercially or is known in the art, or can be prepared by procedures analogous to those in the literature for the known compounds, is treated with benzyltrimethylammonium tetrachloroiodate in a solution of methylene chloride to give a high yield of the mono-chloro product which can be purified by crystallization.

The mono-chloro product is chirally reduced to the intermediate XV

(XV)

with borane-THF and a chiral auxilary agent such as (R)-tetrahydro-1-methyl-3,3-diphenyl-1H, 3H-pyrrolo[1,2-c][1, 3,2]oxazaborole as described by Corey, E. J. et al., *J. Org. Chem*, (1991), 56, 442.

Subsequent reaction of the intermediate XI with sodium azide and an excess of sodium iodide in dimethylsulfoxide (DMSO) at 40° C. to 60° C. for 24 to 168 hours followed by reduction of the intermediate azide with hydrogen at 45 PSI over 10% palladium on carbon provides the compounds of formula VIII.

Alternatively, compounds of formula I where $Z=SO_2$ can be prepared in simultaneous fashion using a technique known as "solution phase parallel synthesis" as described by Balkenhohl in *Angew. Chem. Int. Ed. Engl.*, 1996, 35, 2288–2337. In this procedure two or more reaction products are simultaneously prepared in separate vessels. The number of reaction vessels being equal to the number of expected products. The ease of solution phase parallel synthesis is aided through the addition of "resin bound reagents" to the reaction mixture which can be filtered through glass or polypropylene frits or other filtration methods known to those skilled in the art. Resin bound reagents are chemicals that are attached to polymeric materials, such as polystyrene, typically through covalent or ionic chemical bonds, and can assist in the reaction process itself or scavenge side products/excess starting materials from a reaction mixture. At the conclusion of the reaction the resin bound reagents are filtered from the reaction medium to provide a highly purified product which may now be obtained through solvent evaporation of the filtrate.

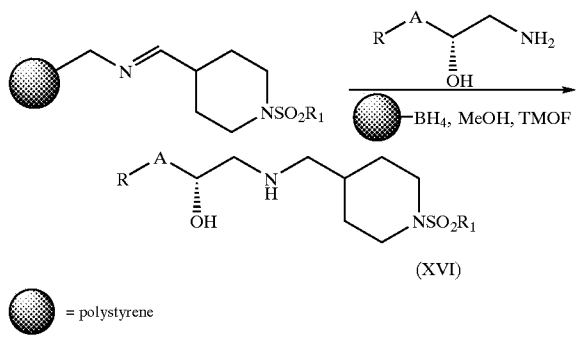

According to the description above compounds of formula I where $Z=SO_2$ can be prepared from resin bound imines of formula XVI by suspending the resin in a suitable, anhydrous solvent mixture such as 50:50 methanol-trimethylorthoformate (TMOF), distributing the resin suspension to separate vessels, adding a different amine of type V as the limiting reagent and resin bound reducing agent, such as borohydride on resin, to each vessel. The mixtures can be shaken 1–48 hours and then filtered. The filtrate can then be evaporated to obtain products.

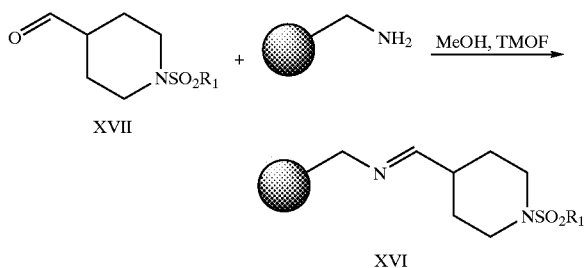

Resin bound imines of the type XVI can be prepared as described by Look in *Tetrahedron Lett.*, 1995, 36, 2937–2940 by suspending a resin bound primary amine, either commercially available or available through literature procedures, treating the suspension with an aldehyde of the type XVII and removal of water by physical or chemical means. Typically, water is removed by chemical means through the use of trimethylorthoformate as the primary solvent. After 1–48 hours of agitation the suspension is filtered to obtain the resin bound imine as the residue. The filtration step also removes unreactive impurities in the aldehyde from the product resin. For example, a mixture of an aldehyde and an alcohol are reacted with aminomethyl resin and filtered. The filtrate contains alcohol impurity only while none of the impurity resides on the resin.

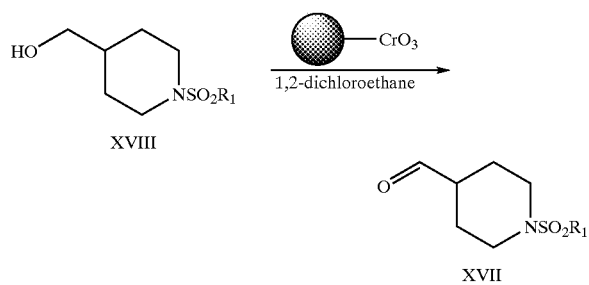

Aldehydes of the type XVII are prepared by oxidation of corresponding sulfonamide alcohols of the type XVIII. In particular the alcohols are oxidized with resin bound chromium trioxide in 1,2-dichloroethane according to the method of Cainelli as described in *J. Am. Chem. Soc.*, 1976, 98, 6737–6738. Filtration of the reaction suspension and evaporation of the solvent leads to the isolation of aldehydes XVII contaminated with up to 25% of the starting sulfonamide alcohol XVIII.

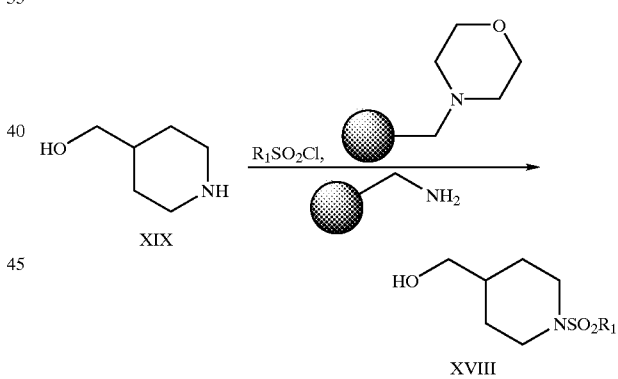

Sulfonamide alcohols of the type XVIII can be prepared according to the procedure of Flynn as described in *J. Am. Chem. Soc.*, 1997, 119, 4874–4881 by reacting an excess of the sulfonyl chloride (table 1 or 2) with 4-(hydroxymethyl) piperidine XIX in an appropriate solvent such as dichloromethane. Addition of an insoluble resin bound tertiary amine such as morpholinomethylpolystyrene reacts with and retains hydrogen chloride byproduct on the insoluble resin. After an appropriate reaction time of 1–48 hours a primary or secondary amine resin such as aminomethylpolystyrene can be added to react with the excess sulfonyl chloride which will retain the excess starting material on the insoluble resin. Filtration of the resulting suspension and evaporation of the solvent provides pure product that is free of byproducts and unreacted starting materials.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was confirmed with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., *Eur. J. Biochem.*, 196:357–361(1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5' CTGGCGCCCAACGGCCAGTGGC-CAGTC3'; a NarI-AccI fragment, 5' TTGGCGCTGATG-GCCACTGGCCGTTTG3' as sense and 5' GCGCGTAGACGAAGAGCATCACGAG3' as anti-sense primer; an AccIi-StyI fragment, sense primer 5' CTCGT-GATGCTCTTCGTCTCACGCGC3' and anti-sense primer 5' GTGAAGGTGCCCATGATGAGACCCAAGG3' and a StyI-TAG fragment, with sense primer 5' CCCTGTGCAC-CTTGGGTCTCATCATGG3' and anti-sense primer 5' CCTCTGCCCCGGTTACCTACCC3'. The corresponding primer sequences are described in Mantzoros, C. S., et.al, *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$_AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

$$IA = \frac{\% \text{ activity compound}}{\% \text{ activity isoproterenol}}$$

Table I shows the $\beta_3$-adronergic receptor $EC_{50}$ and IA values for the representative compounds of this invention that were evaluated in this standard pharmacological test procedure. These results show that compounds of the present invention have activity at the $\beta_3$-adrenergic receptor. The compounds of this inventon had weaker or no activity at $\beta_1$ and/or $\beta_2$-adrenergic receptor.

TABLE I

| Compound No. | $EC_{50}(\beta 3, \mu M)$ | $IA(\beta 3)$ |
|---|---|---|
| Example 8 | 0.870 | 0.56 |
| Example 9 | 0.047 | 0.39 |
|  | 0.287 | 1.06 |
| Example 10 | 0.187 | 0.99 |
| Example 13 | 0.596 | 0.62 |
| Example 14 | 0.219 | 0.75 |
| Example 15 | 12.495 | 0.52 |
| Example 19 | 1.245 | 0.82 |
| Example 22 | 1.210 | 0.53 |
| Example 23 | 1.090 | 0.66 |
| Example 24 | 0.943 | 0.98 |
| Example 25 | 2.066 | 0.93 |
|  | 0.319 | 0.43 |
| Example 26 | 0.665 | 0.79 |
| Example 27 | 1.034 | 0.51 |
| Example 30 | 1.240 | 0.53 |
| Example 31 | 0.133 | 0.32 |
|  | 0.380 | 0.49 |
| Example 32 | 0.123 | 0.8 |
| Example 33 | 0.141 | 0.68 |
| Example 34 | 7.000 | 0.36 |
| Example 37 | 0.376 | 1.04 |
| Example 38 | 0.365 | 0.36 |
| Example 39 | 0.030 | 0.81 |
| Example 40 | 0.490 | 0.23 |
| Example 41 | 0.095 | 0.65 |
| Example 42 | 0.150 | 0.69 |
| Example 43 | 0.880 | 0.68 |
| Example 44 | 0.421 | 0.46 |
| Example 45 | 0.610 | 1 |
| Example 46 | 0.222 | 0.81 |
| Example 47 | 0.250 | 0.7 |
| Example 49 | 2.360 | 0.4 |
| Example 52 | 0.305 | 0.9 |
| Example 56 | 0.110 | 0.53 |
| Example 57 | 3.190 | 0.46 |
| Example 58 | 0.048 | 0.62 |
| Example 59 | 0.040 | 0.83 |
| Example 60 | 0.010 | 0.53 |
| Example 61 | 0.097 | 0.4 |
| Example 62 | 0.010 | 0.68 |
| Example 63 | 0.135 | 1.05 |
| Example 64 | 0.060 | 1.1 |
| Example 65 | 0.126 | 0.9 |
| Example 66 | 0.026 | 0.92 |
| Example 67 | 0.020 | 1.2 |
| Example 69 | 0.069 | 1 |
|  | 0.066 | 1.01 |
|  | 0.047 | 0.94 |
|  | 0.049 | 1 |
|  | 0.046 | 0.86 |
|  | 0.071 | 0.77 |
| Example 70 | 0.055 | 0.52 |
| Example 71 | 0.096 | 0.6 |
| Example 73 | 0.006 | 1 |
| Example 74 | 0.005 | 0.91 |
| Example 75 | 0.020 | 0.95 |
| Example 77 | 0.029 | 0.82 |

TABLE I-continued

| Compound No. | EC$_{50}$(β3, μM) | IA(β3) |
|---|---|---|
| Example 78 | 0.045 | 0.94 |
| Example 79 | 0.001 | 1 |
| Example 81 | 0.005 | 1.1 |
| Example 83 | 0.112 | 1.2 |
| Example 84 | 0.027 | 0.93 |
| Example 85 | 0.029 | 1.2 |
| Example 86 | 0.003 | 0.78 |
| Example 87 | 0.007 | 1 |
| Example 88 | 0.022 | 1 |
| Example 89 | 0.035 | 1 |
| Example 90 | 0.269 | 0.91 |
| Example 91 | 0.110 | 0.72 |
| Example 92 | 0.160 | 0.82 |
| Example 93 | 0.347 | 0.99 |
| Example 94 | 0.510 | 0.76 |
| Example 95 | 0.125 | 0.82 |
| Example 96 | 0.013 | 0.85 |
| Example 97 | 0.011 | 0.96 |
| Example 98 | 0.025 | 1 |
| Example 99 | 0.009 | 1 |
| Example 100 | 0.041 | 1 |
| Example 101 | 0.043 | 0.93 |
| Example 104 | 0.008 | 1 |
| Example 105 | 0.034 | 0.94 |
| Example 106 | 0.001 | 0.97 |
|  | 0.001 | 0.97 |
| Example 107 | 0.010 | 1.2 |
| Example 108 | 0.006 | 0.96 |
| Example 109 | 0.031 | 1.2 |
| Example 110 | 0.045 | 0.72 |
| Example 111 | 0.095 | 0.9 |
| Example 112 | 0.131 | 0.93 |
| Example 114 | 0.010 | 1 |
| Example 115 | 0.066 | 1 |
| Example 124 | 0.055 | 1 |
| Example 143 | 0.810 | 1.34 |
| Example 153 | 0.042 | 0.76 |
| Example 157 | 0.670 | 1 |
| Example 160 | 0.346 | 0.85 |
| Example 162 | 0.011 | 0.64 |
|  | 0.035 | 0.94 |
| Example 163 | 0.040 | 0.85 |
| Example 168 | 0.940 | 0.72 |
| Example 173 | 0.388 | 1.34 |
|  | 0.380 | 1.15 |
| Example 178 | 0.210 | 0.84 |
| Example 183 | 1.410 | 0.72 |

Evaluation in β$_3$ Knockout(KO) and β$_3$ Transgenic(Tg) Mice: The ability of compounds of this invention to treat or inhibit disorders related to insulin resistance or hyperglycemia was also confirmed with representative compounds of this invention in an in vivo standard pharmacological test procedure which compared thermogenesis in transgenic mice (Tg mice) and β$_3$-knockout (KO mice). The procedure used and results obtained are provided below.

β$_3$-Adrenergic receptor knockout mice and β$_3$ human transgenic mice are created on an inbred FVB background (Susulic, V. S., et.al., *J. Biol. Chem.*, 1995, 270 (49), 29483–29492). Female FVB β$_3$ transgenic and β$_3$ knockout mice were used to determine in vivo activity and selectivity of β$_3$ agonists. Compounds selected for in vivo testing had β$_3$ EC$_{50}$<30 nm and were full agonists in CHO cells expressing human β$_3$ receptors. These compounds were also selective in being 100-fold less responsive and partial agonists when tested in β$_1$ and β$_2$ transfected CHO cells. Compounds were tested for increased thermogenesis using the Oxymax indirect calorimeter (Columbus Instruments, Columbus, Ohio). Fed animals were placed in chambers for 3 hours to obtain baseline O$_2$ and CO$_2$ values. Eight fed mice were weighed in pairs and placed in 4 chambers, two per chamber. The relative gas content of each chamber was sampled and recorded at 10 to 12 minute intervals. For each sample, energy expenditure values were calculated by the Oxymax and expressed as kcal/hr. After 3 hours of baseline measurement, the mice were removed, treated and replaced in the chambers. The β$_3$ agonists were injected at doses between 0.1 and 20 mg/kg i.p. and between 1.0 and 30 mg/kg for oral administration. Compounds in 10 mM or 10 mg/ml DMSO solutions were suspended in 0.5% methylcellulose: 0.1% tween-80 and injected i.p. or administered by oral gavage. Some compounds were suspended in 5.0% tween-80 for oral administration. Post-treatment kcal/hr values were taken between 40 minutes and 2.5 hours later. The 6 to 10 sample sections of the pre-treatment and post-treatment periods, which appear to best represent stable resting thermogenesis, were selected. Each of these sample values was corrected for body weight and used such that each pair of mice serves as its own baseline for both T test and percent increase in thermogenesis calculations. An ANOVA and a one sided T test (H1: Post>Pre) are performed using the SAS software modified to down weight extreme values. In a separate set of calculations, values that appear to be too high to represent resting thermogenesis are discarded (activity monitor sampling associated spikes in thermogenesis with ambulatory activity). The mean baseline value for each chamber is subtracted from mean post-treatment value for that chamber. This baseline-subtracted value is divided by the mean baseline value and multiplied by 100 to obtain a percent increase in thermogenesis for each chamber. The combined mean percent increase, standard deviation, and standard error of the mean for each chamber is calculated. Compounds were considered active if they were able to produce a statistically significant 15% increase in thermogenesis in β$_3$ transgenic mice and no significant increase in β$_3$ knockout mice. The results are shown in the table below.

Thermogenesis in β3 Knockout(KO) and β3 Transgenic(Tg) Mice

| | | Transgenic Mice | | | | Knock Out Mice | |
|---|---|---|---|---|---|---|---|
| Example # | Mouse type | IP % | (10 mg/kg) sd | Gavage % | (30 mg/kg) sd | IP % | (10 mg/kg) sd |
| 10 | hetero | −15 | 5 | | | | |
| 58 | hetero | −3 | 5 | | | | |
| 59 | homo | 5 | 5 | | | | |
| 63 | homo | 3 | 7 | | | | |
| 66 | homo | 4 | 3 | | | | |
| 69 | hetero | 24 | 7 | 14 | 7 | −3 | 6 |
|  | homo | 24 | 7 | | | | |
|  | hetero | 30 | 14 | | | | |
| 74 | homo | 18 | 2 | | | | |
| 75 | homo | 5 | 1 | | | | |
| 77 | homo | 4 | 8 | | | | |
| 79 | homo | 10 | 5 | | | | |

Based on the results obtained id these standard pharmacological test procedures, representative compounds of this invention have been shown to be selective β$_3$ adrenergic receptor agonists and are therefore useful in treating metabolic disorders related to insulin, resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following describe the preparation of representative examples of this invention.

INTERMEDIATE 1

4-[(2S)-Oxiranylmethoxy]-9H-carbazole

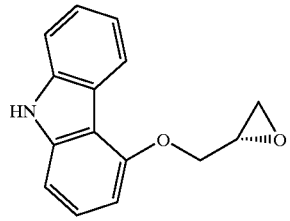

The starting material 4-hydroxycarbazole was prepared from a combination of procedures described in Berridge, M. et al *Nucl. Med. Biol.* (1992), 19, 563 for the intermediate hydrazone, and E. Dubois et al. *J. Med. Chem.* (1996), 39, 3260 for the Fisher indole and aromatization of the intermediate 4-oxo-tetrahydrocarbazole. A mixture of 4-hydroxycarbazole (18.6 9, 102 mmol), (S)-glycidyl nosylate (26.3 g, 102 mmol) and potassium carbonate (14 g, 102 mmol) in 400 mL of 2-butanone was heated at reflux for 18 hours. The reaction mixture was partitioned with ethyl acetate (EtOAc) and $H_2O$. The organic phase was washed with brine and dried with sodium sulfate ($Na_2SO_4$). The solvent was removed in vacuo and the residual solids were purified by flash chromatography (methylene chloride-hexane 3:1) to give 13 g product as a white solid.

NMR (DMSO-$d_6$, 400 MHz): δ 2.84 (m, 1H), 2.915 (m, 1H), 3.533 (m, 1H), 4.07 (m, 1H), 4.54 (m, 1H), 6.68 (d, 1H, J=7.9 Hz), 7.08 (d, 1H, J=8.1 Hz), 7.14 (dt, 1H), 7.28 (m, 2H), 7.44 (dd, 1H), 8.15 (dd, 1H). MS (EI, m/z): 239 (M$^+$); Anal calc'd. for $C_{18}H_{17}ClN_2S$: C, 65.55; H, 5.23; N, 8.57 Found: C, 65.14; H, 5.19; N, 8.31.

INTERMEDIATE 2

1-Bromo-4-[(2S)-oxiranylmethoxy]-9H-carbazole

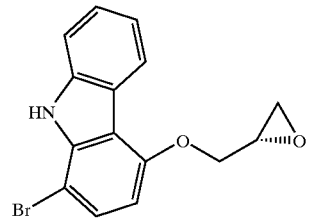

A solution of 4-[(2S)-oxiranylmethoxy]-9H-carbazole (0.750 g, 3.13 mmol) and N-bromosuccinimide (0.57 g, 3.2 mmol) in 10 mL dry dimethylformamide (DMF) was stirred at ambient temperature for 48 hours. The reaction mixture was partitioned with EtOAc and $H_2O$. The organic phase was washed with $H_2O$ and dried with $Na_2SO_4$. The solvent was removed (rotovap) and the residue purified by flash chromatography (hexane-EtOAc 5:1) afforded 0.10 g of the title compound.

NMR (DMSO-$d_6$, 400 MHz): 82.83 (m, 1H), 2.925 (m, 1H), 3.53 (m, 1H), 4.09 (m, 1H), 4.55 (m, 1H), 6.70 (d, 1H, J=8.56 Hz), 7.21 (dt, 1H), 7.406 (dt, 1H), 7.48 (d, 1H, J=8.56 Hz), 7.55 (d, 1H, J=8.12 Hz), 8.16 (d, 1H, J=7.69 Hz)), 11.42 (s, 1H). MS (ESI$^+$, m/z): 318, 320 [M+H]$^+$; 335, 337 [M+NH$_4$]$^+$.

INTERMEDIATE 3

3-Bromo-4-[(2S)-oxiranylmethoxy]-9H-carbazole

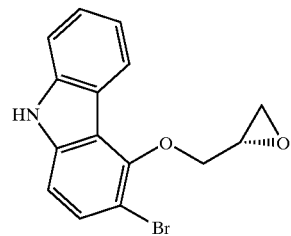

Obtained from the previous prep as major product using the following chromatography conditions:(methylene chloride-hexane-1:1) to give 0.210 g of title compound.

NMR (DMSO-$d_6$, 400 MHz): δ 2.73 (m, 1H), 2.87 (m, 1H), 3.54 (m, 1H), 3.96 (m, 1H), 4.45 (m, 1H), 7.22 (m, 2H), 7.42 (m, 1H), 7.50 (m, 2H), 8.21 (d, 1H), 11.5 (s, 1H). MS (ESI$^+$, m/z): 335, 337 [M+NH$_4$]$^+$.

INTERMEDIATE 4

1-Chloro-4-[(2S)-oxiranylmethoxy]-9H-carbazole

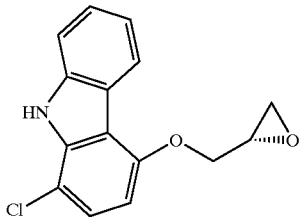

A solution of 4-[(2S)-oxiranylmethoxy]-9H-carbazole (0.50 g, 2.09 mmol) and N-chlorosuccinimide (0.280 g, 2.09 mmol) in 5 mL dry DMF was stirred at ambient temperature for 48 hours. The reaction mixture was partitioned with EtOAc and H$_2$O. The organic phase was washed with H$_2$O and dried with Na$_2$SO$_4$. The solvent was removed (rotovap) and the residue purified by flash chromatography (methylene chloride-hexane-1:1) afforded 0.10 g of the title compound plus 0.50 g of 3-Chloro-4-[(2S)-oxiranylmethoxy]-9H-carbazole.

NMR (DMSO-d$_6$, 400 MHz): δ 2.82 (m, 1H), 2.90(m, 1H), 3.51 (m, 1H), 4.08 (m, 1H), 4.55 (m, 1H), 6.71 (d, 1H, J=8.56 Hz), 7.19 (dt, 1H), 7.39 (m, 2H), 7.52 (m, 1H), 8.15 (d, 1H), 11.542 s, 1H). MS (EI, m/z): 273, 275 (M$^+$).

INTERMEDIATE 5

3-Chloro-4-[(2S)-oxiranylmethoxy]-9H-carbazole

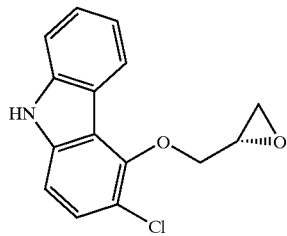

Obtained from the previous prep as major product.

NMR (DMSO-d$_6$, 400 MHz): δ 2.71 (m, 1H), 2.86 (m, 1H), 3.52 (m, 1H), 3.97 (m, 1H), 4.49 (m, 1H), 7.19 (m, 1H), 7.28 (d, 1H, J=8.56 Hz), 7.42 (m, 2H), 7.50 (d, 1H, J=8.34 Hz), d, 1H), 11.514 (s, 1H). MS (ESI$^+$, m/z): 274 [M+H]$^+$, 291 [M+NH$_4$]$^+$.

INTERMEDIATE 6

3-Hydroxy-4-[(2S)-oxiranylmethoxy]-9H-carbazole

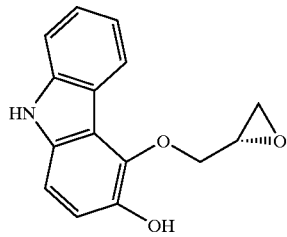

A solution of 4-[(2S)-oxiranylmethoxy]-9H-carbazole (0.183 g, 0.76 mmol) in 20 mL dry methylene chloride was treated with 0.258 g of 56–86% m-chloroperbenzoic acid. The reaction was stirred at ambient temperature for 45 minutes. The reaction mixture was partitioned with saturated sodium bicarbonate (sat'd NaHCO$_3$) The organic phase was dried (Na$_2$SO$_4$) and concentrated to a dark red oil. Purification by flash chromatography eluting with methylene chloride (CH$_2$Cl$_2$), afforded 0.040 g of the title compound.

NMR (DMSO-d$_6$, 400 MHz): δ 2.71 (m, 1H), 2.837 (m, 1H), 3.458 (m, 1H), 4.016 (m, 1H), 4.46 (m, 1H), 6.97 (d, 1H, J=8.56 Hz), 7.06 (m, 2H), 7.315 (dt, 1H), 7.38 (dt, 2H), 8.22 (d, 1/H, J=7.9 Hz), 8.8 (s, 1H), 10.9479 (s, 1H). MS (EI, m/z): 255 (M$^+$).

INTERMEDIATE 7

4-[(2S)-Oxiranylmethoxy]-9-fluorenone

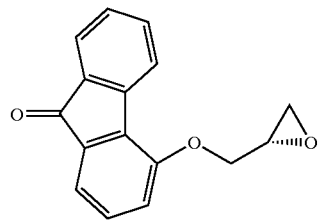

A stirred suspension of hexane washed potassium hydride (0.204 g, 5 mmol) in THF was treated in one portion with 4-hydroxy-9-fluorenone (1.0 g, 5.1 mmol). To the purple suspension was added (S)-glycidyl nosylate (1.0 g, 5 mmol) and the mixture was stirred at ambient temperature overnight. The reaction was partitioned with EtOAc. The organic phase was washed with H$_2$O, brine and dried (Na$_2$SO$_4$). The solvent was removed in vacuo to provide crude product. Purification by flash chromatography (CH$_2$Cl$_2$-hexane 3:1) provided 0.210 g of product as a yellow solid.

NMR (DMSO-d$_6$, 400 MHz): δ 2.48 (m, 1H), 2.9068 (m, 1H), 3.4775 (m, 1H), 4.07 (m, 1H), 4.57 (m, 1H), 7.23 (dd, 1H), 7.33 (d, 3H), 7.59 (m, 1H), 7.82 (m, 1H), MS (EI, m/z): 252 (M$^+$).

INTERMEDIATE 8

1-[(2S)-Oxiranylmethoxy]-9-fluorenone

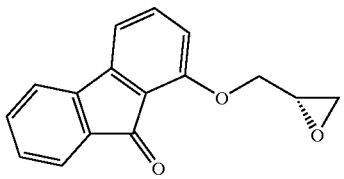

Prepared from 1-hydroxy-9-fluorenone (3.0 g, 15.2 mmol), (S)-glycidyl nosylate (3.06 g, 15.2 mmol) and potassium carbonate (2.1 g, 15.2 mmol) according to the procedure used for Intermediate 1 to give 0.78 g product as a yellow solid.

NMR (DMSO-d$_6$, 400 MHz): δ 2.489 (m, 1H), 2.8459 (m, 1H), 3.3687 (m, 1H), 4.07 (m, 1H), 4.50 (m, 1H), 7.03 (d, 1H, J=8.57 Hz), 7.37 (m, 2H), 7.544 (m, 3H), 7.28 (m, 2H), 7.75 (m, 1H). MS (ESI$^+$, m/z): 253 [M+H]$^+$, 270 [M+NH$_4$]$^+$.

INTERMEDIATE 9

4-[(2S)-Oxiranylmethoxy]-1H-indole

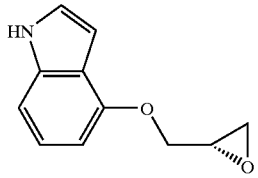

A solution of 4-hydroxyindole (0.53 g, 4.0 mmol), (R+)-glycidol (0.3 mL, 4.4 mmol), and triphenylphosphine (1.26 g, 4.8 mmol) in dry THF was treated dropwise with diethylazodicarboxylate (0.76 mL, 4.8 mmol). After stirring the reaction mixture at ambient temperature overnight, the solvent was removed in vacuo and the residue purified by flash chromatography ($CH_2Cl_2$) to give 0.20 g product as a white solid.

TLC (rf=0.40, $CH_2Cl_2$). NMR (DMSO-$d_6$, 400 MHz): δ 2.75 (m, 1H), 2.871 (m, 1H), 3.402 (m, 1H), 3.94 (m, 1H), 4.41 (m, 1H), 6.445 (s, 1H), 6.49 (dd, 1H), 6.995 (m, 2H), 7.227 (m, 1H), 11.09 (s, 1H). MS (ESI$^+$, m/z): 190 [M+H]$^+$, 207 [M+NH$_4$]$^+$.

INTERMEDIATE 10

5-[(2S)-Oxiranylmethoxy]-1H-indole

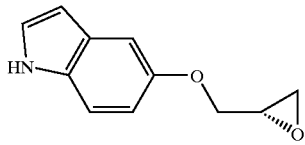

Prepared from 5-hydroxyindole (0.37 g, 2.78 mmol), (R+)-glycidol (0.202 mL, 3.06 mmol), diethylazodicarboxylate (0.52 mL, 3.3 mmol), and triphenylphosphine (0.87 g, 3.3 mmol) according to the procedure used for Intermediate 9 (silica Merck 60, $CH_2Cl_2$) to give 0.060 g product as a white solid.

TLC (rf=0.37, $CH_2Cl_2$). NMR (DMSO-$d_6$, 300 MHz): δ 2.70 (m, 1H), 2.82 (m, 1H), 3.60 (m, 1H), 3.80 (m, 1H), 4.25 (m, 1H), 6.32 (s, 1H), 6.75 (dd, 1H), 7.05 (m, 2H), 7.3 (m, 1H), 10.85 (s, 1H).

INTERMEDIATE 11

4-[(2S)-Oxiranylmethoxy]-benzimidazol-2-one
(CAS #197774-51-9)

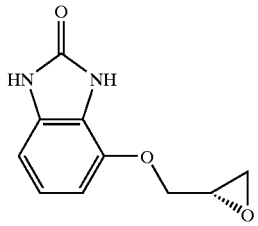

A solution of 2-amino-3-nitrophenol is reacted with (R+) glycidol to give the intermediate 2-amino-3-nitrobenzylmethoxy-(S)-oxirane via the procedure used for Intermediate 9. The intermediate (0.250 g, 1.2 mmol) was hydrogenated under an atmosphere of hydrogen over a catalytic amount of Raney nickel. The catalyst was filtered and the intermediate diamine was reacted with 1.9 M phosgene in toluene and an excess of diisopropylethyl amine to give 0.170 g of the title compound as a light pink solid.

NMR (DMSO-$d_6$, 300 MHz): δ 2.82 (m, 1H), 3.35 (m, 1H), 3.94 (m, 1H), 4.38 (m, 1H), 6.6 (m, 2H), 6.82 (t, 1H), 10.56 (s, 1H), 10.75 (s, 1H).

INTERMEDIATE 12

4-[(2S)-Oxiranylmethoxy]-2-methylindole

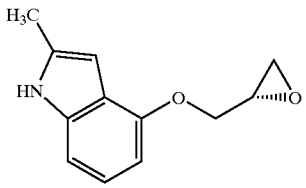

Prepared from 2-methyl-4-hydroxyindole (5 g, 33 mmol), (S)-glycidyl nosylate (8.78 g, 33 mmol) and potassium carbonate (4.56 g, 33 mmol) according to the procedure used for Intermediate 1 to give 3.4 g product as a white solid.

NMR (DMSO-$d_6$, 400 MHz): δ 2.345 (s, 3H), 2.739 (m, 1H), 2.841 (m, 1H), 3.37 (m, 1H), 3.91 (m, 1H), 4.36 (m, 1H), 6.128 (s, 1H), 6.438 (m, 1H,), 6.87 (m, 2H), 10.8703 (s, 1H). MS (ESI$^+$, m/z): 204 [M+H]$^+$.

INTERMEDIATE 13

4-[(2S)-Oxiranylmethoxy]-2-oxindole

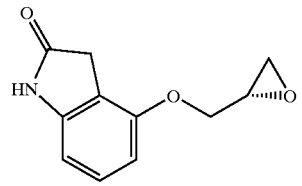

Step A: 2-Methoxy-6-nitrobenzyl Bromide

A solution of 2-methoxy-6-nitrotoluene (28.2 g, 159 mmol) and N-bromosuccinimide (26.5 g, 159 mmol) in 350 mL $CCl_4$ was treated with a catalytic amount of t-butylhydroperoxide and irradiated with a floodlamp while stirring for 3 hours. The solids formed were filtered and the filtrate concentrated to give 4.0 g of a yellow solid.

NMR (DMSO-$d_6$, 300 MHz): d 3.95 (s, 3H), 4.75 (s, 2H), 7.45 (m, 1H), 7.6 (m, 2H).

Step B: 2-Methoxy-6-nitrobenzylcyanide

Prepared according to the procedure described by Beckett et. al., Tetr, (1968), 24, 6093 to give 39.1 g of an amber colored solid.

NMR (DMSO-$d_6$, 400 MHz): δ 3.9425 (s, 3H), 3.9645 (s, 2H), 7.49 (dd, 1H), 7.61 (m, 2H). MS (EI, m/z): 192 [M]$^+$.

Step C: 2-Methoxy-6-nitrophenylacetic Acid

A solution of 2-methoxy-6-nitrobenzylcyanide (29 g, 151 mmol) in 200 mL conc. HCl and 20 mL conc.$H_2SO_4$ was heated at reflux for 3 hours. The reaction mixture was poured into ice/water. The resulting solids that formed were filtered, washed with water and dried (high vac) to give 31 g of a light tan solid.

NMR (DMSO-$d_6$, 400 MHz): δ 3.8332 (s, 2H), 3.8667 (s, 3H), 7.491 (dd, 1H), 7.5097 (t, 1H), 7.58 (dd, 1H), 12.4249 (broad, 1H). MS (EI, m/z): 211 [M]$^+$.

Step D: 4-Methoxy-2-oxindole

A mixture of 2-methoxy-6-nitrophenylacetic acid (31 g, 150 mmol), and 3.0 g of 10% palladium on carbon in 200 mL of glacial acetic acid was stirred under an atmosphere of $H_2$ gas until uptake ceased. The catalyst was filtered and the solvent evaporated in vacuo. The crude product was crystallized from methanol to give 9.0 g of the title compound.

NMR (DMSO-$d_6$, 400 MHz): δ 3.7652 (s, 3H), 6.451 (dd, 1H), 6.58 (dd, 1H), 7.13 (dt, 1H), 10.3236 (s, 1H). MS (EI, m/z): 163 [M]$^+$.

Step E: 4-Hydroxy-2-oxindole

A mixture of 4-methoxy-2-oxindole (3.5 g, 21.4 mmol) and 3.0 g of aluminum chloride was heated at 235° C. for 10 minutes with stirring. On cooling the sludge was triturated with $H_2O$. The solids were filtered washed with $H_2O$ and dried to give 3.0 g of product as an orange solid. Purified by flash chromatography (hexane-ethyl acetate 3:1) to give 1.1 g of pure title compound.

NMR (DMSO-$d_6$, 400 MHz): δ 3.2622 (s, 2H), 6.28 (dd, 1H), 6.38 (dd, 1H), 6.95 (dt, 1H), 9.4468 (s, 1H), 10.2226 (s, 1H). MS (EI, m/z): 149M]$^+$.

Step F: 4-[(2S)-Oxiranylmethoxy]-2-oxindole

Prepared from 4-hydroxy-2-oxindole (1.1 g, 7.38 mmol), (S)-glycidyl nosylate (1.91 g, 7.38 mmol) and potassium carbonate (1.1 g, 8 mmol) according to the procedure used for Intermediate 1 to give 0.33 g product as a white solid.

NMR (DMSO-$d_6$, 300 MHz): δ 2.75 (m, 1H), 2.85 (m, 1H), 3.37 (m, 1H), 3.95 (m, 1H), 4.4 (m, 1H), 6.5 (d, 1H), 6.65 (d, 1H), 7.18 (t, 1H), 10.4 (s, 1H).

INTERMEDIATE 14 t-Butyl-[4-(2S)-oxiranylmethoxy-phenoxy]-diphenylsilane

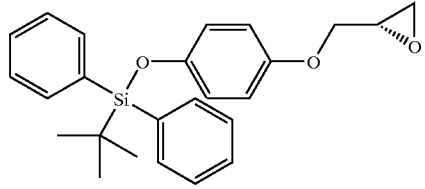

Step A: t-Butyl-[4-benzyloxyphenoxy]-diphenylsilane

A mixture of 4-benzyloxyphenol (100 g, 360 mmol), t-butylchlorodiphenylsilane (72.8 g, 360 mmol), and imidazole (24.5 g, 360 mmol) in 1 L of methylene chloride was stirred overnight at ambient temperature. The reaction mixture was washed with water, sat'd $NaHCO_3$ and brine. After drying ($Na_2SO_4$), the solvent was evaporated to provide, 155 g of the title compound NMR (DMSO-$d_6$, 300 MHz): δ 1.02 (s, 9H), 5.95 (s, 2H), 6.62 (d, 2H), 6.77 (d, 2H), 7.38 (m, 11H), 7.64 (dd, 4H).

Step B: t-Butyl-[4-hydroxyphenoxy]-diphenylsilane

A mixture of t-butyl-[4-benzyloxyphenoxy]-diphenylsilane (170 g, 388 mmol) and 10 g of 10% palladium on carbon in ethanol-cyclohexene (2:1, v/v) was heated at reflux for 48 hours. The catalyst was filtered and the solvent was removed in vacuo to provide 134 g of product as an oil.

NMR (DMSO-$d_6$, 300 MHz): δ 1.02 (s, 9H), 6.55 (m, 4H), 7.42 (m, 6H), 7.64 (dd, 4H)., 8.9 (s, 1H).

Step C: t-Butyl-[4-(2S)-oxiranylmethoxy-phenoxy]-diphenylsilane

Prepared from t-butyl-[4-hydroxyphenoxy]-diphenylsilane (1.34 g, 380 mmol), (R+)-glycidol (26.5 mL, 400 mmol), diethylazodicarboxylate (70.8 mL, 450 mmol), and triphenylphosphine (118 g, 450 mmol) according to the procedure used for Intermediate 9 (hexane-$Et_2O$) to give 50 g product as a white solid.

NMR (DMSO-$d_6$, 300 MHz): δ 2.68 (m, 1H), 2.82 (m, 1H), 3.28 (m, 1H), 3.72 (m, 1H), 4.25 (m, 1H), 6.73 (q, 4H), 7.48 (m, 6H), 7.7 (m, 4H).

INTERMEDIATE 15

2-(S)-(4-Benzyloxy-phenoxymethyl)-oxirane CAS #122797-04-0

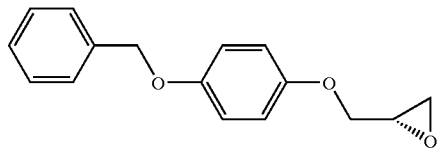

Prepared from 4-benzyloxyphenol (1 eq.), (S)-glycidyl nosylate (1 eq.) and potassium carbonate (1 eq.) according to the procedure used for Intermediate 1 to give the product as a white solid.

INTERMEDIATE 16

8-(Benzyloxy)-5-[(2S)oxiranylmethoxy]-3,4-dihydro-2(1H)-quinolinone

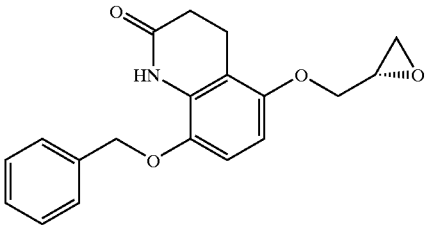

Step A. 5,8-Dihydroxy-3,4-dihydro-2(1H)-quinolinone 5,8-Dimethoxy-3,4-dihydro-2(1H-quinolinone (prepared as described in Chem. Pharm. Bull., (1981), 129, 2161) (1.5 g, 7.24 mmol) was heated at 120° C. in 40% HBr (15 mL) for 4 hours. The reaction mixture was cooled in ice and the solid filtered and washed with water. The aqueous phase was extracted with ethyl acetate. The solvent was removed and the residue combined with the filtrate to give crude title compound (1.04 g, 5.80 mmol).

MS (ESI$^+$, m/z): 180 [M+H]$^+$, 359 [2M+H]$^+$.

Step B:. 8-(Benzyloxy)-5-hydroxy-3,4-dihydro-2(1H)-quinolinone 5,8-Dihydroxy-3,4-dihydro-2(1H)-quinolinone (2.0 g, 11.16 mol) and potassium carbonate (1.8 g, 13.02 mol) were stirred at reflux in acetone (35 mL). Benzyl bromide (1.33 mL, 11.2 mmol) was added and refluxing continued for 4 hours. The solvents were removed and the reaction mixture partitioned between chloroform and water. The organic phase was washed with brine and dried over anhydrous magnesium sulfate. The solution was filtered and the solvent evaporated to dryness in vacuo. The residue was purified by flash chromatography on silica gel Merck-60 (eluant: 1:1 hexane-ethyl acetate) to yield the title compound (0.80 g, 2.97 mmol).

MS (ESI$^+$, m/z): 270 [M+H]$^+$.

Step C:. 8-(Benzyloxy)-5-[(2S)oxiranylmethoxy]-3,4-dihydro-2(1H-quinolinone

A mixture of 8-(benzyloxy)-5-hydroxy-3,4-dihydro-2 (1H)-quinolinone (0.20 g, 0.743 mmol), (S)-(+)-glycidyl 3-nitrobenzenesulfonate (0.193 g, 0.743 mmol) and potassium carbonate (0.113 g, 0.817 mmol) in 2-butanone (10 mL) was heated at reflux for 16 hours. The solvent was removed in vacuo and the residue purified by flash chromatography (chloroform-methanol, 50:1) to yield the title compound (0.210 g, 0.61 mmol).

MS (APCI$^+$, m/z): 326 [M+H]$^+$.

INTERMEDIATE 17 t-Butyl-{3-chloro-4-[(2S)oxiranylmethoxy]phenoxy}-diphenylsilane

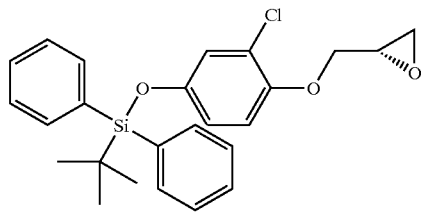

Step A: 4-{[t-Butyl(diphenyl)silyl]oxy}-2-chlorobenzaldehyde

To a solution of imidazole (4.28 g, 62.89 mmol) and 2-chloro-4-hydroxybenzaldehyde (8.95 g, 57.16 mmol) in CH$_2$Cl$_2$ (500 ml) was added dropwise a solution of t-butyldiphenylchlorosilane (17.27 g, 62.86 mmol) in CH$_2$Cl$_2$, (200 mL). The solution was stirred overnight at ambient temperature. The mixture was then poured into H$_2$O (500 mL) and the organic layer washed with NaHCO$_3$, H$_2$O, brine, and dried (MgSO$_4$). The solvent was removed in vacuo to provide 24.2 g of the title compound.

$^1$H NMR (DMSO-d$_6$, 300 MHz): δ 1.11 (s, 9H), 6.88 (dd, 1H), 6.94 (d, 1H), 7.40 (m, 1H), 7.51 (m, 6H), 7.75 (m, 4H), 10.13 (s, 1H).

Step B: 4-{[t-Butyl(diphenyl)silyl]oxy}-2-chlorophenyl Formate

4-{[t-butyl(diphenyl)silyl]oxy}-2-chlorobenzaldehyde (11.00 g, 28 mmol) was dissolved in CHCl$_3$ (150 ml). In one portion m-chloroperbenzoic acid (MCPBA) (7.21 g, 41.8 mmol) was added and the solution heated to reflux for 72 h. The solution was diluted with CH$_2$Cl$_2$, washed with sat. NaHSO$_3$, sat. NaHCO$_3$, brine and dried (MgSO$_4$). The solvent was removed to provide 9.42 g of the title compound.

$^1$H NMR (DMSO-d$_6$, 300 MHz): δ 1.11 (s, 9H), 6.69 (dd, 1H), 6.94 (d, 1H), 7.16 (d, 1H), 7.42 (m, 6H), 7.68 (m, 4H), 8.13 (s, 1H).

Step C: 4-{[t-Butyl(diphenyl)silyl]oxy}-2-chlorophenol

4-{[t-butyl(diphenyl)silyl]oxy}-2-chlorophenyl formate (9.42 g, 22.4 mmol) was dissolved in methanol (50 mL). 10% KOH (15 mL) was added. The solution was stirred for 30 minutes at ambient temperature. The solvent was removed in vacuo and the solid partitioned between ethyl acetate and water. The aqueous phase was acidified with HCl and extracted three times with ethyl acetate. The organic layers were combined and the solvent dried over anhydrous magnesium sulfate. The solution was filtered and the solvent evaporated to dryness in vacuo to yield crude title compound (8.04 g, 21 mmol).

$^1$H NMR (DMSO-d$_6$, 300 MHz): δ 1.11 (s, 9H), 6.58 (dd, 1H), 6.67 (d, 1H), 6.78 (d, 1H), 7.46 (m, 6H), 7.70 (m, 4H), 9.64 (s, 1H).

Part D: t-Butyl-{3-chloro-4-[(2S)oxiranylmethoxy]phenoxy}-diphenylsilane

4-{[t-butyl(diphenyl)silyl]oxy}-2-chlorophenol (8.04 g, 21 mmol) was dissolved in THF (100 ml). R(+)-glycidol (2.49 g, 33.6 mmol) and triphenylphosphine (8.81 g, 33.6 mmol) were added. Diethylazodicarboxylate (6.035 g, 34.7 mmol) was added dropwise. The solution was stirred overnight. The solvent was removed and the solid was filtered through a silica gel plug eluting with (2:1 hexane:ether). (4.8 g, 10.9 mmol).

$^1$H NMR (DMSO-d$_6$, 300 MHz): δ 1.11 (s, 9H), 2.69 (m, 1H), 2.81 (m, 1H), 3.33 (m, 1H), 3.82 (m, 1H), 4.28 (dd, 1H), 6.62 (dd, 1H), 6.81 (d, 1H), 6.94 (d, 1H), 7.46 (m, 6H), 7.70 (m, 4H).

INTERMEDIATE 18 t-Butyl-{2-fluoro-4-[(2S)oxiranylmethoxy]phenoxy}-diphenylsilane

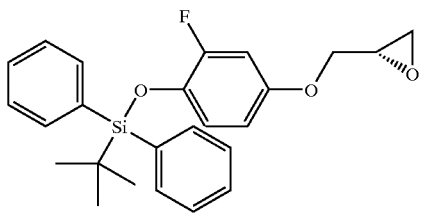

Step A: 2-Fluorophenyl Acetate

2-Fluorophenol (99.4 g, 886.7 mmol) was stirred in thionyl chloride (71.2 mL) and acetic acid (51 mL) added. After the initial reaction had subsided the mixture was heated to reflux for 4 hours. The solution was then heated at 150° C. overnight. The resulting dark solution was distilled under reduced pressure at an oil bath temperature of 190° C. to give the title compound as a pale yellow oil (120.9 g, 784.4 mmol).

MS (EI, m/z): 154 [M]$^+$.

Step B: 1-(3-Fluoro-4-hydroxyphenyl)-1-ethanone

2-Fluorophenyl acetate (91.0 g, 590.4 mmol) was added to a solution of anhydrous aluminum chloride (98.3 g, 737.2 mmol) in carbon disulfide (150 mL). The reaction was heated to reflux for 48 hours. The excess solvent was removed by heating at 80° C. for 3 hours followed by 2 hours heating at 140° C. The dark reaction was sonicated under ice/HCl. The solid was removed by filtration, dissolved in ether and filtered. Removal of the solvent gave a solid which was recrystallized twice from toluene to give the title compound (51.0 g, 330.9 mmol).

Step C: 1-(4-{[t-Butyl(diphenyl)silyl]oxy}-3-fluorophenyl)-1-ethanone

To a solution of imidazole (7.29 g, 107.0 mmol) and 1-(3-fluoro-4-hydroxyphenyl)-1-ethanone (15.0 g, 97.3 mmol) in anhydrous dichloromethane (500 mL) was added drop-wise a solution of t-butyldiphenylchlorosilane (28.09 g, 102.0 mmol) in anhydrous dichloromethane (100 mL). The solution was stirred overnight at room temperature. The mixture was poured into water (500 mL) and the organic layer separated and washed with saturated sodium hydrogen carbonate, water, brine and dried over anhydrous magnesium sulfate. The solution was filtered and the solvent evaporated to dryness in vacuo to give the title compound which was used without further purification (37.9 g, 96.55 mmol). MS (APCI$^+$, m/z): 393 [M+H]$^+$.

Step D: 4-{[t-Butyl(diphenyl)silyl]oxy}-3-fluorophenyl Acetate 1-(4-{[t-Butyl(diphenyl)silyl]oxy}-3-fluorophenyl)-1-ethanone (8.27 g, 21.07 mmol) was dissolved in chloroform (300 mL). 3-Chloroperoxybenzoic acid (4.0 g, 23.18 mmol) was added and the solution heated to reflux for 72 hours. The solution was diluted with dichloromethane, washed with saturated sodium hydrogen sulfate, saturated sodium hydrogen carbonate, brine and dried over anhydrous magnesium sulfate. The solution was filtered and the solvent evaporated to dryness in vacuo to yield the title compound which was used without further purification (5.28 g, 12.92 mmol).

MS (APCI$^+$, m/z): 426 [M+NH$_4$]$^+$.

Step E: 4-{[t-Butyl(diphenyl)silyl]oxy}-3-fluorophenol

4-{[t-Butyl(diphenyl)silyl]oxy}-3-fluorophenyl acetate (5.28 g, 12.92 mmol) was dissolved in methanol (100 mL). 1N NaOH (15.5 mL) was added. The solution was stirred for 30 minutes at ambient temperature. 1N HCl (16 mL) was added. The solvent was removed in vacuo and the solid partitioned between dichloromethane and water. The aqueous phase was washed with dichloromethane. The organic layers were combined and the solvent dried over anhydrous magnesium sulfate. The solution was filtered and the solvent evaporated to dryness in vacuo to yield crude title compound (4.5 g, 12.28 mmol).

MS (ESI$^-$, m/z): 365 [M−H]$^{--}$.

Step F: t-Butyl{2-fluoro-4-[(2S)oxiranylmethoxy]phenoxy}diphenylsilane

4-{[t-Butyl(diphenyl)silyl]oxy}-3-fluorophenol (4.5 g, 12.28 mmol) was dissolved in anhydrous tetrahydrofuran (50 mL). R-(+)-glycidol (1.0 g, 13.5 mmol) and triphenylphosphine (3.86 g, 14.76 mmol) were added. Diethylazodicarboxylate (2.32 g, 14.76 mmol) was added drop-wise. The solution was stirred overnight at ambient temperature. The solvent was removed in vacuo and the solid passed through a silica gel pad (eluant: 2:1 hexane-diethyl ether) to yield the title compound (2.64 g, 6.25 mmol).

INTERMEDIATE 19

2-{[t-butyl(diphenyl)silyl]oxy}-5-[(2S)-oxiranylmethoxy]phenyl(methylsulfonyl)-carbamate

Step A: (4-t-Butyl-diphenyl-silyloxy)-3-nitro-acetophenone

To a solution of imidazole (9.0 g, 132 mmol) and 4-hydroxy-3-nitro-acetophenone (22.83 g, 126 mmol) in dichloromethane (500 mL) was added drop-wise a solution of t-butyldiphenylchlorosilane (36.37 g, 132 mmol) in anhydrous dichloromethane (100 mL). The solution was stirred overnight at ambient temperature. The mixture was poured into water (500 mL) and the organic layer separated and washed with saturated sodium hydrogen carbonate, water, brine and dried over anhydrous magnesium sulfate. The solution was filtered and the solvent evaporated to dryness in vacuo to give the title compound as a solid (51.63 g, 123 mmol).

$^1$H NMR (DMSO-d$_6$, 300 MHz): δ 1.10 (s, 9H), 2.48 (s, 3H), 6.64 (d, 1H), 7.55 (m, 6H), 7.76 (m, 4H), 7.93 (dd, 1H), 8.46 (d, 1H).

Step B: Acetic Acid 3-Nitro-4-(t-butyl-diphenyl-silanyloxy)-phenyl Ester (4-t-Butyl-diphenyl-silyloxy)-3-nitro-acetophenone (51.63 g, 123 mmol) was dissolved in chloroform (300 mL). 3-Chloroperoxybenzoic acid (31.85 g, 184 mmol) was added and the solution heated to reflux for 48 hours. The solution was diluted with dichloromethane, washed with saturated sodium hydrogen sulfate, saturated sodium hydrogen carbonate, brine and dried over anhydrous magnesium sulfate. The solution was filtered and the solvent evaporated to dryness in vacuo to yield crude title compound (45.29 g, 104 mmol).

$^1$H NMR (DMSO-d$_6$, 300 MHz): δ 1.10 (s, 9H), 2.25 (s, 3H), 6.58 (d, 1H), 7.19 (dd, 1H), 7.41 (m, 1H), 7.52 (m, 6H), 7.73 (m, 4H).

Step C: Acetic Acid 3-Amino-4-(t-butyl-diphenyl-silanyloxy)-phenyl Ester

Acetic acid 3-nitro-4-(t-butyl-diphenyl-silanyloxy)-phenyl ester (5.0 g, 11.86 mmol) was dissolved in anhydrous tetrahydrofuran (100 mL). Excess Raney Ni was added and the mixture placed under an atmospheric of hydrogen overnight. The mixture was filtered through a Celite pad and the solvent removed to give the title compound as a solid (3.5 g, 8.6 mmol).

$^1$H NMR (DMSO-d$_6$, 300 MHz): δ 1.08 (s, 9H), 2.20 (s, 3H), 4.97 (s, 2H), 5.92 (dd, 1H), 6.51 (d, 1H), 7.44 (m, 6H), 7.73 (m, 4H).

Step D: 4-{[t-Butyl(diphenyl)silyl]oxy}-3-[(methylsulfonyl)amino]phenyl Acetate

Acetic acid 3-amino-4-(t-butyl-diphenyl-silanyloxy)-phenyl ester (3.5 g, 8.6 mmol) was dissolved in anhydrous dichloromethane (150 mL) and anhydrous N,N-diisoproplyamine (1.5 mL) added. The solution was cooled to −78° C. and methanesulfonyl chloride (1.08 g, 9.05 mmol) added. The solution was stirred for 30 minutes and allowed to come to room temperature. The solution was stirred overnight. The reaction mixture was washed with water. The organic solvent was dried over anhydrous magnesium sulfate. The solution was filtered and the solvent evaporated to dryness in vacuo to yield the title compound as a solid (2.8 g, 5.7 mmol).

$^1$H NMR (DMSO-d$_6$, 300 MHz): δ 1.08 (s, 9H), 2.22 (s, 3H), 3.13 (s, 3H), 6.31 (d, 1H), 6.62 (dd, 1H), 7.18 (d, 1H), 7.44 (m, 6H), 7.76 (m, 4H), 8.92 (s, 2H),

Step E: 3-[(t-Butoxycarbonyl)(methylsulfonyl)amino]-4-{[t-bulyl(diphenyl)-silyl]oxy}phenyl Acetate 4-{[t-Butyl(diphenyl)silyl]oxy}-3-[(methylsulfonyl)amino]phenyl acetate (2.8 g, 5.7 mmol) was dissolved in anhydrous dichloromethane (100 mL) and 4-(dimethylamino)-pyridine (0.069 g, 5.7 mmol) added. Di-t-butyl dicarbonate (1.39 g, 6.37 mmol) in anhydrous dichloromethane was added drop-wise over 1 hour. The solution was stirred overnight at ambient temperature. The solvent was washed with water, 1N HCl, and dried over anhydrous magnesium sulfate. The solution was filtered and the solvent evaporated to dryness in vacuo to give the title compound (3.20 g, 5.48 mmol).

Step F: 2-{[t-butyl(diphenyl)silyl]oxy}-5-hydroxyyhenyl (methylsulfonyl)carbamate 3-[(t-Butoxycarbonyl)(methylsulfonyl)amino]-4-{[t-butyl(diphenyl)silyl]-oxy}phenyl acetate was dissolved in methanol (25 mL), 1N NaOH (5.5 mL) was added and the solution stirred for 30 minutes at ambient temperature. 1N HCl (5.5 mL) was added, the solvent removed in vacuo and the residue partitioned between dichloromethane and water. The aqueous phase was washed with dichloromethane. The combined organic extracts were dried over anhydrous magnesium sulfate. The solution was filtered and the solvent evaporated to dryness in vacuo to give the title compound (2.34 g, 4.31 mmol).

$^1$H NMR (DMSO-d$_6$, 300 MHz): δ 0.94 (s, 9H), 1.41 (s, 9H), 3.49 (s, 3H), 6.06 (d, 1H), 6.37 (dd, 1H), 6.75 (d, 1H), 7.40 (m, 6H), 7.71 (m, 4H), 9.10 (s, 2H),

Step G: 2-{[t-butyl(diphenyl)silyl]oxy}-5-[(2S)-oxiranylmethoxy]phenyl(methylsulfonyl)carbamate 2-{[t-butyl(diphenyl)silyl]oxy}-5-hydroxyphenyl(methylsulfonyl)carbamate (2.34 g, 4.31 mmol) was dissolved in anhydrous tetrahydrofuran (50 mL). R-(+)-glycidol (0.511 g, 6.9 mmol) and triphenylphosphine (1.81 g, 6.9 mmol) were added. Diethylazodicarboxylate (1.23 g, 7.11 mmol) was added drop-wise. The solution was stirred overnight at ambient temperature. The solvent was removed in vacuo and residue purified by passage through a silica gel pad (eluant: 2:1 hexane-ether). The solvent was removed in vacuo to yield the title compound as a solid (1.8 g, 3.0 mmol).

INTERMEDIATE 20

2-(4-Hydroxy-3-methanesulfonamido-phenyl)-2-hydroxy-ethyl Amine

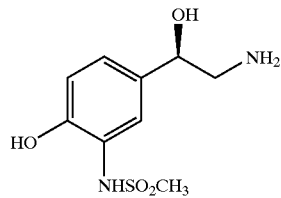

Step A: 5-Chloroacetyl-2-benzyloxy-methanesulfonanilide [ref, Kajigaeshi et al, *Synthesis* (1988), 546]

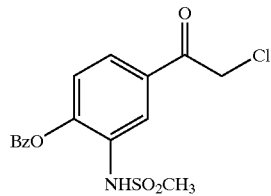

A solution of 5-acetyl-2-benzyloxy-methanesulfonanilide (10 g, 31.3 mmol) in 400 mL $CH_2Cl_2$—$CH_3OH$ (20:1, v/v) was treated in one portion with benzyltrimethylammonium tetrachloroiodate (13.4 g, 32 mmol). After stirring at ambient temperature for 2 hours, the reaction mixture was washed with dilute $Na_2S_2O_3$ solution. The organic phase was clarified (Norite A) and dried ($Na_2SO_4$). The reaction mixture was concentrated to ⅓ volume and the solids formed were collected and dried to give 4.0 g of title compound (m.p.-130° C.).

NMR (DMSO-$d_6$, 400 MHz): δ 2.9371 (s, 3H), 5.093 (s, 2H), 5.2934 (s, 2H), 7.23 (d, 1H), 7.34 (m, 1H), 7.39 (dt, 2H), 7.53 (dd, 2H), 7.85 (m, 2H), 9.2382 (s, 1H). MS (APCI$^+$, m/z): 354 [M+H]$^+$, 371 [M+NH$_4$]$^+$.

Step B: 5-[2-Chloro-1-(R)-hydroxy-ethyl]-2-benzyloxy-methanesulfonanilide (ref E. J. Corey et al., *JOC*, (1991), 56, 442.)

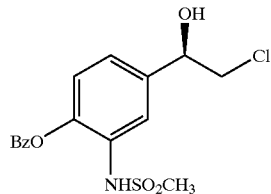

To a stirred solution of (R)-tetrahydro-1-methyl-3,3-diphenyl-1H, 3H-pyrrolo[1,2-c][1,3,2]oxazaborole (2.25 mL of a 1M solution in toluene) and borane-THF (18 mL of a 1M solution) in 80 mL of THF was added 5-chloroacetyl-2-benzyloxy-methanesulfonanilide (7.9 g, 22.4 mmol) portionwise. After stirring for 1 hour the reaction was treated with excess 1N HCl. The reaction was extracted with ethyl acetate. The organic phase was washed with brine and dried ($Na_2SO_4$). Removal of solvent afforded 6.9 g of the title compound as an amber oil which solidified on standing.

NMR (DMSO-$d_6$, 400 MHz): δ 2.897 (s, 3H), 3.62 (m, 1H), 3.68 (m, 1H), 4.68 (m, 1H), 5.156 (s, 2H), 5.73 (d, 1H), 7.07 (d, 1H), 7.17 (dd, 1H), 7.29 (m, 2H), 7.38 (dt, 2H), 7.52 (dd, 2H), 8.9262 (s, 1H). MS (APCI$^-$, m/z): 354 [M−H]$^-$; OR (CH$_3$OH, 8.88 mg/mL): [a]$_D^{25}$ −15.77.

Step C: N-[5-(2-Amino-1-{R}-hydroxyethyl)-2-hydroxyphenyl]-methanesulfonamide

A mixture of 5-[2-chloro-1-(R)-hydroxy-ethyl]-2-benzyloxy-methane-sulfonanilide (6.8 g, 19.2 mmol), sodium azide (5.0 g, 76.8 mmol) and sodium iodide (15 g, 100 mmol) in 100 mL dry DMSO was heated at 60° C. for 7 days. The reaction mixture was poured into $H_2O$ and extracted with ethyl acetate. The organic phase was dried ($Na_2SO_4$) and concentrated in vacuo to give 6.3 g of the intermediate azide.

NMR (DMSO-$d_6$, 300 MHz): δ 2.9 (s, 3H), 3.27 (m, 2H), 4.72 (m, 1H), 5.15 (s, 2H), 5.75 (d, 1H), 7.07 (d, 1H), 7.17 (dd, 1H), 7.38 (m, 4H), 7.5 (dd, 2H), 8.95 (s, 1H).

A mixture of the azide and 1.0 g of 10% palladium on carbon in 100 mL $CH_3OH$ was hydrogenated under 40 PSI of hydrogen overnight. The catalyst was filtered and the filtrate concentrated in vacuo to provide 3.2 g of the title compound as an off-white solid.

NMR (DMSO-$d_6$, 300 MHz): δ 2.58 (m, 2H), 2.85 (s, 3H), 4.35 (m, 1H), 5.5 (broad, 2H), 6.75 (d, 1H), 6.85 (dd, 1H), 7.12 (sharp m, 1H).

INTERMEDIATE 21

(4-Carboxamido-1-piperidinyl)-4-aminobenzenesulfonamide

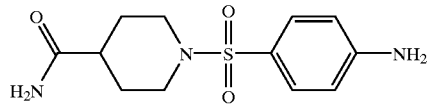

Step A: (4-Carboxamido-1-piperidinyl)-4-nitrobenzenesulfonamide

A solution of isonipecotamide (5.0 g, 39 mmol), 4-nitrobenzenesulfonyl chloride (8.65 g, 39 mmol) and diisopropylethyl amine (6.8 mL, 39 mmol) in 200 mL THF was stirred at ambient temperature overnight. The solids formed were filtered, washed with $H_2O$, $Et_2O$ and dried under high vacuum to provide 10 g of the title compound as a white solid.

NMR (DMSO-$d_6$, 400 MHz): δ 1.5513 (m, 2H), 1.77 (m, 2H), 2.085 (m, 1H), 2.42 (dt, 2H), 3.07 (m, 2H), 3.62 (broad d, 2H), 6.817 (s, 1H), 7.233 (s, 1H), 8.02 (d, 2H), 8.44 (d, 2H). MS (ESI$^+$, m/z): 314 [M+H]$^+$, 331 [M+NH$_4$]$^+$.

Step B: 4-Carboxamido-1-piperidinyl)-4-aminobenzenesulfonamide

A solution of (4-carboxamido-1-piperidinyl)-4-nitrobenzenesulfonamide in ethanol was hydrogenated under an atmosphere of hydrogen over 10% palladium on carbon. The catalyst was filtered and the solvent was removed in vacuo to give 7.2 g of product as a white solid foam.

NMR (DMSO-$d_6$, 400 MHz): δ 1.52 (m, 2H), 1.72 (m, 2H), 1.999 (m, 1H), 2.16 (dt, 2H), 3.45 (broad d, 2H), 6.0265

(s, 2H), 6.62 (dd, 2H), 6.7573 (s, 1H), 7.1598 (s, 1H), 7.32 (dd, 2H). MS (ESI⁺, m/z): 284 [M+H]⁺, 301 [M+NH₄]⁺.

INTERMEDIATE 22

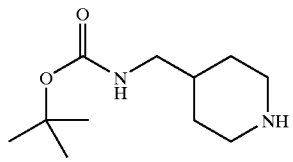

Piperidin-4-ylmethyl-carbamic Acid t-Butyl Ester
Step A: 4-Aminomethyl-1-benzylpiperidine A suspension of 1-benzylisonipecotamide (9.0 g, 41.2 mmol) in 300 mL THF was treated portionwise with LAH (3.13 g, 82.4 mmol). The mixture was heated at reflux overnight. Upon cooling the excess LAH was decomposed by the stepwise addition of 3.13 mL $H_2O$, 3.13 mL 1N NaOH, 9.5 mL $H_2O$ and 36 g $Na_2SO_4$. The solids were filtered and washed with ethyl acetate. The combined filtrates were concentrated in vacuo to give 5.5 g of the product as an oil.

NMR (CDCl₃, 400 MHz): δ 0.90 (dq, 2H), 1.3559 (s, 9H), 1.48 (broad d, 2H), 2.34 (t, 2H), 2.747 (t, 2H), 2.86 (broad d, 2H), 6.759 (t, 1H). MS (ESI⁺, m/z): 205 [M+H]⁺.

Step B: Piperidin-4-ylmethyl-carbamic Acid t-Butyl Ester

A mixture of 4-aminomethyl-1-benzylpiperidine (5.5 g, 27 mmol), di-tert-butyldicarbonate 5.88 g, 27 mmol) and potassium carbonate (7.45 g, 54 mmol) in 200 mL of dioxane-water (1:1, v/v) was stirred at ambient temperature over night. The reaction was partitioned between ethyl acetate and $H_2O$. The organic phase was washed with $H_2O$ and dried ($Na_2SO_4$). Removal of solvent in vacuo afforded 8.3 g of the intermediate 1-benzyl-piperidin-4-ylmethyl-carbamic acid t-butyl ester as a clear oil.

A solution of the intermediate (8.2 g, 27 mmol) in 200 mL ethanol containing 1.0 g of 10% palladium on carbon was stirred under an atmosphere of hydrogen until gas uptake ceased. The catalyst was filtered and the filtrate concentrated in vacuo to give 6.3 g of a wet solid. Recrystallization from Et₂O-pet ether gave 3.2 g of product as a white solid.

NMR (CDCl₃, 400 MHz): δ 1.07 (m, 3H), 1.60 (broad d, 2H), 1.84 (dt, 2H), 2.37 (d, 2H), 2.76 (broad d, 2H), 3.041 (s, 2H), 7.27 (m, 5H). MS (ESI⁺, m/z): 215 [M+H]⁺.

INTERMEDIATE 23

[1-(4-Aminobenzenesulfonyl)-piperidin-4-ylmethyl]-carbamic Acid t-Butyl Ester

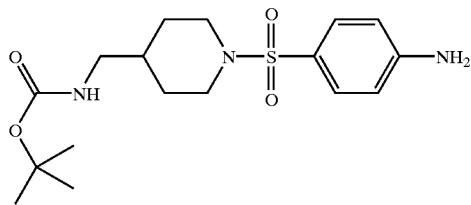

Step A: (4-Aminomethylpiperidin-1-yl)-4-nitrobenzenesulfonamide

A solution of benzaldehyde (20.3 mL, 200 mmol) and 4-aminomethylpiperidine (22.8 g, 200 mmol) in 250 mL toluene was heated at reflux until 3.6 mL of $H_2O$ was collected in a Dean-Stark trap. To the cooled reaction mixture was added 4-nitrobenzenesulfonyl chloride (44.3 g, 200 mmol) and diisopropylethyl amine (34.8 mL, 200 mmol) and stirring was continued for 1 hour. The intermediate imine was decomposed by the addition of 200 mL of 1N KHSO₄ solution. The solids formed were filtered, washed sequentially with water and ether. The collected solids were dried to provide 65 g of the title compound.

NMR (DMSO-d₆, 400 MHz): δ 1.18 (m, 2H), 1.408 (m, 1H), 1.74 (broad d, 2H), 2.33 (dt, 2H), 2.57 (d, 2H), 3.4 (m, 2H), 3.685 (broad d, 2H), 8.0 (d, 2H, J=8.78 Hz), 8,42 (d, 2H), J=8.78 Hz), 6.812 (t, 1H), 7.32 (dd, 2H). MS (ESI⁺, m/z): 300 [M+H]⁺.

Step B: [1-(4-Aminobenzenesulfonyl)-piperidin-4-ylmethyl]-carbamic Acid t-Butyl Ester A solution of 4-aminomethylpiperidin-1-yl-(4-nitrobenzenesulfonamide (15 g, 50 mmol), di-t-butyldicarbonate (10.9 g, 50 mmol) and potassium carbonate (13.8 g, 100 mmol) in 200 mL of dioxane-water (1:1, v/v) was stirred at ambient temperature over night. The reaction mixture was partitioned with ethyl acetate and water. The organic phase was washed with brine and dried ($Na_2SO_4$). to give 15 g of the intermediate. The nitro was reduced in 1 L ethanol over 1.5 g 10% Pd/C by the addition of 11.8 g (187 mmol) of ammonium formate. The reaction was stirred overnight. The catalyst was filtered and the solvent evaporated to give 12 g of an off-white solid.

NMR (DMSO-d₆, 400 MHz): δ 1.097 (m, 2H), 1.26 (m, 1H), 1.340 (s, 9H), 1.62 (broad d, 2H), 2.0644 (t, 2H), 2.75 (t, 2H), 3.47 (broad d, 2H), 6.0265 (s, 2H), 6.61 (dd, 2H), 6.812 (t, 2H), 7.32 (dd, 2H). MS (ESI⁺, m/z): 370 [M+H]⁺, 387 [M+NH₄]⁺.

INTERMEDIATE 24

(1-(4-Amino)benzenesulfonylpiperidin-4ylmethyl) dimethyl Acetal

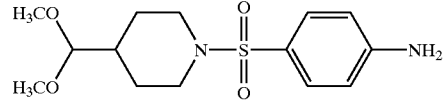

Step A: [1-(4-Nitro-benzenesulfonyl)-piperidin-4-yl]-methanol

Prepared in identical fashion to the 4-carboxamide analog by reacting 4-nitrobenzenesulfonyl chloride with 4-hydroxymethylpiperidine in THF containing 1 equivalent of diisopropyethylamine overnight at ambient temperature.

Step B: 1-(4-Nitro-benzenesulfonyl)-piperidine-4-carbaldehyde

A mixture of 1-hydroxy-1,2-benziodooxol-3(1H)-one-1-oxide (IBX) (8.73 g, 3.12 mmol) in DMSO (30 mL) and THF (15 mL) was stirred at room temperature over a period of 20 minutes. In one portion [1-(4-Nitro-benzenesulfonyl)-piperidin-4-yl]-methanol (4.69 g, 15.6 mmol) was added and the solution heated to 50° C. Water was added to the reaction until a white precipitate formed. The reaction mixture was filtered and washed with ethyl acetate. The filtrate was partitioned with ethyl acetate and water. The organic phase was dried (sodium sulfate) and concentrated in vacuo to give 4.32 g of the product as a tan solid NMR (DMSO-d₆, 400 MHz): δ 1.46–1.56 (m, 2H), 1.88–1.97 (m, 2H), 7.97–7.99 (m, 2H), 8.40–8.44 (m, 1H), MS (ESI⁺, m/z): 298 [M+H]⁺.

Step C: 4-Dimethoxymethyl-1-(4-nitro-benzenesulfonyl)-piperidine 1-(4-Nitro-benzenesulfonyl)-piperidine-4-carboxaldehyde (5 g, 16.8 mmol) was dissolved in methanol (30 mL). Trimethylorthoformate (20 mL) was added, and the resulting solution was heated to 81° C. A catalytic amount of p-toluenesulfonic acid was added. After about 10 minutes the heat was removed, and a solid fell out of solution. Diethyl ether was added, and the reaction filtered to give 3.42 g of the acetal.

NMR (DMSO-$d_6$, 400 MHz): δ 1.20–1.24(m, 2H). 1.50 (m, 1H), 1.64–1.68 (m, 2H), 2.24–2.31 (m, 2H), 3.67–3.68 (m, 2H), 4.00–4.02 (m, 1H), 7.96–8.00 (m, 2H), 8.41–8.44 (m, 2H). MS (APCI$^+$, m/z): 345 [M+H]$^+$.

Step D: [1-(4-Amino)benzenesulfonylpiperidin-4ylmethyl] dimethyl Acetal

A solution of 4-dimethoxymethyl-1-(4-nitro-benzenesulfonyl)-piperidine (8.1 g, 23.5 mmol) and ammonium formate (7.4 g, 117 mmol) in ethanol (100 mL) was heated at reflux over 1.0 g of 10% palladium on carbon for 20 minutes. The catalyst was filtered and the filtrate concentrated in vacuo. The crude product was purified by flash chromatography ($CH_2Cl_2$—$CH_3OH$, 19:1) to give 5.8 g of title compound as a white solid.

NMR (DMSO-$d_6$, 300 MHz): δ 1.20 (s, 2H), 1.45 (m, 1H), 1.62 (broad d, 2H), 2.15 (t, 2H), 3.18 (s, 6H), 3.55 (broad d, 2H), 6.02 (s, 2H), 6.62 (d, 2H), 7.33 (d, 2H).

INTERMEDIATE 25

4-Formylpiperidine Dimethyl Acetal

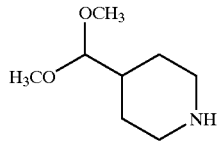

Step A: N-Benzyloxycarbonyl-4-hydroxymethylpiperidine

A solution of benzylchloroformate (17 g, 100 mmol) in 50 mL of 2-butanone was added dropwise to a stirred mixture of 4-hydroxymethylpiperidine (10.3 g, 100 mol) and potassium carbonate (13.8 g, 100 mmol) in 300 mL of 2-butanone. When the addition was complete the stirring was continued for an additional 3 hours. The solids formed were filtered and the filtrate concentrated in vacuo. Pure product was obtained by flash chromatography (hexane-ethyl acetate, 2:1) to give 10.6 g of product as an oil.

NMR (DMSO-$d_6$, 400 MHz): δ 1.0 (m, 2H), 1.51 (m, 1H), 1.61 (broad d, 2H), 2.75 (broad, 2H), 3.22 (d, 2H), 3.98 (d, 2H), 5.0468 (s, 2H), 7.34 (m, 5H). MS (APCI$^+$, m/z): 250 [M+H]$^+$.

Step B: N-Benzyloxycarbonyl-4-formylpiperidine

An ice cold solution of N-benzyloxycarbonyl-4-hydroxymethylpiperidine (2.5 g, 10 mmol) in 100 mL $CH_2Cl_2$ is treated with pyridinium chlorochromate (3.23 g, 15 mmol). The reaction is stirred at ambient temperature for 3 hours. The mixture was diluted with 100 mL $Et_2O$ and filtered through a plug of silica. The filtrate was concentrated in vacuo to provide 2.3 g of the title compound as a pale green liquid.

NMR (DMSO-$d_6$, 400 MHz): δ 1.38 (m, 2H), 1.82 (m, 2H), 2.54 (m, 1H), 2.91 (broad, 2H), 3.87 (m, 2H), 5.054 (s, 2H), 7.34 (m, 5H), 9.5725 (s, 1H).

Step C: N-Benzyloxycarbonyl-4-formylpiperidine Dimethyl Acetal

A solution of N-benzyloxycarbonyl-4-formylpiperidine (2.3 g, 9.3 mmol) in 40 mL of $CH_3OH$-trimethylorthoformate (3:1, v/v) containing a trace amount of p-toluenesulfonic acid was stirred at ambient temperature for 1 hour. Concentrated in vacuo to provide 2.4 g of product as an oil.

NMR (DMSO-$d_6$, 400 MHz): δ 1.06 (m, 2H), 1.62 (broad d, 2H), 1.74 (m, 1H), 2.75 (broad, 2H), 3.2359 (s, 6H), 3.41 (broad, 1H), 4.0 (m, 3H), 5.045 (s, 2H), 7.34 (m, 5H). MS (ESI$^+$, m/z): 294 [M+H]$^+$.

Step D: 4-Formylpiperidine Dimethyl Acetal

A solution of N-benzyloxycarbonyl-4-formylpiperidine dimethyl acetal (2.4 g, 8.2 mmol) in 40 mL ethanol-cyclohexene (3:1, v/v) was heated at reflux over 0.8 g of 10% palladium on carbon for 1.5 hours. The catalyst was filtered and the solvent evaporated in vacuo to give 0.9 g of title compound as a solid.

NMR (DMSO-$d_6$, 300 MHz): δ 1.06 (m, 2H), 1.52 (broad d, 2H), 1.6 (m, 1H), 2.38 (t, 2H), 2.89 (broad d, 2H), 3.22 (s, 6H), 3.98 (d, 1H).

INTERMEDIATE 26

[1-(4-Aminobenzenesulfonyl)-piperidin-4-ylmethyl]-carbamic Acid t-Butyl Ester

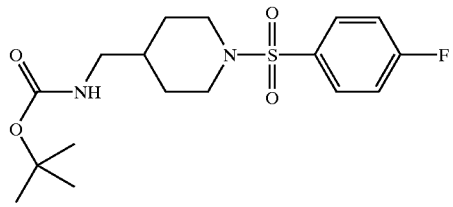

A solution of [piperidin-4-ylmethyl]-carbamic acid t-butyl ester (4.28 g, 20 mmol), 4-fluorobenzenesulfonyl chloride (3.89 g, 20 mmol), and diisopropylethyl amine (3.5 mL, 20 mmol) in 50 mL of $CH_2Cl_2$ was stirred at ambient temperature overnight. The reaction mixture was diluted to twice its volume with $CH_2Cl_2$ and washed with 1N HCl, brine and dried ($Na_2SO_4$). The solvent was evaporated in vacuo to give 8.2 g of product as a white solid.

NMR (DMSO-$d_6$, 400 MHz): δ 1.09 (m, 2H), 1.33 (s+m, 10H), 1.63 (broad d, 2H), 2.18 (t, 2H), 2.75 (t, 2H), 3.58 (broad d, 2H), 6.81 (t, 1H), 7.46 (t, 2H), 7.78 (m, 2H). MS (APCI$^+$, m/z): 373 [M+H]$^+$.

INTERMEDIATE 27

[1-(4-Fluorobenzenesulfonyl)-piperidin-4-yl]-carboxaldehyde Dimethyl Acetal

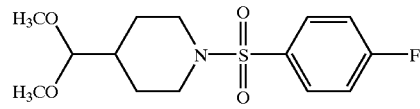

Step A: 1-(4-Hydroxymethylpiperidine)-4-fluorobenzenesulfonamide

A solution of 4-hydroxymethylpiperidine (14.8 g, 128 mmol), 4-fluorobenzenesulfonyl chloride (25 g, 128 mmol), and diisopropylethyl amine (22.25 mL, 128 mmol) 500 mL of $CH_2Cl_2$ was stirred at ambient temperature overnight. The reaction mixture was washed with 1N HCl, brine and dried ($Na_2SO_4$). The solvent was evaporated in vacuo to give 35 g of product as a white solid (m.p. 82–83° C.).

NMR (DMSO-$d_6$, 400 MHz): δ 1.135 (m, 2H), 1.30 (s, 1H), 1.68 (dd, 2H), 2.19 (dt, 2H), 3.19 (d, 2H), 3.61 (d, 2H), 7.46 (t, 2H), 7.79 (m, 2H). MS (APCI$^+$, m/z): 274 [M+H]$^+$.

Step B: [1-(4-Fluorobenzenesulfonyl)-piperidin-4-yl]-carboxaldehyde

A mixture of 1-(4-hydroxymethylpiperidine)-4-fluorobenzenesulfonamide (34.8 g, 127 mmol) and 1-hydroxy-1,2-benziodooxol-3(1H)-one-1-oxide (IBX) [ref M. Frigerio et al. *Tet. Lett*, (1994) 35, 8019] in 250 mL DMSO was heated at 50° C. for 15 minutes and cooled. The reaction mixture was poured into $H_2O$ and filtered. The product was isolated from the filter cake by washing the cake with acetone. The combined acetone layers were concentrated in vacuo. The crude product was triturated with $Et_2O$-hexane (1:1, v/v) to give 34 g of product as a white solid (m.p.-84–85° C.).

NMR (DMSO-$d_6$, 400 MHz): δ 1.50 (m, 2H), 1.88 (dd, 2H), 2.345 (m, 1H), 2.46 (m, 2H), 3.42 (m, 2H), 3.61 (d, 2H), 7.47 (t, 2H), 7.79 (m, 2H), 9.5084 (s, 1H). MS (APCI$^+$, m/z): 272 [M+H]$^+$.

Step C: [1-(4-Fluorobenzenesulfonyl)-piperidin-4-yl]-carboxaldehyde Dimethyl Acetal A solution of 1-[(4-fluorobenzene)-sulfonyl]-piperidin-4-yl-carboxaldehyde (35 g, 125 mmol) in 200 mL methanol, 135 mL (1.25 mol) trimethylorthoformate and a trace of p-toluenesulfonic acid was heated to 50° C. and allowed to cool. The reaction mixture was concentrated in vacuo and the residue triturated with $Et_2O$-hexane to give 22 g product as a white solid (m.p.-86–88° C.).

NMR (DMSO-$d_6$, 400 MHz): δ 1.22 (m, 2H), 1.52 (m, 1H), 1.65 (d, 2H), 2.15 (dt, 2H), 3.182 (s, 6H), 3.34 (broad s, 2H), 3.63 (d, 2H), 4.012 (d, 1H), 7.46 (t, 2H), 7.78 (m, 2H). MS (APCI$^+$, m/z): 318 [M+H]$^+$.

INTERMEDIATE 28

4-(4-(Dimethoxymethyl)piperidinyl)benzoic Acid

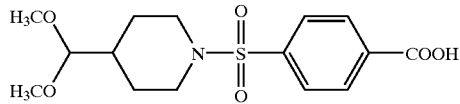

Step A: Methyl 4-((4-Hydroxymethyl)piperidinyl)benzoate

A solution of ethyl 4-fluorobenzoate (54.85 g, 3.262 mmol), 4-hydroxymethylpiperidine (37.57 g, 326.2 mmol) and potassium carbonate (135 g, 979 mmol) in DMF (30 mL) is heated at 100° C. overnight. The reaction is partitioned with water and ethyl acetate. The organic phase is washed with water and dried ($Na_2SO_4$). The solvent is evaporated in vacuo and the remaining solids purified by flash chromatography (ethyl acetate-hexane, 1:1) to give the coupled product (43 g, 50%).

Step B: Methyl 4-(4-Formylpiperidinyl)benzoate

A solution of methyl 4-((4-hydroxymethyl)piperidinyl)benzoate (20 g, 76 mmol) in methylene chloride (760 mL) was chilled in an ice/water bath. Pyridinium chlorochromate (25 g, 114 mmol) was added, and the reaction was allowed to warm to room temperature over three hours. The reaction was diluted with ether, filtered through a pad of silica gel and the filtrate concentrated in vacuo to give the aldehyde which was used directly in the following step.

Step C: Methyl 4-(4-(Dimethoxymethyl)piperidinyl) benzoate

A solution of the crude methyl 4-((4-hydroxymethyl)piperidinyl)benzoate in methanol (120 mL), and trimethylorthoformate (83 mL) containing a catalytic amount of p-toluenesulfonic acid, was heated at 81° C. for 2 hours. On cooling the resulting precipitate was collected, washed with ether and dried to give 5.6 g of product.

Step D: 4-(4-(Dimethoxymethyl)piperidinyl)benzoic Acid

A solution of methyl 4-(4-(dimethoxymethyl)piperidinyl) benzoate(5.6 g, 18.2 mol) was in methanol (50 mL) 1N sodium hydroxide (27 mL) was heated at 80° C. for 5 hours. The reaction was neutralized with 1N HCl (27 ml) and concentrated in vacuo. Additional methanol was added to the residue which was filtered (0.5 micron filter) and evaporated to give 5.0 g of the product.

INTERMEDIATE 29

[1-({4-[Amino(hydroxyimino)methyl] phenyl}sulfonyl)-4-piperidinyl]methyl-carbamic Acid t-Butyl Ester

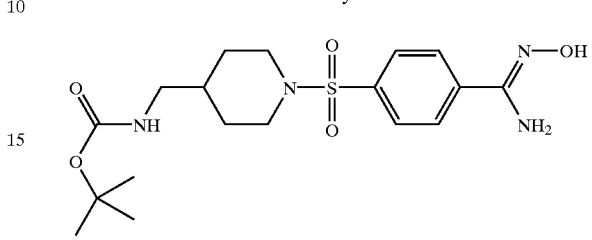

{1-[(4-Cyanophenyl)sulfonyl]-4-piperidinyl}methylcarbamic acid t-butyl ester (1 g, 2.6 mmol), potassium carbonate (1.8 g, 13 mmol), and ammonium hydroxide hydrochloride (0.916 g, 13 mmol) were heated in ethanol (5 ml) at reflux for 2.5 days. The reaction was cooled in an ice-water bath, and filtered. The solid was washed with cold ethanol, and evaporated to a white solid (0.870 g).

MS (APCI$^+$, m/z): 413 [M+H]$^+$.

EXAMPLE 1

(2S)-1-(9H-Carbazol-4-yloxy)-3-{[1-(7-trifluoromethyl-quinolin-4-yl)-piperidin-4-ylmethyl]-amino}-propan-2-ol

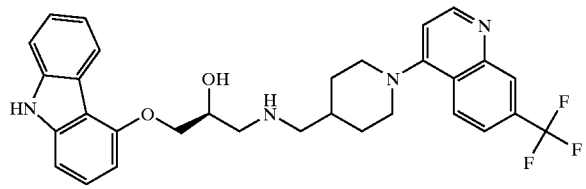

Step A: 1-(7'-Trifluoromethyl-4'-quinolyl)piperidine-4-carboxamide

Under anhydrous conditions, a slurry of hexane washed potassium hydride (1.56 g, 39 mmol) in 50 mL THF was treated portionwise with isonipecotamide (5.0 g, 39 mmol). Stirred at ambient temp until gas evolution ceased. To the mixture was added 4-chloro-7-trifluoromethyl quinoline (9.0 g, 39 mmol). The reaction mixture was heated at reflux for 48 hours, cooled and partitioned between ethyl acetate and $H_2O$. The organic phase was washed with brine and dried ($Na_2SO_4$). Removal of solvent (rotovap) and purification of the residue by flash chromatography ($CH_2Cl_2$—$CH_3OH$, 19:1) afforded 1.4 g of title compound as a white solid.

NMR (DMSO-$d_6$, 400 MHz): δ 1.872 (m, 4H), 2.357 (m, 1H), 2.8585, (m, 2H), 3.555 (broad d, 2H, 6.135 (s, 1H), 7.11 (d, 1H), 7.3497 (s, 1H), 7.77 (dd, 1H), 8.18 (d, 1H), 8.243 (s, 1H), 8.78 (d, 1H). MS (EI, m/z): 323 (M$^+$); Anal. calc'd for $C_{16}H_{16}F_3N_3O$: C, 59.44; H, 4.99; N, 13.00; Found: C, 59.13; H, 5.04; N, 12.96.

Step B: 4-Aminomethyl-1-(7'-trifluoromethyl-4'-quinolyl)-piperidine

A mixture of the amide (1.4 g., 4.3 mmol) in 30 mL of THF was treated in one portion with lithium aluminum hydride (LAH) (0.17 g, 4.3 mmol). The mixture was heated at reflux for 1 hour and allowed to stir at ambient temp overnight. Excess LAH was decomposed by the stepwise addition of 0.17 mL of $H_2O$, 0.17 mL of 1N NaOH, 0.51 mL of water and 2.1 g of $Na_2SO_4$. After stirring for 10 min the solids were filtered and washed with EtOAc. The solvent was removed (rotovap) to provide 1.15 g of the title compound as an amber solid of suitable purity for direct use as an intermediate.

NMR (DMSO-$d_6$, 400 MHz): δ 1.49 (m, 2H), 1.58 (broad, 1H), 1.83 (d, 2H), 2.83, (m, 2H), 3.58 (broad d, 2H), 7.05 (m, 1H), 7.78 (dd, 1H), 8.16 (d, 1H), 8.24 (s, 1H), 8.77 (m, 1H). MS (ESI$^+$, m/z): 310 (M$^+$).

Step C: (2S)-1-(9H-Carbazol-4-yloxy)-3-{[1-(7-trifluoromethyl-quinolin-4-yl)-piperidin-4-ylmethyl]-amino}-propan-2-ol A mixture of 4-[(2S)-oxiranylmethoxy]-9H-carbazole (0.239 g, 1 mmol) and 4-aminomethyl-1-(7'-trifluoromethyl-4'-quinolyl)-piperidine (0.309 g, 1 mmol) was heated as a solution in 5 mL methanol at 60° C. for 24 hours. The reaction mixture was preabsorbed on silica gel and purified. by flash chromatography ($CH_2Cl_2$—$CH_3OH$, 19:1) to give the title compound. The product, 0.06 g, was dissolved in $CH_2Cl_2$ and treated with excess 1N HCl in diethyl ether. The solids were collected and dried to give 0.058 g of the dihydrochloride as a yellow solid.

NMR (DMSO-$d_6$, 400 MHz): δ 1.55 (m, 2H), 2.01 (broad t, 2H), 2.18 (broad, 1H), 3.05, (m, 2H), 3.3 (m, 4H), 4.05 (broad, 2H), 4.236 (m, 2H), 4.45 (m, 1H), 6.006 (s, 1H), 6.71 (m, 1H), 7.09 (m, 2H), 7.24–7.35 (m, 3H), 7.45 (d, 1H), 7.89 (d, 1H) 8.21–8.34 (m, 3H), 8.79.(m, 3H), 11.296 (s, 1H). MS (ESI$^+$, m/z): 549 [M+H]$^+$.

EXAMPLE 2

(2S)-1-(4-Benzyloxy-phenoxy)-3-{[1-(7-trifluoromethyl-quinolin-4-yl)-piperidin-4-ylmethyl]-amino}-propan-2-ol

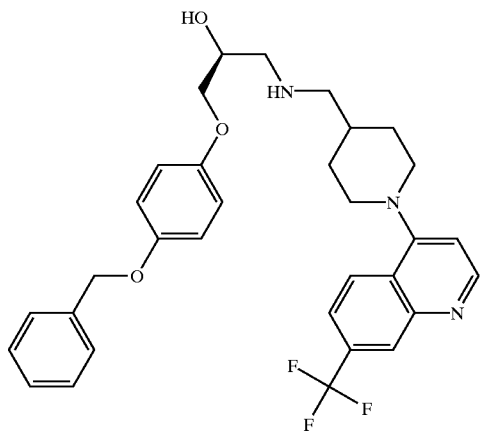

A solution of 2-(S)-(4-benzyloxy-phenoxymethyl)-oxirane (0.198 g, 0.776 mmol) and 4-aminomethyl-1-(7'-trifluoromethyl-4'-quinolyl)-piperidine (0.242 g, 0.766 mmol) in 4 mL methanol was heated at 60° C. overnight. The reaction mixture was preabsorbed on silica gel and purified by flash chromatography ($CH_2Cl_2$—$CH_3OH$, 19:1) to provide 0.065 g of product as a white solid.

NMR (DMSO-$d_6$, 400 MHz): δ 1.45 (m, 2H), 1.61 (broad, 1H), 1.87 (broad d, 2H), 2.52, (m, 4H), 2.81 (broad t, 2H), 3.535 (broad d, 2H), 3.85 (m, 3H), 4.95 (m, 1H), 5.009 (s, 1H), 6.88 (m, 4H), 7.08 (m, 1H), 7.27–7.37 (m, 5H), 7.76 (d, 1H), 8.16 (d, 1H), 8.23 (s, 1H), 8.77.(d, 3H). MS (ESI$^+$, m/z): 566 [M+H]$^+$.

EXAMPLE 3

4-((2S)-2-Hydroxy-3-{[1-(7-trifluoromethyl-quinolin-4-yl)-piperidin-4-ylmethyl]-amino}-propoxy)-fluoren-9-one

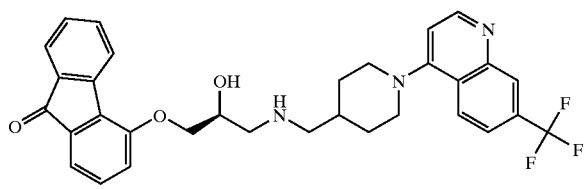

Prepared from 4-[(2S)-oxiranylmethoxy]-9-fluorenone (0.211 g, 0.84 mmol) and 4-aminomethyl-1-(7'-trifluoromethyl-4'-quinolyl)-piperidine (0.260 g, 0.84 mmol) according to the procedure used for Example 2 to provide 0.160 g of product as a yellow solid, m.p.-sinters 88° C.

NMR (DMSO-$d_6$, 400 MHz): δ 1.45 (m, 2H), 1.66 (broad, 1H), 1.87 (broad d, 2H), 2.59, (m, 2H), 2.79 (broad t, 4H), 3.51 (broad d, 2H), 4.0–4.23 (m, 3H), 5.18 (m, 1H), 7.05 (d, 1H), 7.21 (m, 1H), 7.29–7.33 (m, 3H), 7.57 (m, 2H), 7.76 (d, 1H), 7.91 (d, 1H), 8.13. (d, 1H), 8.23 (s, 1H), 8.76 (d, 1H). MS (ESI$^+$, m/z): 562 (M+H)$^+$.

EXAMPLE 4

4-((2S)-2-Hydroxy-3-{[1-(7-trifluoromethyl-quinolin-4-yl)-piperidin-4-ylmethyl]-amino}-propoxy)-fluoren-9-one Oxime

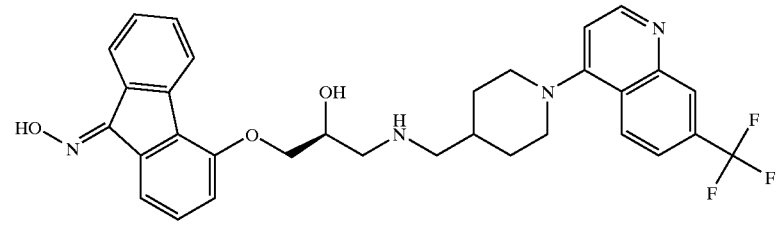

A solution of 4-((2S)-2-hydroxy-3-{[1-(7-trifluoromethyl-quinolin-4-yl)-piperidin-4-ylmethyl]-amino}-propoxy)-fluoren-9-one (0.080 g, 0.14 mmol), hydroxylamine hydrochloride (0.0105 g, 0.15 mmol) and sodium acetate (0.123 g, 0.15 mmol) in 10 mL methanol was stirred overnight at ambient temperature. The reaction mixture was concentrated in vacuo and triturated with a mixture of methylene chloride and water. The solids were filtered and dried to give the crude product. The dihydrochloride salt was prepared with excess 1N HCl in diethyl ether. The solids were collected and dried to give 0.070 g of the title compound as an off-white solid, mp 171° C. sinters.(di-HCl salt)

NMR (DMSO-$d_6$, 400 MHz): δ 1.585 (m, 2H), 1.977 (m, 3H), 2.85 (t, 2H), 3.06 (s, 2H), 3.15 (s, 1H), 3.85 (d, 2H), 4.218 (m, 2H), 4.419 (s, 1H), 6.01 (s, 1H), 7.13 (m, 2H), 7.2–7.5 (m, 4H), 7.68–7.70 (m, 2H), 8.02 (m, 2H), 8.15–8.32 (m, 2H), 8.8 (m, 2H), 12.58 (s, 1H). MS (ESI$^-$, m/z): 575 (M–H)$^-$.

EXAMPLE 5

(2S)-1-(9H-Carbazol-4-yloxy)-3-[(4'-trifluoromethyl-3,4,5,6-tetrahydro-2H-[1,2']bipyridinyl-4-ylmethyl)-amino]-propan-2-ol

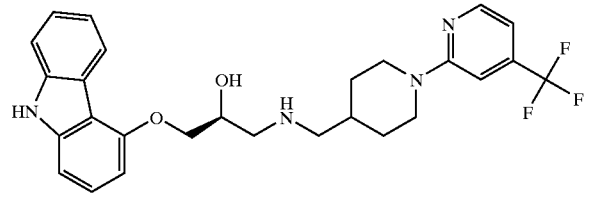

Step A: 4-Aminomethyl-1-(4'-trifluoromethyl-2'-pyridyl)-piperidine

A mixture of the 1-(4'-trifluoromethyl-2'-pyridyl)-piperidine-4-carboxamide (1.0 g., 3.6 mmol, Maybridge) in 20 mL of THF was treated in one portion with lithium aluminum hydride (LAH) (0.274 g, 7.2 mmol). The mixture was heated at reflux for 2 hours. On cooling the excess LAH was decomposed by the stepwise addition of 0.28 mL of H$_2$O, 0.28 mL of 1N NaOH, 0.84 mL of H$_2$O and 2 g of Na$_2$SO$_4$. After stirring for 10 min the solids were filtered and washed with EtOAc. The solvent was removed (rotovap) to provide 0.9 g of the title compound as an amber oil of suitable purity for direct use as an intermediate.

NMR (DMSO-$d_6$, 400 MHz): δ 1.055 (m, 2H), 1.47 (broad, 1H), 1.74 (d, 2H), 2.81, (m, 2H), 4.365 (broad d, 2H), 6.78 (m, 1H), 7.02 (s, 1H), 8.27 (d, 1H). MS (ESI$^+$, m/z): 260 [M+H]$^+$.

Step B: (2S)-1-(9H-Carbazol-4-yloxy)-3-[(4'-trifluoromethyl-3,4,5,6-tetrahydro-2H-[1,2']bipyridinyl-4-ylmethyl)-amino]-propan-2-ol Prepared from 253 mg (1.06 mmol) of 4-[(2S)-oxiranylmethoxy]-9H-carbazole (0.253 g, 1.06 mmol) and 4-aminomethyl-1-(4'-trifluoromethyl-2'-pyridyl)-piperidine (0.285 g, 1.1 mmol) according to the procedure used for Example 2 to give 0.125 g of the title compound as an off-white solid (m.p.-137–138° C., EtOAc/hexane).

NMR (DMSO-$d_6$, 400 MHz): δ 1.07 (m, 2H), 1.745 (broad m, 3H), 2.74, (m, 3H), 2.88 (m, 1H), 4.11 (broad m, 3H), 4.236 (m, 2H), 5.14 (broad, 1H), 6.67 (d, 1H), 6.78 (d, 2H), 7.0–7.13 (m, 3H), 7.25–7.33 (m, 3H), 7.42 (d, 1H) 8.20 (d, 1H), 8.27.(d, 1H), 11.222 (s, 1H). MS (ESI$^+$, m/z): 499 [M+H]$^+$; Anal. calc'd for C$_{27}$H$_{29}$F$_3$N$_4$O$_2$: C, 65.05; H, 5.86; N, 11.24; Found: C, 64.83; H, 5.82; N, 11.14.

EXAMPLE 6

4-{(2S)-2-Hydroxy-3-[(4'-trifluoromethyl-3,4,5,6-tetrahydro-2H-[1,2']bipyridinyl-4-ylmethyl)-amino]-propoxy}-fluoren-9-one

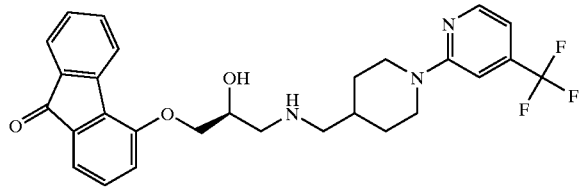

Prepared from 4-[(2S)-Oxiranylmethoxy]-9-fluorenone (0.252 g, 1.0 mmol) and 4-aminomethyl-1-(4'-trifluoromethyl-2'-pyridyl)-piperidine (0.259 g, 1.0 mmol) according to the procedure used for Example 2 to give 0.065 g of the title compound as a yellow solid.

NMR (DMSO-$d_6$, 400 MHz): δ 1.065 (m, 2H), 1.87 (broad d, 3H), 2.77, (m, 4H), 4.0 (broad, 1H), 4.15 (m, 2H), 4.35 (broad d, 2H), 5.185 (broad, 1H), 6.78 (d, 1H), 7.01 (s, 1H), 7.205 (d, 1H), 7.32 (m, 3H), 7.57 (m, 2H), 7.89 (d, 1H), 8.27 (d, 1H). MS (ESI$^+$, m/z): 512 (M+H)$^+$.

EXAMPLE 7

1-{(2S)-2-Hydroxy-3-[(4'-trifluoromethyl-3,4,5,6-tetrahydro-2H-[1.2']bipyridinyl-4-ylmethyl)-amino]-propoxy}-fluoren-9-one

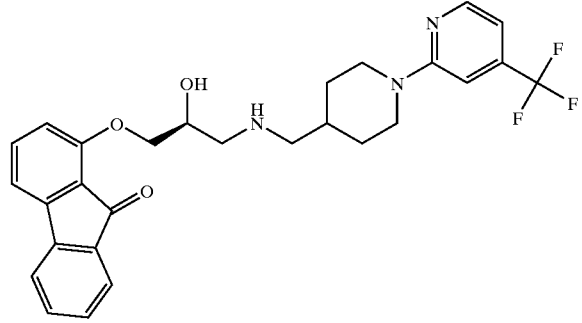

Prepared from 1-[(2S)-Oxiranylmethoxy]-9-fluorenone (0.278 g, 1.1 mmol) and 4-aminomethyl-1-(4'-trifluoromethyl-2'-pyridyl)-piperidine (0.285 g, 1.1 mmol) according to the procedure used for Example 2 to give 0.089 g of the title compound as a yellow solid (m.p.-105–107° C., triturated with Et$_2$O).

NMR (DMSO-$d_6$, 400 MHz): δ 1.09 (m, 2H), 1.78 (broad d, 3H), 2.55 (m, 2H), 2.85 (m, 4H), 4.0 (m, 1H), 4.12 (m, 2H), 4.34 (broad d, 2H), 5.15 (broad, 1H), 6.81 (d, 1H), 7.08 (m, 2H), 7.38 (m, 2H), 7.32 (m, 3H), 7.57 (m, 3H), 7.76 (d, 1H), 8.29 (d, 1H). MS (ESI$^+$, m/z): 511 (M$^+$).

EXAMPLE 8

(2S)-1-(9H-Carbazol-4-yloxy)-3-[(1-propyl-piperidin-4-ylmethyl)-amino]-propan-2-ol

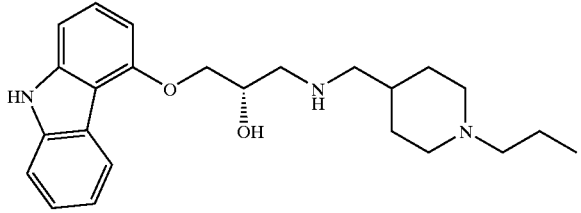

Step A: 1-Propylpiperidine-4-carboxamide

A solution of isonipecotamide (2.0 g, 15.6 mmol), 1-iodopropane (1.52 mL, 15.6 mmol), and potassium carbonate (2.15 g, 15.6 mmol) was heated at reflux in 100 mL of 2-butanone. The solids were filtered and the filtrate concentrated in vacuo to give crude product. Purification by flash chromatography ($CH_2Cl_2$—$CH_3OH$, 12:1) afforded 1.25 9 of the product as an off-white solid.

NMR (DMSO-$d_6$, 400 MHz): δ 0.8378 (m, 3H), 1.42 (m, 2H), 1.5282 (m, 2H), 1.64 (broad d, 2H), 1.8364 (broad t, 2H), 2.0237 (m, 2H), 2.2055 (t, 2H), 2.84 (broad d, 2H), 6.7044 (s, 1H), 7.1943 (s, 1H). MS (EI, m/z): 170 (M)$^+$.

Step B: 4-Aminomethyl-1-propylpiperidine

A mixture of 1-propylpiperidine-4-carboxamide (1.2 g, 7.06 mmol) in 50 mL THF was treated in one portion with LAH (0.98 g, 14.2 mmol). The mixture was heated at reflux for 2 hours. On cooling the excess LAH was decomposed by the stepwise addition of $H_2O$, 1N NaOH, $H_2O$ and $Na_2SO_4$ (v/v/v/w-1;1;3;12.5 based on 1 gram of LAH). After stirring for 10 min the solids were filtered and washed with EtOAc. The solvent was removed (rotovap) to give 0.9 g of title compound as a yellow oil.

NMR (DMSO-$d_6$, 400 MHz): δ 0.8170 (m, 3H), 1.05 (m, 3H), 1.39 (m, 2H), 1.60 (broad d, 2H), 1.75 (dt, 2H), 2.161 (m, 2H), 2.36 (d, 2H), 2.80 (broad d, 2H). MS (EI, m/z): 156 (M)$^+$.

Step C: (2S)-1-(9H-Carbazol-4-yloxy)-3-[(1-propyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-propylpiperidine (0.312 g, 2.0 mmol) according to the procedure used for Example 2 to give 0.145 g of the title compound as an off-white solid.

NMR (DMSO-$d_6$, 400 MHz): δ 0.8235 (m, 3H), 1.09 (m, 2H), 1.22 (m, 4H), 1.3827 (m, 3H), 1.63 (broad d, 2H), 1.723 (dt, 2H), 2.1516 (m, 2H), 2.40 (d, 2H), 2.754 (m, 3H), 2.82 (m, 1H), 4.0718 (m, 1H), 4.1537 (m, 3H), 5.08 (broad, 1H), 6.67 (d, 1H, J=7.9 Hz), 7.06 (d, 1H, J=8.1 Hz), 7.12 (m, 1H), 7.2844 (m, 2H), 7.45 (d, 1H, J=8.1 Hz), 8.20 (d, 1H, J=7.9 Hz), 11.2385 (s, 1H). MS (ESI$^+$, m/z): 396 [M+H]$^+$.

EXAMPLE 9

(2S)-1-(9H-Carbazol-4-yloxy)-3-[(1-isopropyl-piperidin-4-ylmethyl)-amino]-propan-2-ol

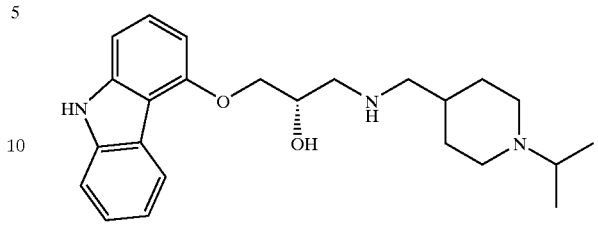

Step A: 1-Isopropylpiperidine-4-carboxamide

Prepared from isonipecotamide (2.0 g, 15.6 mmol), 2-iodopropane (3.10 mL, 31.2 mmol) of potassium carbonate and (2.15 g, 5.6 mmol) according to the procedure used for Example 8 (Step A) to give 2.5 g of the title compound.

NMR (DMSO-$d_6$, 300 MHz): δ 0.94, (d, 6H), 1.48 (m, 2H), 1.62 (broad d, 2H), 2.0 (m, 2H), 2.62 (m, 1H), 2.75 (broad d, 2H), 6.68 (s, 1H), 7.18 (s, 1H).

Step B: 4-Aminomethyl-1-isopropylpiperidine

Prepared from 1-isopropylpiperidine-4-carboxamide (2.5 g, 14.7 mmol) and LAH (1.12 g, 29.4 mmol) according to general the procedure used for Example 8 (Step B) to give 1.75 g of title compound as an oil.

NMR (DMSO-$d_6$, 300 MHz): δ 0.94, (d, 6H), 1.03 (m, 3H), 1.64 (broad d, 2H), 2.02 (dt, 2H), 2.35 (d, 2H), 2.49 (m, 1H), 2.62 (m, 1H), 2.45 (broad d, 2H).

Step C: (2S)-1-(9H-Carbazol-4-yloxy)-3-[(1-isopropyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-isopropylpiperidine (0.312 g, 2.0 mmol) of according to the procedure used for Example 2 to give 0.135 g of the title compound as a white solid.

NMR (DMSO-$d_6$, 400 MHz): δ 0.895, (d, 6H), 1.034 (m, 2H), 1.32 (m, 1H), 1.6277 (broad d, 2H), 1.94 (t, 2H), 2.41 (d, 2H), 2.598 (m, 1H), 2.70 (broad d, 2H), 2.74 (m, 1H), 2.81 (m, 1H), 4.057 (m, 1H), 4.1394 (m, 2H), 5.064 (broad, 1H), 6.66 (d, 1H, J=7.9 Hz), 7.04 (d, 1H, J=8.1 Hz), 7.11 (m, 1H), 7.28 (m, 2H), 7.42 (d, 1H, J=8.1 Hz) 8.18 (d, 1H, J=7.7Hz), 11.219 (s, 1H). MS (ESI$^+$, m/z): 396 [M+H]$^+$.

EXAMPLE 10

(2S)-1-(9H-Carbazol-4-yloxy)-3-{[1-(3,3,3-trifluoro-propyl)-piperidin-4-ylmethyl]-amino}-propan-2-ol

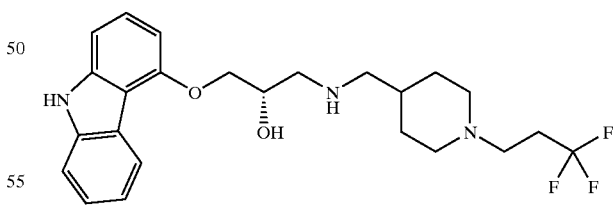

Step A: 1-(3,3,3-Trifluoropropyl)-piperidine-4-carboxamide

Prepared from isonipecotamide (2.85 g, 22.3 mmol), 3,3,3-trifluoropropyl iodide (5 g, 22.3 mmol) and potassium carbonate (3.08 g, 22.3 mmol) of according to the procedure used for Example 8 (Step A) to give 1.17 g of the title compound.

NMR (DMSO-$d_6$, 400 MHz): δ 1.52 (m, 2H), 1.65 (m, 2H), 1.89 (m, 2H), 2.03 (m, 1H), 2.38–2.52 (m, 4H), 2.85 (broad d, 2H), 6.71 (s, 1H), 7.206 (s, 1H). MS (EI, m/z): 224 (M)$^+$.

Step B: 4-Aminomethyl-1-(3,3,3-trifluoropropyl)-piperidine

Prepared from 1-(3,3,3-trifluoropropyl)-piperidine-4-carboxamide (1.0 g, 4.46 mmol) and LAH (0.34 g, 8.9 mmol) according to general the procedure used for Example 8 (Step B) to give 0.9 g of title compound as a white solid.

NMR (DMSO-$d_6$, 400 MHz): δ 1.1 (m, 2H), 1.17 (broad, 1H), 1.64 (m, 2H), 1.86 (m, 2H), 2.37–2.51 (m, 4H), 2.78 (broad d, 2H), MS (EI, m/z): 210 (M)$^+$.

Step C: (2S)-1-(9H-Carbazol-4-yloxy)-3-{[1-(3,3,3-trifluoro-propyl)-piperidin-4-ylmethyl]-amino}-propan-2-ol Prepared from 260 mg (1.09 mmol) of 4-[(2S)-oxiranylmethoxy]-9H-carbazole and 229 mg (1.09 mmol) of 4-aminomethyl-1-(3,3,3-trifluoropropyl)-piperidine according to the procedure used for Example 2 to give 0.089 g of the title compound as a white solid ($Et_2O$, EtOAc/hexane).

NMR (DMSO-$d_6$, 400 MHz): δ 1.10 (m, 2H), 1.426 (broad, 1H), 1.655 (broad d, 2H), 1.81 (broad t, 3H), 2.40, (m, 4H), 2.88 (d, 2H), 2.908 (broad m, 1H), 4.16 (broad m, 3H), 5.14 (broad, 1H), 6.68 (d, 1H, J=7.9 Hz), 7.07 (d, 1H, J=8.1 Hz), 7.13 (m, 1H), 7.29 (m, 2H), 7.44 (d, 1H, J=8.1 Hz) 8.20 (d, 1H, J=7.7 Hz), 11.251 (s, 1H). MS (ESI$^+$, m/z): 450 [M+H]$^+$.

EXAMPLE 11

(2S)-1-(4-Benzyloxy-phenoxy)-3-{[1-(3,3,3-trifluoro-propyl)-piperidin-4-ylmethyl]-amino}-propan-2-ol

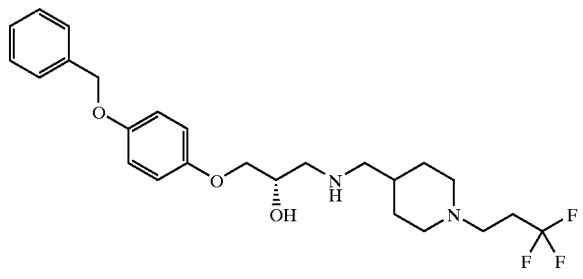

Prepared from 2-(S)-(4-benzyloxy-phenoxymethyl)-oxirane (0.40 g, 1.57 mmol) and 4-aminomethyl-1-(3,3,3-trifluoropropyl)-piperidine (0.329 g, 1.57 mmol) according to the procedure used for Example 2 to provide 0.0280 g of product as a white solid.

NMR (DMSO-$d_6$, 400 MHz): δ 1.07 (m, 2H), 1.369 (broad, 1H), 1.65 (broad d, 2H), 1.87 (broad t, 2H), 2.43 (m, 4H), 2.60 (m, 2H), 2.83 (broad d, 2H), 3.83 (m, 3H), 4.85 (broad, 1H), 5.03 (s, 2H), 6.86 (m, 2H), 6.92 (m, 2H), 7.31–7.44 (m, 5H). MS (ESI$^+$, m/z): 467 [M+H]$^+$.

EXAMPLE 12

4-((2S)-2-Hydroxy-3-{[1-(3,3,3-trifluoro-propyl)-piperidin-4-ylmethyl]-amino}-propoxy)-phenol

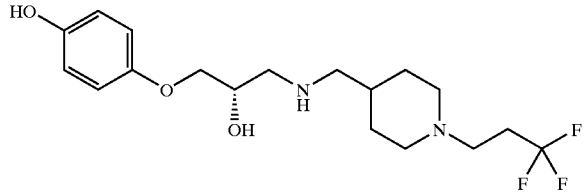

A mixture of (2S)-1-(4-Benzyloxy-phenoxy)-3-{[1-(3,3,3-trifluoro-propyl)-piperidin-4-ylmethyl]-amino}-propan-2-ol (0.20 g, 0.43 mmol) and ammonium formate (0.135 g, 2.15 mmol) in 10 mL of methanol over 0.20 g of 10% palladium on carbon was stirred at ambient temperature for 2 hours. The catalyst was filtered (solka floc) and the filtrate concentrated in vacuo. Crystallization of the crude oil form EtOAc-hexane provided 0.040 g of the title compound as a white solid.

NMR (DMSO-$d_6$, 400 MHz): δ 1.11 (m, 2H), 1.46 (broad, 1H), 1.66 (broad m, 2H), 1.88 (broad t, 2H), 2.4–2.54 (m, 4H), 2.66 (m, 1H), 2.84 (broad d, 3H), 3.78 (m, 3H), 3.92 (m, 1H), 6.66 (m, 2H), 6.74 (m, 2H), 8.263 (s, 1H). MS (ESI$^+$, m/z): 377 [M+H]$^+$.

EXAMPLE 13

4-(2-Hydroxy-3-{[1-(3,3,3-trifluoro-propyl)-piperidin-4-ylmethyl]-amino}-propoxy)-fluoren-9-one

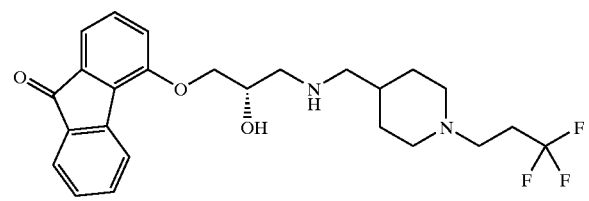

Prepared from 4-[(2S)-oxiranylmethoxy]-9-fluorenone (0.087 g, 0.34 mmol) and 4-aminomethyl-1-(3,3,3-trifluoropropyl)-piperidine (0.126 g, 0.6 mmol) of according to the procedure used for Example 2 to give 0.092 g of the title compound as a yellow solid.

NMR (DMSO-$d_6$, 400 MHz): δ 1.06 (m, 2H), 1.3509 (broad, 1H), 1.625 (broad d, 2H), 1.7903 (t, 2H), 2.41 (m, 6H), 2.74 (m, 4H), 4.007 (m, 1H), 4.112 (m, 1H), 4.1609 (m, 1H), 5.15 (broad, 1H), 7.21 (dd, 1H), 7.3207 (m, 3H), 7.5712 (m, 2H), 7.88 (d, 1H, J=7.25 Hz). MS (APCI$^+$, m/z): 463 [M+H]$^+$.

EXAMPLE 14

4-((2S)-2-Hydroxy-3-{[1-(3,3,3-trifluoro-propyl)-piperidin-4-ylmethyl]-amino}-propoxy)-9H-fluoren-9-ol

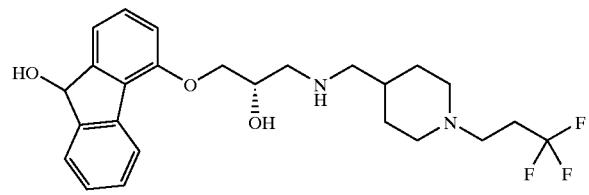

A solution of 4-(2-hydroxy-3-{[1-(3,3,3-trifluoro-propyl)-piperidin-4-ylmethyl]-amino}-propoxy)-fluoren-9-one (0.060 g, 0.13 mmol) in 4 mL THF was treated with LAH (0.010 g, 0.26 mmol) and stirred at ambient temperature overnight. Heated to reflux and cooled. The excess LAH was decomposed by the sequential addition of 0.01 mL of each of water and 1 N NaOH, 0.03 mL of water and 0.5 g $Na_2SO_4$. The solids were filtered and the filtrate concentrated in vacuo to give 0.045 g of the title compound as a yellow solid.

NMR (DMSO-$d_6$, 400 MHz): δ 1.07 (m, 2H), 1.32 (broad, 1H), 1.63 (broad d, 2H), 1.8002 (t, 2H), 2.41 (m, 6H), 2.75

(m, 4H), 4.03 (m, 1H), 4.1 (m, 2H), 5.15 (broad, 1H), 5.43 (d, 1H), J=7.25 Hz), 5.78 (d, 1H, J=7.47 Hz), 6.99 (d, 1H, J=7.9 Hz), 7.16 (d, 1H, J=7.25 Hz), 7.2521 (t, 2H), 7.32 (m, 1H), 7.53 (d, 1H, J=7 Hz), 7.96 (d, 1H, J=7.25 Hz). MS (ESI$^+$, m/z): 465 [M+H]$^+$.

EXAMPLE 15

4-((2S)-2-Hydroxy-3-{[1-(3,3,3-trifluoro-propyl)-piperidin-4-ylmethyl]-amino}-propoxy)-9H-carbazol-3-ol

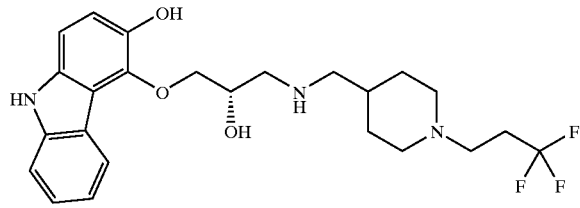

Prepared from 3-hydroxy-4-[(2S)-oxiranylmethoxy]-9H-carbazole (0.260 g, 1.09 mmol) and 4-aminomethyl-1-(3,3,3-trifluoropropyl)-piperidine (0.229 g, 1.09 mmol) according to the procedure used for Example 2 without heating to give 0.084 g of the title compound as a white solid.

NMR (DMSO-d$_6$, 400 MHz): δ 1.10 (m, 2H), 1.45 (broad, 1H), 1.675 (broad d, 2H), 1.872 (t, 2H), 2.40, (m, 5H), 2.81 (m, 4H), 4.05 (m, 3H), 6.91 (d, 1H, J=8.57 Hz), 7.03 (m, 2H), 7.303 (m, 1H), 7.37 (d, 1H, J=8.13 Hz), 8.16 (d, 1H, J=7.9 Hz), 10.95 (s, 1H). MS (ESI$^+$, m/z): 466 [M+H]$^+$.

EXAMPLE 16

(2S)-1-(1-Bromo-9H-carbazol-4-yloxy)-3-{[1-(3,3,3-trifluoro-propyl)-piperidin-4-ylmethyl]-amino}-propan-2-ol

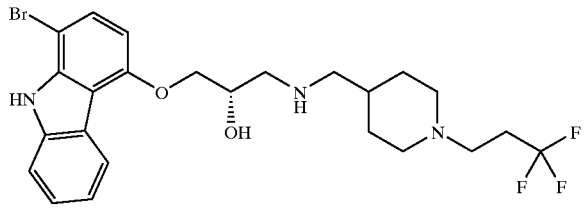

Prepared from 1-bromo-4-[(23)-oxiranylmethoxy]-9H-carbazole (0.075 g, 0.24 mmol) and 4-aminomethyl-1-(3,3,3-trifluoropropyl)-piperidine (0.10 g, 0.48 mmol) of according to the procedure used for Example 2 without heating to give 0.090 g of the title compound as a white solid (m.p. 79° C., hexane-Et$_2$O).

NMR (DMSO-d$_6$, 400 MHz): δ 1.05 (m, 2H), 1.37 (broad, 1H), 1.62 (broad d, 2H), 1.76 (t, 2H), 2.40, (m, 6H), 2.77 (m, 3H), 2.84 (m, 1H), 4.11 (m, 3H), 5.18 (broad, 1H), 6.68 (d, 1H, J=8.56 Hz), 7.18 (dt, 1H), 7.393 (dt, 1H), 7.47 (d, 1H, J=8.35 Hz), 7.53 (dd, 1H), 8.20 (d, 1H, J=7.9 Hz)), 11.3489 (s, 1H). MS (ESI$^+$, m/z): 528, 530 [M+H]$^+$.

EXAMPLE 17

(2S)-1-(1-Chloro-9H-carbazol-4-yloxy)-3-{[1-(3,3,3-trifluoro-propyl)-piperidin-4-ylmethyl]-amino}-propan-2-ol

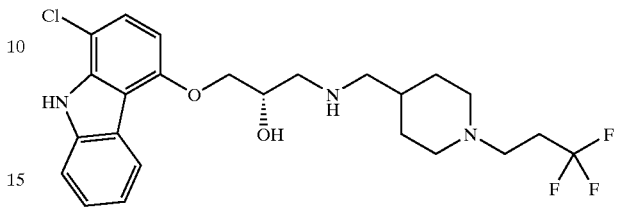

Prepared from 1-chloro-4-[(2S)-oxiranylmethoxy]-9H-carbazole (0.085 g, 0.31 mmol) and 4-aminomethyl-1-(3,3,3-trifluoropropyl)-piperidine (0.10 g, 0.48 mmol) according to the procedure used for Example 2 without heating to give 0.080 g of the title compound as a white solid.

NMR (DMSO-d$_6$, 400 MHz): δ 1.05 (m, 2H), 1.34 (broad, 1H), 1.62 (broad d, 2H), 1.761 (t, 2H), 2.40, (m, 6H), 2.75 (m, 4H), 4.11 (m, 1H), 4.15 (m, 2H), 5.09 (broad, 1H), 6.70 (d, 1H, J=8.56 Hz), 7.18 (dt, 1H), 7.34 (d, 1H, J=8.34 Hz), 7.39 (t, 1H), 7.52 (d, 1H, J=8.13 Hz), 8.21 (d, 1H, J=7.9 Hz)), 11.5014 (s, 1H). MS (ESI$^+$, m/z): 484 [M+H]$^+$.

EXAMPLE 18

(2S)-1-(3-Bromo-9H-carbazol-4-yloxy)-3-{[1-(3,3,3-trifluoro-propyl)-piperidin-4-ylmethyl]-amino}-propan-2-ol

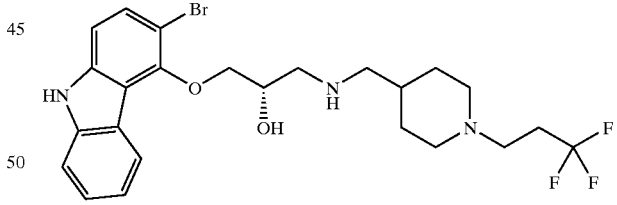

Prepared from 3-bromo-4-[(2S)-oxiranylmethoxy]-9H-carbazole (0.083 g, 0.26 mmol) and 4-aminomethyl-1-(3,3,3-trifluoropropyl)-piperidine (0.10 g, 0.48 mmol) according to the procedure used for Example 2 without heating to give 0.085 g of the title compound as a white solid.

NMR (DMSO-d$_6$, 400 MHz): δ 1.10 (m, 2H), 1.378 (broad, 1H), 1.655 (broad d, 2H), 1.87 (t, 2H), 2.40, (m, 6H), 2.74 (m, 1H), 2.81 (m, 3H), 4.1 (m, 3H), 5.23 (broad, 1H), 7.2 (m, 2H), 7.41 (t, 1H), 7.47 (m, 2H), 8.36 (d, 1H, J=7.9 Hz), 11.4975 (s, 1H). MS (ESI$^+$, m/z): 528, 530 [M+H]$^+$.

EXAMPLE 19

(2S)-1-(3-Chloro-9H-carbazol-4-yloxy)-3-{[1-(3,3,3-trifluoro-propyl)-piperidin-4-ylmethyl]-amino}-propan-2-ol

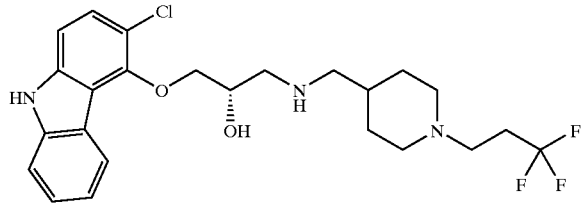

Prepared from 3-chloro-4-[(2S)-oxiranylmethoxy]-9H-carbazole (0.060 g, 0.22 mmol) and 4-aminomethyl-1-(3,3,3-trifluoropropyl)-piperidine (0.10 g, 0.48 mmol) according to the procedure used for Example 2 without heating to give 0.092 g of the title compound as a white solid.

NMR (DMSO-$d_6$, 400 MHz): δ 1.09 (m, 2H), 1.38 (broad, 1H), 1.66 (broad d, 2H), 1.86 (t, 2H), 2.40, (m, 6H), 2.71 (m, 1H), 2.80 (m, 3H), 4.1 (m, 3H), 5.20 (broad, 1H), 7.17 (dt, 1H), 7.25 (d, 1H, J=8.56 Hz), 7.405 (m, 2H), 8.36 (d, 1H, J=7.9 Hz), 11.469 (s, 1H). MS (ESI$^+$, m/z): 484, 486 [M+H]$^+$.

EXAMPLE 20

(2S)-1-(1H-Indol-4-yloxy)-3-{[1-(3,3,3-trifluoro-propyl)-piperidin-4-ylmethyl]-amino}-propan-2-ol

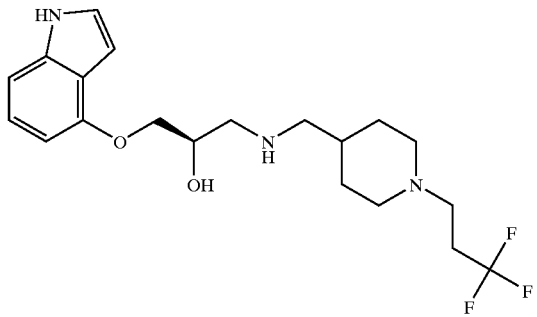

Prepared from 4-[(2S)-oxiranylmethoxy]-1H-indole (0.170 g, 0.9 mmol) 4-aminomethyl-1-(3,3,3-trifluoropropyl)-piperidine and (0.378 g, 0.8 mmol) according to the procedure used for Example 2 to give 0.210 g of the title compound as a white solid.

NMR (DMSO-$d_6$, 400 MHz): δ 1.09 (m, 2H), 1.37 (broad, 1H), 1.65 (broad d, 2H), 1.86 (t, 2H), 2.42, (m, 6H), 2.64 (m, 1H), 2.73 (m, 1H), 2.82 (broad d, 2H), 3.99 (m, 3H), 4.96 (broad, 1H), 6.44 (m, 2H), 6.97 (m, 2H), 7.20 (m, 1H), 11.0408 (s, 1H). MS (ESI$^+$, m/z): 400 [M+H]$^+$.

EXAMPLE 21

(2S)-1-(1H-Indol-5-yloxy)-3-{[1-(3,3,3-trifluoro-propyl)-piperidin-4-ylmethyl]-amino}-propan-2-ol

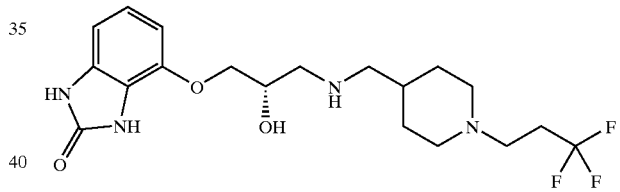

Prepared from 5-[(2S)-oxiranylmethoxy]-1H-indole (0.050 g, 0.25 mmol) and 4-aminomethyl-1-(3,3,3-trifluoropropyl)-piperidine (0.105 g, 0.5 mmol) according to the procedure used for Example 2 to give 0.055 g of the title compound as a white solid.

NMR (DMSO-$d_6$, 400 MHz): δ 1.096 (m, 2H), 1.39 (broad, 1H), 1.66 (broad d, 2H), 1.877 (t, 2H), 2.45, (m, 6H), 2.606 (m, 1H), 2.71 (m, 1H), 2.83 (broad d, 2H), 3.912 (m, 3H), 5.0 (broad, 1H), 6.31 (s, 1H), 6.72 (dd, 1H), 7.0345 (s, 1H), 7.27 (m, 2H), 10.908 (s, 1H). MS (ESI$^+$, m/z): 400 [M+H]$^+$.

EXAMPLE 22

4-((2S)-2-Hydroxy-3-{[1-(3,3,3-trifluoro-propyl)-piperidin-4-ylmethyl]-amino}-propoxy)-1,3-dihydro-benzoimidazol-2-one

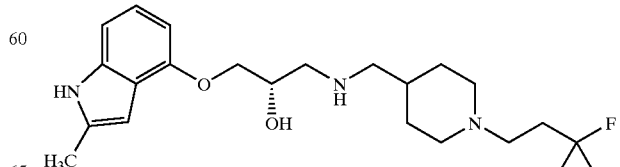

Prepared from 4-[(2S)-oxiranylmethoxy]-benzimidazol-2-one (0.080 g, 0.38 mmol) and 4-aminomethyl-1-(3,3,3-trifluoropropyl)-piperidine (0.250 g, 1.2 mmol) of according to the procedure used for Example 2 to give 0.050 g of the title compound as an off-white solid.

NMR (DMSO-$d_6$, 400 MHz): δ 1.08 (m, 2H), 1.347 (broad, 1H), 1.635 (broad d, 2H), 1.847 (t, 2H), 2.42, (m, 6H), 2.60 (m, 1H), 2.68 (m, 1H), 2.805 (broad d, 2H), 3.88 (m, 2H), 3.995 (m, 1H), 4.83 (broad, 1H), 6.55 (d, 1H, J=7.68 Hz), 6.59 (d, 1H, J=8.3 Hz), 6.82 (t, 1H), 10.5 (s+broad, 2H). MS (APCI$^+$, m/z): 417 [M+H]$^+$.

EXAMPLE 23

(2S)-1-(2-Methyl-1H-indol-4-yloxy)-3-{[1-(3,3,3-trifluoro-propyl)-piperidin-4-ylmethyl]-amino}-propan-2-ol Prepared from 2-methyl-4-[(2S)-oxiranylmethoxy]-indole (0.150 g, 0.74 mmol) and 4-aminomethyl-1-(3,3,3-trifluoropropyl)-piperidine (0. 250 g, 1.2 mmol) of according to the procedure used for Example 2 to give 0.110 g of the title compound as a light yellow solid.

NMR (DMSO-$d_6$, 400 MHz): δ 1.07 (m, 2H), 1.362 (broad, 1H), 1.64 (broad d, 2H), 1.849 (t, 2H), 2.332 (s, 3H), 2.42, (m, 6H), 2.615 (m, 1H), 2.72 (m, 1H), 2.8 (broad d, 2H), 3.92 (m, 3H), 4.93 (broad, 1H), 6.10 (s, 1H), 6.40 (m, 1H), 6.884 (m, 2H), 10.8214 (s, 1H). MS (APCI$^+$, m/z): 414 [M+H]$^+$.

EXAMPLE 24

(2S)-1-(9H-Carbazol-4-yloxy)-3-{[1-(4,4,4-trifluoro-butyl)-piperidin-4-ylmethyl]-amino}-propan-2-ol

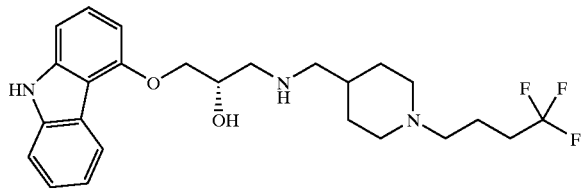

Step A: 1-(4,4,4-Trifluorobutyl)-piperidine-4-carboxamide

Prepared from isonipecotamide (0.422 g, 3.3 mmol), 4,4,4-trifluorobutyliodide (0.82 g, 3.4 mmol) and potassium carbonate (0.47 g, 3.4 mmol) according to the procedure used for Example 8 (Step A) to give 0.84 g of the title compound as a white solid.

NMR (DMSO-$d_6$, 400 MHz): δ 1.5217 (m, 2H), 1.6211 (m, 4H), 1.8363 (t, 2H), 2.012 (m, 1H), 2.21–2.29 (m, 4H), 2.80 (broad d, 2H), 6.68 (s, 1H), 7.174 (s, 1H). MS (APCI$^+$, m/z): 239 [M+H]$^+$.

Step B: 4-Aminomethyl-1-(4,4,4-trifluorobutyl)-piperidine

Prepared from 1-(4,4,4-trifluorobutyl)-piperidine-4-carboxamide (0.82 g, 3.3 mmol) and LAH (0.25 g, 6.6 mmol) according to general the procedure used for Example 8 (Step B) to give 0.73 g of title compound as a clear oil.

NMR (DMSO-$d_6$, 400 MHz): δ 1.078 (m, 3H), 1.635 (m, 4H), 1.82 (dt, 2H), 2.17–2.31 (m, 4H), 2.38 (d, 1H), 2.80 (broad d, 2H), MS (ESI$^+$, m/z): 225 [M+H]$^+$.

Step C: (2S)-1-(9H-Carbazol-4-yloxy)-3-{[1-(4,4,4-trifluoro-butyl)-piperidin-4-ylmethyl]-amino}-propan-2-ol Prepared from 4-[(2S)-oxiranylmethoxy]-9H-carbazole (0.125 g, 0.52 mmol) and 4-aminomethyl-1-(4,4,4-trifluorobutyl)-piperidine (0.224 g, 1.0 mmol) according to the procedure used for Example 2 to give 0.110 g of the title compound as a tan solid.

NMR (DMSO-$d_6$, 400 MHz): δ 1.0807 (m, 2H), 1.3597 (mm, 1H), 1.618 (m, 4H), 1.746 (dt, 2H), 2.23 (m, 4H), 2.44 (d, 2H), 2.74 (m, 3H), 2.82 (m, 1H), 4.05 (m, 1H) 4.14 (m, 3H), 5.08 (broad, 1H), 6.6 (d, 1H, J=7.9 Hz), 7.04 (d, 1H, J=8.1 Hz), 7.11 (m, 1H), 7.27 (m, 2H), 7.42 (d, 1H), J=7.9 Hz), 8.18 (d, 1H, J=7.7 Hz), 11.2226 (s, 1H). MS (APCI$^+$, m/z): 464 [M+H]$^+$.

EXAMPLE 25

(2S)-1-(9H-Carbazol-4-yloxy)-3-[(1-pentyl-piperidin-4-ylmethyl)-amino]-propan-2-ol

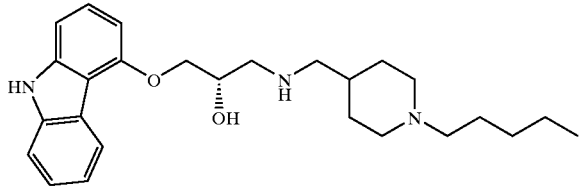

Step A: 1-Pentyl-piperidine-4-carboxamide

Prepared from isonipecotamide (3.3, 25.7 mmol), 1-iodopentane (5.1 g, 25.7 mmol) and potassium carbonate (3.54 g, 25.7 mmol) according to the procedure used for Example 8 (Step A) to give 3.05 g of the title compound as an off-white solid.

NMR (DMSO-$d_6$, 400 MHz): δ 0.8647 (m, 3H), 1.26 (m, 4H), 1.40 (m, 2H), 1.51 (m, 2H), 1.64 (broad d, 2H), 1.82 (broad t, 2H), 2.012 (m, 1H), 2.209 (t, 2H), 2.84 (broad d, 2H), 6.695 (s, 1H), 7.188 (s, 1H). MS (EI, m/z): 198 (M)$^+$.

Step B: 4-Aminomethyl-1-pentyl-piperidine

Prepared from 1-pentyl-piperidine-4-carboxamide (3.0 g, 15.1 mmol) and LAH (1.14 g, 30.2 mmol) according to general the procedure used for Example 8 (Step B) to give 2.2 g of title compound as an oil.

NMR (DMSO-$d_6$, 400 MHz): δ 0.845 (m, 3H), 1.048 (m, 3H), 1.20–1.40 (m, 6H), 1.64 (broad d, 2H), 1.75 (broad t, 2H), 2.181 (m, 2H), 2.38 (d, 2H), 2.79 (broad d, 2H). MS (EI, m/z): 184 (M)$^+$.

Step C: (2S)-1-(9H-Carbazol-4-yloxy)-3-[(1-pentyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-pentyl-piperidine (0.368 g, 2.0 mmol) according to the procedure used for Example 2 to give 0.210 g of the title compound as a white solid (Et$_2$O).

NMR (DMSO-$d_6$, 400 MHz): δ 0.8472 (m, 3H), 1.08 (m, 2H), 1.22 (m, 4H), 1.377 (m, 3H), 1.639 (broad d, 2H), 1.76 (broad t, 2H), 2.2039 (m, 2H), 2.46 (m, 2H), 2.77 (m, 3H), 2.865 (m, 1H), 4.15 (m, 3H), 5.15 (broad, 1H), 6.66 (d, 1H, J=7.9 Hz), 7.05 (d, 1H, J=8.1 Hz), 7.11 (m, 1H), 7.27 (m, 2H), 7.43 (d, 1H, J=8.1 Hz), 8.18 (d, 1H, J=7.9 Hz), 11.2251 (s, 1H). MS (ESI$^+$, m/z): 424 [M+H]$^+$.

EXAMPLE 26

(2S)-1-(9H-Carbazol-4-yloxy)-3-[(1-hexyl-piperidin-4-ylmethyl)-amino]-propan-2-ol

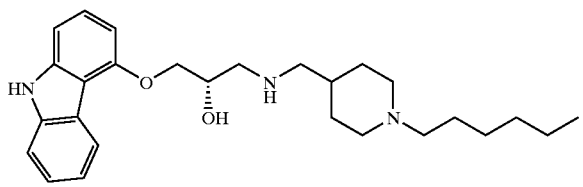

Step A: 1-Hexyl-piperidine-4-carboxamide

Prepared from isonipecotamide (4.04 g, 31.6 mmol), 1-iodohexane (6.7 g, 31.6 mmol) and potassium carbonate (4.36 g, 31.6 mmol) according to the procedure used for Example 8 (Step A) to give 6.9 g of the title compound as a white solid.

NMR (DMSO-$d_6$, 400 MHz): δ 0.862 (m, 3H), 1.245 (m, 6H), 1.3915 (m, 2H), 1.51 (m, 2H), 1.64 (broad d, 2H), 1.798

(broad t, 2H), 2.015 (m, 1H), 2.207 (t, 2H), 2.82 (broad d, 2H), 6.695 (s, 1H), 7.187 (s, 1H). MS (EI, m/z): 212 (M)+.

Step B: 4-Aminomethyl-1-hexyl-piperidine

Prepared from 1-hexylpiperidine-4-carboxamide (6.6 g, 31.0 mmol) and LAH (1.93 g, 62.0 mmol) according to general the procedure used for Example 8 (Step B) to give 4.6 g of title compound as a waxy solid.

NMR (DMSO-$d_6$, 400 MHz): δ 0.843 (m, 3H), 1.0487 (m, 3H), 1.2266 (m, 6H), 1.374 (m, 2H), 1.641 (broad d, 2H), 1.75 (broad t, 2H), 2.1831 (m, 2H), 2.36 (d, 2H), 2.79 (broad d, 2H). MS (EI, m/z): 198 (M)+.

Step C: (2S)-1-(9H-Carbazol-4-yloxy)-3-[(1-hexyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-hexylpiperidine (0.396 g, 2.0 mmol) according to procedure used for Example 2 to give 0.225 g of the title compound as a white solid.

NMR (DMSO-$d_6$, 400 MHz): δ 0.8428 (m, 3H), 1.079 (m, 2H), 1.224 (m, 6H), 1.36 (m, 3H), 1.62 (broad d, 2H), 1.711 (broad t, 2H), 2.1654 (m, 2H), 2.42 (d, 2H), 2.7744 (m, 3H), 2.817 (m, 1H), 4.15 (m, 3H), 5.05 (broad, 1H), 6.66 (d, 1H, J=7.9 Hz), 7.04 (d, 1H, J=8.1 Hz), 7.11 (m, 1H), 7.28 (m, 2H), 7.42 (d, 1H, J=8.1 Hz), 8.18 (d, 1H, J=7.9 Hz), 11.2221 (s, 1H). MS (ESI+, m/z): 438 [M+H]+.

EXAMPLE 27

2S)-1-(9H-Carbazol-4-yloxy)-3-[(1-octyl-piperidin-4-ylmethyl)-amino]-propan-2-ol

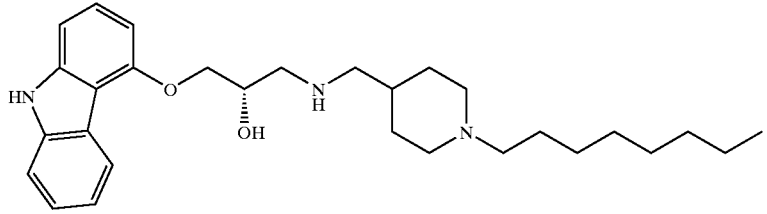

Step A: 1-Octyl-piperidine-4-carboxamide

Prepared from isonipecotamide (2.7 g, 21.0 mmol), 1-iodooctane (5.05 g, 21.0 mmol) and potassium carbonate (2.9 g, 21.0 mmol) of according to procedure used for Example 8 (Step A) to give 5.6 g of the title compound as a white solid.

NMR (DMSO-$d_6$, 400 MHz): δ 0.8625 (m, 3H), 1.252 (m, 10H), 1.42 (m, 2H), 1.52 (m, 2H), 1.675 (broad d, 2H), 1.79–2.015 (m, 3H), 2.32 (broad, 2H), 2.91 (broad, 2H), 6.733 (s, 1H), 7.2202 (s, 1H). MS (EI, m/z): 240 (M)+.

Step B: 4-Aminomethyl-1-octane-piperidine

Prepared from 1-octylpiperidine-4-carboxamide (5.0 g, 20.8 mmol) and LAH (1.58 g, 41.6 mmol) according to general procedure used for Example 8 (Step B) to give 4.06 g of title compound as an oil.

NMR (DMSO-$d_6$, 400 MHz): δ 0.8428 (m, 3H), 1.046 (m, 3H), 1.2290 (m, 8H), 1.369 (m, 2H), 1.62 (broad d, 2H), 1.7485 (broad t, 2H), 2.1792 (m, 2H), 2.36 (d, 2H), 2.79 (broad d, 2H). MS (EI, m/z): 226 (M)+.

Step C: (2S)-1-(9H-Carbazol-4-yloxy)-3-[(1-octyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-octylpiperidine (0.452 g, 2.0 mmol) according to procedure used for Example 2 to give 0.180 g of the title compound as a white solid.

NMR (DMSO-$d_6$, 400 MHz): δ 0.8423 (m, 3H), 1.073 (m, 2H), 1.2268 (m, 8H), 1.35 (m, 3H), 1.62 (broad d, 2H), 1.712 (broad t, 2H), 2.167 (m, 2H), 2.43 (d, 2H), 2.775 (m, 3H), 2.81 (m, 1H), 4.15 (m, 3H), 5.05 (broad, 1H), 6.66 (d, 1H, J=7.9 Hz), 7.04 (d, 1H, J=8.1 Hz), 7.11 (m, 1H), 7.27 (m, 2H), 7.42 (d, 1H, J=8.1 Hz), 8.18 (d, 1H, J=7.9 Hz), 11.2221 (s, 1H). MS (ESI+, m/z): 466 [M+H]+.

EXAMPLE 28

2S)-1-(9H-Carbazol-4-yloxy)-3-[(1-tridecyl-piperidin-4-ylmethyl)-amino]-propan-2-ol

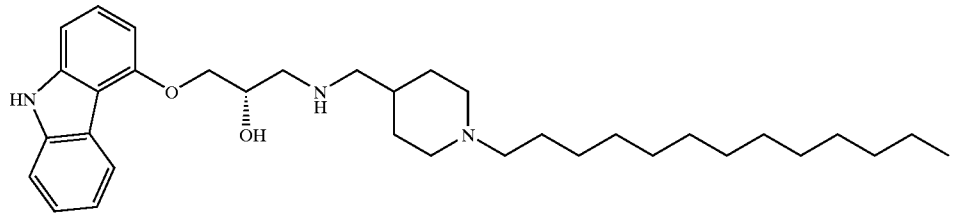

Step A: 1-Tridecyl-piperidine-4-carboxamide

Prepared from isonipecotamide (2.0 g, 15.6 mmol), 1-bromotridecane (4.0 mL, 15.6 mmol) and potassium carbonate (2.16 g, 15.6 mmol) of according to procedure used for Example 8 (Step A) to give 4.9 g of the title compound as a white solid.

NMR (DMSO-$d_6$, 400 MHz): δ 0.8439 (m, 3H), 1.2272 (m, 18H), 1.369 (m, 3H), 1.50 (m, 2H), 1.61 (broad d, 2H), 1.787 (m, 3H), 1.9959 (m, 2H), 2.1919 (t, 2H), 2.81 (broad d, 2H), 6.674 (s, 1H), 7.166 (s, 1H). MS (EI, m/z): 310 (M)+.

Step B: 4-Aminomethyl-1-tridecyl-piperidine

Prepared from 1-tridecylpiperidine-4-carboxamide (4.7 g, 15.1 mmol) and LAH (1.14 g, 30.0 mmol) according to general procedure used for Example 8 (Step B) to give 3.6 g of title compound as a pale yellow solid.

NMR (CDCl$_3$, 400 MHz): δ 0.8767 (m, 3H), 1.2506 (m, 18H), 1.428 (m, 3H), 1.70 (broad d, 2H), 1.87 (t, 2H), 2.29 (m, 2H), 2.57 (d, 2H), 2.93 (broad d, 2H). MS (ESI$^+$, m/z): 297 [M+H]$^+$.

Step C: (2S)-1-(9H-Carbazol-4-yloxy)-3-[(1-tridecyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-tridecylpiperidine (0.596 g, 2.0 mmol) of according to procedure used for Example 2 to give 0.240 g of the title compound as a white solid (mp-70–72° C., Et$_2$O).

NMR (DMSO-d$_6$, 400 MHz): δ 0.8396 (m, 3H), 1.069 (m, 2H), 1.2234 (m, 20H), 1.348 (m, 3H), 1.61 (broad d, 2H), 1.7049 (broad t, 2H), 2.157 (m, 2H), 2.42 (d, 2H), 2.738 (m, 3H), 2.811 (m, 1H), 4.06 (m, 1H), 4.137 (m, 2H), 5.05 (broad, 1H), 6.66 (d, 1H, J=7.9 Hz), 7.04 (d, 1H, J=8.1 Hz), 7.12 (m, 1H), 7.27 (m, 2H), 7.42 (d, 1H, J=8.1 Hz), 8.18 (d, 1H, J=7.9 Hz), 11.2140 (s, 1H).
MS (EI, m/z): 535 (M)$^+$.

EXAMPLE 29

(2S)-1-(9H-Carbazol-4-yloxy)-3-[(1-pentadecyl-piperidin-4-ylmethyl)-amino]-propan-2-ol

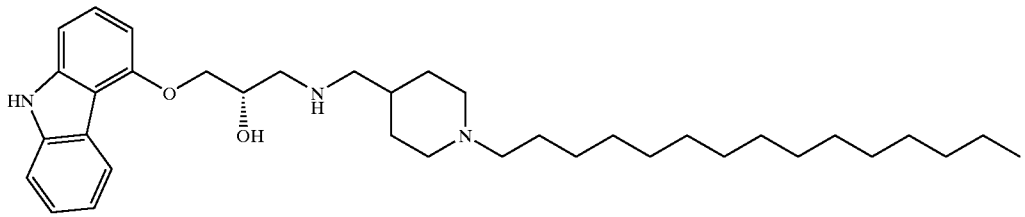

Step A: 1-Pentadecyl-piperidine-4-carboxamide

Prepared from isonipecotamide (2.0 g, 15.6 mmol), 1-bromopentadecane (4.5 g, 15.6 mmol) and potassium carbonate (2.16 g, 15.6 mmol) according to procedure used for Example 8 (Step A) to give 4.5 g of the title compound as a white solid.

NMR (DMSO-d$_6$, 400 MHz): δ 0.85 (m, 3H), 1.2268 (m, 22H), 1.39 (m, 3H), 1.50 (m, 2H), 1.61 (broad d, 2H), 1.78 (m, 3H), 1.99 (m, H), 2.19 (t, 2H), 2.8 (broad d, 2H), 6.677 (s, 1H), 7.167 (s, 1H). MS (EI, m/z): 338 (M)$^+$.

Step B: 4-Aminomethyl-1-pentadecyl-piperidine

Prepared from 1-pentadecylpiperidine-4-carboxamide (4.3 g, 12.7 mmol) and LAH (0.97 g, 21.2 mmol) according to general procedure used for Example 8 (Step B) to give 4.3 g of title compound as a pale yellow solid.

NMR (CDCl$_3$, 400 MHz): δ 0.873 (m, 3H), 1.2462 (m, 26H), 1.481 (m, 3H), 1.70 (broad d, 2H), 1.874 (t, 2H), 2.282 (m, 2H), 2.56 (d, 2H), 2.935 (broad d, 2H). MS (ESI$^+$, m/z): 325 [M+H]$^+$.

Step C: (2S)-1-(9H-Carbazol-4-yloxy)-3-[(1-pentadecyl-piperidin-4-ylmethyl)-amino]-propan-2-ol Prepared from 4-[(2S)-oxiranylmethoxy]-9H-carbazole (0.239 g, 1.0 mmol) and 4-aminomethyl-1-pentadecylpiperidine (0.650 g, 2.0 mmol) according to procedure used for Example 2 to give 0.298 g of the title compound as a white solid (mp-69–71° C., Et$_2$O).

NMR (DMSO-d$_6$, 400 MHz): δ 0.836 (m, 3H), 1.067 (m, 2H), 1.2196 (m, 20H), 1.347 (m, 3H), 1.615 (broad d, 2H), 1.7035 (broad t, 2H), 2.155 (m, 2H), 2.42 (d, 2H), 2.73 (m, 3H), 2.8 (m, 1H), 4.056 (m, 1H), 4.135 (m, 2H), 5.02 (broad, 1H), 6.65 (d, 1H, J=7.9 Hz), 7.04 (d, 1H), J=8.1 Hz), 7.112 (m, 1H), 7.265 (m, 2H), 7.42 (d, 1H, J=8.1 Hz), 8.18 (d, 1H, J=7.9 Hz), 11.2177 (s, 1H). MS (ESI$^+$, m/z): 564 [M+H]$^+$.

EXAMPLE 30

12-(4-{[(2S)-3-(9H-Carbazol-4-yloxy)-2-hydroxy-propylamino]-methyl}-piperidin-1-yl)-dodecan-1-ol

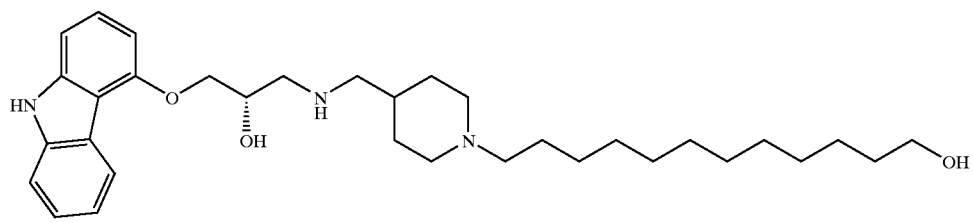

Step A: 1-(12-Hydroxydodecyl)-piperidine-4-carboxamide

Prepared from isonipecotamide (2.0 g, 15.6 mmol), 12-bromododecanol (4.15 g, 15.6 mmol) potassium carbonate and (2.16 g, 15.6 mmol) according to procedure used for Example 8 (Step A) to give 3.35 g of the title compound as a white solid.

NMR (DMSO-d$_6$, 400 MHz): δ 1.2288 (m, 16H), 1.37 (m, 4H), 1.506 (m, 2H), 1.606 (broad d, 2H), 1.78 (broad t, 2H), 1.99 (m, 2H), 2.1847 (t, 2H), 2.8 (broad d, 2H), 3.35 (m, 2H), 4.2975 (t, 1H), 6.673 (s, 1H), 7.1657 (s, 1H).

MS (EI, m/z): 312 (M)$^+$.

Step B: 4-Aminomethyl-1-(12-hydroxydodecyl)-piperidine

Prepared from 1-(12-hydroxydodecyl)-piperidine-4-carboxamide (3.3 g, 10.6 mmol) and LAH (0.8 g, 21.2 mmol) according to general procedure used for Example 8 (Step B) to give 3.1 g of title compound as a white solid.

NMR (CDCl$_3$, 400 MHz): δ 1.2495 (m, 18H), 1.4669 (m, 3H), 1.53 (m, 2H), 1.69 (broad d, 2H), 1.868 (t, 2H), 2.27 (m, 2H), 2.55 (d, 2H), 2.93 (broad d, 2H), 3.601 (t, 2H).

MS (ESI$^+$, m/z): 299 (M+H)$^+$.

Step C: 12-(4-{[(2S)-3-(9H-Carbazol-4-yloxy)-2-hydroxypropylamino]-methyl}-piperidin-1-yl)-dodecan-1-ol Prepared from 4-[(2S)-oxiranylmethoxy]-9H-carbazole (0.239 g, 1.0 mmol) and 4-aminomethyl-1-(12-hydroxydodecyl)-piperidine (0.586 g, 2.0 mmol) according to procedure used for Example 2 to give 0.175 g of the title compound as an off-white solid (mp-110° C. (sinters) 166° C. (melts), Et$_2$O).

NMR (CDCl$_3$, 400 MHz): δ 1.05 (m, 2H), 1.225 (m, 16H), 1.365 (m, 5H), 1.62 (broad d, 2H), 1.7079 (t, 2H), 2.15 (t, 2H), 2.42 (d, 2H), 2.74 (m, 3H), 2.8 (m, 1H), 3.3463 (m, 2H), 4.01 )m, 1H), 4.137 (m, 2H), 4.30 (broad t, 1H), 5.06 (broad, 1H), 6.66 (d, 1H, J=7.9 Hz), 7.04 (d, 1H, J=8.1 Hz), 7.112 (m, 1H), 7.265 (m, 2H), 7.42 (d, 1H, J=8.1 Hz), 8.18 (d, 1H, J=7.9 Hz), 11.2188 (s, 1H). MS (ESI$^+$, m/z): 538 [M+H].

EXAMPLE 31

(2S)-1-(9H-Carbazol-4-yloxy)-3-{[1-(naphthalene-2-sulfonyl)-piperidin-4-ylmethyl]-amino}-propan-2-ol

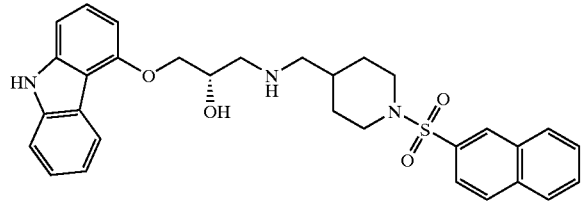

Step A: 4-Carboxamido-1-piperidinyl)2-naphthylsulfonamide

A solution of isonipecotamide (5.0 g, 39 mmol), 2-naphthylsulfonyl chloride (8.85 g, 39 mmol) and 5.5 mL of triethyl amine was stirred at ambient temperature until a solution resulted. After stirring over night the solids that reformed were filtered, washed with methylene chloride, water, and dried under high vacuum to give to give 8.2 g of product as a white solid (m.p. 202–203° C.).

NMR (DMSO-d$_6$, 400 MHz): δ 1.565 (m, 2H), 1.53 (m, 2H), 1.77 (m, 2H), 2.035 (m, 1H), 2.35 (dt, 2H), 3.66 (broad d, 2H), 6.292 (t, 1H), 6.7808 (s, 1H), 7.70 (m, 3H), 8.08 (d, 1H, J=8.13 Hz), 8.17 (d, 1H, J=8.78 Hz), 8.22 (d, 1H, J=7.9HZ), 8.438 (s, 1H). MS (ESI$^+$, m/z): 319 [M+H]$^+$, 336 [M+NH$_4$]$^+$; Anal. calc'd for C$_{16}$H$_{18}$N$_2$O$_3$S: C, 60.36; H, 5.70; N, 8.80; Found: C, 60.23; H, 5.61; N, 8.77.

Step B: (4-Aminomethyl-1-piperidinyl)2-naphthylsulfonamide

A solution of (4-carboxamido-1-piperidinyl) 2-naphthylsulfonamide (7.9 g, 25 mmol) in dioxane was treated with an excess of BH$_3$-THF (50 mL, 1.0 M solution in THF). The mixture was heated at reflux for 0.5 to 2 hours. On cooling the excess BH$_3$-THF was decomposed by the addition of CH$_3$OH, The solvent was removed (rotovap) to provide crude product. Pure compound was obtained by flash chromatography (CH$_2$Cl$_2$—CH$_3$OH, NH$_4$OH— 19:1:0.1) to give 2.4 g product as an oil.

NMR (DMSO-d$_6$, 400 MHz): δ 1.130 (m, 3H), 1.73 (m, 2H), 2.248 (m, 2H), 2.35 (d, 2H), 3.72 broad d, 2H), 7.71 (m, 3H), 8.08 (d, 1H, J=7.9 Hz), 8.16 (d, 1H, J=8.57 Hz), 8.21 (d, 1H, J=12 Hz), 8.438 (s, 1H). MS (ESI$^+$, m/z): 305 [M+H]$^+$.

Step C: (2S)-1-(9H-Carbazol-4-yloxy)-3-{[1-(naphthalene-2-sulfonyl)-Piperidin-4-ylmethyl]-amino}-propan-2-ol Prepared from 4-[(2S)-Ooxiranylmethoxy]-9H-carbazole (0.239 g, 1.0 mmol) and (4-aminomethyl-1-piperidinyl) 2-naphthylsulfonamide (0.608 g, 2.0 mmol) of according to procedure used for Example 2 to give 0.380 g of the title compound as a white solid.

NMR (DMSO-d$_6$, 400 MHz): δ 1.09 (m, 2H), 1.3 (m, 1H), 1.70 (broad d, 2H), 2.07 (dt, 2H), 2.38 (d, 2H), 2.659 (m, 1H), 2.753 (m, 1H), 3.64 (broad d, 2H), 4.076 (broad, 1H), 4.086 (d, 2H), 5.03 (broad, 1H), 6.62 (d, 1H), 7.02 (m, 2H), 7.22 (m, 2H), 7.35 (d, 1H), J=8.1 Hz), 7.7151 (m, 4H), 8.3907 (s, 1H), 11.20 (s, 1H). MS (ESI$^+$, m/z): 544 [M+H]$^+$.

EXAMPLE 32

(2S)-1-(9H-Carbazol-4-yloxy)-3-{[1-(ropane-2-sulfonyl)-piperidin-4-ylmethyl]-amino}-propan-2-ol

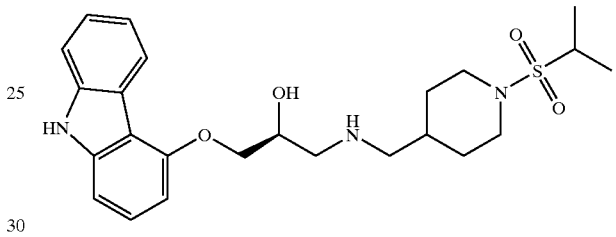

Step A: 4-Carboxamido-1-piperidinyl)-propane-2-sulfonamide

A mixture of isopropylsulfonyl chloride (1.75 mL, 15.6 mmol), 1-hydroxybenzotriazine (2.1 g, 15.6 mmol) and 2.7 mL of diisopropylethyl amine in 100 mL methylene chloride was stirred at ambient temperature for 10 minutes. In one portion isonipecotamide (2.0 g, 15.6 mmol) was added and stirring was continued overnight, The reaction mixture was concentrated to a residue and purified by flash chromatography (CH$_2$Cl$_2$—CH$_3$OH: 19:1) to give 0.320 g of product as a white solid.

NMR (DMSO-d$_6$, 400 MHz): δ 1.185 (d, 6H), 1.46 (m, 2H), 1.71 (broad d, 2H), 2.223 (m, 1H), 2.85 (dt, 2H), 3.286 (m, 1H), 3.62 (broad d, 2H), 6.8105 (s, 1H), 7.279 (s, 1H), MS (ESI$^+$, m/z): 235 [M+H]$^+$, 252 [M+NH$_4$]$^+$.

Step B: (4-Aminomethyl-1-piperidinyl)-propane-2-sulfonamide

Prepared from (4-carboxamido-1-piperidinyl)-propane-2-sulfonamide (0.30 g, 1.3 mmol) and BH$_3$-THF (3.0 mL, 1.0 M solution in THF) according to procedure used for Example 31 (Step B). Isolation by flash chromatography (silica Merck 60: CH$_2$Cl$_2$, CH$_3$OH, NH$_4$OH— 9:1:0.1) afforded 0.15 g product as a white solid.

NMR (DMSO-d$_6$, 400 MHz): δ 1.04 (m, 2H), 1.18 (d, 6H), 1.33 (M, 1H), 1.71 (broad d, 2H), 2.40 (d, 2H), 2.80 (dt, 2H), 3.269 (m, 1H), 3.62 (d, 2H). MS (ESI$^+$, m/z): 221 [M+H]$^+$.

Step C: (2S)-1-(9H-Carbazol-4-yloxy)-3-{[1-(propane-2-sulfonyl)-piperidin-4-ylmethyl]-amino}-propan-2-ol Prepared from 4-[(2S)-oxiranylmethoxy]-9H-carbazole (0.084 g, 0.35 mmol) and (4-aminomethyl-1-piperidinyl)-propane-2-sulfonamide (0.120 g, 0.55 mmol) of according to procedure used for Example 2 to give 0.055 g of the title compound as a white solid.

NMR (DMSO-d$_6$, 400 MHz): 81.02 (m, 2H), 1.17 (d, 6H), 1.53 (m, 1H), 1.68 (broad d, 2H), 2.47 (d, 2H), 2.62 (dt, 2H), 2.79 (m, 1H), 2.86 (m, 1H), 3.2144 (m, 1H), 3.54 (broad d, 2H), 4.078 (broad, 1H), 4.17 (d, 2H), 5.10 (broad, 1H), 6.68 (d, 1H), 7.07 (m, 2H), 7.30 (m, 2H), 7.35 (dd, 1H), 7.45 (d, 1H), 8.21 (s, 1H), 11.2533 (s, 1H). MS (ESI⁺, m/z): 460 [M+H]⁺.

EXAMPLE 33

(2S)-1-(9H-Carbazol-4-yloxy)-3-{[1-(4-methoxy-benzenesulfonyl)-piperidin-4-ylmethyl]-amino}-propan-2-ol

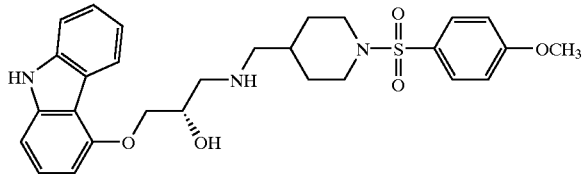

Step A: 4-Carboxamido-1-piperidinyl)-4-methoxybenzenesulfonamide

Prepared from isonipecotamide (4.0 g, 31.25 mmol), 4-methoxybenzenesulfonyl chloride (6.45 g, 31.25 mmol) and 5.45 mL of diisopropylethyl amine according to procedure used for Example 31 (Step A) to give 6.7 g of product as a white solid.

NMR (DMSO-d₆, 400 MHz): δ 1.53 (m, 2H), 1.74 (broad d, 2H), 2.018 (m, 1H), 2.22 (dt, 2H), 3.50 (broad d, 2H), 3.8423 (s, 3H), 6.8105 (s, 1H), 7.13 (d, 2H, J=9 Hz), 7.1757 (s, 1H), 7.65 (d, 2H, J=9 Hz). MS (ESI⁺, m/z): 299 [M+H]⁺, 316 [M+NH₄]⁺.

Step B: (4-aminomethyl-1-piperidinyl)4-methoxybenzenesulfonamide

Prepared from (4-carboxamido-1-piperidinyl) 4-methoxybenzenesulfonamide (6.5 g, 21.8 mmol) and BH₃-THF (43.8 mL, 1.0 M solution in THF) according to procedure used for Example 31 (Step B). Isolation by flash chromatography (silica Merck 60: CH₂Cl₂, CH₃OH, NH₄₀H— 19:1:0.1) to give 1.4 g product as an oil.

NMR (DMSO-d₆, 400 MHz): δ 1.0962 (m, 3H), 1.70 (broad d, 2H), 2.123 (broad t, 2H), 2.35 (d, 2H), 3.57 (broad d, 2H), 3.839 (s, 3H), 7.13 (d, 2H, J=8.8 Hz), 7.645 (d, 2H, J=9 Hz). MS (ESI⁺, m/z): 285 [M+H]⁺.

Step C: (2S)-1-(9H-Carbazol-4-yloxy)-3-{[1-(4-methoxy-benzenesulfonyl)-piperidin-4-ylmethyl]-amino}-propan-2-ol Prepared from 4-[(2S)-Oxiranylmethoxy]-9H-carbazole (0.125 g, 0.52 mmol) and (4-aminomethyl-1-piperidinyl) 4-methoxybenzenesulfonamide (0.255 g, 0.9 mmol) according to procedure used for Example 2 to give 0.170 g of the title compound as a white solid.

NMR (DMSO-d₆, 400 MHz): δ 1.11 (m, 2H), 1.3 (m, 1H), 1.72 (broad d, 2H), 2.03 (dt, 2H), 2.42 (d, 2H), 2.703 (m, 1H), 2.80 (m, 1H), 3.55 (broad d, 2H), 4.053 (broad, 1H), 4.12 (d, 2H), 5.08 (broad, 1H), 6.65 (d, 1H), 7.05 (m, 2H), 7.15 (dd, 2H), 7.25 (m, 2H), 7.42 (d, 1H, J=8.12 Hz), 7.62 (d, 2H, J=8.8 Hz), 8.15 (d, 1H, J=7.25 Hz), 11.2325 (s, 1H). MS (ESI⁺, m/z): 524 [M+H]⁺.

EXAMPLE 34

(2S)-1-(3-Bromo-9H-carbazol-4-yloxy)-3-{[1-(4-methoxy-benzenesulfonyl)-piperidin-4-ylmethyl]-amino}-propan-2-ol

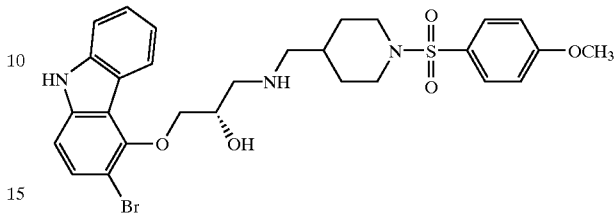

Prepared from 3-bromo-4-[(2S)-oxiranylmethoxy]-9H-carbazole (0.083 g, 0.26 mmol) and (4-aminomethyl-1-piperidinyl) 4-methoxybenzenesulfonamide (0.142 g, 0.5 mmol) according to procedure used for Example 2 to give 0.079 g of the title compound as a white solid.

NMR (DMSO-d₆, 400 MHz): δ 1.13 (m, 2H), 1.32 (m, 1H), 1.73 (broad d, 2H), 2.12 (dt, 2H), 2.41 (d, 2H), 2.653 (m, 1H), 2.749 (m, 1H), 3.57 (broad d, 2H), 3.836 (s, 3H), 4.0007 (m, 1H), 4.05 (m, 2H), 5.18 (broad, 1H), 7.119 (m, 2H), 7.21 (d, 1H, J=8.57 Hz), 7.395 (t, 1H), 7.48 (m, 2H), 7.63 (m, 2H), 8.33 (d, 1H, J=7.9 Hz), 11.4898 (s, 1H). MS (ESI⁺, m/z): 602, 604 [M+H]⁺.

EXAMPLE 35

(2S)-1-(3-Chloro-9H-carbazol-4-yloxy)-3-{[1-(4-methoxy-benzenesulfonyl)-piperidin-4-ylmethyl]-amino}-propan-2-ol

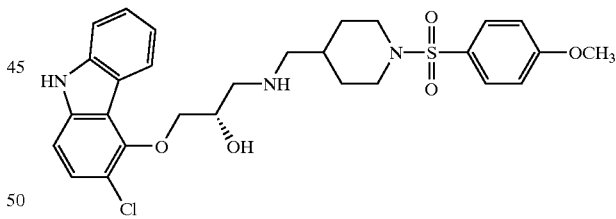

Prepared from 3-chloro-4-[(2S)-oxiranylmethoxy]-9H-carbazole (0.060 g, 0.22 mmol) and (4-aminomethyl-1-piperidinyl) 4-methoxybenzenesulfonamide (0.125 g, 0.5 mmol) according to procedure used for Example 2 to give 0.075 g of the title compound as a white solid.

NMR (DMSO-d₆, 400 MHz): δ 1.12 (m, 2H), 1.3 (m, 1H), 1.715 (broad d, 2H), 2.11 (dt, 2H), 2.39 (d, 2H), 2.658 (m, 1H), 2.722 (m, 1H), 3.56 (broad d, 2H), 3.836 (s, 3H), 4.05 (m, 3H), 5.17 (broad, 1H), 7.12 (m, 3H), 7.24 (d, 1H, J=8.57 Hz), 7.39 (m, 2H), 7.47 (d, 1H, J=7.9 Hz), 7.64 (m, 2H), 8.33 (d, 1H, J=7.7 Hz), 11.48 (s, 1H). MS (ESI⁺, m/z): 558, 560 [M+H]⁺.

EXAMPLE 36

2S)-1-(1-Bromo-9H-carbazol-4-yloxy)-3-{[1-(4-methoxy-benzenesulfonyl)-piperidin-4-ylmethyl]-amino}-propan-2-ol

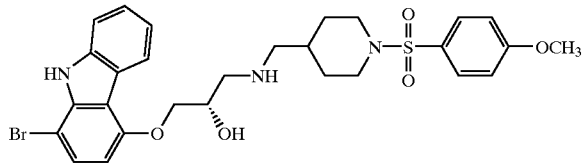

Prepared from 1-bromo-4-[(2S)-oxiranylmethoxy]-9H-carbazole (0.050 g, 0.15 mmol) and (4-aminomethyl-1-piperidinyl) 4-methoxybenzenesulfonamide (0.085 g, 0.3 mmol) of according to procedure used for Example 2 to give 0.035 g of the title compound as a white solid.

NMR (DMSO-$d_6$, 400 MHz): δ 1.10 (m, 2H), 1.31 (m, 1H), 1.70 (broad d, 2H), 2.028 (t, 2H), 2.41 (d, 2H), 2.69 (m, 1H), 2.76 (m, 1H), 3.53 (broad d, 2H), 3.8448 (s, 3H), 4.03 (m, 1H), 4.12 M.2H), 5.084 (broad, 1H), 6.65 (d, 1H, J=8.56 Hz), 7.12 (m, 3H), 7.35 (dt, 1H), 7.45 (d, 1H, J=8.56 Hz), 7.52 (d, 1H, J=8.12 Hz), 8.15 (d, 1H, J=7.7 Hz), 11.3657 (s, 1H). MS (ESI$^+$, m/z): 602, 604 [M+H]$^+$.

EXAMPLE 37

4-((2S)-2-Hydroxy-3-{[1-(4-methoxy-benzenesulfonyl)-piperidin-4-ylmethyl]-amino}-propoxy)-phenol

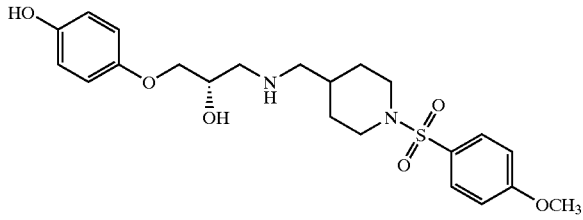

A mixture of t-butyl-[4-(2S)-oxiranylmethoxy-phenoxy]-diphenylsilane (0.078 g, 0.19 mmol) and an excess of and (4-aminomethyl-1-piperidinyl)-4-methoxybenzenesulfonamide (0.109 g, 0.38 mmol) was heated as a solution in methanol at 60° C. for 24 hours. The reaction mixture was preabsorbed on silica gel and purified by flash chromatography ($CH_2Cl_2$—$CH_3OH$, 19:1) to give the intermediate silyl-protected product. Deprotection to the phenol was accomplished by treatment of the silyl intermediate with 1M TBAF in THF. After stirring 15 minutes the solvent was evaporated and the product isolated by flash chromatography ($CH_2Cl_2$—$CH_3OH$, 12:1) to give 0.049 g of the title compound as a white solid.

NMR (DMSO-$d_6$, 400 MHz): δ 1.10 (m, 2H), 1.35 (m, 1H), 1.72 (broad d, 2H), 2.115 (t, 2H), (d, 2H), 2.54 (m, 1H), 2.64 (m, 1H), 3.55 (broad d, 2H), 3.798 (m, 3H), 3.839 (s, 3H), 4.975 (broad, 1H), 6.65 (dd, 2H), 6.69 (dd, 2H), 7.13 (d, 2H, J=8.79 Hz), 7.64 (dd, 2H), 8.8773 (s, 1H). MS (ESI$^-$, m/z): 449 [M−H]$^-$.

EXAMPLE 38

4-((2S)-2-Hydroxy-3-{[1-(4-methoxy-benzenesulfonyl)-piperidin-4-ylmethyl]-amino}-propoxy)-fluoren-9-one

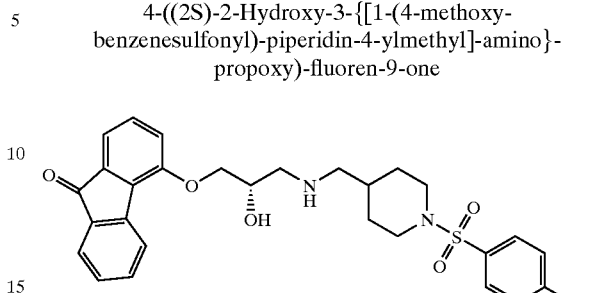

Prepared from 4-[(2S)-Ooxiranylmethoxy]-9-fluorenone (0.251 g, 1.0 mmol) and (4-aminomethyl-1-piperidinyl) 4-methoxybenzenesulfonamide (0.568 g, 2.00 mmol) according to procedure used for Example 2 to give 0.340 g of the title compound as a yellow solid.

NMR (DMSO-$d_6$, 400 MHz): δ 1.10 (m, 2H), 1.29 (m, 1H), 1.70 (broad d, 2H), 2.037 (t, 2H), 2.38 (d, 2H), 2.66 (m, 3H), 3.54 (broad d, 2H), 3.95 (broad, 1H), 4.14 (m, 2H), 5.058 (broad, 1H), 7.13 (d, 2H, J=9.0 Hz), 7.2 (m, 1H), 7.291 (m, 3H), 7.55 (m, 2H), 7.61 (dd, 2H), 7.84 (d, 1H, J=7.2 Hz). MS (ESI$^+$, m/z): 537 [M+H]$^+$.

EXAMPLE 39

4-((2S)-2-Hydroxy-3-{[1-(4-methoxy-benzenesulfonyl)-piperidin-4-ylmethyl]-amino}-propoxy)-1,3-dihydro-benzoimidazol-2-one

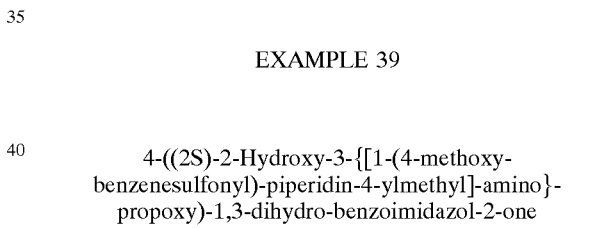

Prepared from 4-[(2S)-oxiranylmethoxy]-2-benzimidazolone (0.062 g, 0.3 mmol) and (4-aminomethyl-1-piperidinyl) 4-methoxybenzenesulfonamide (0.142 g, 0.5 mmol) according to procedure used for Example 2 to give 0.045 g of the title compound as a solid.

NMR (DMSO-$d_6$, 400 MHz): δ 1.10 (m, 2H), 1.33 (m, 1H), 1.715 (broad d, 2H), 2.1045 (t, 2H), 2.37 (d, 2H), 2.56 (m, 1H), 2.65 (m, 1H), 3.56 (broad d, 2H), 3.84 (s, 3H), 3.87 (m, 1H), 3.95 (m, 1H), 4.81 (broad, 1H), 6.55 (m, 2H), 6.81 (t, 1H), 7.13 (dd, 2H), 7.64 (dd, 2H), 10.54–10.65 (s+broad, 2H); MS (ESI$^+$, m/z): 491 [M+H]$^+$.

EXAMPLE 40

4-((2S)-2-Hydroxy-3-{[1-(4-methoxy-benzenesulfonyl)-piperidin-4-ylmethyl]-amino}-propoxy)-2-methyl-1H-indole

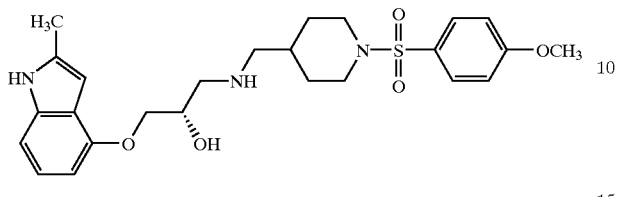

Prepared from 2-methyl-4-[(2S)-Ooxiranylmethoxy]-indole (0.050 g, 0.25 mmol) and (4-aminomethyl-1-piperidinyl) 4-methoxybenzenesulfonamide (0.10 g, 0.35 mmol) of according to procedure used for Example 2 to give 0.055 g of the title compound as a solid.

NMR (DMSO-$d_6$, 400 MHz): δ 1.08 (m, 2H), 1.33 (m, 1H), 1.71 (broad d, 2H), 2.08 (t, 2H), 2.29 (s, 3H), 2.38 (d, 2H), 2.57 (m, 1H), 2.65 (m, 1H), 3.55 (broad d, 2H), 3.823 (s, 3H), 3.9 (m, 3H), 4.92 (broad, 1H), 6.06 (s, 1H), 6.36 (m, 1H), 6.81 (m, 2H), 7.11 (dd, 2H), 7.62 (dd, 2H), 10.795 (s, 1H). MS (ESI$^+$, m/z): 488 [M+H]$^+$.

EXAMPLE 41

4-((2S)-3-{[1-(4-Methoxy-benzenesulfonyl)-piperidin-4-ylmethyl]-amino}-2-hydroxy-propoxy)-1,3-dihydro-indol-2-one

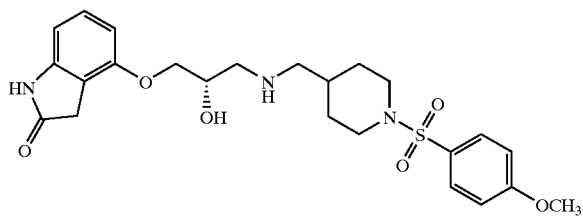

Prepared from 4-[(2S)-Oxiranylmethoxy]-2-oxindole (0.205 g, 1.0 mmol), (4-aminomethyl-1-piperidinyl) 4-methoxybenzenesulfonamide-TFA salt (0.70 g, 1.75 mmol) and diisopropylethyl amine (0.31 mL, 1.75 mmol) according to procedure used for Example 2 to give 0.30 g of the title compound as a solid. Dissolved in methanol and treated with excess 1N HCl in Et$_2$O. The solids were filtered and dried to give 0.086 g of the title compound as an HCl salt.

NMR (DMSO-$d_6$, 400 MHz): δ 1.233 (m, 3H), 1.61 (m, 1H), 1.766 (broad t, 2H), 2.14 (t, 2H), 2.78 (broad s, 2H), 2.88 (m, 1H), 3.03 (m, 1H), 3.59 (broad d, 2H), 3.8418 (s, 3H), 3.954 (m, 2H), 4.065 (m, 1H), 5.65 (broad, 1H), 6.46 (d, 1H, J=7.69 Hz), 6.57 (d, 1H, J=8.35 Hz), 7.12 (m, 3H), 7.66 (d, 2H, J=8.78 Hz), 8.25 (broad, 2H), 10.3609 (s, 1H). MS (ESI$^+$, m/z): 490 [M+H]$^+$.

EXAMPLE 42

4-((2S)-2-Hydroxy-3-{[1-(3,4-dimethoxy-benzenesulfonyl)-piperidin-4-ylmethyl]-amino}-propoxy)-1,3-dihydro-benzoimidazol-2-one

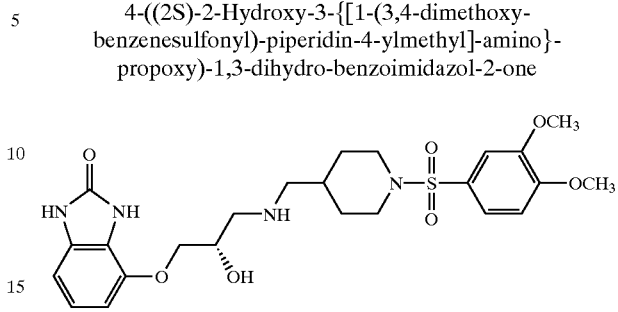

Step A: (4-Carboxamido-1-piperidinyl)-3,4-dimethoxybenzenesulfonamide

Prepared from isonipecotamide (5.4 g, 42 mmol), 3,4-dimethoxybenzenesulfonyl chloride (10 g, 42 mmol) and 7.3 mL of diisopropylethyl amine according to procedure used for Example 31 (Step A) to give 10.5 g of product as a white solid.

NMR (DMSO-$d_6$, 400 MHz): δ 1.53 (m, 2H), 1.74 (broad d, 2H), 2.027 (m, 1H), 2.26 (dt, 2H), 3.55 (broad d, 2H), 3.8198 (s, 3H), 3.8402 (s, 3H), 6.7705 (s, 1H), 7.17 (m, 2H), 7.30 (dd, 1H). MS (ESI$^+$, m/z): 329 [M+H]$^+$.

Step B: (4-Aminomethyl-1-piperidinyl)3,4-dimethoxybenzenesulfonamide

Prepared from (4-carboxamido-1-piperidinyl) 3,4-dimethoxybenzene-sulfonamide (10.3 g, 31.4 mmol) and BH$_3$-THF (50 mL, 1.0 M solution in THF) according to procedure used for Example 31 (Step B). Isolation by flash chromatography (CH$_2$Cl$_2$, CH$_3$OH, NH$_4$OH— 19:1:0.1) to give 1.2 g product as a white solid.

NMR (DMSO-$d_6$, 400 MHz): δ 1.107 (m, 3H), 1.71 (broad d, 2H), 2.16 (broad t, 2H), 2.35 (d, 2H), 3.59 (broad d, 2H), 3.8171 (s, 3H), 3.837 (s, 3H), 7.13 (m, 2H), 7.29 (dd, 1H). MS (ESI$^+$, m/z): 315 [M+H]$^+$.

Step C: 4-((2S)-2-Hydroxy-3-{[1-(3,4-dimethoxy-benzenesulfonyl)-piperidin-4-ylmethyl]-amino}-propoxy)-1,3-dihydro-benzoimidazol-2-one Prepared from 4-[(2S)-oxiranylmethoxy]-2-benzimidazolone (0.170 g, 0.825 mmol) and (4-aminomethyl-1-piperidinyl)-3,4-dimethoxybenzenesulfonamide (0.389 g, 1.24 mmol) according to procedure used for Example 2 to give 0.102 g of the title compound as a solid.

NMR (DMSO-$d_6$, 400 MHz): δ 1.09 (m, 2H), 1.36 (m, 1H), 1.74 (broad d, 2H), 2.1648 (t, 2H), 2.39 (d, 2H), 2.58 (m, 1H), 2.67 (m, 1H), 3.60 (broad d, 2H), 3.834 (s, 3H), 3.835 (s, 3H), 3.88 (m, 2H), 3.97 (m, 1H), 4.83 (broad, 1H), 6.56 (m, 2H), 6.83 (t, 1H), 7.15 (m, 2H), 7.28 (dd, 1H), 10.54–10.65 (s+broad, 2H). MS (ESI$^+$, m/z): 521 [M+H]$^+$.

EXAMPLE 43

4-((2S)-2-Hydroxy-3-{[1-(3,4-dimethoxy-benzenesulfonyl)-piperidin-4-ylmethyl]-amino}-propoxy)-phenol

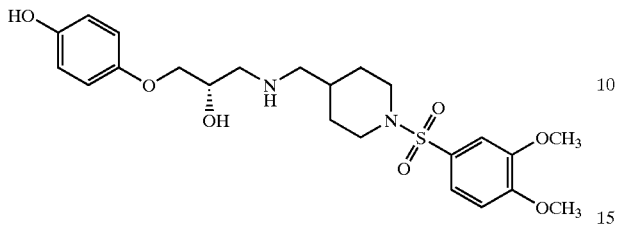

Prepared from t-butyl-[4-(2S)-oxiranylmethoxy-phenoxy]-diphenylsilane (0.365 g, 0.9 mmol) and an excess of and (4-aminomethyl-1-piperidinyl)-3,4-dimethoxybenzene-sulfonamide (0.439 g, 1.4 mmol) according to the procedure used in example 37 to give 0.227 g of the title compound as a white solid.

NMR (DMSO-$d_6$, 400 MHz): δ 1.11 (m, 2H), 1.36 (m, 2H), 1.73 (broad d, 2H), 2.17 (t, 2H), 2.40 (m, 2H), 2.54 (m, 1H), 2.61 (m, 1H), 3.07 (m, 2H), 3.61 (broad d, 2H), 3.8 (m, 3.8329 (s, 3H), 3.8532 (s, 3H), 4.94 (broad, 1H), 6.64 (dd, 2H), 6.72 (dd, 2H), 7.16 (m, 2H), 7.30 (dd, 1H), 8.886 (s, 1H). MS (ESI$^+$, m/z): 481 [M+H]$^+$; Anal. calc'd for $C_{23}H_{32}N_2O_7S$: C, 57.48; H, 6.71; N, 5.83; Found: C, 57.44; H, 6.96; N, 5.43.

EXAMPLE 44

4-((2S)-3-{[1-(3,4-Dimethoxy-benzenesulfonyl)-piperidin-4-ylmethyl]-amino}-2-hydroxy-propoxy)-1,3-dihydro-indol-2-one

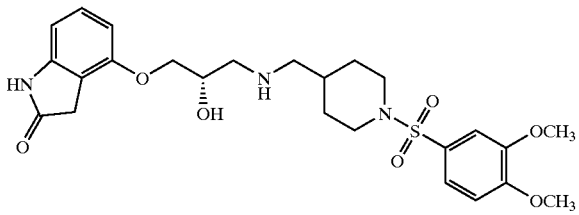

Prepared from 4-[(2S)-oxiranylmethoxy]-2-oxindole (0.205 g, 1.0 mmol) and 4-aminomethyl-1-piperidinyl-3,4-dimethoxybenzenesulfonamide (0.628 g, 2.0 mmol) according to procedure used for Example 2 to give 0.145 g of the title compound as a rose colored solid. Dissolved in $CH_2Cl_2$ and treated with 0.5 mL of 1N HCl in $Et_2O$. Resulting solids filtered and dried to give 0.140 g of title compound as the HCl salt.

NMR (DMSO-$d_6$, 400 MHz): δ 1.125 (m, 2H), 1.70 (m, 1H), 1.838 (t, 2H), 2.196 (t, 2H), 2.85 (m, 2H), 2.94 (m, 1H), 3.10 (m, 1H), 3.38 (m, 2H), 3.615 (broad d, 2H), 3.8339 (s, 3H), 3.8398 (s, 3H), 3.97 (m, 2H), 4.15 (broad, 1H), 5.78 (broad, 1H), 6.46 (d, 1H, J=7.75 Hz), 6.58 (d, 1H), J=8.1 Hz)), 7.14 (m, 3H), 7.30 (dd, 1H), 8.61 (broad, 2H), 10.3544 (s, 1H). MS (APCI$^+$, m/z): 520 [M+H]$^+$.

EXAMPLE 45

4-((2S)-2-Hydroxy-3-{[1-(4-nitro-benzenesulfonyl)-piperidin-4-ylmethyl]-amino}-propoxy)-phenol

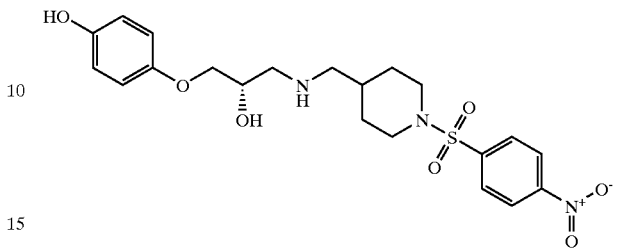

Step A: (4-Carboxamido-1-piperidinyl)-4-nitrobenzenesulfonamide

Prepared from isonipecotamide (5.0 g, 39 mmol), 4-nitrobenzenesulfonyl chloride (8.65 g, 39 mmol) and 6.8 mL of diisopropylethyl amine according to procedure used for Example 31 (Step A) to give 10.0 g of product as a white solid.

NMR (DMSO-$d_6$, 400 MHz): 81.5513 (m, 2H), 1.77 (m, 2H), 2.085 (m, 1H), 2.42 (dt, 2H), 3.07 (m, 2H), 3.62 (broad d, 2H), 6.817 (s, 1H), 7.233 (s, 1H), 8.02 (d, 2H), 8.44 (d, 2H). MS (ESI$^+$, m/z): 314 [M+H]$^+$, 331 [M+NH$_4$]$^+$.

Step B: (4-Aminomethyl-1-piperidinyl)-4-nitrobenzenesulfonamide

Prepared from (4-carboxamido-1-piperidinyl)-4-nitrobenzenesulfonamide (9.0 g, 28.7 mmol) and BH$_3$-THF (57 mL, 1.0 M solution in THF) according to procedure used for Example 31 (Step B). Pure compound was Isolated by flash chromatography (silica Merck 60: $CH_2Cl_2$, $CH_3OH$, $NH_4OH$— 19:1:0.1) to give 0.9 g product as a white solid.

NMR (DMSO-$d_6$, 400 MHz): δ 1.25 (m, 2H), 1.65 (broad, 1H), 1.806 (broad d, 2H), 2.33 (dt, 2H), 2.67 (d, 2H), 3.124 (m, 2H), 3.595 (m, 2H), 3.69 (broad d, 2H), 8.02 (d, 2H), J=8.78 Hz), 8.44 (d, 2H, J=8.78 Hz). MS (ESI$^+$, m/z): 300 [M+H]$^+$.

Step C: 4-((2S)-2-Hydroxy-3-{[1-(4-nitro-benzenesulfonyl)-piperidin-4-ylmethyl]-amino}-propoxy)-phenol Prepared from t-butyl-[4-(2S)-oxiranylmethoxy-phenoxy]-diphenylsilane (0.225 g, 0.55 mmol) and (4-aminomethyl-1-piperidinyl)-4-nitrobenzenesulfonamide (0.250 g, 0.83 mmol) of according to procedure used for Example 37 to give 0.029 g of the title compound as a light yellow solid.

NMR (DMSO-$d_6$, 400 MHz): δ 1.12 (m, 2H), 1.37 (m, 2H), 1.72 (broad d, 2H), 2.280 (t, 2H), 2.39 (m, 2H), 2.509 (m, 1H), 2.59 (m, 1H), 3.635 (broad d, 2H), 3.74 (m, 3H), 4.91 (broad, 1H), 6.61 (d, 2H, J=9 Hz), 6.68 (d, 2H, J=9 Hz), 7.97 (d, 2H, J=8.78 Hz), 8.41 (d, 2H, J=8.78 Hz), 8.8379 (s, 1H). MS (APCI$^-$, m/z): 465 [M]$^-$.

EXAMPLE 46

4-((2S)-2-Hydroxy-3-{[1-(4-trifluoromethoxy-benzenesulfonyl)-piperidin-4-ylmethyl]-amino}-propoxy)-1,3-dihydro-indol-2-one

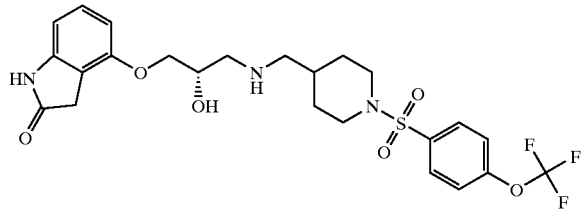

Step A: (4-Aminomethyl-1-piperidinyl)4-trifluoromethoxybenzenesulfonamide

Part 1

A solution of piperidin-4-ylmethyl-carbamic acid t-butyl ester (0.750 g, 3.5 mmol), 4-trifluoromethoxybenzenesulfonyl chloride (0.857 g, 3.5 mmol) and 0.61 mL of diisopropylethyl amine in methylene chloride was stirred at ambient temperature overnight. The reaction mixture was washed with dilute $KHSO_4$, brine and dried ($Na_2SO_4$). Removal of solvent in vacuo afforded 1.35 g of the intermediate [1-(4-trifluoromethoxybenzenesulfonyl)-piperidin-4-ylmethyl]-carbamic acid t-butyl ester.

NMR (DMSO-$d_6$, 400 MHz): δ 1.09 (m, 2H), 1.24 (m, 1H), 1.3389 (s, 9H), 1.63 (broad d, 2H), 2.24 (broad t, 2H), 2.758 (t, 2H), 3.61 (broad d, 2H), 6.811 (t, 1H), 7.60 (d, 2H, J=7.9 Hz), 7.85 (d, 2H, J=8.78 Hz). MS (ESI$^+$, m/z): 439 [M+H]$^+$, 456 [M+NH$_4$]$^+$.

Part 2:

A solution of [1-(4-trifluoromethoxybenzenesulfonyl)-piperidin-4-ylmethyl]-carbamic acid t-butyl ester (1.3 g, 2.96 mmol)in 3 mL TFA was stirred at ambient temperature for 15 minutes. The TFA was removed in vacuo to provide the 1.3 g of the TFA salt of the amine as an off-white solid.

NMR (DMSO-$d_6$, 400 MHz): δ 1.23 (m, 2H), 1.521 (m, 1H), 1.75 (broad d, 2H), 2.25 (dt, 2H), 2.68 (t, 2H), 3.65 (broad d, 2H), 7.62 (d, 2H), 7.73 (broad, 3H), 7.87 (d, 2H). MS (ESI$^+$, m/z): 339 [M+H]$^+$.

Step B: 4-((2S)-2-Hydroxy-3-{[1-(4-trifluoromethoxy-benzenesulfonyl)-piperidin-4-ylmethyl]-amino}-propoxy)-1,3-dihydro-indol-2-one Prepared from 4-[(2S)-oxiranylmethoxy]-2-oxindole (0.154 g, 0.75 mmol), (4-aminomethyl-1-piperidinyl) 4-trifluoromethoxybenzenesulfonamide-TFA salt (0.565 g, 1.25 mmol) and diisopropylethyl amine (0.22 mL, 1.25 mmol) according to procedure used for Example 2 to give 0.285 g of the title compound as a solid. Dissolved in methanol and treated with excess of 1N HCl in Et$_2$O. The solids were filtered and dried to give 0.085 g of the title compound as an HCl salt.

NMR (DMSO-$d_6$, 400 MHz): δ 1.24 (m, 4H), 1.70 (m, 1H), 1.792 (broad t, 2H), 2.26 (t, 2H), 2.83 (m, 2H), 2.93 (m, 1H), 3.08 (m, 1H), 3.66 (broad d, 2H), 3.96 (m, 2H), 4.097 (m, 1H), 5.74 (broad s, 1H), 6.47 (d, 1H, J=7.69 Hz), 6.58 (d, 1H, J=8.35 Hz), 7.128 (t, 1H), 7.63 (d, 2H), J=8.13 Hz), 7.88 (d, 2H, J=8.78 Hz), 8.34 (broad, 2H), 10.357 (s, 1H). MS (ESI$^-$, m/z): 542 [M−H]$^-$.

EXAMPLE 47

4-((2S)-2-Hydroxy-3-{[1-(4-trifluoromethoxy-benzenesulfonyl)-piperidin-4-ylmethyl]-amino}-propoxy)-phenol

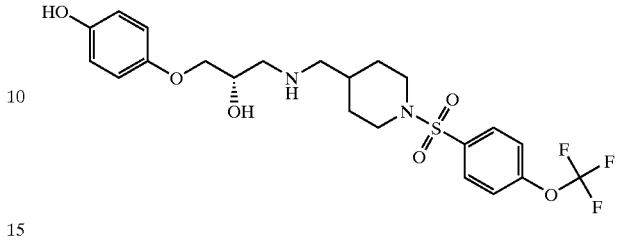

Prepared from t-Butyl-[4-(2S)-oxiranylmethoxy-phenoxy]-diphenylsilane (0.303 g, 0.75 mmol), (4-aminomethyl-1-piperidinyl) 4-trifluoromethoxybenzenesulfonamide-TFA salt (0.109 g, 0.38 mmol) and diisopropylethyl amine (0.22 mL, 1.25 mmol) according to procedure used for Example 37 to provide 0.110 g of product as a white solid. Dissolved in methanol and treated with an excess of 1N HCl in Et$_2$O. The solids were filtered and dried to give 0.121 g of the title compound as an HCl salt.

NMR (DMSO-$d_6$, 400 MHz): δ 1.23 (m, 2H), 1.72 (m, 1H), 1.806 (broad t, 2H), 2.255 (t, 2H), 2.839 (m, 2H), 2.9 (m, 1H), 3.1 (m, 1H), 3.64 (broad d, 2H), 3.82 (m, 2H), 4.107 (m, 1H), 5.76 (d, 1H), 6.65 (dd, 2H), 6.74 (dd, 2H), 7.63 (dd, 2H), 7.88 (dd, 2H), 8.55 (broad s, 2H), 8.961 (s, 1H). MS (ESI$^+$, m/z): 505 [M+H]$^+$; Anal. calc'd for $C_{22}H_{27}F_3N_2O_6S·HCl$: C, 48.84; H, 5.22; N, 5.18; Found: C, 48.82; H, 5.21; N, 4.97.

EXAMPLE 48

(1R)-1-(3-Chloro-phenyl)-2-{[1-(4-trifluoromethoxy-benzenesulfonyl)-piperidin-4-ylmethyl]-amino}-ethanol

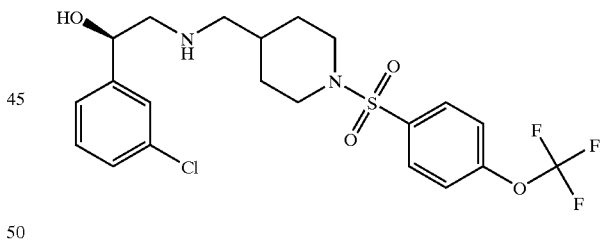

Prepared from 2-(3-chlorophenyl)-(2R)-oxirane (0.050 g, 0.33 mmol), (4-aminomethyl-1-piperidinyl) 4-trifluoromethoxybenzenesulfonamide-TFA salt (0.210 g, 0.46 mmol) and diisopropylethyl amine (0.08 mL, 0.46 mmol) according to procedure used for Example 37 to provide 0.060 g of product as a white solid. Dissolved in CH$_3$OH and treated with excess 1N HCl in Et$_2$O. The solids were filtered and dried to give 0.065 g of the title compound as an HCl salt.

NMR (DMSO-$d_6$, 400 MHz): δ 1.22 (m, 2H), 1.74 (m, 1H), 1.826 (broad t, 2H), 2.253 (t, 2H), 2.84 (m, 2H), 2.93 (m, 1H), 3.12 (m, 1H), 3.64 (m, 2H), 4.95 (m, 1H), 6.26 (d, 1H), 7.4 (m, 4H), 7.63 (dd, 2H), 7.88 (dd, 2H), 8.55 (broad s, 1H), 8.81 (broad s, 1H). MS (ESI$^+$, m/z): 493 [M+H]$^+$; Anal. calc'd for $C_{21}H_{24}ClF_3N_2O_4S·HCl$: C, 47.64; H, 4.76; N, 5.29; Found: C, 47.71; H, 4.72; N, 5.23.

EXAMPLE 49

4-((2S)-2-Hydroxy-3-{[1-(1-methyl-1H-imidazole-4-sulfonyl)-piperidin-4-ylmethyl]-amino}-propoxy)-phenol

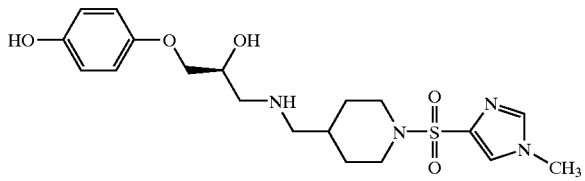

Step A: [1-(1-Methyl-1H-imidazole-4-sulfonyl)-piperidin-4-ylmethyl Amine

Prepared from piperidin-4-ylmethyl-carbamic acid t-butyl ester (0.428 g, 2.0 mmol), 1-methyl-1H-imidazole-4-sulfonyl chloride (0.361 g, 2.0 mmol) and 0.35 mL of diisopropylethyl amine according to the procedure used in example 46 (Step A, Part 1) to give 0.650 g of the intermediate [1-(1-methyl-1H-imidazole-4-sulfonyl)-piperidin-4-ylmethyl]-carbamic acid t-butyl ester.

NMR (DMSO-$d_6$, 400 MHz): δ 1.06 (m, 2H), 1.25 (m, 1H), 1.3476 (s, 9H), 1.62 (broad d, 2H), 2.4 (broad t, 2H), 2.767 (t, 2H), 3.56 (broad d, 2H), 6.826 (t, 1H), 7.764 (s, 1H), J=8.78 Hz). MS (APCI$^+$, m/z): 359 [M+H]$^+$.

The title compound was prepared according to the procedure used in example 46 (Step A, Part 2) to give 0.670 g of the title compound as the TFA salt.

NMR (DMSO-$d_6$, 400 MHz): δ 1.21 (m, 2H), 1.52 (m, 1H), 1.74 (broad d, 2H), 2.43 (dt, 2H), 2.688 (t, 2H), 3.60 (broad d, 2H), 3.700 (s, 3H), 7.758 (broad, 2H), 7.79 (s, 1H). MS (ESI$^+$, m/z): 259 [M+H]$^+$.

Step B: 4-((2S)-2-Hydroxy-3-{[1-(1-methyl-1H-imidazole-4-sulfonyl)-piperidin-4-ylmethyl]-amino}-propoxy)-phenol Prepared from t-butyl-[4-(2S)-oxiranylmethoxy-phenoxy]-diphenylsilane (0.404 g, 1.0 mmol) and [1-(1-methyl-1H-imidazole-4-sulfonyl)-piperidin-4-ylmethyl amine (0.650 g, 1.8 mmol) according to the procedure used in example 37 to give 0.045 g of the title compound as a white solid.

NMR (DMSO-$d_6$, 400 MHz): δ 1.10 (m, 2H), 1.349 (m, 2H), 1.71 (broad d, 2H), 2.4 (m, 3H), 2.51 (m, 1H), 2.59 (m, 1H), 3.57 (broad d, 2H), 3.69 (s, 3H), 3.75 (m, 3H), 4.853 (broad, 1H), 6.63 (d, 2H, J=9 Hz), 6.71 (d, 2H, J=9 Hz), 7.7568 (s, 1H), 7.782 (s, 1H), 8.8472 (s, 1H). MS (ESI$^+$, m/z): 425 [M+H]$^+$.

EXAMPLE 50

3-[(4-{[(2S)-3-(9H-Carbazol-4-yloxy)-2-hydroxy-propylamino]-methyl}-piperidine-1-carbonyl)-amino]-benzoic Acid Ethyl Ester

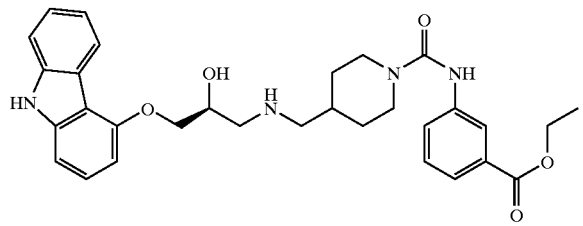

Step A: —(4-Carboxamide-1-piperidinyl)-1-(3-carbonylethoxy-phenyl)-urea

A mixture of isonipecotamide (5.0 g, 40 mmol) and 3-ethoxycarbonylphenyl isocyanate (7.6 g, 40 mmol) was heated at reflux in dioxane for 1 hour. On cooling the reaction mixture was concentrated in vacuo and the residue triturated with diethyl ether. The solids were collected and dried to give 12.0 g of the title compound as a white solid (mp-160° C., Et$_2$O).

NMR (DMSO-$d_6$, 400 MHz): δ 1.322 (t, 3H), 1.47 (m, 2H), 1.73 (m, 2H), 2.31 (m, 1H), 2.81, (t, 2H), 4.12 (broad d, 2H), 4.32 (q, 2H), 6.80 (s, 1H), 7.28 (s, 1H), 7.36 (t, 1H), 7.52 (d, 1H), 7.77 (dd, 1H), 8.103 (s, 1H), 8.7257 (s, 1H). MS (ESI$^+$, m/z): 320 [M+H]$^+$, 337 [M+NH$_4$]$^+$; Anal. calc'd for $C_{16}H_{21}N_3O_4$: C, 60.17; H, 6.63; N, 13.16; Found: C, 59.86; H, 6.59; N, 12.79.

Step B: 3-(4-Aminomethyl-1-piperidinyl)-1-(3-carbonylethoxy-phenyl)urea

A mixture of 3-(4-carboxamide-1-piperidinyl)-1-(3-carbonylethoxy-phenyl) urea (0.127 g, 40 mmol) and BH$_3$-THF (220 mL, 1.0 M solution in THF) was stirred at ambient temperature overnight. The reaction mixture was treated with dilute 1N HCl and extracted with ethyl acetate. The solvent was removed (rotovap) to provide crude product. Pure compound was obtained by flash chromatography (CH$_2$Cl$_2$—CH$_3$OH—NH$_4$OH: (9:1:0.1) to give 1.2 product as a waxy solid.

NMR (DMSO-$d_6$, 400 MHz): δ 1.01 (m, 2H), 1.3026 (t, 3H), 1.41 (m, 1H), 1.68 (broad d, 2H), 2.3 (m, 2H), 2.73, (t, 2H), 4.125 (broad d, 2H), 4.29 (q, 2H), 7.34 (t, 1H), 7.50 (d, 1H), 7.76 (dd, 1H), 8.08 (s, 1H), 8.672 (s, 1H). MS (EI, m/z): 305 (M)$^+$.

Step C: 3-[(4-{[(2S)-3-(9H-Carbazol-4-yloxy)-2-hydroxy-propylamino]-methyl}-piperidine-1-carbonyl)-amino]-benzoic Acid Ethyl Ester Prepared from 4-[(2S)-oxiranylmethoxy]-9H-carbazole (0.190 g, 0.8 mmol) and 3-(4-aminomethyl-1-piperidinyl)-1-(3-carbonylethoxy-phenyl) urea (0.50 g, 1.43 mmol) according to the procedure used in example 2 to give 0.160 g of the title compound as a white solid.

NMR (DMSO-$d_6$, 400 MHz): δ 1.055 (m, 2H), 1.316 (t, 3H), 1.65 (m, 1H), 1.68 (broad d, 2H), 2.3 (m, 2H), 2.66, (t, 2H), 2.78 (m, 1H), 2.86 (m, 1H), 4.15 (broad d, 3H), 4.18 (m, 2H), 4.30 (q, 2H), 5.13 (broad, 1H), 6.69 (d, 1H), 7.06 (d, 1H), 7.14 (t, 1H), 7.33 (m, 3H), 7.44 (dd, 1H), 7.50 (dd, 1H), 7.74 (dd, 1H), 8.09 (s, 1H), 8.22 (d, 1H), 8.665 (s, 1H), 11.244 (s, 1H). MS (ESI$^+$, m/z): 545 [M+H]$^+$.

EXAMPLE 51

3-[(4-{[(2S)-3-(9H-Carbazol-4-yloxy)-2-hydroxy-propylamino]-methyl}-piperidine-1-carbonyl)-amino]-benzoic Acid

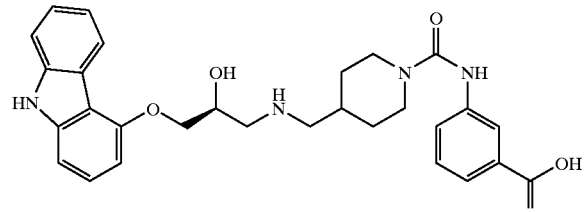

A solution of 3-[(4-{[(2S)-3-(9H-carbazol-4-yloxy)-2-hydroxy-propylamino]-methyl}-piperidine-1-carbonyl)-amino]-benzoic acid ethyl ester (50 mg, 0.1 mmol) in 5 mL methanol-and 1 mL of 1 N NaOH aqueous solution was stirred at ambient temperature overnight. The reaction mixture was concentrated in vacuo and neutralized with 1 mL of 1 N HCl solution. The solids were filtered, washed with water followed by diethyl ether and dried under high vacuum to give 0.053 g of the title compound as a white solid (mp-238–240° C. with decomposition).

NMR (DMSO-d$_6$, 400 MHz): δ 1.06 (m, 2H), 1.71 (m, 3H), 2.56 (m, 2H), 2.67 (t, 2H), 2.8–3.0 (m, 2H), 4.08 (broad d, 3H), 4.16 (m, 3H), 5.12 (broad, 1H), 6.69 (d, 1H), 7.07 (d, 1H), 7.14 (t, 1H), 7.29–7.35 (m, 3H), 7.49 (m, 2H), 7.69 (dd, 1H), 8.06 (s, 1H), 8.22 (d, 1H), 8.61 (s, 1H), 11.251 (s, 1H). MS (ESI$^+$, m/z): 517 [M+H]$^+$.

EXAMPLE 52

3-[(4-{[(2S)-2-Hydroxy-3-(4-hydroxy-phenoxy)-propylamino]-methyl}-piperidine-1-carbonyl)-amino]-benzoic Acid Ethyl Ester

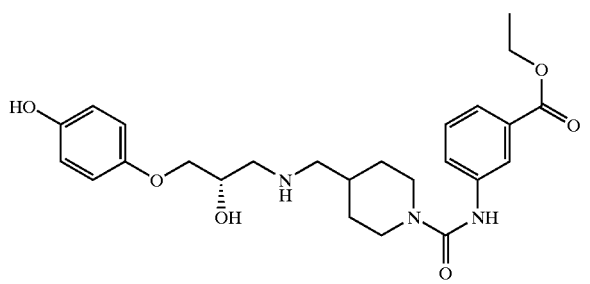

Step A: 3-[(4-{[(2S)-2-benzyloxy-3-(4-hydroxy-phenoxy)-propylamino]-methyl}-piperidine-1-carbonyl)-amino]-benzoic Acid Ethyl Ester Prepared from the (2S)-4-benzyloxy-phenoxymethyl)-oxirane (0.178 g, 0.7 mmol) and 3-(4-aminomethyl-1-piperidinyl)-1-(3-carbonylethoxy-phenyl) urea (0.40 g, 1.3 mmol) of according to the procedure used in example 2 to provide 0.117 g of the title compound as a white solid.

NMR (DMSO-d$_6$, 400 MHz): δ 1.056 (m, 2H), 1.317 (t, 3H), 1.65 (m, 1H), 1.70 (broad d, 2H), 2.4 (m, 2H), 2.6–2.8 (m, 4H), 3.85 (m, 3H), 4.13 (broad d, 2H), 4.30 (q, 2H), 5.0 (broad, 1H), 5.0325 (s, 2H), 6.9 (q, 4H), 7.38 (m, 6H), 7.14 (t, 1H), 7.51 (m, 1H), 7.76 (m, 1H), 8.101 (s, 1H), 8.665 (s, 1H). MS (ESI$^-$, m/z): 560 [M–H]$^-$.

Step B: 3-[(4-{[(2S)-2-Benzyloxy-3-(4-hydroxy-phenoxy)-propylamino]-methyl}-piperidine-1-carbonyl)-amino]-benzoic Acid A mixture of 3-[(4-{[(2S)-2-benzyloxy-3-(4-hydroxy-phenoxy)-propylamino]-methyl}-piperidine-1-carbonyl)-amino]-benzoic acid ethyl ester (0.112 g, 0.43 mmol) and ammonium formate (0.063 g, 1 mmol) in 5 mL of methanol over 0.112 g of 10% palladium on carbon was stirred at ambient temperature overnight. The catalyst was filtered (solka floc) and the filtrate concentrated in vacuo. Trituration of the crude solid foam with Et$_2$O provided 0.057 g of the title compound as an off-white solid.

NMR (DMSO-d$_6$, 400 MHz): δ 1.05 (m, 2H), 1.3026 (t, 3H), 1.604 (m, 1H), 1.70 (broad d, 2H), 2.41 (m, 2H), 2.61 (m, 2H), 2.74 (t, 3H), 3.80 (m, 3H), 4.10 (broad d, 2H), 4.30 (q, 2H), 4.87 (broad, 1H), 6.7 (q, 4H), 7.34 (t, 1H), 7.49 (d, 1H), 7.74 (d 1H), 8.08 (s, 1H), 8.668 (s, 1H), 8.86 (s, 1H). MS (ESI$^+$, m/z): 472 [M+H]$^+$.

EXAMPLE 53

4-[(4-{[(2S)-3-(9H-Carbazol-4-yloxy)-2-hydroxy-propylamino]-methyl}-piperidine-1-carbonyl)-amino]-benzoic Acid Ethyl Ester

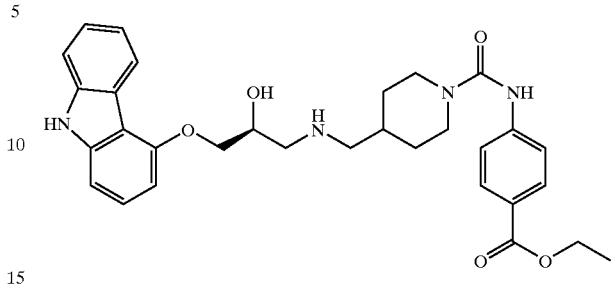

Step A: 3-(4-Carboxamido-1-piperidinyl)-1-(4-ethoxycarbonyl-phenyl)urea

Prepared from isonipecotamide (6.7 g, 52.3 mmol) and 4-ethoxycarbonylphenyl isocyanate (10 g, 52.3 mmol) according to the procedure used in example 50 (Step A) to give 5.5 g of the title compound as a white solid (mp-217° C., Et$_2$O).

NMR (DMSO-d$_6$, 400 MHz): δ 1.289 (t, 3H), 1.46 (m, 2H), 1.70 (m, 2H), 2.298 (m, 1H), 2.81, (t, 2H), 4.09 (broad d, 2H), 4.25 (q, 2H), 6.78 (s, 1H), 7.27 (s, 1H), 7.59 (d, 2H, J=8.78 Hz), 7.81 (d, 2H, J=8.56 Hz), 8.8575 (s, 1H); Anal. calc'd for C$_{16}$H$_{21}$N$_3$O$_4$: C, 60.17; H, 6.63; N, 13.16; Found: C, 59.98; H, 6.26; N, 12.90.

Step B: 3-(4-Aminomethyl-1-piperidinyl)-1-(4-ethoxycarbonylphenyl)urea

Prepared from 3-(4-carboxamido-1-piperidinyl)-1-(4-ethoxy carbonylphenyl)-urea (5.3 g, 16.6 mmol) and BH$_3$-THF (20 mL, 1.0 M solution in THF). according to the procedure used in example 50 (Step B) to give 0.76 g product as a waxy solid.

NMR (DMSO-d$_6$, 400 MHz): δ 1.01 (m, 2H), 1.2877 (t, 3H), 1.406 (m, 1H), 1.68 (broad d, 2H), 2.41 (d, 2H), 2.73, (t, 2H), 4.12 (broad d, 2H), 4.25 (q, 2H), 7.59 (d, 2H, J=8.78 Hz), 7.80 (d, 2H, J=8.78 Hz), 8.8213 (s, 1H). MS (ESI$^+$, m/z): 306 [M+H]$^+$.

Step C: 4-[(4-{[(2S)-3-(9H-Carbazol-4-yloxy)-2-hydroxy-propylamino]-methyl}-piperidine-1-carbonyl)-amino]-benzoic Acid Ethyl Ester Prepared from 4-[(2S)-oxiranylmethoxy]-9H-carbazole (0.150 g, 0.63 mmol) and 3-(4-aminomethyl-1-piperidinyl)-1-(4-ethoxycarbonylphenyl) urea (0.305 g, 1.0 mmol) according to the procedure used in example 2 to give 0.080 g of the title compound as a white solid.

NMR (DMSO-d$_6$, 400 MHz): δ 1.04 (m, 2H), 1.286 (t, 3H), 1.65 (m, 1H), 1.69 (broad d, 2H), 2.659 (broad t, 2H), 2.78, (m, 1H), 2.85 (m, 1H), 4.15 (m, 4H), 4.24 (q, 2H), 5.15 (broad, 1H), 6.67 (d, 1H), 7.05 (d, 1H), 7.12 (t, 1H), 7.30 (m, 2H), 7.43 (d, 1H), 7.58 (d, 2H), 7.80 (d, 2H), 8.20 (d, 1H), 8.799 (s, 1H), 11.228 (s, 1H). MS (ESI$^+$, m/z): 545 [M+H]$^+$.

EXAMPLE 54

4-[(4-{[(2S)-2-Hydroxy-3-(4-hydroxy-phenoxy)-propylamino]-methyl}-piperidine-1-carbonyl)-amino]-benzoic Acid Ethyl Ester

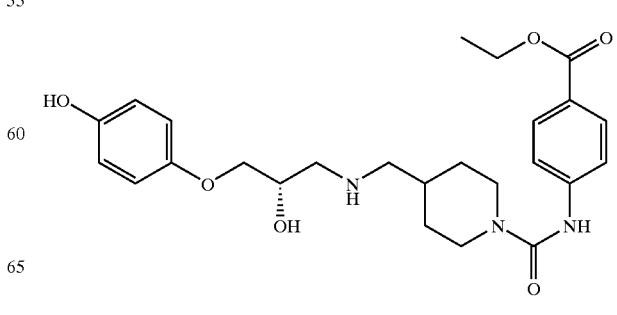

Step A: 4-[(4-{[(2S)-2-Hydroxy-3-(4-benzyloxy-phenoxy)-propylamino]-methyl}-piperidine-1-carbonyl)-amino]-benzoic Acid Ethyl Ester Prepared from the (2S)-(4-benzyloxy-phenoxymethyl)-oxirane (0.158 g, 0.62 mmol) and 3-(4-aminomethyl-1-piperidinyl)-1-(4-ethoxycarbonylphenyl) urea (0.305 g, 1.0 mmol) of according to the procedure used in example 2 to provide 0.115 g of the intermediate as a white solid.

NMR (DMSO-d$_6$, 400 MHz): δ 1.0515 (m, 2H), 1.303 (t, 3H), 1.65 (m, 1H), 1.74 (broad d, 2H), 2.4 (m, 2H), 2.6–2.8 (m, 4H), 3.84 (m, 3H), 4.13 (broad d, 2H), 4.26 (q, 2H), 5.0 (broad, 1H), 5.0325 (s, 2H), 6.85 (d, 2H), (6.90 d, 2H), 7.40 (m, 5H), 7.605 (d, 2H), 7.82 (d, 2H), 8.843 (s, 1H).

MS (ESI$^+$, m/z): 562 [M+H]$^+$.

Step B: 4-[(4-{[(2S)-2-Hydroxy-3-(4-benzyloxy-phenoxy)-propylamino]-methyl}-piperidine-1-carbonyl)-amino]-benzoic Acid A mixture of 4-[(4-{[(2S)-2-hydroxy-3-(4-benzyloxy-phenoxy)-propylamino]-methyl}-piperidine-1-carbonyl)-amino]-benzoic acid ethyl ester (0.11 g, 0.43 mmol) and ammonium formate (0.063 g, 1 mmol) in 5 mL of methanol over 0.110 g of 10% palladium on carbon was stirred at ambient temperature overnight. The catalyst was filtered (solka floc) and the filtrate concentrated in vacuo. Trituration of the crude solid foam with Et$_2$O provided 0.061 g of the title compound as a white solid.

NMR (DMSO-d$_6$, 400 MHz): δ 1.03 (m, 2H), 1.2877 (t, 3H), 1.6068 (m, 1H), 1.695 (broad d, 2H), 2.42 (d, 2H), 2.54 (m, 1H), 2.62 (m, 1H), 2.76 (t, 3H), 3.80 (m, 3H), 4.10 (broad d, 2H), 4.25 (q, 2H), 4.9 (broad, 1H), 6.64 (d, 2H), 6.72 (d, 2H), 7.59 (d, 2H), 7.805 (d, 2H), 8.82 (s, 1H), 8.87 (s, 1H). MS (ESI$^+$, m/z): 472 [M+H]$^+$.

EXAMPLE 55

4-{[(2S)-3-(9H-Carbazol-4-yloxy)-2-hydroxy-propylamino]-methyl}-piperidine-1-carboxylic Acid Hexylamide

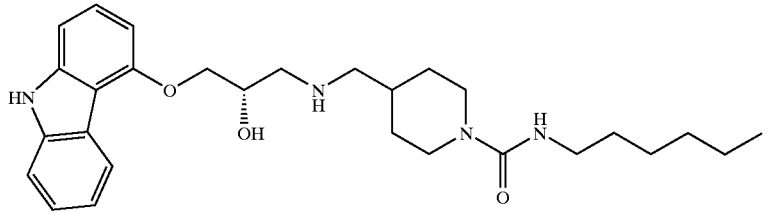

Step A: 3-(4-Carboxamido-1-piperidinyl)-1-hexyl Urea

Prepared from isonipecotamide (3.0 g, 23.4 mmol) and n-hexylisocyanate (3.0 g, 23.4 mmol) according to the procedure used in example 50 (Step A) to give 4.0 g of the title compound as a white solid.

NMR (DMSO-d$_6$, 400 MHz): δ 0.8478 (t, 3H), 1.2288 (m, 8H), 1.3469 (m, 2H), 1.61 (m, 2H), 2.2012 (m, 1H), 2.60, (dt, 2H), 2.96 (m, 2H), 3.90 (broad d, 2H), 6.3652 (t, 1H, J=5.49 Hz), 6.7287 (s, 1H), 7.2146 (s, 1H). MS (EI, m/z): 255 (M)$^+$; Anal. calc'd for C$_{13}$H$_{25}$N$_3$O$_2$: C, 61.15; H, 9.87; N, 16.46; Found: C, 61.15; H, 9.56; N, 16.44.

Step B: 3-(4-Aminomethyl-1-piperidinyl)-1-hexyl Urea

Prepared from 3-(4-carboxamido-1-piperidinyl)-1-hexylurea (3.9 g, 15.3 mmol) and BH$_3$-THF (30 mL, 1.0 M solution in THF). according to the procedure used in example 50 (Step B) to give 2.0 g product as a waxy solid.

NMR (DMSO-d$_6$, 400 MHz): δ 0.85 (m, 5H), 1.2255 (m, 8H), 1.3573 (m, 2H), 1.60 (m, 2H), 2.36 (d, 2H), 2.54, (m, 2H), 2.97 (m, 2H), 3.91 (broad d, 2H), 6.3207 (t, 1H, J=5.49 Hz). MS (EI, m/z): 241 (M)$^+$.

Step C: 4-{[(2S)-3-(9H-Carbazol-4-yloxy)-2-hydroxy-propylamino]-methyl}-piperidine-1-carboxylic Acid Hexylamide Prepared from 4-[(2S)-oxiranylmethoxy]-9H-carbazole (0.150 g, 0.63 mmol) and 3-(4-aminomethyl-1-piperidinyl)-1-hexyl urea (0.305 g, 1.0 mmol) according to the procedure used in example 2 to give 0.85 g of the title compound as a white solid.

NMR (DMSO-d$_6$, 400 MHz): δ 0.8581 (m, 3H), 0.95 (m, 2H), 1.2366 (m, 6H), 1.3662 (m, 2H), 1.605 (m, 3H), 2.78 (m, 1H), 2.875, (m, 1H), 3.869 (m, 2H), 4.108 (m, 3H), 5.15 (broad, 1H), 6.3287 (t, 1H), 6.68 (d, 1H), 7.06 (d, 1H), 7.13 (t, 1H), 7.30 (m, 2H), 7.44 (d, 1H), 8.20 (d, 1H), 11.2468 (s, 1H). MS (ESI$^+$, m/z): 241 [M+H]$^+$.

EXAMPLE 56

4-{[(2S)-3-(9H-Carbazol-4-yloxy)-2-hydroxy-propylamino]-methyl}-piperidine-1-carboxylic Acid Cyclohexylamide

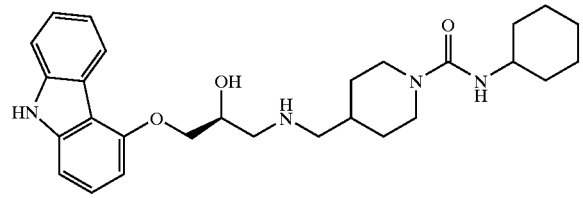

Step A: 3-(4-Carboxamido-1-piperidinyl)-1-cyclohexyl Urea

Prepared from isonipecotamide (3.0 g, 23.4 mmol) and cyclohexylisocyanate (3.0 mL, 23.4 mmol) according to the procedure used in example 50 (Step A) to give 4.5 g of the title compound as a white solid.

NMR (DMSO-d$_6$, 400 MHz): δ 1.167 (m, 5H), 1.295 (m, 2H), 1.65 (m, 7H), 2.1927 (m, 1H), 2.58 (dt, 2H), 3.38 (m, 1H), 3.92 (broad d, 2H), 6.05 (d, 1H), 6.724 (s, 1H), 7.2105 (s, 1H). MS (ESI$^+$, m/z): 254 [M+H]$^+$.

Step B: 3-(4-Aminomethyl-1-piperidinyl)-1-cyclohexyl Urea

Prepared from 3-(4-carboxamido-1-piperidinyl)-1-cyclohexylurea (3.9 g, 15.3 mmol) and BH$_3$-THF (36 mL, 1.0 M solution in THF). according to the procedure used in example 50 (Step B) to give 1.1 g product as a waxy solid.

NMR (DMSO-d$_6$, 400 MHz): δ 0.89 (m, 2H), 1.163 (m, 5H), 1.305 (m, 1H), 1.60 (m, 7H), 2.36 (d, 2H), 2.53, (dt, 2H), 3.36 (m, 2H), 3.92 (broad d, 2H), 6.0 (d, 1H, J=7.9Hz). MS (ESI$^+$, m/z): 240 [M+H]$^+$.

Step C: 4-{[(2S)-3-(9H-Carbazol-4-yloxy)-2-hydroxy-propylamino]-methyl}-piperidine-1-carboxylic Acid Cyclohexylamide Prepared from 4-[(2S)-oxiranylmethoxy]-9H-carbazole (0.175 g, 0.73 mmol) and 3-(4-aminomethyl-1-piperidinyl)-1-cyclohexyl urea (0.360 g, 1.5 mmol) according to the procedure used in example 2 to give 0.095 mg of the title compound as an off white solid.

NMR (DMSO-$d_6$, 400 MHz): δ 0.91 (m, 2H), 1.18 (m, 5H), 1.52–1.70 (m, 8H), 2.437 (m, 4H), 2.78 (m, 1H), 2.75, (m, 1H), 2.83 (m, 1H), 3.3 (m, 1H), 3.88 (broad d, 2H), 4.08 (m, 1H), 4.1456 (m, 1H), 5.08 (broad, 1H), 5.98 (d, 1H, J=7.9 Hz), 6.66 (d, 1H), 7.04 (d, 1H), 7.117 (t, 1H), 7.27 (m, 2H), 7.41 (d, 1H), 8.19 (d, 1H), 11.2186 (s, 1H). MS (ESI$^+$, m/z): 479 [M+H]$^+$.

EXAMPLE 57

4-{[(2S)-2-Hydroxy-3-(4-hydroxy-phenoxy)-propylamino]-methyl}-piperidine-1-carboxylic Acid Cyclohexylamide

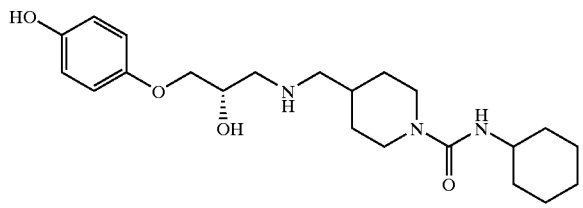

Prepared from the t-butyl-[4-(2S)-oxiranylmethoxy-phenoxy]-diphenylsilane (0.324 g, 0.8 mmol) and 3-(4-aminomethyl-1-piperidinyl)-1-cyclohexyl urea (0.359 g, 1.6 mmol) according to the procedure used in example 2 to provide 0.204 g of silylated product as a white solid. The silyl group was removed by dissolving the compound in THF and treating with 0.793 mL of TBAF. The solvent was evaporated and the residue purified by flash chromatography (CH$_2$Cl$_2$—CH$_3$OH, 9:1) to give 0.077 g of product as a white solid.

NMR (DMSO-$d_6$, 400 MHz): δ 0.92 (m, 2H), 1.19 (m, 5H), 1.52–1.70 (m, 8H), 2.43 (d, 2H), 2.54 (m, 3H), 3.8 (m, 3H), 3.92 (broad d, 2H), 5.0 (broad, 1H), 6.02 (d, 1H), 6.63 (d, 2H), 6.72 (d, 2H) 8.8828 (s, 1H). MS (ESI$^+$, m/z): 406 [M+H]$^+$.

EXAMPLE 58

1-[4-(4-{[(2S)-3-(9H-Carbazol-4-yloxy)-2-hydroxy-propylamino]-methyl}-piperidine-1-sulfonyl)-phenyl]-3-hexyl-urea Step A: 1-[(4-Carboxamido)-piperidine-1-sulfonylphenyl]-3-hexyl-urea Prepared from isonipecotamide (0.401 g, 3.13 mmol), 4-hexylureidobenzenesulfonyl chloride (1.0 g, 3.134 mmol) and 2.5 mL of triethyl amine according to the procedure used in Example 31 (Step A) to give 0.450 g of product as a white solid.

NMR (DMSO-$d_6$, 400 MHz): δ 0.860 (m, 3H), 1.263 (s, 6H), 1.415 (m, 2H), 1.53 (m, 2H), 1.726 (m, 2H), 2.011 (m, 1H), 2.209 (m, 2H), 3.07 (m, 2H), 3.50 (broad d, 2H), 6.292 (t, 1H), 6.78 (s, 1H), 7.16 (s, 1H), 7.57 (q, 4H), 8.9 (s, 1H). MS (ESI$^+$, m/z): 411 [M+H]$^+$, 428 [M+NH$_4$]$^+$.

Step B: 1-[(4-Aminomethyl)-piperidine-1-sulfonylphenyl]-3-hexyl-urea

Prepared from 1-[(4-carboxamido)-piperidine-1-sulfonylphenyl]-3-hexyl-urea (0.450 g, 1.1 mmol) and BH$_3$-THF (9 mL, 1.0 M solution in THF). according to the procedure used in Example 31 (Step B) to give 0.165 g of product as a waxy solid.

NMR (DMSO-$d_6$, 400 MHz): δ 0.874 (m, 3H), 1.17 (m, 2H), 1.277 (s, 8H), 1.429 (m, 2H), 1.72 (m, 2H), 1.726 (m, 2H), 2.13 (t, 2H), 2.43 (d, 1H), 3.08 (m, 2H), 3.44 (m, 2H), 3.57 (broad d, 2H), 6.36 (t, 1H), 7.58 (q, 4H), 9.0003 (s, 1H). MS (ESI$^+$, m/z): 397 [M+H]$^+$.

Step C: 1-[4-(4-{[(2S)-3-(9H-Carbazol-4-yloxy)-2-hydroxy-propylamino]-methyl}-piperidine-1-sulfonyl)-phenyl]-3-hexyl-urea Prepared from 4-[(2S)-oxiranylmethoxy]-9H-carbazole (0.097 g, 0.4 mmol) and 1-[(4-aminomethyl)-piperidine-1-sulfonylphenyl]-3-hexyl-urea (0.160 g, 0.4 mmol) according to the procedure used in Example 2 to give 0.058 g of the title compound as a white solid (mp-87° C., sinters).

NMR (DMSO-$d_6$, 400 MHz): δ 0.8577 (m, 3H), 1.079 (m, 2H), 1.2623 (s, 7H), 1.41 (m, 2H), 1.70 (m, 2H), 2.014 (m, 2H), 2.44 (m, 2H), 2.71 (m, 1H), 2.805 (m, 1H), 3.08 (m, 2H), 3.44–3.57 (m, 4H), 4.05 (broad, 1H), 4.112 (s, 2H), 5.11 (broad, 1H), 6.31 (t, 1H), 6.64 (d, 1H), J=7.9 Hz), 7.04 (m, 2H), 7.258 (m, 2H), 7.4 (d, 1H, J=7.9 Hz), 7.56 (q, 4H), 8.13 (d, 1H), J=7.7 Hz), 8.9358 (s, 1H), 11.2007 (s, 1H). MS (ESI$^+$, m/z): 636 [M+H]$^+$.

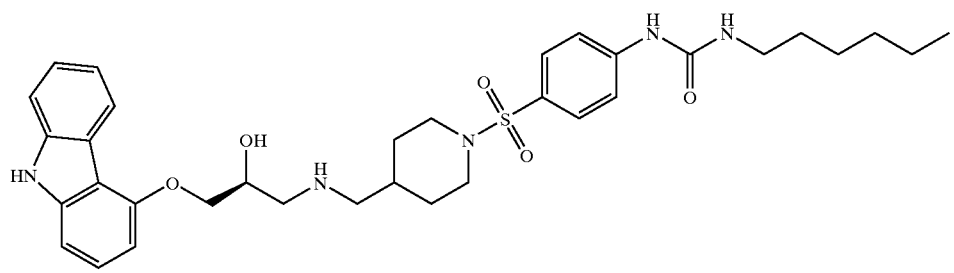

EXAMPLE 59

1-Hexyl-3-[4-(4-{[(2S)-2-hydroa-3-(4-hydroxy-phenoxy)-propylamino]-methyl}-piperidine-1-sulfonyl)-phenyl]-urea

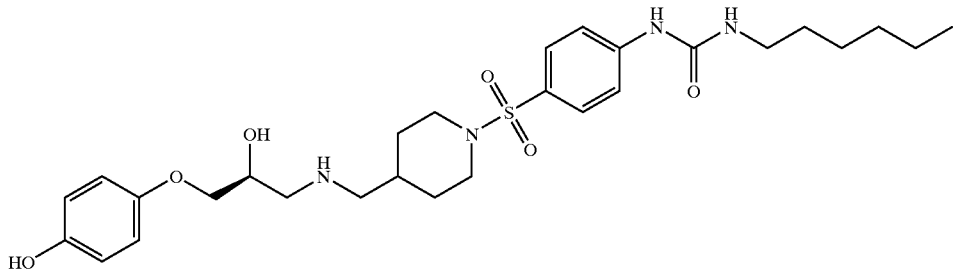

Prepared from t-butyl-[4-(2S)-oxiranylmethoxy-phenoxy]-diphenylsilane (0.150 g, 0.37 mmol) and 1-[(4-aminomethyl)-piperidine-1-sulfonylphenyl]-3-hexyl-urea (0.155 g, 0.39 mmol) of according to the procedure used in Example 37 to give 0.060 g of the title compound as a white solid.

NMR (DMSO-$d_6$, 400 MHz): δ 0.8593 (m, 3H), 1.12 (m, 2H), 1.2625 (s, 8H), 1.414 (m, 2H), 1.72 (broad d, 2H), 2.1078 (t, 2H), 2.37 (m, 2H), 2.58 (m, 1H), 3.07 (m, 2H), 3.54 (broad d, 2H), 3.8 (m, 3H), 4.88 (broad, 1H), 6.3046 (t, 1H), 6.63 (dd, 2H), 6.69 (dd, 2H), 7.56 (q, 4H), 8.8625 (s, 1H), 8.933 (s, 1H). MS (APCI$^+$, m/z): 563 [M+H]$^+$.

EXAMPLE 60

1-Hexyl-3-[4-(4-{[(2S)-2-hydroxy-3-(2-oxo-2,3-dihydro-1H-benzoimidazol-4-yloxy)-propylamino]-methyl}-piperidine-1-sulfonyl)-phenyl]-urea Prepared from 4-[(2S)-oxiranylmethoxy]-2-benzimidazolone (0.62 g, 0.3 mmol) and 1-[(4-aminomethyl)-piperidine-1-sulfonylphenyl]-3-hexyl-urea (0.135 g, 0.34 mmol) according to the procedure used in Example 2 to give 0.039 g of the title compound as a white solid.

NMR (DMSO-$d_6$, 400 MHz): δ 0.8588 (m, 3H), 1.12 (m, 2H), 1.2634 (s, 6H), 1.40 (m, 2H), 1.73 (broad d, 2H), 2.1238 (t, 2H), 2.43 (m, 2H), 2.65 (m, 2H), 3.07 (m, 2H), 3.55 (broad d, 2H), 3.90 (m, 2H), 3.96 (m, 1H), 4.9 (broad, 1H), 6.3065 (t, 1H), 6.56 (m, 2H), 6.818 (t, 1H), 7.57 (q, 4H), 8.9343 (s, 1H), 10.6 (s+broad, 2H). MS (ESI$^-$, m/z): 601 [M−H]$^-$.

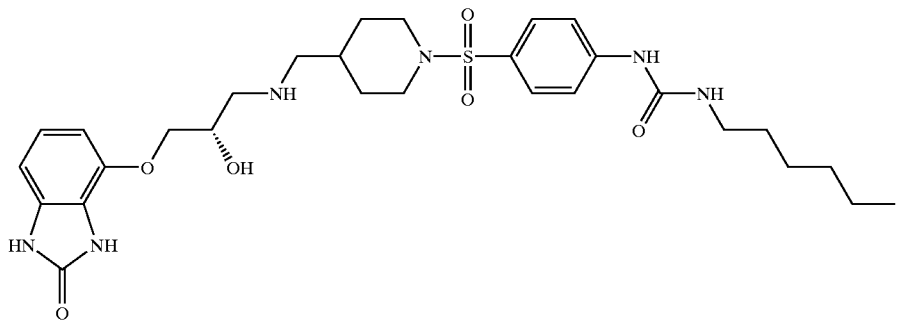

EXAMPLE 61

1-[4-(4-{[(2S)-2-Hydroxy-3-(2-methyl-1H-indol-7-yloxy)-propylamino]-methyl}-piperidine-1-sulfonyl)-phenyl]-3-phenyl-urea

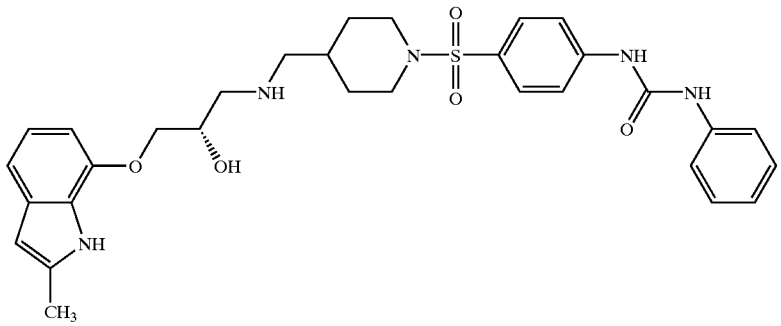

Step A: 1-[(4-Carboxamido)-piperidine-1-sulfonylphenyl]-3-phenyl-urea

Prepared from 1-[(4-carboxamido)-piperidin-1-yl]-4-aminobenzene-sulfonamide (1.5 g, 5.3 mmol) and phenyl-isocyanate (0.58 mL, 5.3 mmol) was stirred at ambient temperature in dioxane for 24 hours. The reaction mixture was preabsorbed on silica gel and purified by flash chromatography ($CH_2Cl_2$—$CH_3OH$, 19:1) to 1.45 g of product as an off-white solid.

NMR (DMSO-$d_6$, 400 MHz): δ 1.54 (m, 2H), 1.76 (m, 2H), 2.046 (m, 1H), 2.26 (dt, 2H), 3.55 (broad d, 2H), 6.8 (s, 1H), 7.008 (t, 1H), 7.1998 (s, 1H), 7.305 (t, 2H), 7.46 (dd, 2H), 7.66 (q, 4H), 8.8383 (s, 1H), 9.2079 (s, 1H). MS (ESI$^+$, m/z): 403 [M+H]$^+$, 420 [M+NH$_4$]$^+$.

Step B: 1-[(4-Aminomethyl)-piperidine-1-sulfonylhenyl]-3-phenyl-urea

A solution of 1-[(4-carboxamido)-piperidine-1-sulfonylphenyl]-3-phenyl-urea (1.31 g, 3.2 mmol) and BH$_3$-THF (5 mL, 1.0 M solution in THF) was stirred overnight at ambient temperature. The excess borane was decomposed with the addition of methanol. The solvent was evaporated and the residue purified by flash chromatography ($CH_2Cl_2$—$CH_3OH$, 9:1 gradient to $CH_3OH$—$NH_4OH$, 19:1) to give 0.230 g product as a white solid.

NMR (DMSO-$d_6$, 400 MHz): δ 1.17 (m, 3H), 1.72 (m, 2H), 2.137 (t, 2H), 2.43 (d, 1H), 3.57 (broad d, 2H), 6.959 (t, 1H), 7.247 (t, 2H), 7.48 (dd, 2H), 7.57 ((d, 2H, J=8.78 Hz), 7.70 (dd, 2H), 9.3027 (s, 1H), 9.683 (s, 1H). MS (APCI$^+$, m/z): 389 [M+H]$^+$.

Step C: 1-[4-(4-{[(2S)-2-Hydroxy-3-(2-methyl-1H-indol-7-yloxy)-propylamino]-methyl}-piperidine-1-sulfonyl)-phenyl]-3-phenyl-urea Prepared from 2-methyl-4-[(2S)-oxiranylmethoxy]-indole (0.041 g, 0. 2 mmol) and 1-[(4-aminomethyl)-piperidine-1-sulfonylphenyl]-3-phenyl-urea (0.107 g, 0.28 mmol) according to the procedure used in Example 2 to give 0.060 g of the title compound as a white solid.

NMR (DMSO-$d_6$, 400 MHz): δ 1.10 (m, 2H), 1.346 (broad, 1H), 1.73 (m, 2H), 2.128 (t, 2H), 2.307 (s, 3H), 2.42 (d, 2H), 2.60 (m, 1H), 2.68 (m, 1H), 3.58 (broad d, 2H), 3.92 (m, 3H), 4.937 (broad, 1H), 6.07 (s, 1H), 6.38 (m, 1H), 6.82 (m, 2H), 6.97 (dt, 1H), 7.27 (dt, 2H), 7.44 (dd, 2H), 7.64 (q, 4H), 8.844 (s, 1H), 9.2099 (s, 1H), 11.2007 (s, 1H). MS (ESI$^+$, m/z): 592 [M+H]$^+$.

EXAMPLE 62

1-[4-(4-{[2-Hydroxy-3-(2-oxo-2,3-dihydro-1H-benzoimidazol-4-yloxy)-propylamino]-methyl}-piperidine-1-sulfonyl)-phenyl]-3-phenyl-urea

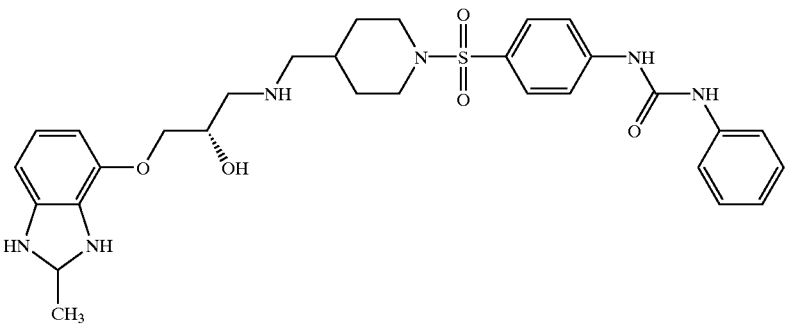

Prepared from 4-[(2S)-oxiranylmethoxy]-2-benzimidazolone (0.103 g, 0.5 mmol) and 1-[(4-aminomethyl)-piperidine-1-sulfonylphenyl]-3-phenyl-urea) .(0.230 g, 0.59 mmol) according to the procedure used in Example 2 to give 0.057 g of the title compound as a white solid.

NMR (DMSO-$d_6$, 400 MHz): δ 1.07 (m, 2H), 1.364 (broad, 1H), 1.73 (m, 2H), 2.14 (t, 2H), 2.39 (m, 2H), 2.58 (m, 1H), 2.608 (m, 1H), 3.57 (broad d, 2H), 3.86 (m, 2H), 3.96 (m, 1H), 4.89 (broad, 1H), 6.52 (m, 2H), 6.8 (m, 1H), 7.28 (t 2H), 7.45 (d, 1H), 7.64 (q, 4H), 8.843 (s, 1H), 9.2074 (s, 1H), 10.54 (s, 1H). MS (APCI$^+$, m/z): 595 [M+H]$^+$.

EXAMPLE 63

1-[4-(4-{[(2S)-2-Hydroxy-3-(4-hydroxy-phenoxy)-propylamino]-methyl}-piperidine-1-sulfonyl)-phenyl]-3-phenyl-urea

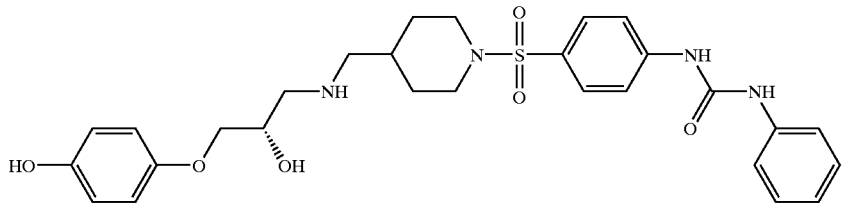

Prepared from t-butyl-[4-(2S)-oxiranylmethoxy-phenoxy]-diphenylsilane (0.121 g, 0.3 mmol) and 1-[(4-aminomethyl)-piperidine-1-sulfonylphenyl]-3-phenyl-urea (0.150 g, 0.35 mmol) according to the procedure used in Example 37 to give 0.044 g of the title compound as a white solid.

NMR (DMSO-$d_6$, 400 MHz): δ 0.8609 (m, 3H), 1.11 (m, 2H), 1.33 (broad, 1H), 1.73 (m, 2H), 2.139 (t, 2H), 2.37 (m, 2H), 2.60 (m, 1H), 3.58 (broad d, 2H), 3.75 (m, 3H), 4.90

(broad, 1H), 6.63 (dd, 2H), 6.69 (dd, 2H), 6.988 (t, 1H), 7.286 (t, 2H), 7.45 (d, 2H, J=7.69 ), 7.638 (q, 4H), 8.886 (d, 2H), 9.220 (s, 1H). MS (APCI+, m/z): 555 [M+H]+.

EXAMPLE 64

1-Cyclohexyl-3-[4-(4-{[(2S)-2-hydroxy-3-(4-hydroxy-phenoxy)-propylamino]-methyl}-piperidine-1-sulfonyl)-phenyl]-urea

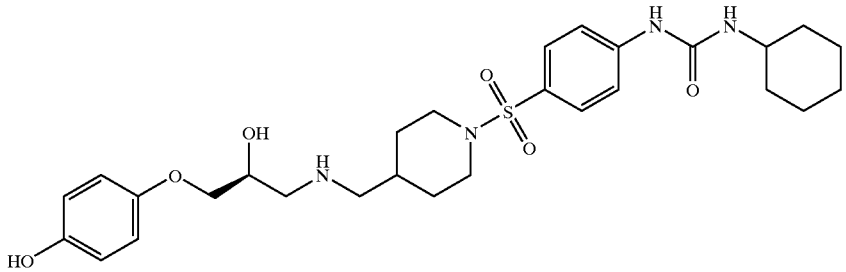

Step A: 1-[(4-Aminomethyl)-piperidine-1-sulfonylphenyl]-3-cyclohexyl-urea

A solution of 1 equivalent of [1-(4-aminobenzenesulfonyl)-piperidin-4-ylmethyl]-carbamic acid t-butyl ester (0.498 g, 1.35 mmol) in THF was added dropwise slowly to a stirred solution of triphosgene (0.133 g, 0.45 mmol) and diisopropylethyl amine (0.470 mL, 2.7 mmol) in $CH_2Cl_2$. When the addition was complete cyclohexylamine (0.155 mL, 1.35 mmol) was added in one portion and the reaction was monitored by TLC until completion. The reaction mixture was washed with 1N HCl, brine and was dried ($Na_2SO_4$). The solvent was evaporated to provide the Boc protected intermediate. A solution of the intermediate in excess TFA was stirred at ambient temperature for 15 minutes. The TFA was removed in vacuo to provide 0.610 g of product as the TFA salt.

NMR (DMSO-$d_6$, 400 MHz): δ 1.2 (m, 8H), 1.51 (m, 2H), 1.65 (m, 2H), 1.75 (m, 4H), 2.13 (dt, 2H), 2.677 (m, 2H), 3.46 (m, 1H), 3.585 (broad d, 2H), 6.36 (d, 1H), 7.57 (m, 4H), 7.679 (broad, 3H), 8.9229 (s, 1H). MS (ESI+, m/z): 395 [M+H]+.

Step B: 1-Cyclohexyl-3-[4-(4-{[(2S)-2-hydroxy-3-(4-hydroxy-phenoxy)-propylamino]-methyl}-piperidine-1-sulfonyl)-phenyl]-urea Prepared from t-butyl-[4-(2S)-oxiranylmethoxy-phenoxy]-diphenylsilane (0.404 g, 1.0 mmol), 1-[(4-aminomethyl)-piperidine-1-sulfonylphenyl]-3-cyclohexyl-urea (0.60 g, 1.15 mmol) and diisopropylethyl amine (0.2 mL, 1.15 mmol) according to the procedure used in Example 37 to give 0.067 g of the title compound as a white solid.

NMR (DMSO-$d_6$, 400 MHz): δ 1.178 (m, 6H), 1.30 (m, 2H), 1.4 (broad, 1H), 1.55 (m, 2H), 1.75 (m, 4H), 2.11 (t, 2H), 2.60 (m, 1H), 2.7 (m, 1H), 3.15 (m, 1H), 3.45 (m, 1H), 3.55 (broad d, 2H), 3.758 (m, 2H), 3.82 (m, 1H), 5.1 (broad, 1H), 6.26 (d, 1H), 6.71 (dd, 2H), 7.56 (m, 4H), 8.824 (s, 1H), 8.886 (s, 1H). MS (ESI+, m/z): 561 [M+H]+.

EXAMPLE 65

1-[4-(4-{[2-Hydroxy-3-(4-hydroxy-phenoxy)-propylamino]-methyl}-piperidine-1-sulfonyl)-phenyl]-3-isobutyl-urea

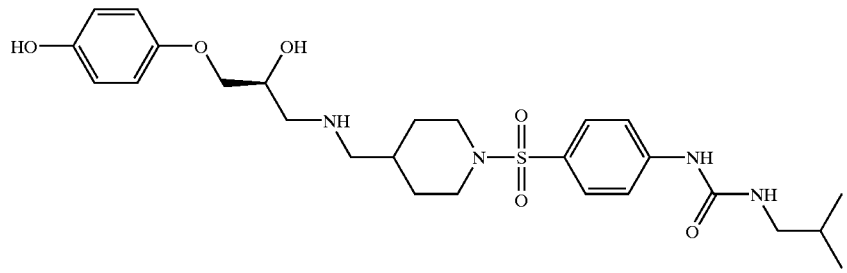

Step A: 1-[(4-Aminomethyl)-piperidine-1-sulfonylphenyl]-3-isobutyl-urea

Prepared from [1-(4-aminobenzenesulfonyl)-piperidin-4-ylmethyl]-carbamic acid t-butyl ester (0.498 g, 1.35 mmol), isobutylamine (0.135 mL, 1.35 mmol), triphosgene (0.133 g, 0.45 mmol) and diisopropylethyl amine (0.470 mL, 2.7 mmol) according to procedure used for example 64 to give 0.650 g product as the TFA salt.

NMR (DMSO-$d_6$, 400 MHz): δ 0.87 (d, 6H), 1.22 (m, 2H), 1.479 (m, 1H), 1.68 (m, 3H), 2.14 (dt, 2H), 2.679 (m, 2H), 2.92 (t, 2H), 3.60 (broad d, 2H), 6.43 (d, 1H), 7.58 (m, 4H), 7.670 (broad, 3H), 9.007 (s, 1H). MS (ESI+, m/z): 369 [M+H]+.

Step B: 1-[4-(4-{[2-Hydroxy-3-(4-hydroxy-phenoxy)-propylamino]-methyl}-piperidine-1-sulfonyl)-phenyl]-3-isobutyl-urea Prepared from t-butyl-[4-(2S)-oxiranylmethoxy-phenoxy]-diphenylsilane (0.404 g, 1.0 mmol), 1-[(4-aminomethyl)-piperidine-1-sulfonylphenyl]-3-isobutyl-urea (0.709 g, 1.47 mmol) and diisopropylethyl amine (0.2 mL, 1.15 mmol) according to the procedure used in Example 37 to give 0.066 g of the title compound as a white solid.

NMR (DMSO-$d_6$, 400 MHz): δ 0.86 (d, 6H), 1.09 (m, 2H), 1.303 (m, 1H), 1.7 (m, 3H), 2.11 (t, 2H), 2.34 (d, 2H), 2.44 (m, 1H), 2.58 (m, 1H), 2.921 (t, 1H), 3.55 (broad d, 2H), 3.758 (m, 3H), 4.816 (broad, 1H), 6.447 (t, 1H), 6.62 (d, 2H), 6.695 (dd, 2H), 7.565 (m, 4H), 8.85 (s, 1H), 9.0169 (s, 1H). MS (ESI$^+$, m/z): 535 [M+H]$^+$.

EXAMPLE 66

1-[4-(4-{[(2S)-2-Hydroxy-3-(4-hydroxy-phenoxy)-proplamino]-methyl}-piperidine-1-sulfonyl)-phenyl]-3-pyridin-2-yl-urea

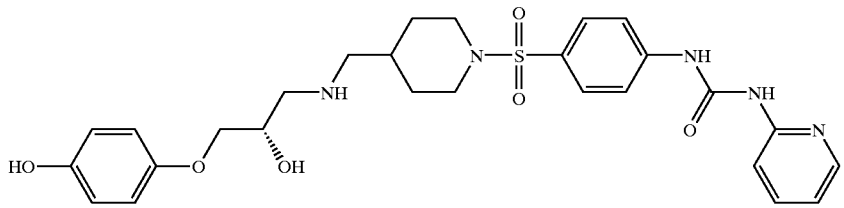

Step A: 1-[(4-Aminomethyl)-piperidine-1-sulfonylphenyl]-3-(2-pyridyl)-urea

Prepared from [1-(4-aminobenzenesulfonyl)-piperidin-4-ylmethyl]-carbamic acid t-butyl ester (1.0 g, 2.7 mmol), 2-aminopyridine (0.253 g, 2.5 mmol), triphosgene (0.267 g, 0.9 mmol) and diisopropylethyl amine (1.0 mL, 5.4 mmol) according to the procedure used for example 64 to give the TFA salt. The crude salt was triturated with sat'd NaHCO$_3$ to give 0.9 g product.

NMR (DMSO-$d_6$, 400 MHz): δ 1.15 (m, 2H), 1.3 (m, 1H), 1.69 (m, 2H), 2.147 (t, 2H), 2.36 (d, 1H), 2.777 (t, 2H), 3.57 (m, 2H), 7.02 (m, 1H), 7.53 (m, 2H), 7.64 (m, 2H), 7.77 (m, 3H), 8.28 (dd, 1H), 9.65 (broad, 1H), 10.91 (broad, 1H). MS (APCI$^+$, m/z): 369 [M+H]$^+$.

Step B: 1-[4-(4-{[(2S)-2-Hydroxy-3-(4-hydroxy-phenoxy)-propylamino]-methyl}-piperidine-1-sulfonyl)-phenyl]-3-pyridin-2-yl-urea Prepared according to a procedure described by R. Hett et al, *Tet Lett*, 38, 1125 (1997), a mixture of 1-[(4-aminomethyl)-piperidine-1-sulfonylphenyl]-3-(2-pyridyl)-urea (0.45 g, 1.15 mmol) and trimethylsilylacetamide (0.164 g, 1.25 mmol) in 5 mL of DMSO was stirred at ambient temperature for 1 hour. To the intermediate silylated amine was added t-Butyl-[4-(2S)-oxiranylmethoxy-phenoxy]-diphenylsilane (0.444 g, 1.1 mmol). The mixture was heated at 70° C. overnight and poured into H$_2$O. The solids formed (0.60 g) were collected and purified by flash chromatography (CH$_2$Cl$_2$—CH$_3$OH, 19:1). to give 0.22 g of 0-silyl protected title compound. The silyl compound was stirred overnight in 2 mL of 4N HCl in dioxane. The crude reaction mixture was basified with triethyl amine, concentrated in vacuo and purified by flash chromatography (CH$_2$C$_{12}$—CH$_3$OH, 9:1) to give 0.085 g of the title compound (m.p. 189° C., ethanol).

NMR (DMSO-$d_6$, 400 MHz): δ 1.12 (m, 2H), 1.322 (m, 1H), 1.715 (broad d, 2H), 2.214 (t, 2H), 2.36 (d, 2H), 2.61 (m, 1H), 3.58 (broad d, 2H), 3.76 (m, 3H), 4.87 (broad, 1H), 6.62 (d 2H), 6.68 (d, 2H), 7.52 (d, 1H, J=8.35, Hz), 7.64 (d, 2H, J=9.26HZ), 7.75 (m, 3H), 8.28 (sharp m, 1H), 8.857 (s, 1H), 9.5666 (s, 1H), 10.8354 (s, 1H). MS (APCI$^+$, m/z): 556 [M+H]$^+$.

EXAMPLE 67

N-{2-Hydroxy-5-[(1R)-1-hydroxy-2-({1-[4-(3-pyridin-2-yl-ureido)-benzenesulfonyl]-piperidin-4-ylmethyl}-amino)-ethyl]-phenyl}-methanesulfonamide

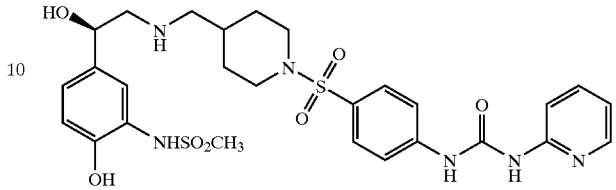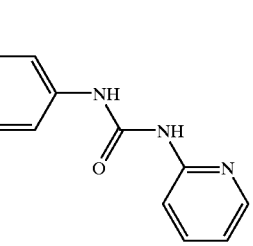

Step A: 1-[(4-{2-Pyridyl}-ureidobenzene)-sulfonyl]-piperidin-4-yl-carboxaldehyde A solution of from 1-[(4-amino)benzenesulfonylpiperidin-4ylmethyl]-dimethyl acetal (1.5 g, 4.77 mmol) and diisopropylethyl amine (0.84 mL, 4.8 mmol) in 70 mL THF was added dropwise over 1 hour to a stirred solution of triphosgene (0.47 g, 1.6 mmol) in 10 mL THF. When the addition was complete 2-aminopyridine (0.49, 4.77 mmol) and diisopropylethyl amine (0.84 mL, 4.8 mmol) was added and the solution was stirred at ambient temperature overnight. The reaction mixture was partitioned with ethyl acetate and water. The organic phase was washed with brine and dried (Na$_2$SO$_4$). Removal of solvent afforded 0.35 g of a white solid. The solid was dissolved in formic acid and gently heated until aldehyde formation was deemed complete by TLC. The acid was removed to give 0.3 g of product as a white solid.

NMR (DMSO-$d_6$, 300 MHz): δ 1.25 (s, 2H), 1.53 (m, 2H), 1.9 (broad d, 1H), 2.14 (m, 1H), 2.4 (m, 1H), 3.4 (m, 1H), 3.6 (m, 1H), 7.04 (m, 1H), 7.55 (d, 1H), 7.65 (m, 2H), 7.75 (m, 3H), 8.83 (d, 1H), 9.55 (s, 1H), 9.60 (s, 1H), 10.86 (s, 1H).

Step B: N-{2-Hydroxy-5-[(1R)-1-hydroxy-2-({1-[4-(3-pyridin-2-yl-ureido)-benzenesulfonyl]-piperidin-4-ylmethyl}-amino)-ethyl]-phenyl}-methanesulfonamide A solution of N-[5-(2-amino-1-{R}-hydroxyethyl)-2-hydroxyphenyl]-methanesulfonamide (0.209 g, 0.85 mmol), 1-[(4-{2-pyridyl}-ureidobenzene)-sulfonyl]-piperidin-4-yl-carboxaldehyde (0.33 g, 0.85 mmol), and glacial acetic acid (0.051 g, 0.85 mmol) in 5 mL methanol was stirred for 1 hour over 4A molecular sieves. In one portion sodium cyanoborohydride (0.053 g, 0.85 mmol) was added and the mixture stirred over night at ambient temperature. The sieves were filtered and the filtrate was preabsorbed on silica gel. The solids were purified by flash chromatography (CH$_2$Cl$_2$—CH$_3$OH, 19:1) to give 0.075 g of product as an off white solid.

NMR (DMSO-$d_6$, 400 MHz): δ 1.10 (m, 2H), 1.31 (m, 1H), 1.71 (broad d, 2H), 2.16 (m, 2H), 2.37 (d, 1H), 3.585 (broad d, 2H), 4.44 (t, 1H), 6.77 (d, 1H), 6.95 (dd, 1H), 7.03 (dt, 2H), 7.12 (s, 2H), 7.53 (d, 1H), 7.65 (d, 2H, J=8.78 Hz), 7.74 (d, 2H, J=9.0 Hz), 8.29 (dd, 1H), 9.5566 (s, 1H), 108249 (s, 1H). MS (APCI$^-$, m/z): 617 [M−H]$^-$.

EXAMPLE 68

N-{5-[1-Hydroxy-2-({1-[4-(3-pyridin-2-yl-ureido)-benzenesulfonyl]-piperidin-4-ylmethyl}-amino)-ethyl]-1H-indol-7-yl}-methanesulfonamide

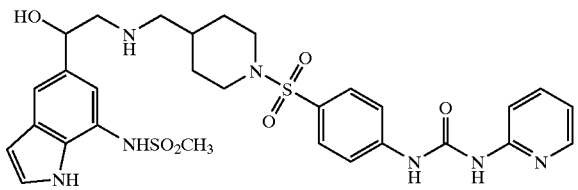

Prepared from 2-(7-methanesulfonamido-1H-indol-5-yl)-2-hydroxy-ethyl amine (0.06 g, 0.22 mmol), 1-[(4-{2-pyridyl}-ureidobenzene)-sulfonyl]-piperidin-4-yl-carboxaldehyde (0.108 g, 0.28 mmol), glacial acetic acid (0.017 g, 0.28 mmol) and sodium cyanoborohydride (0.018 g, 0.28 mmol) according to the procedure used in example 67 (Step B) to give 0.075 g of the title compound as a white solid as the dihydrochloride salt.

NMR (DMSO-$d_6$, 400 MHz): δ 1.07 (m, 2H), 1.721 (m, 1H), 1.819 (broad t, 2H), 2.208 (t, 2H) 2.86 (m, 2H), 2.965 (s, 3H), 3.079 (m, 1H), 3.6 (broad d, 2H), 4.96 (d, 1H), 6.43 (m, 1H), 7.06 (m, 2H), 7.36 (dd, 2H), 7.58 (d, 1H), 7.67 (d, 2H), 7.78 (m, 3H), 8.29 (m, 1H), 8.6 (broad d, 2H), 9.4144 (s, 1H), 9.7532 (s, 1H), 10.9441 (s, 1H). MS (APCI$^-$, m/z): 640 [M−H]$^-$.

EXAMPLE 69

1-[4-(4-{[(2S)-2-Hydroxy-3-(4-hydroxy-phenoxy)-propylamino]-methyl}-piperidine-1-sulfonyl)-phenyl]-3-octyl-urea

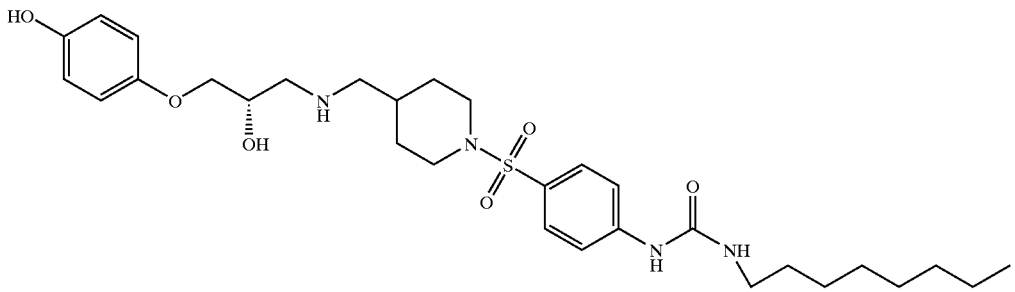

Step A: 1-[(4-Carboxamido)-piperidine-1-sulfonylphenyl]-3-octyl-urea

A solution of (4-carboxamido-1-piperidinyl)-4-aminobenzenesulfonamide (1.5 g, 5.3 mmol) and octylisocyanate (1.88 mL, 10.6 mmol) was stirred at ambient temperature in dioxane for 48 hours. The reaction mixture was preabsorbed on silica gel and purified by flash chromatography (CH$_2$Cl$_2$—CH$_3$OH, 19:1) to give 1.0 g of product as a white solid.

NMR (DMSO-$d_6$, 400 MHz): δ 0.830 (m, 3H), 1.23 (s, 10H), 1.40 (m, 2H), 1.50 (m, 2H), 1.72 (m, 2H), 1.9975 (m, 1H), 2.20 (dt, 2H), 3.05 (q, 2H), 3.48 (broad d, 2H), 6.273 (t, 1H), 6.74 (s, 1H), 7.151 (s, 1H), 7.55 (q, 4H), 8.9036 (s, 1H). MS (ESI$^+$, m/z): 439 [M+H]$^+$.

Step B: 1-[(4-Aminomethyl)-piperidine-1-sulfonylphenyl]-3-octyl-urea

Prepared from 1-[(4-carboxamido)-piperidine-1-sulfonylphenyl]-3-octyl-urea (0.950 g, 3.36 mmol) and BH$_3$-THF (5 mL, 1.0 M solution in THF). according to the procedure used in Example 31 (Step B) to give 0.158 g product as a waxy solid.

NMR (DMSO-$d_6$, 400 MHz): δ 0.824 (m, 3H), 1.099 (m, 2H), 1.2217 (s, 10H), 1.386 (m, 2H), 1.69 (broad d, 2H), 2.093 (t, 2H), 2.37 (broad, 2H), 3.04 (m, 2H), 3.54 (broad d, 2H), 6.56 (t, 1H), 7.50 (d, 2H), 7.59 (d, 2H), 9.1726 (s, 1H). MS (ESI$^+$, m/z): 425 [M+H]$^+$.

Step C: 1-[4-(4-{[(2S)-2-Hydroxy-3-(4-hydroxy-phenoxy)-propylamino]-methyl}-piperidine-1-sulfonyl)-phenyl]-3-octyl-urea Prepared from t-butyl-[4-(2S)-oxiranylmethoxy-phenoxy]-diphenylsilane (0.202 g, 0.5 mmol) and 1-[(4-aminomethyl)-piperidine-1-sulfonylphenyl]-3-octyl-urea (0.150 g, 0.35 mmol) according to the procedure used in Example 37 to give 0.080 g of the title compound as a white solid.

NMR (DMSO-$d_6$, 400 MHz): δ 0.8609 (m, 3H), 1.14 (m, 2H), 1.2745 (s, 12H), 1.41 (m, 2H), 1.73 (broad d, 2H), 2.12 (t, 2H), 2.40 (m, 2H), 2.61 (m, 1H), 3.08 (m, 2H), 3.57 (broad d, 2H), 3.38 (m, 3H), 4.933 (broad, 1H), 6.321 (t, 1H), 6.64 (dd, 2H), 6.66 (dd, 2H), 7.58 (q, 4H), 8.8833 (s, 1H), 8.9536 (s, 1H). MS (APCI$^+$, m/z): 591 [M+H]$^+$.

EXAMPLE 70

1-[4-(4-{[(2S)-2-Hydroxy-3-(2-oxo-2,3-dihydro-1H-indol-4-yloxy)-propylamino]-methyl}-piperidine-1-sulfonyl)-phenyl]-3-octyl-urea

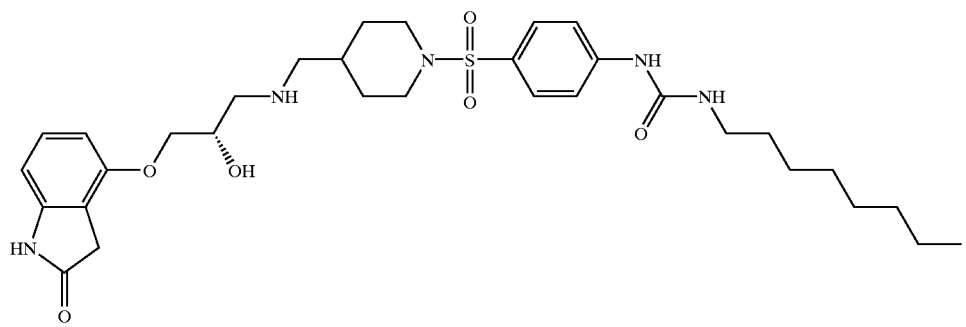

Prepared from 4-[(2S)-oxiranylmethoxy]-2-oxindole (0.205 g, 1.0 mmol) and 1-[(4-aminomethyl)-piperidine-1-sulfonylphenyl]-3-octyl-urea (0.840 g, 2.0 mmol) according to the procedure used in Example 2 to give 0.030 g of the title compound as a rose colored solid.

NMR (DMSO-d$_6$, 400 MHz): δ 0.844 (t, 3H), 1.103 (m, 2H), 1.25 (s, 10H), 1.41 (m, 3H), 1.72 (broad d, 2H), 2.118 (t, 2H), 2.41 (m, 2H), 2.51 (m, 1H), 2.634 (m, 1H), 3.06 (m, 2H), 3.56 (broad d, 2H), 3.9 (m, 3H), 4.954 (broad, 1H), 6.290 (t, 1H), 6.43 (d, 1H, J=7.46 Hz), 6.55 (d, 1H, J=8.1 Hz)), 7.08 (t, 1H), 7.56 (q, 4H), 8.9142 (s, 1H), 10.2978 (s, 1H). MS (ESI$^+$, m/z): 630 [M+H]$^+$.

EXAMPLE 71

4-[2-Hydroxy-3-({1-[4-(3-octyl-ureide)-benzenesulfonyl]-piperidin-4-ylmethyl}-amino)-propoxy]-1H-indole-2-carboxylic Acid Amide

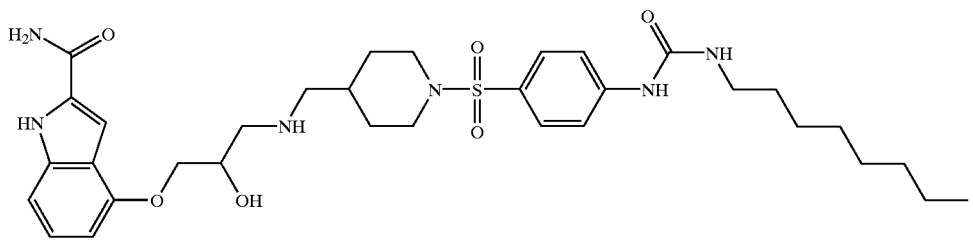

A mixture of 1-[(4-aminomethyl)-piperidine-1-sulfonylphenyl]-3-octyl-urea (0.212 g, 0.5 mmol) and trimethylsilylacetamide (0.072 g, 0.5 mmol) in 5 mL of DMSO was stirred at ambient temperature for 1 hour. To the intermediate silylated amine was added 4-(-2-Oxiranylmethoxy)-2-indolecarboxamide (0.221 g, 0.5 mmol, Aldrich). The mixture was heated at 70° C. overnight and poured into water. The solids were collected and purified by flash chromatography (CH$_2$Cl$_2$—CH$_3$OH, 19:1) to give the title compound. The product was treated with excess 1N HCl, the solids formed were collected and dried to give 0.070 g of the title compound as the HCl salt.

NMR (DMSO-d$_6$, 400 MHz): δ 0.8406 (t, 3H), 1.247 (s, 13H), 1.4075 (m, 2H), 1.56 (m, 1H), 1.77 (broad t, 2H), 2.131 (t, 2H), 2.69 (m, 2H), 2.86 (broad, 1H), 3.0 (broad, 1H), 3.06 (m, 2H), 3.57 (broad d, 2H), 4.04 (m, 2H), 4.125 (m, 1H), 5.52 (broad, 1H), 6.405 (t, 1H), 6.47 (d, 1H), J=7.68 Hz), 6.98 (m, 1H), 7.049 (m, 1H), 7.16 (s, 1H), 7.26 (broad s, 1H), 7.57 (q, 4H), 7.889 (broad s, 1H), 9.0998 (s, 1H), 11.508 (s, 1H). MS (APCI$^+$, m/z): 657 [M+H]$^+$.

EXAMPLE 72

1-[4-(4-{[(2S)-2-Hydroxy-3-(1H-indol-5-yloxy)-propylamino]-methyl}-piperidine-1-sulfonyl)-phenyl]-3-octyl-urea

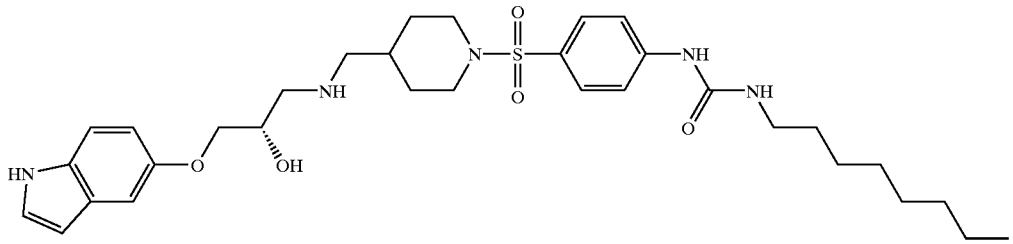

Prepared from 5[-(2S)-oxiranylmethoxy]-1H-indole (0.189 g, 1.0 mmol), 1-[(4-aminomethyl)-piperidine-1-sulfonylphenyl]-3-octyl-urea (0.466 g, 1.1 mmol) and trimethylsilylacetamide (0.157 g, 1.2 mmol) according to the procedure used for example 71 to give 287 mg of the title compound.

NMR (DMSO-d$_6$, 400 MHz): δ 0.8444 (t, 3H), 1.135 (m, 2H), 1.25 (s, 10H), 1.40 (m, 3H), 1.73 (broad d, 2H), 2.12 (t, 2H), 2.41 (d, 2H), 2.56 (m, 1H0, 2.67 (m, 1H), 3.0 (broad, 1H), 3.06 (m, 2H), 3.56 (broad d, 2H), 3.86 (m, 3H), 4.94 (broad, 1H), 6.29 (m, 2H), 6.69 (dd, 1H), (dd, 1H), 6.99 (sharp m, 1H), 7.24 (m, 2H), 7.56 (q, 4H), 8.9355 (s, 1H), 10.867 (s, 1H). MS (APCI$^+$, m/z): 614 [M+H]$^+$.

EXAMPLE 73

(R)-N-{2-Hydroxy-5-[1-hydroxy-2-({1-[4-(3-octyl-ureido)-benzenesulfonyl]-piperidin-4-ylmethyl}-amino)-ethyl]-phenyl}-methanesulfonamide Step D: 1-[(4-Formylpiperidine-1-sulfonylphenyl]-3-octyl-urea A solution of 1-[(4-hydroxymethyl)-piperidine-1-sulfonylphenyl]-3-octyl-urea (1.1 g, 2.6 mmol) and pyridinium chlorochromate (0.836 g, 4.0 mmol) in methylene stirred for three hours at ambient temperature. The reaction was diluted with ether and filtered through Celite. The solvent was evaporated and adsorbed onto silica gel. The compound was purified with flash chromatography (elute:chloroform/methanol) to give 0.700 g (1.68 mmol).

Step E: (R)-N-{2-Hydroxy-5-[1-hydroxy-2-({1-[4-(3-octyl-ureido)-benzenesulfonyl]-piperidin-4-ylmethyl}-amino)-ethyl]-phenyl}-methanesulfonamide A solution of N-[5-(2-amino-1-{R}-hydroxyethyl)-2-hydroxyphenyl]-methane-sulfonamide (0.395 g, 1.6 mmol),

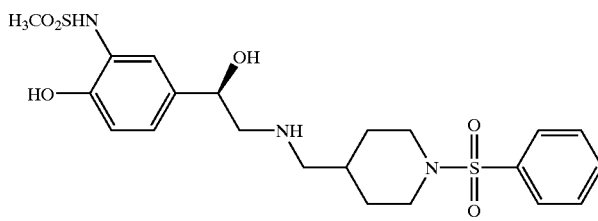
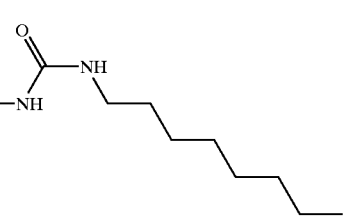

Step A: N-Octyl-N'-phenylurea

A solution of octyl amine (22.79 g, 176 mmol) and phenyl isocyanate (21 g, 176 mmol) in THF (200 ml) at 0° C. was stirred for 2 hours. The solvent was evaporated in vacuo and the residue was triturated with hexane to give 43 g of final product (173 mmol).

Step B: 4-{[(Octylamino)carbonyl]amino}benzenesulfonyl Chloride

N-octyl-N'-phenylurea (10 g, 215 mmol) was dissolved in chlorosulfonic acid 925 g and stirred for 14 hours at ambient temperature. The reaction was poured into ice and extracted with ethyl acetate. The organic layer was washed with cold, dilute aqueous sodium bicarbonate, then dried (Na$_2$SO$_4$). The solvent was evaporated in vacuo to give the product as a white solid (11.46 g, 33 mmol).

Step C: 1-[(4-Hydroxymethyl)-piperidine-1-sulfonylphenyl]-3-octyl-urea

4-{[(octylamino)carbonyl]amino}benzenesulfonyl chloride 11.44 g (33 mmol) was added in two portions to a stirred solution of 4-piperidinylmethanol 3.4 g (33 mmol) in 50 ml acetone with 50 ml of 1N aqueous sodium hydroxide. After 1 hour the reaction was diluted with water and filtered. The solid was washed with water and hexane, and dried in a vacuum oven at 60° C. for 3 hours. The reaction material was then put into a round bottom flask and evaporated with acetone and ethyl acetate. The solid was passed through a pad of silica gel with ethyl acetate. chloride (5 mL) was 1-[(4-formylpiperidine-1-sulfonylphenyl]-3-octyl-urea (0.68 g, 1.6 mmol) and glacial acetic acid (0.10 g, 1.66 mmol) in 5 mL of methanol-THF (4:1, v/v) was stirred for 1 hour over 4A molecular sieves. In one portion sodium cyanoborohydride (0.10 g, 1.61 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 20:1). to give the product (0.37 g).

NMR (DMSO-d$_6$, 400 MHz): δ 1.14–1.26 (m, 13), 1.40–1.45 (m, 2H), 1.72–1.79 (m, 2H), 2.18 (m, 2H), 3.56–3.58 (m, 2H), 4.65–4.67 (s, 1H), 6.28–6.31 (t, 1H), 6.83–6.85 (d, 1H), 6.99–7.02 (d, 1H), 7.18–7.19 (s, 1H), 7.55–7.61 (m, 4H), 8.92 (s, 1H). MS (APCI$^+$, m/z): 654 [M+H]$^+$.

EXAMPLE 74

1-[4-(4-{[(2S)-2-Hydroxy-3-(8-hydroxy-2-oxo-1,2,3,4-tetrahydro-quinolin-5-yloxy)-propylamino]-methyl}-piperidine-1-sulfonyl)-phenyl]-3-octyl-urea

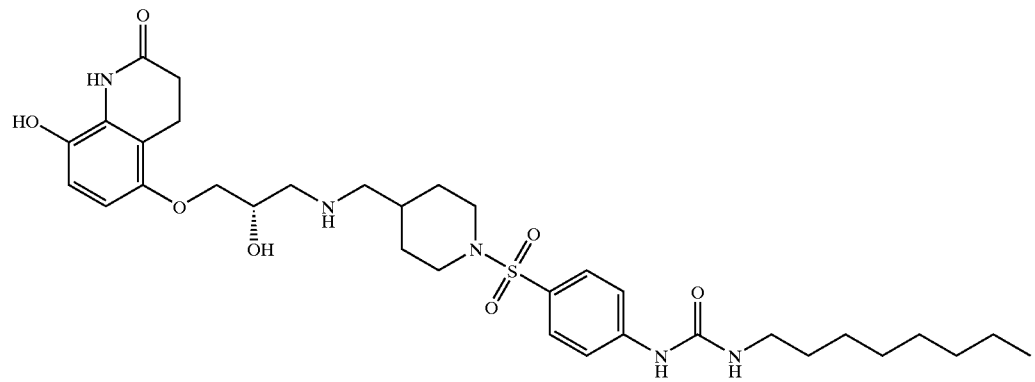

A solution of 8-(benzyloxy)-5-[(2S)oxiranylmethoxy]-3,4-dihydro-2(1H)-quinolinone (0.18 g, 0.55 mmol) and 1-[(4-aminomethyl)-piperidine-1-sulfonylphenyl]-3-octyl-urea (0.235 g, 0.55 mmol) in 40 mL ethanol was heated at 60° C.

for 86 hours. The intermediate benzyl protected product was isolated by flash chromatography (CHCl₃—CH₃OH, 10:1) to give 0.1 g product. The benzyl group was removed by reflux in ethanol and cyclohexene over 10% palladium on carbon for 1 hour. The catalyst was filtered and the solvent removed in vacuo. Flash chromatography (CHCl₃—CH₃OH, 10:1) afforded 0.045 g of the title compound as a white solid.

NMR (DMSO-d₆, 400 MHz): δ 1.06–1.13 (m, 3H), 1.38–1.44 (m, 2H), 1.25–1.26 (m, 10H), 1.71–1.77 (m, 2H), 2.34–2.39 (m, 2H), 2.73–2.80 (m, 2H), 3.52–3.58 (m, 2H), 3.73–3.85 (m, 3H), 6.28–6.31 (m, 1H), 6.40–6.43 (m, 1H), 7.53–7.59 (q, 4H), 8.66–8.70 (broad s, 1H), 8.89–9.06 (broad s, 1H), 9.12–9.20 (broad s, 1H), MS (ESI⁺, m/z): 660 [M+H]⁺.

EXAMPLE 75

1-[4-(4-1{[(2S)-2-Hydroxy-3-(4-hydroxy-phenoxy)-propylamino]-methyl}-piperidine-1-sulfonyl)-phenyl]-3-(3-thiophen-2-yl-propyl)-urea Step B: [1-(4-Aminomethyl-piperidine-1-sulfonyl)-phenyl]-3-(3-thiophen-2-yl-propyl)-urea A solution of [1-({4-[({[3-(2-thienyl)propyl]amino{carbonyl)amino]phenyl}-sulfonyl)-4-piperidinyl]methylcarbamic acid t-butyl ester (0.55 g, 0.8 mmol) was heated as a solution in formic acid at 40° C. for 1 hour. Concentrated in vacuo to provide the title compound as a formate salt. Used directly in the following prep.

Step C: 1-[4-(4-4-{[(2S)-2-Hydroxy-3-(4-hydroxy-phenoxy)-propylamino]-methyl}-piperidine-1-sulfonyl)-phenyl]-3-(3-thiophen-2-yl-propyl)-urea Prepared from t-butyl-[4-(2S)-oxiranylmethoxyphenoxy]-diphenylsilane (0.32 g, 0.79 mmol), 1-[(4-aminomethyl)-piperidine-1-sulfonylphenyl]-3-[3-(2-thienylpropyl)]-urea formate salt (0.54 g, 0.79 mmol) and diisopropylethyl amine (0.24 mL) according to the procedure used for example 37 to give 0.95 g of the title compound as a white solid.

NMR (DMSO-d₆, 400 MHz): δ 1.10–1.14 (m, 2H) 1.72–1.79 (m, 4H), 2.08–2.14 (m, 2H), 3.11–3.16 (m, 2H), 3.54–3.57 (m, 2H), 3.76–3.81 (m, 3H), 6.41–6.44 (m, 1H),

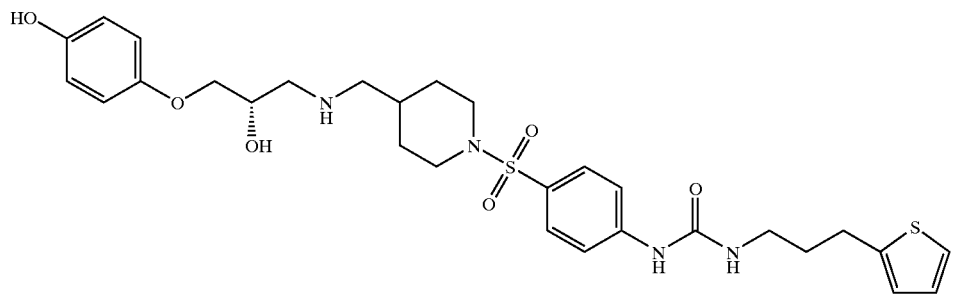

Step A: [1-({4-[({[3-(2-Thienyl)propyl]amino}-carbonyl)amino]phenyl}sulfonyl)-4-piperidinyl]methylcarbamic Acid t-Butyl Ester A solution of 4-(2-thienyl)butanoic acid (1.35 g, 7.90 mmol), [1-(4-aminobenzen-esulfonyl)-piperidin-4-ylmethyl]-carbamic acid t-butyl ester (2.90 g, 7.90 mmol) and carbonyldiimidazole (1.27 g, 7.9 mmol) in methylene chloride was stirred overnight at ambient temperature. The reaction mixture was washed with 1N NaOH, 1N HCl, and brine. The organic phase was dried (Na₂SO₄) and concentrated in vacuo to give near quantitative yield of the title compound.

MS (ESI⁺, m/z): 514 [M+H]⁺.

6.61–6.65 (m, 2H), 6.69–6.73 (m, 2H), 6.86–6.87 (m, 1H), 6.92–6.94 (m, 1H), 7.30–7.31 (m, 1H), 7.54–7.61 (m, 4H), 8.87–8.88 (s, 1H), 8.98–9.86 (s, 1H). MS (APCI⁺, m/z): 603 [M+H]⁺.

EXAMPLE 76

1-(2,5-Difluoro-benzyl)-3-[4-(4-{[(2S)-2-hydroxy-3-(1H-indol-5-yloxy)-propylamino]-methyl}-piperidine-1-sulfonyl)-phenyl]-urea

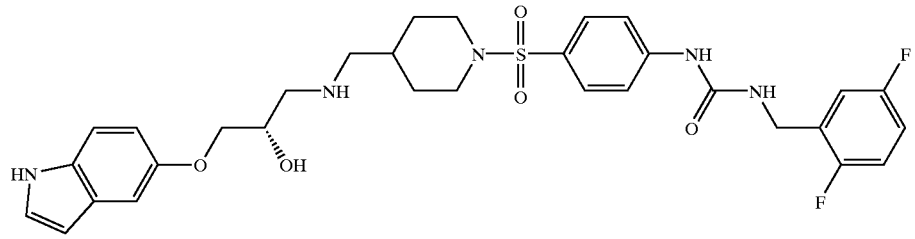

Step A: 1-[(4-Aminomethyl)-piperidine-1-sulfonylphenyl]-3-(2,5-difluorobenzyl)-urea Prepared from [1-(4-aminobenzenesulfonyl)-piperidin-4-ylmethyl]-carbamic acid t-butyl ester (4.0 g, 10.8 mmol), 2,5-difluorobenzyl amine (1.26 mL, 10.8 mmol), triphosgene (1.07 g, 3.6 mmol) and diisopropylethyl amine (3.84 mL, 22 mmol) according to the procedure used for 64 (Step A) to give the product as the TFA salt. The free base was isolated by trituration of the salt with sat'd NaHCO$_3$. The solids were collected washed with water and dried to give 3.0 g of the title compound.

NMR (DMSO-d$_6$, 300 MHz): δ 1.1 (m, 2H), 1.25 (m, 1H), 1.62 (m, 2H), 2.14 (t, 2H), 2.35 (m, 1H), 2.85 (t, 1H), 3.58 (broad d, 2H), 7.18 (m, 3H), 7.58 (m, 4H), 9.25 (s, 1H). MS (ESI$^+$, m/z): 439 [M+H]$^+$.

Step B: 1-(2,5-Difluoro-benzyl)-3-[4-(4-{[(2S)-2-hydroxy-3-(1H-indol-5-yloxy)-propylamino]-methyl}-piperidine-1-sulfonyl)-phenyl]-urea Prepared from 5-[(2S)-oxiranylmethoxy]-indole (0.104 g, 0.55 mmol), 1-[(4-aminomethyl)-piperidine-1-sulfonylphenyl]-3-(2,5-difluorobenzyl)-urea (0.265 g, 0.6 mmol) and trimethylsipylacetamide (0.085 g, 0.65 mmol) according to the procedure used for example 71 to give 0.105 g of the title compound as a white solid.

NMR (DMSO-d$_6$, 400 MHz): δ 1.105 (m, 2H), 1.42 (broad, 1H), 1.74 (m, 2H), 2.122 (t, 2H), 2.65 (m, 1H), 2.78 (m, 1H), 3.56 (broad d, 2H), 3.89 (m, 3H), 4.33 (d, 2H), 5.17 (broad, 1H), 6.292 (sharp m, 1H), 6.70 (dd, 1H), 6.93 (t, 1H), 7.0 (s, 1H), 7.15 (m 2H), 7.21 (m, 3H), 7.59 (q, 4H), 9.2739 (s, 1H), 10.888 (s, 1H). MS (APCI$^+$, m/z): 628 [M+H]$^+$.

EXAMPLE 77

1-(2,5-Difluoro-benzyl)-3-[4-(4-{[(2S)-2-hydroxy-3-(4-hydroxy-phenoxy)-propylamino]-methyl}-piperidine-1-sulfonyl)-phenyl]-urea

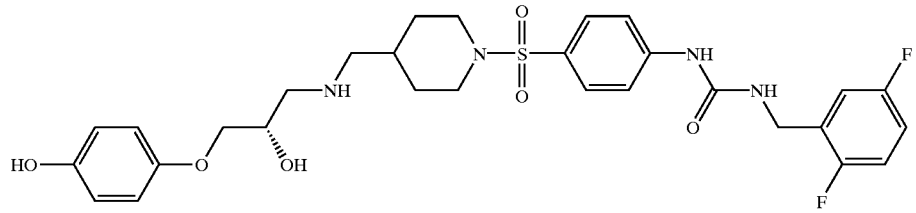

N-(4-{[4-(aminomethyl)-1-piperidinyl]sulfonyl}phenyl)-N'-(2,5-difluorobenzyl)urea formate (0.433 g, 1.00 mmol) was reacted with t-butyl-(4-oxiranylmethoxy-phenoxy)-diphenyl-silane (0.404 g, 1.00 mmol) according to example 37 to give the title compound (0.084 g, 0.13 mmol).

$^1$H NMR (DMSO-d$_6$, 400 MHz): δ 1.12 (q, 2H), 1.30 (m, 1H), 1.71 (d, 2H) 2.11 (t, 2H), 2.38 (m, 2H), 2.49 (s, 1H), 2.59 (m, 1H), 3.54 (d, 2H), 3.75 (m, 3H), 4.33 (d, 2H), 4.93 (s, 1H), 6.65 (q, 4H), 6.89 (t, 1H), 7.20 (m, 3H), 7.57 (m, 4H), 8.86 (s, 1H), 9.20 (s, 1H). MS (APCI$^+$, m/z): 605 [M+H]$^+$.

EXAMPLE 78

1-(2,5-Difluoro-benzyl)-3-[4-(4-{[(2S)-3-(3-fluoro-4-hydroxy-phenoxy)-2-hydroxy-propylamino]-methyl}-piperidine-1-sulfonyl)-phenyl]-urea

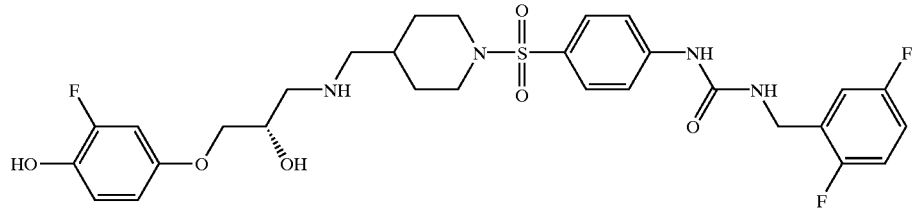

N-(4-{[4-(aminomethyl)-1-piperidinyl]sulfonyl}phenyl)-N'-(2,5-difluoro-benzyl)urea formate (0.433 g, 1.00 mmol) was reacted with t-butyl(diphenyl)silyl 2-fluoro-4-[(2S) oxiranylmethoxy]phenyl ether (0.422 g, 1.00 mmol) according to example 37 to give the title compound (0.1 g, 0.16 mmol).

$^1$H NMR (DMSO-d$_6$, 400 MHz): δ 1.12 (q, 2H), 1.29 (m, 1H), 1.72 (d, 2H) 2.09 (t, 2H), 2.34 (d, 2H), 2.49 (s, 1H), 3.57 (d, 2H), 3.76 (m, 3H), 4.33 (d, 2H), 4.89 (s, 1H), 6.54 (dt, 1H), 6.69 (t, 1H), 6.75 (dd, 1H), 6.80 (t, 1H), 6.87 (t, 1H), 7.14 (m, 2H), 7.24 (m, 1H), 7.60 (m, 4H), 9.17 (s, 1H). MS (ESI$^+$, m/z): 623 [M+H]$^+$.

EXAMPLE 79

N-(5-{(2S)-3-[(1-{4-[3-(2,5-Difluoro-benzyl)-ureido]-benzenesulfonyl}-piperidin-4-ylmethyl)-amino]-2-hydroxy-propoxy}-2-hydroxy-phenyl)-methanesulfonamide

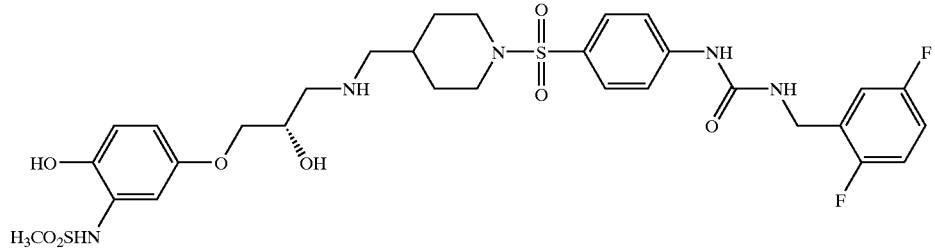

N-(4-{[4-(aminomethyl)-1-piperidinyl]sulfonyl}phenyl)-N'-(2,5-difluorobenzyl)urea formate (0.285 g, 0.535 mmol) was reacted with 2-{[t-butyl(diphenyl)silyl]oxy}-5-[(2S) oxiranylmethoxy]phenyl(methylsulfonyl)carbamate (0.322 g, 0.535 mmol) according to example 37 to give the title compound (0.03 g, 0.04 mmol).

$^1$H NMR (DMSO-d$_6$, 400 MHz): δ 1.15 (q, 2H), 1.34 (m, 1H), 1.72 (d, 2H), 2.12 (t, 2H), 2.12 (t, 2H), 2.42 (m, 2H), 2.49 (s, 1H), 2.59 (m, 1H), 2.91 (s, 3H), 3.54 (d, 2H), 3.75 (m, 3H), 4.33 (d, 2H), 6.58 (dd, 1H), 6.75 (d, 2H), 6.88 (t, 1H), 7.20 (m, 3H), 7.60 (m, 4H), 9.19 (s, 1H). MS (ESI$^-$, m/z): 696 [M−H]$^-$.

EXAMPLE 80

1-[4-(4-{[(2S)-3-(2-Chloro-4-hydroxy-phenoxy)-2-hydroxy-propylamino]-methyl}-piperidine-1-sulfonyl}-phenyl]-3-(2,5-difluoro-benzyl)-urea N-(4-{[4-(aminomethyl)-1-piperidinyl]sulfonyl}phenyl)-N'-(2,5-difluorobenzyl)urea formate (0.827 g, 1.72 mmol) was reacted with t-butyl(diphenyl)silyl 3-chloro-4-[(2S) oxiranylmethoxy]phenyl ether (0.516 9,1.17 mmol) according to example 37 to give the title compound (0.15 g, 0.23 mmol).

$^1$H NMR (DMSO-d$_6$, 400 MHz): δ 1.12 (q, 2H), 1.33 (m, 1H), 1.69 (d, 2H) 2.08 (t, 2H), 2.40 (m, 2H), 2.49 (s, 1H), 2.56 (m, 1H), 3.53 (d, 2H), 3.81 (s, 1H), 4.33 (d, 2H), 4.91 (s, 1H), 6.62 (dd, 1H), 6.79 (s, 1H), 6.92 (m, 2H) 6.89 (t, 1H), 7.20 (m, 3H), 7.59 (m, 4H), 9.19 (s, 1H), 9.29 (s, 1H). MS (ESI$^+$, m/z): 639 [M+H]$^+$.

EXAMPLE 81

N-{5-[(1R)-2-({[1-({4-[({[2-(2,5-difluorophenyl)ethyl]amino]-carbonyl)amino}-phenyl}sulfonyl)piperidin-4-yl]methyl}amino)-1-hydroxyethyl]-2-hydroxyphenyl}-methanesulfonamide

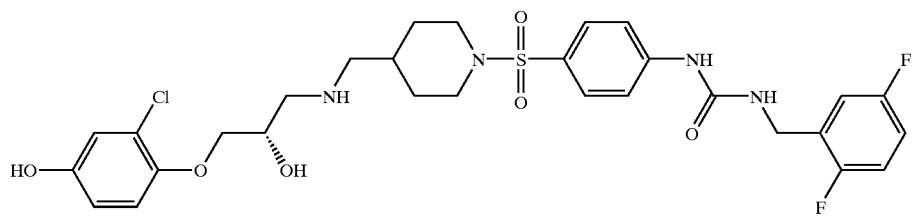

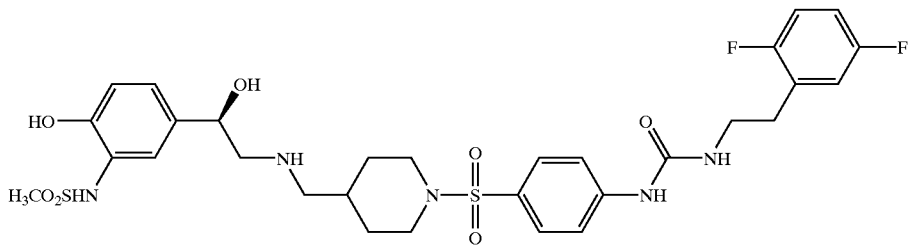

Step A: 1-[2-(2,5-Difluoro-phenyl)-ethyl]-3-[4-(4-dimethoxymethyl-piperidine-1-sulfonyl)-phenyl]-urea To a solution of (2,6-difluorobenzyl) propionic acid (0.591 g, 3.18 mmol), and triethylamine (0.488 mL, 3.5 mmol) in dry toluene (34 mL) is added diphenylphosphoryl azide (0.822 mL, 4 mmol). The solution is stirred at room temperature for 30 minutes, then heated to 85° C. for 1 hour. At 85° C., [1-(4-amino)benzenesulfonylpiperidin-4ylmethyl]dimethyl acetal (1 g, 3.18 mmol) is added. The reaction is allowed to continue heating until complete by TLC. The solvent was removed in vacuo, and the residue partitioned with ethyl acetate and an aqueous solution of potassium hydrogen sulfate (10%). The organic phase was washed with aqueous sodium bicarbonate solution (5%), brine, dried with sodium sulfate. The solvent was removed in vacuo and the crude residue was purified by flash chromatography ($CH_3Cl$, $CH_3OH$, 100:1) to give 0.170 g of the title compound.

NMR (DMSO-$d_6$, 400 MHz): δ 1.21–1.22 (m, 2H), 1.63–1.66 (d, 2H), 2.08–2.09 (t, 2H), 2.77–2.80 (t, 2H), 3.56–3.59 (m, 2H), 6.37 (t, 1H), 7.09–7.21 (m, 3H), 7.53–7.59 (m, 4H), 9.00 (bs, 1H). MS (APCI$^+$, m/z): 498 [M+H]$^+$.

Step B: 1-[2-(2,5-Difluoro-phenyl)-ethyl]-3-[4-(4-formyl-piperidine-1-sulfonyl)-phenyl]-urea A solution of 1-[2-(2,5-difluoro-phenyl)-ethyl]-3-[4-(4-dimethoxymethyl-piperidine-1-sulfonyl)-phenyl]-urea (0.170 g, 0.3 mmol) in 2 mL TFA was stirred for 15 minutes at ambient temperature. The excess TFA was removed in vacuo and the residue partitioned between ethyl acetate and water. The organic base was dried ($Na_2SO_4$) and the solvent evaporated to provide the title compound which was used directly in the next step.

Step C: N-{5-[(1R)-2-({[1-({4-[({[2-(2,5- Difluorophenyl) ethyl]amino}-carbonyl)-amino]-phenyl}-sulfonyl) piperidin-4-yl]methyl}amino)-1-hydroxyethyl]-2-hydroxyphenyl}methanesulfonamide The title compound was prepared from 1-[2-(2,5-difluoro-phenyl)-ethyl]-3-[4-(4-formyl-piperidine-1-sulfonyl)-phenyl]-urea (0.3 mmol) according to the procedure used in example 67 (Step B) to give the final product (0.0379, 6.5%).

NMR (DMSO-$d_6$, 400 MHz): δ 1.17–1.20 (m, 2H), 1.73–1.74 (m, 2H), 2.11–2.17 (m, 2H), 2.11–2.17 (m, 2H), 3.56–3.58 (m, 2H), 6.37–6.89 (m, 1H), 6.98–7.00 (m, 1H), 7.05–7.20 (m, 2H), 7.21–7.24 (m, 3H), 7.54–7.60 (m, 4H), 9.02 (broad s, 1H). MS (ESI$^+$, m/z): 682 [M+H]$^+$.

EXAMPLE 82

1-[2-(2,4-Difluoro-phenyl)-ethyl]-3-[4-(4-{[(2S)-2-hydroxy-3-(4-hydroxy-phenoxy)-propylamino]-methyl}-piperidine-1-sulfonyl)-phenyl]-urea

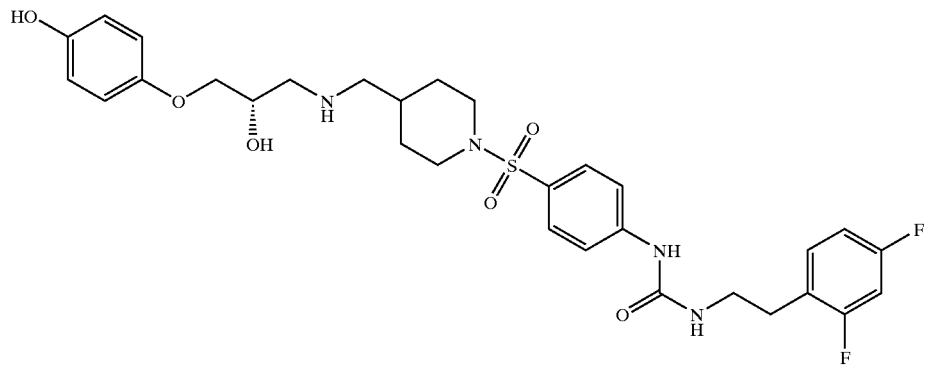

Prepared from t-butyl-[4-(2S)-oxiranylmethoxyphenoxy]-diphenylsilane (0.173 g,. 0.43 mmol), and 1-[(4-aminomethyl)-piperidine-1-sulfonylphenyl]-3-[3-(2,2-difluorophenethyl-]urea (0.213 g, 0.45 mmol) according to the procedure used for example 37 to give 0.68 g of the title compound as a white solid.

NMR (DMSO-$d_6$, 400 MHz): δ 3.54–3.56 (m, 2H), 3.69–3.80 (m, 3H), 6.33–6.36 (m, 1H), 6.61–6.72 (m, 4H), 7.00–7.05 (m, 1H), 7.15–7.21 (m, 1H), 7.32–7.38 (m, 1H), 7.53–7.60 (m, 4H), 8.84 (s, 1H), 8.98 (s, 1H). MS (APCI$^+$, m/z): 619 [M+H]$^+$.

EXAMPLE 83

1-(2,6-Difluoro-phenyl)-3-[4-(4-{[(2S)-2-hydroxy-3-(4-hydroxy-phenoxy)-propylamino]-methyl}-piperidine-1-sulfonyl)-phenyl-urea

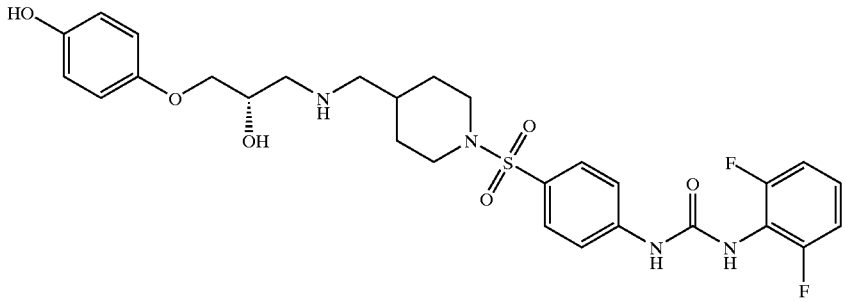

Step A: (1-{4-[3-(2,6-Difluoro-phenyl)-ureido]-benzenesulfonyl}-piperidin-4-ylmethyl)-carbamic Acid tert-Butyl Ester The title compound was prepared from 2,6-difluoroaniline (0.324 mL, 2.71 mmol), (1-(4-amino)benzenesulfonylpiperidin-4ylmethyl) dimethyl acetal (1 g, 2.71 mol) according to the procedure used for example 64 (Step A) to give 0.660 g (45%) of product. NMR (DMSO-d$_6$, 400 MHz): δ 1.06–1.14 (m, 2H), 1.34 (s, 9H), 1.62–1.65 (d, 2H), 2.11–2.17 (t, 2H), 2.74–2.77 (m, 2H), 3.55–3.58 (d, 2H), 6.81–6.84 (t, 1H), 7.11–7.19 (m, 2H), 7.29–7.37 (m, 1H), 7.60–7.62 (d, 2H), 7.65–7.68 (d, 2H), 8.27 (s, 1H), 9.46 (s, 1H). MS (ESI$^+$, m/z): 525 [M+H]$^+$.

Step B: 1-[(4-Aminomethyl)-piperidine-1-sulfonylphenyl]-3-(2,6-difluorophenyl)-urea A solution of (1-{4-[3-(2,6-difluoro-phenyl)-ureido]-benzenesulfonyl}-piperidin-4-ylmethyl)-carbamic acid tert-butyl ester (0.66 g, 1.2 mmol) in formic acid (5 mL) was stirred at ambient temperature until the reaction was complete. The formic acid was evaporated in vacuo to give the title compound as the formate salt. It was used directly in the next step.

Step C: 1-(2,6-Difluoro-phenyl)-3-[4-(4-{[(2S)-2-hydroxy-3-(4-hydroxy-phenoxy)-propylamino]-methyl}-piperidine-1-sulfonyl)-phenyl]-urea Prepared from t-butyl-[4-(2S)-oxiranylmethoxy-phenoxy]-diphenyl silane (0.495 g, 1.2 mmol) diisopropyl-ethyl amine (0.321 mL, 1.84 mmol) and 1-[(4-aminomethyl)-piperidine-1-sulfonylphenyl]-3-(2,6-difluorophenyl)-urea (0.508 g, 1.2 mmol) according to the procedure used for example 37 to give 0.12 g of the product.

NMR (DMSO-d$_6$, 400 MHz): δ 1.13–1.16 (m, 2H), 1.71–1.73 (m, 2H), 2.12–2.16 (t, 2H), 3.55–3.58 (m, 2H), 6.61–6.72 (m, 4H), 7.13–7.19 (m, 2H), 7.30–7.36 (m, 1H), 7.66–7.68 (m, 4H), 8.32 (broad s, 1H), 8.87 (broad s, 1H), 9.50 (broad s, 1H). MS (ESI$^-$, m/z): 589 [M–H]$^-$.

EXAMPLE 84

N-(5-{(1R)-2-[(1-{4-[3-(2,6-Difluoro-benzyl)-3-isopropyl-ureido]-benzenesulfonyl}-piperidin-4-ylmethyl)-amino]-1-hydroxy-ethyl}-2-hydroxy-phenyl)-methane-sulfonamide

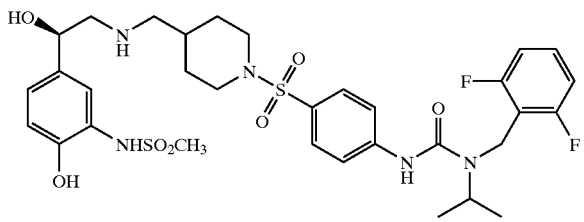

Step A: N-Isopropyl-2,6-difluorobenzamide

A solution of 2,6-difluorobenzoic acid (10 g, 63 mmol) and carbonyldiimidazole (10.26 g, 63.5 mmol) in 300 mL methylene chloride was stirred for 1 hour at ambient temperature. Isopropyl amine (5.39 mL, 63.25 mmol) was added and stirring was continued over night. An equivalent volume of methylene chloride was added, and the reaction mixture was washed with water, 1M NaOH, 1M HCl, and brine. The organic phase was dried (Na$_2$SO$_4$) and concentrated in vacuo to give a near quantitative yield of the amide as a white solid.

NMR (DMSO-d$_6$, 400 MHz): δ 1.11–1.12 (d, 6H), 3.97–4.05 (m, 1H), 7.10–7.16 (m, 2H), 7.44–7.51 (m, 1H), 8.57–8.59 (broad d, 1H). MS (ESI$^+$, m/z): [M+H]$^+$.=200.

Step B: 2,6-Difluoro-N-isopropyl-benzamine

A solution of N-isopropyl-2,6-difluorobenzamide (0.50 g, 3.0 mmol) in toluene (25 mL) was treated with borane-methylsulfide complex (0.772 mL of a 2 M solution in toluene). The reaction was heated at reflux for 8 hours, and acidified with 6N HCl upon cooling. The mixture was stirred vigorously overnight at ambient temperature until the evolution of gas ceased. The reaction was basified with 1N NaOH and extracted with ethyl acetate. The organic phase was dried (Na$_2$SO$_4$) and concentrated in vacuo to give 0.38 g of the title compound.

NMR (DMSO-d$_6$, 400 MHz): δ 1.11–1.12 (d, 6H), 3.97–4.05 (m, 1H), 7.10–7.16 (m, 2H), 7.44–7.51 (m, 1H), 8.57–8.59 (broad s, 1H). MS (ESI$^+$, m/z): 200 [M+H]$^+$.

123

Step C: 1-(2,6-Difluoro-benzyl)-3-[4-(4-dimethoxymethyl-piperidine-1-sulfonyl)-phenyl]-1-isopropyl-urea A solution of from 1-[(4-amino)benzenesulfonylpiperidin-4ylmethyl]-dimethyl acetal (0.5 g, 1.66 mmol) and diisopropylethyl amine (0.61 mL, 3.5 mmol) in 50 mL THF was added dropwise over 1 hour to a stirred solution of triphosgene (0.184 g, 0.48 mmol) in 10 mL THF. When the addition was complete N-isopropyl-2,6-difluorobenzyl amine (0.272 g, 1.6 mmol) and diisopropylethyl amide (0.61 mL, 3.5 mmol) was added and the solution was stirred at ambient temperature overnight. The reaction mixture was partitioned with ethyl acetate and water. The organic phase was washed with brine and dried ($Na_2SO_4$). Removal of solvent afforded 0.33 g of a white solid.

NMR (DMSO-$d_6$, 400 MHz): δ 1.10–1.12 (d, 6H), 1.18–1.23 (m, 2H), 1.63–1.66 (m, 2H), 2.07–2.12 (m, 2H), 3.18 (s, 6H), 3.57–3.60 (m, 2H), 4.00–4.01 (d, 1H), 4.22–4.26 (m, 1H), 4.60 (s, 2H), 7.02–7.06 (m, 2H), 7.35 (m, 1H), 7.54–7.57 (m, 2H), 7.66–7.68 (m, 2H), 8.96 (broad s, 1H). MS ($ESI^+$, m/z): $[M+H]^+$.=526, MS ($ESI^+$, m/z): 543 $[M+NH_4]^+$.

Step D: 1-(2,6-Difluoro-benzyl)-3-[4-(4-formyl-piperidine-1-sulfonyl)-phenyl]-1-isopropyl-urea Under anhydrous conditions, a solution of 1-(2,6-difluoro-benzyl)-3-[4-(4-dimethoxymethyl-piperidine-1-sulfonyl)-phenyl]-1-isopropyl-urea (0.32 g, 0.6 mmol), sodium iodide (0.228 g, 1.5 mmol), and trichloromethylsilane (0.143 mL, 1.2 mmol) in acetonitrile (2.5 mL) was stirred at ambient temperature for 15 minutes. The reaction mixture was quenched with water and partitioned with methylene chloride. The organic phase was washed with $Na_2S_2O_3$ dilute solution and dried ($Na_2SO_4$). Removal of solvent afforded the crude product which was used directly in the next step without characterization.

Step E: N-(5-{(1R)-2-[(1-{4-[3-(2,6-Difluoro-benzyl)-3-isopropyl-ureido]-benzenesulfonyl}-piperidin-4-ylmethyl)-amino]-1-hydroxy-ethyl}-2-hydroxy-phenyl)-methanesulfonamide A solution of N-[5-(2-amino-1-{R}-hydroxyethyl)-2-hydroxyphenyl]-methanesulfonamide (0.159 g, 0.65 mmol), 1-(2,6-difluoro-benzyl)-3-[4-(4-formyl-piperidine-1-sulfonyl}-phenyl]-1-isopropyl-urea (0.6 mol),and glacial acetic acid (0.037 g, 0.65 mmol) in 5 mL methanol was stirred for 1 hour over 4A molecular sieves. In one portion sodium cyanoborohydride (0.041 g, 0.65 mmol) was added and the mixture stirred over night at ambient temperature. The sieves were filtered and the filtrate was preabsorbed on silica gel. The solids were purified by flash chromatography ($CH_2Cl_2$—$CH_3OH$, 19:1) to give 0.12 g of product as an off white solid.

NMR (DMSO-$d_6$, 400 MHz): δ 1.10–1.12 (d, 6H), 1.71–1.75 (m, 2H), 2.11–2.16 (t, 2H), 3.56–3.58 (d, 2H), 4.54–4.55 (m, 1H), 4.56–4.60 (m, 1H), 6.80–6.82 (d, 1H), 6.97–7.16 (m, 3H), 7.31–7.35 (m, 1H), 7.36–7.39 (m, 1H), 7.55–7.57 (m, 2H), 7.65–7.69 (m, 2H), 8.97 (s, 1H), MS ($APCI^+$, m/z): 710 $[M+H]^+$.

124

EXAMPLE 85

N-(5-{2-[(1-{4-[3-(2,6-Difluoro-benzyl)-3-methyl-ureido]-benzenesulfonyl}-piperidin-4-ylmethyl)-amino]-1-hydroxy-ethyl}-2-hydroxy-phenyl)-methanesulfonamide

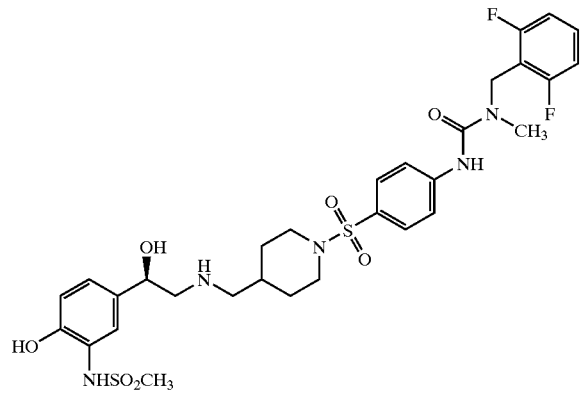

Step A: 2,6-Difluoro-N-methyl-benzamide

The title compound was prepared from 2,6-difluorobenzoic acid (10 g, 63.2 mmol), carbonyldiimidazole (10.26 g, 63.5 mmol), methylamine hydrochloride (4.27 g, 63.25 mmol) and diisopropylethyl amine according to the procedure used for example 84 (Step A) to give near quantitative yield of the title compound.

NMR (DMSO-$d_6$, 400 MHz): δ 2.74–2.76 (d, 3H), 7.12–7.18 (m, 2H), 7.45–7.53 (m, 1H), 8.6 (broad s, 1H).

MS ($ESI^+$, m/z): 172 $[M+H]^+$, 189 $[M+NH_4]^+$.

Step B: 2,6-Difluoro-N-methyl-benzylamine

Prepared from 2,6-difluoro-N-methyl-benzamide (3.2 g, 18.7 mmol) and borane-methylsulfide (47 mL of a 2 M solution in toluene) according to the procedure used for example 84 (Step B) to give 1.5 g of the title compound which was used directly in the next prep.

Step C: 1-(2,6-Difluoro-benzyl)-3-[4-(4-dimethoxymethyl-piperidine-1-sulfonyl)-phenyl]-1-methyl-urea The title compound was prepared from N-methyl-2,6-difluorobenzylamine (0.250 g, 1.6 mmol), (1-(4-amino)benzenesulfonylpiperidin-4ylmethyl)dimethyl acetal (0.500 g, 1.6 mmol), triphosgene (0.184 g, 0.62 mmol) and diisopropylethyl amine (1.28 mL, 2.48 mmol) according to the procedure used for example 84 (Step C) to give 0.250 g.

NMR (DMSO-$d_6$, 400 MHz): δ 1.19–1.25 (m, 2H), 1.63–1.66 (m, 2H), 2.07–2.12 (m, 2H), 2.90 (s, 3H), 3.18 (s, 6H), 3.58–3.61 (d, 2H), 4.65 (s, 2H), 7.08–7.12 (t, 2H), 7.41 (m, 1H), 7.55–7.58 (d, 2H), 7.69–7.71 (d, 2H), 8.88 (broad s, 1H). MS ($ESI^+$, m/z): 498 $[M+H]^+$; 515 $[M+NH_4]^+$.

Step D: 1-(2,6-Difluoro-benzyl)-3-[4-(4-formyl-piperidine-1-sulfonyl)-phenyl]-1-methyl-urea The title compound was prepared from 1-(2,6-difluoro-benzyl)-3-[4-(4-dimethoxymethyl-piperidine-1-sulfonyl)-phenyl]-1-methyl-urea (0.250 g, 0.5 mmol), sodium iodide (0.188 g, 1.26 mmol), and trichloromethylsilane (0.118 mL, 1.0 mmol) according to the procedure used for example 84 (Step D) and used directly in the next step.

Step E: N-(5-{2-[(1-[4-[3-(2,6-Difluoro-benzyl)-3-methyl-ureido]-benzene-sulfonyl)-piperidin-4-ylmethyl)-amino]-1-hydroxy-ethyl}-2-hydroxy-phenyl)-methanesulfonamide The title compound was prepared from N-[5-(2-amino-1-{R}-hydroxyethyl)-2-hydroxyphenyl]-methanesulfonamide (0.126 g, 0.51 mmol), 1-(2,6-Difluoro-benzyl)-3-[4-(4-formyl-piperidine-1-sulfonyl)-phenyl]-1-methyl-urea (0.5 mmol), glacial acetic acid (0.028 g, 0.49 mmol) and sodium cyanoborohydride (0.031 g, 0.49 mmol) according to the general procedure used for example 84 (Step E) to give the final product (0.136 g).

NMR (DMSO-d$_6$, 400 MHz): δ 1.17–1.20 (m, 2H), 1.73–1.75 (m, 2H), 2.13–2.18 (m, 2H), 2.66–2.89 (m, 4H), 2.91 (s, 6H), 3.57–3.59 (m, 2H), 4.65 (s, 3H), 6.82–6.84 (m, 1H), 6.99–7.01 (m, 1H), 7.07–7.11 (t, 2H), 7.17–7.18 (s, 1H), 7.38–7.42 (m, 1H), 7.57–7.59 (m, 2H), 7.69–7.71 (m, 2H), 8.88 (broad s, 1H). MS (ESI$^+$, m/z): 172 [M+H]$^+$., MS (ESI$^+$, m/z): 189 [M+NH$_4$]$^+$.

EXAMPLE 86

N-5-{(1R)-2-[(1-{4-[3-(2,5-Difluoro-benzyl)-3-isopropyl-ureido]-benzenesulfonyl}-piperidin-4-ylmethyl)-amino]-1-hydroxy-ethyl}-2-hydroxy-phenyl)-methane-sulfonamide

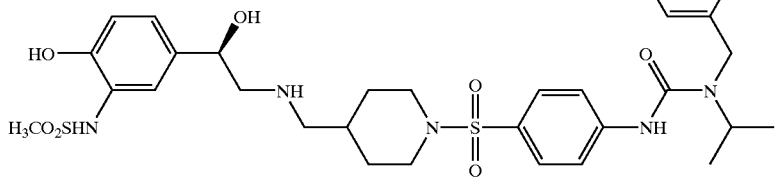

Step A: 2,5-Difluoro-N-isopropyl-benzamide

The title compound was prepared from 2,5-difluorobenzoic acid (10 g, 63.2 mmol), carbonyldiimidazole (9.57 g, 61 mmol) and isopropyl amine (5.15 mL, 60.5 mmol) according to the procedure used for example 84 (Step A) to give near quantitative yield of the title compound.

NMR (DMSO-d$_6$, 400 MHz): δ 1.12–1.13 (d, 6H), 3.99–4.04 (m, 1H), 7.31–7.36 (m, 3H), 8.24–8.26 (broad s, 1H). MS (ESI$^+$, m/z): 200 [M+H]$^+$.

Step B: 2,5-Difluoro-N-isopropyl-benzylamine 2,5-Difluoro-N-isopropyl-benzamide (0.5 g, 0.0025 mol) was dissolved in THF (8 mL). Lithium aluminum hydride (8 mL of a 1M solution in THF) was added, and the reaction was heated at reflux. When complete by TLC (methanol/methylene chloride), the reaction was cooled, and quenched with water, aqueous NaOH (15%), water and Na$_2$SO$_4$. The white solid is filtered off, and the filtrate is concentrated in vacuo to give 0.3 g of the amine. The product was used in the next step without characterization.

Step C: 1-(2,5-Difluoro-benzyl)-3-[4-(4-dimethoxymethyl-piperidine-1-sulfonyl)-phenyl]-1-isopropyl-urea The title compound was prepared from N-isopropyl-2,5-difluorobenzylamine (0.294 g, 1.6 mol), (1-(4-amino)benzenesulfonylpiperidin-4ylmethyl)dimethyl acetal (0.50 9, 1.6 mol) triphosgene (0.184 g, 0.62 mmol) and diisopropylethyl amine (1.28 mL, 2.48 mmol) according to the procedure used for example 84 (Step C) to give 0.530 g of the title compound.

NMR (DMSO-d$_6$, 400 MHz): δ 1.08–1.12 (d, 6H), 1.19–1.25 (m, 2H), 1.63–1.66 (m, 2H), 2.07–2.13 (m, 2H), 3.18–3.19 (s, 6H), 3.56–3.61 (m, 2H), 3.99–4.01 (d, 2H), 4.45–4.50 (m, 1H), 6.97–7.07 (m, 1H), 7.09–7.13 (m, 1H), 7.20–7.32 (m, 1H), 7.55–7.58 (m, 2H), 7.69–7.72 (m, 2H), 8.91 (broad s, 1H). MS (ESI$^+$, m/z): 526 [M+H]$^+$.

Step D: 1-(2,5-Difluoro-benzyl)-3-[4-(4-formyl-piperidine-1-sulfonyl)-phenyl]-1-isopropyl-urea The title compound was prepared from 1-(2,5-difluoro-benzyl)-3-[4-(4-dimethoxymethyl-piperidine-1-sulfonyl)-phenyl]-1-isopropyl-urea (0.530 g, 0.001 mol), sodium iodide (0.188 g, 1.26 mmol), and trichloromethylsilane (0.118 mL, 1.0 mmol) according to the procedure used for example 84 (Step D) and used directly in the next step.

Step E: N-(5-{(1R)-2-[(1-{4-[3-(2,5-Difluoro-benzyl)-3-isopropyl-ureido]-benzenesulfonyl}-piperidin-4-ylmethyl)-amino]-1-hydroxy-ethyl}-2-hydroxy-phenyl)-methanesulfonamide The title compound was prepared from N-[5-(2-amino-1-{R}-hydroxyethyl)-2-hydroxyphenyl]-methanesulfonamide (0.154 g, 0.63 mmol), 1-(2,5-difluoro-benzyl)-3-[4-(4-formyl-piperidine-1-sulfonyl)-phenyl]-1-isopropyl-urea (1.0 mmol), glacial acetic acid (0.036 g, 0.63 mmol) and sodium cyanoborohydride (0.039 g, 0.63 mmol) according to the general procedure used for example 84 (Step E) to give the final product (0.131 g).

NMR (DMSO-d$_6$, 400 MHz): δ 1.10–1.12 (d, 6H), 1.14–1.23 (m, 2H), 1.79 (m, 2H), 2.12–2.18 (t, 2H), 3.57–3.59 (m, 2H), 4.53 (s, 2H), 4.64–4.65 (broad s, 1H), 6.83–6.85 (d, 1H), 6.97–7.26 (m, 6H), 7.57–7.60 (m, 2H), 7.70–7.72 (m, 2H), 8.94 (broad s, 1H). MS (APCI$^-$, m/z): 708 [M-H]$^-$.

EXAMPLE 87

N-[5-[(R)-2-[[[1-[[4-[[[[(2,5-Difluorophenyl)methyl]-methylamino]-carbonyl]amino]-phenyl]sulfonyl]-4-piperidinyl]methyl]amino]-1-hydroxyethyl]-2-hydroxyphenyl]-methanesulfonamide

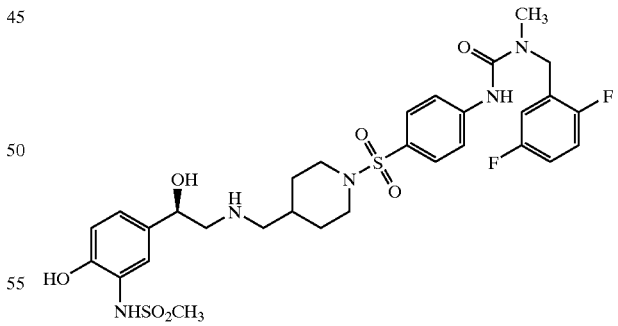

Step A: 2,5-Difluoro-N-methyl-benzamide

The title compound was prepared from 2,6-difluorobenzoic acid (9.52 g, 60 mmol), carbonyldiimidazole (9.76 g, 60.2 mmol), methylamine hydrochloride (4.06 g, 60 mmol) and diisopropylethyl amine (12 mL, 66 mmol) according to the procedure used for example 84 (Step A) to give near quantitative yield of the title compound.

NMR (DMSO-d$_6$, 400 MHz): δ 2.75–2.77 (m, 3H), 7.31–7.43 (m, 3H), 8.26–8.40 (broad s, 1H). MS (ESI$^+$, m/z): 172 [M+H]$^+$.

Step B: 2,5-Difluoro-N-methyl-benzamine 2,5-Difluoro-N-methyl-benzamide (0.300 g, 0.0018 mol), borane-methylsulfide complex (4.3 mL of a 2 M solution in toluene) according to the procedure used for example 84 (Step B) to give 0.106 g of the amine. Used in the following step without characterization

EXAMPLE 88

[3-Fluoro-4-[[[[4-[[4-[[[(R)-2-hydroxy-2-[4-hydroxy-3-[(methylsulfonyl)amino]-phenyl]ethyl]amino]-methyl]-1-piperidinyl]sulfonyl]phenyl]amino]-carbonyl]-amino]methyl]phenoxy]acetic Acid, Methyl Ester

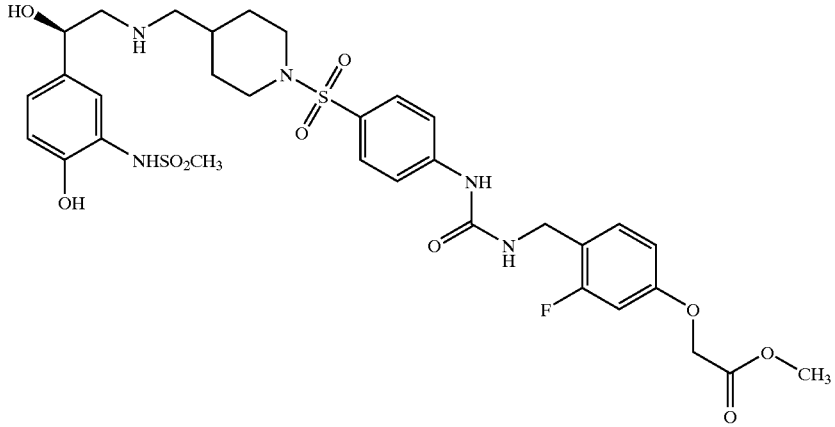

Step C: 1-(2,5-Difluoro-benzyl)-3-[4-(4-dimethoxymethyl-piperidine-1-sulfonyl)-phenyl]-1-methyl-urea The title compound was prepared from N-methyl-2,5-difluorobenzylamine (0.250 g, 1.6 mol), (1-(4-amino)benzenesulfonylpiperidin-4ylmethyl)dimethyl acetal (0.50 g, 1.6 mol) triphosgene (0.184 g, 0.62 mmol) and diisopropylethyl amine (1.28 mL, 2.48 mmol) according to the procedure used for example 84 (Step C) to give 0.410 g of the title compound.

NMR (DMSO-$d_6$, 400 MHz): δ 1.19–1.21 (m, 2H), 1.63 (d, 2H), 2.07–2.12 (t, 2H), 3.18 (s, 9H), 3.58–3.61 (d, 2H), 4.59 (s, 2H), 7.16 (m, 1H), 7.24–7.26 (m, 1H), 7.27 (m, 1H), 7.56–7.58 (m, 2H), 7.71–7.73 (m, 2H), 8.90 (broad s, 1H).

Step D: 1-(2,5-Difluoro-benzyl)-3-[4-(4-formyl-piperidine-1-sulfonyl)-phenyl]-1-methyl-urea The title compound was prepared from 1-(2,5-Difluoro-benzyl)-3-[4-(4-dimethoxy-methyl-piperidine-1-sulfonyl)-phenyl]-1-methyl-urea (0.410 g, 0.8 mmol), sodium iodide (0.309 g, 2.06 mmol), and trichloromethylsilane (0.194 mL, 1.65 mmol) according to the procedure used for example 84 (Step D) and used directly in the next step Step E: N-[5-[(R)-2-[[[1-[[4-[[[[(2,5-Difluorophenyl)methyl]methylamino]-carbonyl]-amino]phenyl]sulfonyl]-4-piperidinyl]methyl]amino]-1-hydroxyethyl]-2-hydroxyphenyl]methanesulfonamide The title compound was prepared from N-[5-(2-amino-1-{R}-hydroxyethyl)-2-hydroxyphenyl]-methanesulfonamide (0.130 g, 0.53 mmol), 1-(2,5-difluoro-benzyl)-3-[4-(4-formyl-piperidine-1-sulfonyl)-phenyl]-1-methyl-urea (0.8 mmol), glacial acetic acid (0.029 mL, 0.5 mmol) and sodium cyanoborohydride (0.031 g, 0.5 mmol) according to the general procedure used for example 84 (Step E) to give the final product (0.135 g).

NMR (DMSO-$d_6$, 400 MHz): δ 1.16–1.21 (m, 2H), 1.72–1.75 (m, 2H), 2.07–2.19 (m, 2H), 3.57–3.59 (m, 2H), 4.60 (m, 3H), 6.81–6.84 (d, 1H), 6.98–7.29 (m, 6H), 7.58–7.61 (m, 2H), 7.73–7.75 (m, 2H), 8.91 (s, 1H). MS (ESI$^+$, m/z): 682 [M+H]$^+$.

Step A: 4-(t-Butyl-diphenyl-silanyloxy)-2-fluoro-benzonitrile

A solution of 2-fluoro-4-hydroxybenzonitrile (19.85 g, 145 mmol), imidazole (10.86 g, 160 mmol), and t-butylchlorodiphenylsilane (39.60 mL, 152 mmol in methylene chloride (400 mL) was stirred overnight at ambient temperature. The reaction was washed with water, dried (Na$_2$SO$_4$), and the solvent removed in vacuo to give the silylated alcohol (49.28 g).

NMR (DMSO-$d_6$, 400 MHz): δ 1.04 (s, 9H), 6.58–6.61 (m, 1H), 6.87–6.90 (m, 1H), 7.42–7.55 (m, 6H), 7.60–7.71 (m, 5H). MS (EI, M+): 375 (M$^+$); Analysis calculated for C$_{23}$H$_{22}$ NOFSi: C, 73.57; H, 5.91; N, 3.73 Found: C, 73.08; H, 6.00; N, 3.36.

Step B: 4-(t-Butyl-diphenyl-silanyloxy)-2-fluoro-benzylamine

To a solution of the 4-(t-butyl-diphenyl-silanyloxy)-2-fluoro-benzonitrile (2.07 g, 5.52 mmol) in ether (17 mL) was added a solution of lithium aluminum hydride (6.6 mL, 1M in THF) slowly. The reaction was heated at reflux for two hours and allowed to stir overnight at ambient temperature. The reaction was quenched with 1.17 mL of water, then 1.17 mL of NaOH (15%), and 1.17 mL of water. The white solid was filtered, washed with methylene chloride. The filtrate was dried (Na$_2$SO$_4$), and concentrated in vacuo to give the benzylamine (1.66 g,) as a yellow oil, which was used directly in the next step.

Step C: [4-(t-Butyl-diphenyl-silanyloxy)-2-fluoro-benzyl]-carbamic Acid tert-Butyl Ester A solution of 4-(t-butyl-diphenyl-silanyloxy)-2-fluoro-benzylamine (1.66 g, 4.38 mmol) and ditertbutyldicarbonate (1.05 g, 4.82 mmol) in 9 mL THF was stirred at ambient temperature for 2 hours. When the reaction was finished, the THF was removed in vacuo and the residue was partitioned with Et$_2$O and phosphoric acid (aqueous 20% solution). The organic phase was washed with saturated sodium bicarbonate, brine and dried (Na$_2$SO$_4$). The solvent evaporated in vacuo to give the product (2.1 g).

NMR (DMSO-$d_6$, 400 MHz): δ 1.02 (s, 9H), 1.34–1.45 (s, 9H), 3.99–4.01 (d, 2H), 6.44–6.48 (m, 1H), 6.50–6.53 (m, 1H), 7.00–7.04 (t, 1H), 7.19–7.22 (t, 1H), 7.41–7.51 (m, 6H), 7.63–7.66 (m, 4H). MS (ESI$^+$, m/z): 497 [M+NH$_4$]$^+$.

Step D: (2-Fluoro-4-hydroxy-benzyl)-carbamic Acid tert-Butyl Ester

A solution of [4-(t-butyl-diphenyl-silanyloxy)-2-fluoro-benzyl]-carbamic acid tert-butyl ester (2.1 g, 4.38 mmol) in 5 mL of THF was treated with tetrabutylammonium fluoride (4.5 ml of a 1M solution) and stirred at ambient temperature for 1 hour. The reaction was concentrated in vacuo and purified by flash chromatography (chloroform-methanol, 5:1) to give 0.46 g of the phenol.

NMR (DMSO-$d_6$, 400 MHz): δ 1.37 (s, 9H), 4.01–4.03 (m, 2H), 6.47–6.50 (m, 1H), 6.53–6.56 (m, 1H), 7.05–7.09 (t, 1H), 7.22 (t, 1H), 9.72 (s, 1H). MS (ESI$^+$, m/z): 242 [M+H]$^+$., 483 [2M+H]$^+$.

Step E: [4-(t-Butoxycarbonylamino-methyl)-3-fluoro-phenoxyl]-acetic Acid Methyl Ester A solution of (2-fluoro-4-hydroxy-benzyl)-carbamic acid t-butyl ester (0.47 g, 1.95 mmol), methyl bromoacetate (0.203 mL, 2.15 mmol) and potassium carbonate (0.431 g, 3.12 mmol) in DMF (5 mL) was stirred at ambient temperature overnight. The reaction mixture was partitioned with water and ethyl acetate. The organic phase was washed with water and dried ($Na_2SO_4$). Removal of solvent in vacuo afforded 0.59 g of the title compound.

NMR (DMSO-$d_6$, 400 MHz): δ 1.37 (s, 9H), 3.69 (s, 3H), 4.06–4.07 (d, 2H), 4.80 (s, 2H), 6.74–6.78 (m, 1H), 6.80–6.81 (m, 1H), 7.17–7.21 (t, 1H), 7.29 (t, 1H). MS (APCI$^+$, m/z): 331 [M+NH$_4$]$^+$.

Step F: [4-(Aminomethyl)-3-fluoro-phenoxy]-acetic Acid Methyl Ester

[4-(tert-Butoxycarbonylamino-methyl)-3-fluoro-phenoxy]-acetic acid methyl ester (0.94 g, 3.0 mmol) was dissolved in formic acid (13 mL) and heated to 60° C. When the reaction was complete, the formic acid was removed under reduced pressure, and co-evaporated with chloroform and ethanol (1:1) to remove any excess formic acid. The resulting formate salt was taken up in ethyl acetate and shaken with saturated sodium bicarbonate. The organic layer was dried ($Na_2SO_4$) concentrated in vacuo to provide 0.56 g of product which was used directly in the next step.

Step G: (4-{3-[4-(4-Dimethoxymethyl-piperidine-1-sulfonyl)-phenyl]-ureido-methyl}-3-fluoro-phenoxy)-acetic Acid Methyl Ester A solution of from 1-[(4-amino) benzenesulfonylpiperidin-4ylmethyl]-dimethyl acetal (0.5 g, 1.6 mmol) and diisopropylethyl amine (0.28 mL, 1.6 mmol) in 20 mL THF was added dropwise over 1 hour to a stirred solution of triphosgene (0.155 g, 0.53 mmol) in 10 mL THF. When the addition was complete from [4-(aminomethyl)-3-fluoro-phenoxy]-acetic acid methyl ester (0.339 g, 1.6 mmol) and diisopropylethyl amine (0.28 mL, 1.6 mmol) was added and the solution was stirred at ambient temperature overnight. The reaction mixture was partitioned with ethyl acetate and water. The organic phase was washed with brine and dried ($Na_2SO_4$). Removal of solvent afforded 0.274 g of product as a white solid.

NMR (DMSO-$d_6$, 400 MHz): δ 1.19–1.21 (m, 2H), 1.50 (broad s, 1H), 1.63–1.66 (m, 2H), 2H), 2.06–2.08 (m, 2H), 3.31 (s, 6H), 3.57–3.60 (d, 2H), 3.99–4.01 (d, 1H), 4.25–4.26 (d, 2H), 4.81 (s, 2H), 6.74–6.77 (m, 2H), 6.82–6.85 (m, 1H), 7.24–7.28 (t, 1H), 7.53–7.60 (m, 4H), 9.05 (broad s, 1H). MS (APCI$^+$, m/z): 522 [M+H]$^+$.

Step H: (4-{3-[4-(4-Formyl-piperidine-1-sulfonyl)-phenyl]-ureidomethyl}-3-fluoro-phenoxy)-acetic Acid Methyl Ester The title compound was prepared from (4-{3-[4-(4-dimethoxymethyl-piperidine-1-sulfonyl)-phenyl]-ureidomethyl}-3-fluoro-phenoxy)-acetic acid methyl ester (0.274 g, 0.5 mmol), sodium iodide (0.185 g, 1.2 mmol), and trichloromethylsilane (0.118 mL, 1.0 mmol) according to the procedure used for example 84 (Step D) and used directly in the next step Step I: [3-Fluoro-4-[[[[[4-[[4-[[[(R)-2-hydroxy-2-[4-hydroxy-3-[(methylsulfonyl)-amino]phenyl]ethyl]amino]-methyl]-1-piperidinyl]sulfonyl]phenyl]amino]-carbonyl]amino]-methyl]phenoxy]acetic Acid, Methyl Ester The title compound was prepared from N-[5-(2-amino-1-{R}-hydroxyethyl)-2-hydroxyphenyl]-methanesulfonamide (0.128 g, 0.52 mmol), (4-{3-[4-(4-formyl-piperidine-1-sulfonyl)-phenyl]-ureidomethyl}-3-fluoro-phenoxy)-acetic acid methyl ester (0.5 mmol), glacial acetic acid (0.03 mL, 0.5 mmol) and sodium cyanoborohydride (0.031 g, 0.5 mmol) according to the general procedure used for example 84 (Step E) to give the final product (0.21 g).

NMR (DMSO-$d_6$, 400 MHz): δ 1.14–1.20 (m, 2H), 1.71–1.76 (t, 2H), 2.11–2.17 (t, 2H), 3.55–3.58 (t, 2H), 3.68 (s, 3H), 4.25–4.26 (d, 2H), 4.59 (broad s, 1H), 4.81 (s, 2H), 6.74–6.86 (m, 4H), 6.98–7.00 (m, 1H), 7.16–7.17 (m, 1H), 7.24–7.29 (t, 1H), 7.55–7.61 (m, 4H), 9.07 (broad s, 1H). MS (ESI$^-$, m/z): 736 [M-H]$^-$.

EXAMPLE 89

[3-Fluoro-4-[[[[[4-[[4-[[[(R)-2-hydroxy-2-[4-hydroxy-3-[(methylsulfonyl)amino]phenyl]-ethy]amino]-methyl]-1-piperidinyl]sulfonyl]phenyl]amino]carbonyl]-amino]-methyl]phenoxy]acetic Acid

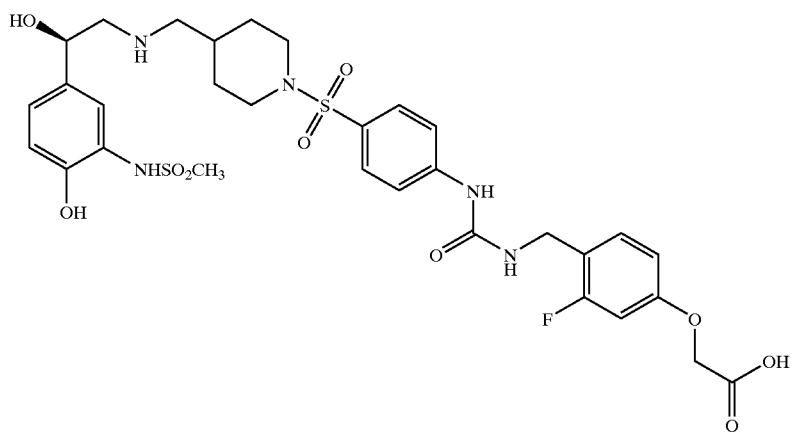

A solution of [3-fluoro-4-[[[[[4-[[4-[[[(R)-2-hydroxy-2-[4-hydroxy-3-[(methylslulfonyl)-amino]phenyl]ethyl]amino]methyl]-1-piperidinyl]sulfonyl]-phenyl]amino]-carbonyl]amino]methyl]phenoxy]acetic acid, methyl ester (0.200 g, 0.271 mmol) in 1N sodium hydroxide (0.55 mL) and methanol (2 mL) was stirred overnight at ambient temperature. The reaction was neutralized with 1N HCl (0.55 mL) and concentrated in vacuo. The residue was dissolved in methanol, filtered, and evaporated to give 0.048 g of the title compound.

NMR (DMSO-$d_6$, 400 MHz): δ 1.02–1.23 (m, 2H), 1.73–1.90 (m, 2H), 2.07–2.10 (m, 2H), 3.47–3.49 (d, 2H), 4.21–4.22 (d, 2H), 6.60–6.68 (m, 2H), 6.82–6.99 (m, 2H), 7.14–7.30 (m, 3H), 7.52–7.62 (m, 4H), 9.74 (broad s, 1H). MS (ESI$^-$, m/z): 706 [M–H]$^-$.

EXAMPLE 90

Heptanoic Acid [4-(4-{[(2S)-2-Hydroxy-3-(4-hydroxy-phenoxy)-propylamino]-methyl}-piperidine-1-sulfonyl)-phenyl]-amide

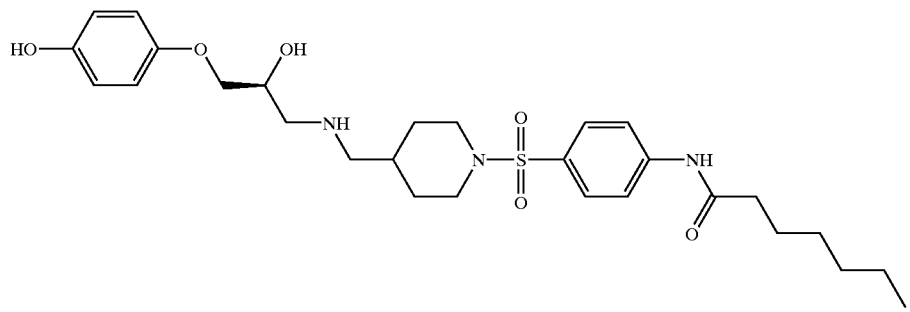

Step A: 1-(4-Heptylamidobenzenesulfonyl)-piperidin-4-ylmethyl]-carbamic Acid t-Butyl Ester A solution of 1-(4-aminobenzenesulfonyl)-piperidin-4-ylmethyl]-carbamic acid t-butyl ester (0.37 g, 1 mmol), diisopropylethyl amine (0.19 mL, 1 mmol) in 4 mL THF was treated with heptanoyl chloride (0.155 mL, 1 mmol) and stirred at ambient temperature for 3 hours. The reaction mixture was partitioned with ethyl acetate and $H_2O$. The organic phase was washed with brine and dried ($Na_2SO_4$). Removal of solvent in vacuo afforded 0.375 g of product as an amber solid.

NMR (DMSO-$d_6$, 400 MHz): δ 0.853 (m, 3H), 1.099 (m, 2H), 1.263 (m, 7H), 1.3367 (s, 9H), 1.415 (m, 2H), 1.6 (m, 4H), 2.143 (m, 2H), 2.332 (t, 2H), 2.75 (t, 2H), 3.55 (broad d, 2H), 6.798 (t, 1H), 7.63 (d, 1H, J=8.78 Hz), 7.80 (d, 2H, J=8.78 Hz). MS (ESI$^+$, m/z): 482 [M+H]$^+$, 499 [M+NH$_4$]$^+$.

Step B: 4-Aminomethyl-1-piperidinyl-benzene-4-sulfonyl Heptanamide

A solution of 1-(4-heptylamidobenzenesulfonyl)-piperidin-4-ylmethyl]-carbamic acid t-butyl ester (0.350 g, 0.72 mmol) in 5 mL of trifluoroacetic acid was stirred at ambient for 30 minutes. The solvent was removed in vacuo and partitioned with ethyl acetate and sat'd $NaHCO_3$. The organic phase was washed with brine and dried ($Na_2SO_4$), Removal of solvent provided 0.260 g of title compound.

NMR (DMSO-$d_6$, 400 MHz): δ 0.854 (m, 3H), 1.16 (m, 2H), 1.26 (m, 7H), 1.57 (m, 2H), 1.70 (m, 2H), 2.13 (t, 2H), 2.34 (t, 2H), 2.46 (m, 2H), 3.58 (broad d, 2H), 7.64 (d, 1H, J=9.24 Hz), 7.82 (d, 2H, J=8.56 Hz), 10.3537. MS (APCI$^+$, m/z): 382 [M+H]$^+$.

Step C: Heptanoic Acid [4-(4-{[(2S)-2-hydroxy-3-(4-hydroxy-phenoxy)-propylamino]-methyl}-piperidine-1-sulfonyl)-phenyl]-amide Prepared from t-butyl-[4-(2S)-oxiranylmethoxy-phenoxy]-diphenylsilane (0.121 g, 0.3 mmol) and 4-(4-aminomethyl-1-piperidinyl-sulfonyl)-phenyl-heptanamide (0.150 g, 0.35 mmol) according to the procedure used for example 37 to give 0.044 g of the title compound as a white solid.

NMR (DMSO-$d_6$, 400 MHz): δ 0.8541 (m, 3H), 1.11 (m, 2H), 1.26 (broad, 7H), 1.580 (m, 2H), 1.72 (broad d, 2H), 2.131 (t, 2H), 2.35 (m, 4H), 2.57 (m, 1H), 3.57 (broad d, 2H), 3.75 (m, 3H), 4.84 (broad, 1H), 6.63 (dd, 2H), 6.70 (dd, 2H), 7.63 (d 2H), 7.80 (d, 2H), 8.847 (s, 1H), 10.270 (s, 1H). MS (APCI$^+$, m/z): 548 [M+H]$^+$.

EXAMPLE 91

N-(2,6-Difluoro-benzyl)-4-(4-{[(2S)-2-hydroxy-3-(4-hydroxy-phenoxy)-propylamino]-methyl}-piperidine-1-sulfonyl)-benzamide

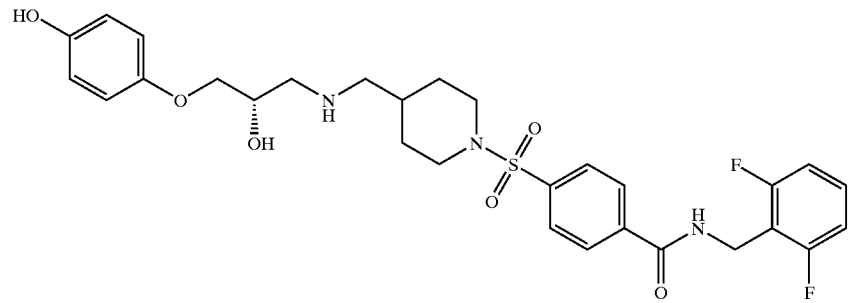

Step A: 1-(2,6-Difluorobenzylaminocarbonyl-benzenesulfonyl)-piperidin-4-ylmethyl]-carbamic Acid t-Butyl Ester A solution of 1-(4-hydroxycarbonylbenzenesulfonyl)-piperidin-4-ylmethyl]-carbamic acid t-butyl ester (1.0 g, 2.51 mmol), benzyltriazol-1-yloxytris(dimethylamino)-phosphonium hexafluorophosphate (1.22 g, 2.51 mmol), triethyl amine (0.52 mL, 2.51 mmol) and 2,6-difluorobenzyl amine (0.359 g, 2.51 mmol) in 10 mL DMF was stirred at ambient temperature for 18 hours. The reaction mixture was partitioned with ethyl acetate and $H_2O$. The organic phase was washed with brine and dried ($Na_2SO_4$). Removal of solvent in vacuo afforded 0.98 g of product as an amber solid.

NMR (DMSO-$d_6$, 300 MHz): δ 1.1 (m, 2H), 1.34 (s, 9H), 1.62 (m, 2H), 2.20 (t, 2H), 2.65 (t, 2H), 3.62 (broad d, 2H), 4.52 (d, 2H), 6.82 (t, 1H), 7.10 (t, 2H), 7.40 (m, 1H), 7.79 (d, 2H), 8.05 (d, 2H), 9.15 (t, 1H).

Step B: [(4-Aminomethylpiperidinyl)-1-sulfonyl]-N-(2,6-difluorobenzyl)-benzamide A solution of 1-(2,6-difluorobenzylaminocarbonyl-benzenesulfonyl)-piperidin-4-ylmethyl]-carbamic acid t-butyl ester (0.350 g, 0.72 mmol) in 5 mL of trifluoroacetic acid was stirred at ambient for 30 minutes. The solvent was removed in vacuo and partitioned with ethyl acetate and sat'd $NaHCO_3$. The organic phase was washed with brine and dried ($Na_2SO_4$), Removal of solvent provided 0.260 g of title compound.

NMR (DMSO-$d_6$, 400 MHz): δ 1.08 (m, 2H), 1.26 (m, 1H), 1.67 (m, 2H), 2.18 (t, 2H), 2.33 (d, 1H), 2.72 (t, 1H), 3.61 (t, 2H), 4.52 (d, 2H), 6.58 (broad, 1H), 7.085 (t, 2H), 7.391 (m, 1H), 7.78 (d, 2H), 8.02 (d, 2H), 9.13 (t, 1H). MS (ESI⁻, m/z): 422 [M–H]⁻.

Step C: N-(2,6-Difluoro-benzyl)-4-(4-{[(2S)-2-hydroxy-3-(4-hydroxy-phenoxy)-propylamino]-methyl}-piperidine-1-sulfonyl)-benzamide Prepared from t-butyl-[4-(2S)-oxiranylmethoxy-phenoxy]-diphenylsilane (0.404 g, 1 mmol) and [(4-aminomethylpiperidinyl)-1-sulfonyl]-N-(2,6-difluorobenzyl)-benzamide (0.318 g, 0.76 mmol) according to the procedure used for example 37 to give 0.66 g of the title compound as a white solid.

NMR (DMSO-$d_6$, 400 MHz): δ 0.8541 (m, 3H), 1.115 (m, 2H), 1.306 (m, 1H), 1.72 (broad d, 2H), 2.17 (t, 2H), 2.36 (d, 2H), 2.6 (m, 1H), 3.61 (d, 2H), 3.75 (m, 3H), 4.53 (d, 2H), 4.885 (broad, 1H), 6.63 (dd, 2H), 6.69 (dd, 2H), 7.08 (t, 2H), 7.393 (m, 1H), 7.78 (d, 2H), 8.03 (d, 2H), 8.868 (s, 1H), 9.133 (t, 1H). MS (APCI⁺, m/z): 590 [M+H]⁺.

EXAMPLE 92

1H-Indazole-3-carboxylic Acid [4-(4-{[(2S)-2-Hydroxy-3-(4-hydroxy-phenoxy)-propylamino]-methyl}-piperidine-1-sulfonyl)-phenyl]-amide

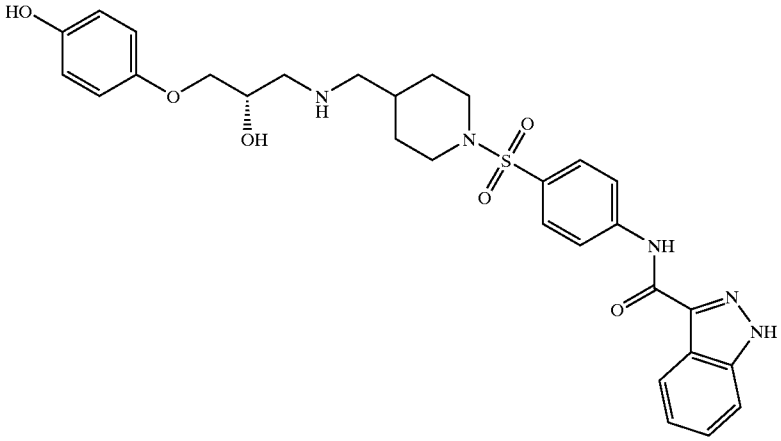

Step A: [1-({4-[(1H-Indazol-3-ylcarbonyl)amino]phenyl}sulfonyl)-4-piperidinyl]-methylcarbamic Acid t-Butyl Ester Oxalyl chloride (0.538 ml) was added to a solution of 1H-indazole-3-carboxylic acid (1.0 g, 6.2 mmol) and DMF (0.014 ml) in THF., and the reaction was stirred at 35° C. for 10 minutes. The solvent was removed in vacuo, and the resulting oil was dissolved in THF. The solution was chilled to 0° C., and (1-(4-amino)benzenesulfonylpiperidin-4ylmethyl)dimethyl acetal (2.28 g, 6.2 mmol) was added with diisopropylethyl amine (1.65 ml, 9.3 mmol). The reaction was stirred for 2.5 hours. The THF was removed in vacuo, methylene chloride and water were added. The organic layer was sequentially washed with aqueous HCl and brine and dried ($Na_2SO_4$). The product was purified by flash chromatography (chloroform-methanol, 50:1) to give 0.890 g of product.

Step B: (1H)-Indazole-3-carboxylic Acid [4-(4-Aminomethyl-1-piperidinyl-sulfonyl)-phenyl]-amide A solution of [1-({4-[(1H-indazol-3-ylcarbonyl)amino]phenyl}sulfonyl)-4-piperidinyl]methylcarbamic acid t-butyl ester (0.89 g) in formic acid was heated at 40° C. for 1 hour. Evaporated to give 0.71 g of the formate salt of the product, which was used directly in the following step.

Step C: 1H-Indazole-3-carboxylic Acid [4-(4-{[(2S)-2-Hydroxy-3-(4-hydroxy-phenoxy)-propylamino]-methyl}-piperidine-1-sulfonyl)-phenyl]-amide Prepared from t-butyl-[4-(2S)-oxiranylmethoxy-phenoxy]-diphenylsilane (0.623 g, 1.54 mmol), (1H)-Indazole-3-carboxylic acid [4-(4-aminomethyl-1-piperidinyl-sulfonyl)-phenyl]-amide formate salt (0.71 g, xx mmol) and diisopropylethyl amine (0.41 mL) according to the procedure used for example 37 to give 0.12 g of the title compound as a white solid.

NMR (DMSO-$d_6$, 400 MHz): δ 1.11–1.15 (m, 2H), 1.72–1.76 (m, 2H), 2.14–2.20 (m, 2H), 3.60–3.62 (m, 2H), 3.69–3.79 (m, 3H), 4.89–4.92 (s, 1H), 6.61–6.72 (m, 4H), 7.29–7.33 (m, 1H), 7.45–7.49 (m, 1H), 7.67–7.71 (m, 3H), 8.16–8.22 (m, 4H), 8.86 (s, 1H), MS (APCI⁺, m/z): 580 [M+H]⁺.

EXAMPLE 93

4-(2-Hydroxy-3-{[1-(4-pyrazol-1-yl-benzenesulfonyl)-piperidin-4-ylmethyl]-amino}-propoxy)-phenol

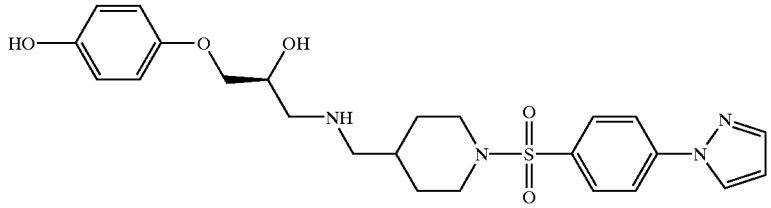

Step A: [1-(4-(Pyrazol-1-yl)-benzenesulfonyl)-piperidin-4-ylmethyl]-carbamic Acid t-Butyl Ester To a stirred mixture of hexane washed potassium hydride (0.08 g, 2 mmol) in 5 mL of DMF was added pyrazole (0.136 g, 2 mmol) in one portion. Stirring was continued until gas evolution ceased. A solution of [1-(4-aminobenzenesulfonyl)-piperidin-4-ylmethyl]-carbamic acid t-butyl ester (0.745 g, 2 mmol) in 5 mL DMF was added and the solution was heated at 70° C. overnight. The reaction mixture was poured into water and the solids formed collected and dried (high vac). The crude product was purified by flash chromatography (silica Merck 60, $CH_2Cl_2$—$CH_3OH$, 19:1) to give 0.258 g of the product as a white solid.

NMR (DMSO-$d_6$, 400 MHz): δ 1.12 (m, 2H), 1.328 (s+m, 10H), 1.64 (broad d, 2H), 2.22 (dt, 2H), 2.755 (t, 2H), 3.615 (broad d, 2H), 6.61 sharp m, 1H), 6.824 (t, 1H), 7.82 (td, 2H), 8.08 (td, 2H), 8.66 (d, 1H, J=1.6 Hz). MS (APCI$^+$, m/z): 421 [M+H]$^+$.

Step B: 4-Aminomethyl-1-piperidinyl-4-(pyrazol-1-yl)-benzenesulfonamide

The intermediate [1-(4-(pyrazol-1-yl)-benzenesulfonyl)-piperidin-4-ylmethyl]-carbamic acid t-butyl ester was dissolved in TFA (2 mL) and stirred for 15 minutes. The excess TFA was removed in vacuo and the residue triturated with sat'd $NaHCO_3$. The solids were filtered, Washed with $H_2O$ and dried (high vac) to give 0.140 g of the title compound.

NMR (DMSO-$d_6$, 400 MHz): δ 1.123 (m, 2H), 1.31 (m, 1H), 1.72 (m, 2H), 2.226 (m, 2H), 2.226 (m, 2H), 2.38 (d, 1H), 2.76 (t, 1H), 3.62 (broad d, 2H), 6.61 sharp (m, 1H), 6.824 (t, 1H), 7.82 (td, 2H), 8.09 (td, 2H), 8.65 (d, 1H, J=2.6 Hz). MS (APCI$^+$, m/z): 321 [M+H]$^+$.

Step C: 4-(2-Hydroxy-3-{[1-(4-pyrazol-1-yl-benzenesulfonyl)-piperidin-4-ylmethyl]-amino}-propoxy)-phenol Prepared from t-butyl-[4-(2S)-oxiranylmethoxy-phenoxy]-diphenylsilane (0.174 g, 0.43 mmol), (4-aminomethyl-1-piperidinyl-4-(pyrazol-1-yl)-benzenesulfonamide (0.138 g, 0.43 mmol) and trimethylsilylacetamide (0.062 g, 0.43 mmol) according to the procedure used for example 66 to give 0.040 g of the title compound (m.p. 169–171° C., EtOH).

NMR (DMSO-$d_6$, 400 MHz): δ 1.14 (m, 2H), 1.371 (m, 1H), 1.73 (broad d, 2H), 2.212 (t, 2H), 2.4 (broad s, 2H), 2.61 (broad m, 1H), 3.63 (broad d, 2H), 3.76 (m, 3H), 4.94 (broad, 1H), 6.62 (m, 3H), 6.69 (d, 2H), 7.82 (d, 2H), 8.10 (d, 2H), 8.66 (s, 1H), 8.86 (s, 1H). MS (APCI$^+$, m/z): 487 [M+H]$^+$.

EXAMPLE 94

1-[4-(4-{[2-Hydroxy-3-(4-hydroxy-phenoxy)-propylamino]-methyl}-piperidine-1-sulfonyl)-phenyl]-3-methyl-imidazolidin-2-one

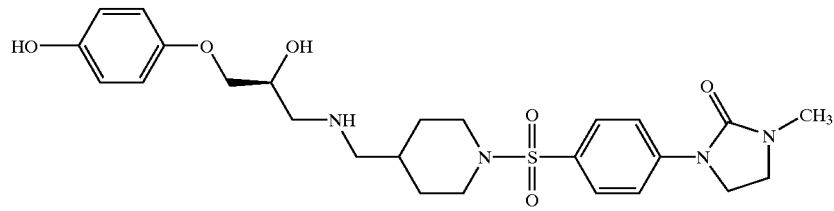

Step A: 1-Methyl-2-phenyl-ethylenediamine

A stirred mixture of aniline hydrochloride (12.8 g, 100 mmol) and 3-methyl-2-oxazolidinone was heated at 180° C. for 2 hours. The cooled solid was partitioned with ethyl acetate and 2.5N NaOH solution. the organic phase was washed with water and dried ($Na_2SO_4$). The solvent was removed in vacuo and the crude product purified by flash chromatography ($CH_2Cl_2$—$CH_3OH$, $NH_4OH$, 9:1:0.1) to give 11.4 g of the title compound.

NMR (DMSO-$d_6$, 400 MHz): δ 2.28 (s, 3H), 2.64 (t, 2H), 3.05 (m, 2H), 5.42 (broad t, 1H), 6.477 (t, 1H), 6.52 (dd, 1H), 7.04 (dt, 2H). MS (ESI$^+$, m/z): 151 [M+H]$^+$.

Step B: 1-Methyl-3-phenylimidazol-2-one

A solution of triphosgene (7.3 g, 24.6 mmol) in 50 mL dry $CH_2Cl_2$ was added dropwise to a stirred solution of 1-methyl-2-phenyl-ethylenediamine (11.1 g, 74 mmol) and diisopropylethyl amine (26.3 mL, 148 mmol) in 150 mL $CH_2Cl_2$ over 30 minutes. After stirring at ambient temperature for 2 hours the reaction mixture was washed with 2N HCl and brine. After drying ($Na_2SO_4$) the solvent was removed in vacuo and the crude product recrystallized from ethyl acetate to give 8.5 g of title compound.

NMR (DMSO-$d_6$, 400 MHz): δ 2.749 (s, 3H), 3.39 (m, 2H), 3.74 (m, 2H), 6.96 (t, 1H), 7.29 (tt, 1H), 7.55 (dd, 2H). MS (APCI$^+$, m/z): 177 [M+H]$^+$.

137

Step C: 4-(3-Methyl-2-oxo-imidazolidin-1-yl)-benzenesulfonyl Chloride

A solution of 1-methyl-3-phenylimidazol-2-one (5.7 g, 32.3 mmol) in 10 mL of chlorosulfonic acid was stirred at ambient temperature for 30 minutes. The reaction mixture was poured into ice/water and extracted with ethyl acetate. The organic phase was separated, dried ($Na_2SO_4$) and concentrated in vacuo to a white solid (7.4 g). Used as is in the following prep.

NMR (DMSO-$d_6$, 400 MHz): δ 2.7482 (s, 3H), 3.42 (m, 2H), 3.75 (m, 2H), 7.50 (m, 4H). MS (APCI$^+$, m/z): 275 [M+H]$^+$.

Step D {1-[4-(3-Methyl-2-oxo-imidazolidin-1-yl)-benzenesulfonyl]-piperidin-4-ylmethyl}-carbamic Acid t-Butyl Ester Prepared according to the procedure used for example 46 (Step A, part 1) from piperidin-4-ylmethyl-carbamic acid t-butyl ester (1.09 g, 5.1 mmol), 4-(3-methyl-2-oxo-imidazolidin-1-yl)-benzenesulfonyl chloride (1.4 g, 5.1 mmol) and 0.89 mL of diisopropylethyl amine to give 1.5 g of the title compound NMR (DMSO-$d_6$, 400 MHz): δ 1.09 (m, 2H), 1.24 (m, 1H), 1.3389 (s, 9H), 1.63 (broad d, 2H), 2.24 (broad t, 2H), 2.758 (t, 2H), 3.61 (broad d, 2H), 6.811 (t, 1H), 7.60 (d, 2H, J=7.9 Hz), 7.85 (d, 2H, J=8.78 Hz). MS (ESI$^+$, m/z): 439 [M+H]$^+$, 456 [M+NH$_4$]$^+$.

Step E: 1-[(Aminomethyl-piperidine)-1-sulfonyl-phenyl]-3-methyl-1-imidazol-2-one The intermediate {1-[4-(3-methyl-2-oxo-imidazolidin-1-yl)-benzenesulfonyl]-piperidin-4-ylmethyl}-carbamic acid t-butyl ester (1.4 g, 3.1 mmol) was dissolved in 3 mL TFA. After stirring 5 minutes the excess TFA was removed in vacuo and the residue was stirred in sat'd NaHCO$_3$. The solids were filtered, washed with water and dried (high vacuum) to give 0.875 g product NMR (DMSO-$d_{6, 400}$ MHz): δ 1.09 (m, 3H), 1.70 (m, 2H), 2.12 (m, 2H), 2.34 (d, 1H), 2.78 (s, 3H), 3.48 (m, 2H), 3.58 (broad d, 2H), 3.82 (m, 2H), 7.63 (d, 2H), 7.77 (d, 2H). MS (APCI$^+$, m/z): 353 [M+H]$^+$.

Step F: 1-[4-(4-{[2-Hydroxy-3-(4-hydroxy-phenoxy)-propylamino]-methyl}-piperidine-1-sulfonyl)-phenyl]-3-methyl-imidazolidin-2-one Prepared from t-butyl-[4-(2S)-oxiranylmethoxy-phenoxy]-diphenylsilane (0.404 g, 1.0 mmol), 1-[(Aminomethyl-piperidine)-1-sulfonyl-phenyl]-3-methyl-1-imidazol-2-one (0.352 g, 1.0 mmol) and trimethylsilylacetamide (0.157 g, 1.2 mmol) according to the procedure used for example 66 to give 0.115 g of the title compound as a white solid.

NMR (DMSO-$d_{6, 400}$ MHz): δ 1.14 (m, 2H), 1.370 (m, 1H), 1.74 (broad d, 2H), 2.131 (t, 2H), 2.44 (d, 2H), 2.56 (m, 1H), 2.66 (m, 1H), 3.47 (m, 2H), 3.57 (broad d, 2H), 3.8 (m, 5H), 5.02 (broad, 1H), 6.63 (d, 2H), 6.70 (d, 2H), 7.64 (d, 2H), 7.77 (d, 2H), 8.66 (s, 1). MS (APCI$^+$, m/z): 519 [M+H]$^+$.

138

EXAMPLE 95

1-[4-(4-{[(2R)-2-Hydroxy-2-(4-hydroxy-3-methanesulfonylamino-phenyl)-ethyl-amino]-methyl}-piperidine-1-sulfonyl)-phenyl]-1H-indole-2-carboxalic Acid Ethyl Ester

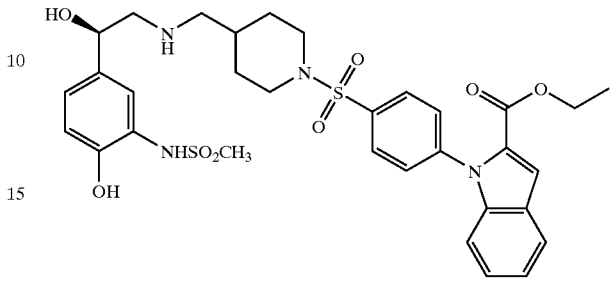

Step A: [1-(4-{2-Ethoxycarbonylindol-1yl}-benzenesulfonyl)-piperidin-4-yl]-carboxaldehyde Dimethyl Acetal To a stirred mixture of hexane washed potassium hydride (0.192 g, 4.8 mmol) in 5 mL of DMF was added 2-ethoxycarbonylindole (0.85 g, 4.73 mmol) in one portion. Stirring was continued until gas evolution ceased. A solution of [1-(4-fluorobenzenesulfonyl)-piperidin-4-yl]-carboxaldehyde dimethyl acetal (1.5 g, 2 mmol) in 5 mL DMF was added and the solution was heated at 100° C. for 48 hours. The reaction mixture was poured into water and extracted with ethyl acetate. The organic phase was washed with H$_2$O and dried (Na$_2$SO$_4$). Removal of solvent in vacuo provided crude product which was purified by flash chromatography (hexane-ethyl acetate; 2:1) to give 0.50 g of the product as a white solid.

NMR (DMSO-$d_{6, 400}$ MHz): δ 1.12 (m, 2H), 1.55 (m, 1H), 1.69 (broad d, 2H), 2.31 (t, 2H), 3.213 (s, 6H), 3.73 (broad d, 2H), 4.14 (m, 2H), 7.13 (m, 2H), 7.227 (t, 1H), 7.66 (d, 2H), 7.87 (d, 1H). MS (ESI$^+$, m/z): 487 [M+H]$^+$.

Step B: [1-(4-{2-Ethoxycarbonylindol-1yl}-benzenesulfonyl)-piperidin-4-yl]-carboxaldehyde The intermediate [1-(4-{2-ethoxycarbonylindol-1yl}-benzenesulfonyl)-piperidin-4-yl]-carboxaldehyde dimethyl acetal was dissolved in formic acid (2 mL) and stirred for 15 minutes. The excess formic acid was removed in vacuo to give 0.450 g of the title compound which was used directly in the following step.

Step C: 1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indole-2-carboxylic Acid Ethyl Ester Prepared from N -[5-(2-amino-1-{R}-hydroxyethyl)-2-hydroxyphenyl]-methanesulfonamide (0.250 g, 0.1.0 mmol), 1-[(4-{2-ethoxycarbonylindol-1yl}-benzene)-sulfonyl]-piperidin-4-yl-carboxaldehyde (0.44 g, 1.1 mmol), glacial acetic acid (0.060 g, 1.0 mmol) and sodium cyanoborohydride (0.063 g, 1.0 mmol) according to the procedure used for example 67 (Step B) to give 0.065 g of the title compound as a white solid.

NMR (DMSO-$d_6$, 400 MHz): δ 1.079 (t, 3H), 1.19 (t, 3H), 1.57 (m, 1H), 1.79 (broad t, 2H), 2.263 (t, 2H), 2.58 (broad s, 1H), 2.67 (m, 2H), 2.9108 (s, 3H), 3.73 (broad d, 2H), 4.10 (q, 2H), 4.57 (m, 1H), 6.82 (d, 1H), 6.99 (dd, 1H), 7.18 (m, 2H), 7.22 (dt, 2H), 7.31 (dt, 1H), 7.53 (s, 1H), 7.67 (dd, 2H), 7.79 (d, 1H), 7.88 (dd, 2H). MS (ESI$^+$, m/z): 671 [M+H]$^+$.

EXAMPLE 96

{1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indol-3-yl}-acetic Acid Ethyl Ester

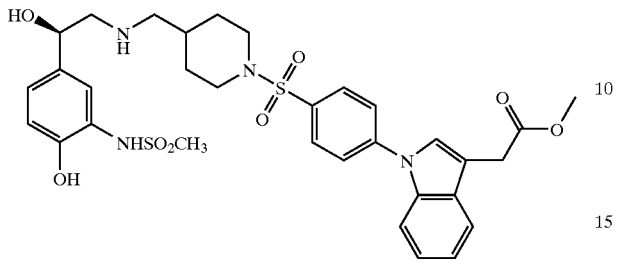

Step A: [1-(4-{3-Ethoxyacetylindol-1yl}-benzenesulfonyl)-piperidin-4-yl]-carboxaldehyde Dimethylacetal To a stirred mixture of hexane washed potassium hydride (0.192 g, 4.8 mmol) in 5 mL of DMF was added 3-ethoxyacetylindole (0.96 g, 4.73 mmol) in one portion. Stirring was continued until gas evolution ceased. A solution of [1-(4-fluorobenzenesulfonyl)-piperidin-4-yl]-carboxaldehyde dimethyl acetal (1.5 g, 2 mmol) in 5 mL DMF was added and the solution was heated at 60° C. for 18 hours. The reaction mixture was poured into water and extracted with ethyl acetate. The organic phase was washed with H$_2$O and dried (Na$_2$SO$_4$). Removal of solvent in vacuo provided crude product which was purified by flash chromatography (hexane-ethyl acetate; 2:1) to give 0.600 g of the intermediate as a white solid.

NMR (DMSO-d$_6$, 400 MHz): δ 1.19 (t, 3H), 1.23 (m, 2H), 1.57 (m, 1H), 1.67 (broad d, 2H), 2.264 (t, 2H), 3.1936 (s, 6H), 3.349 (broad s, 1H), 3.65 (broad d, 2H), 4.02 (d, 1H), 4.10 (q, 2H), 7.188 (t, 1H), 7.26 (dt, 1H), 7.62 (d, 2H), 7.69 (m, 2H), 7.86 (q, 4H). MS (ESI$^+$, m/z): 501 [M+H]$^+$.

Step B: [1-(4-{3-Ethoxyacetylindol-1yl)-benzenesulfonyl)-piperidin-4-yl]-carboxaldehyde The intermediate [1-(4-{3-ethoxyacetylindol-1yl}-benzenesulfonyl)-piperidin-4-yl]-carboxaldehyde dimethyl acetal (0.59 g, 1.18 mmol), methyltrichlorosilane (0.264 g, 1.77 mmol), and sodium iodide (0.442 g, 2.95 mmol) in 10 mL acetonitrile was stirred at ambient temperature for 1 hour. The reaction was diluted with methylene chloride and washed with Na$_2$S$_2$O$_3$ dilute solution. The organic phase was dried (Na$_2$SO$_4$) and concentrated to an orange solid foam.

NMR (DMSO-d$_6$, 400 MHz): δ 1.197 (t, 3H), 1.52 (m, 2H), 1.94 (dd, 2H), 2.39 (m, 1H), 2.557 (m, 2H), 3.450 (m, 2H), 3.83 (s, 2H), 4.02 (d, 1H), 4.10 (q, 2H), 7.19 (dt, 1H), 7.26 (dt, 1H), 7.63 (dd, 2H), 7.70 (m, 2H), 7.86 (q, 4H), 9.534 (s, 1H). MS (APCI$^+$, m/z): 455 [M+H]$^+$.

Step C: {1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indol-3-yl}-acetic Acid Ethyl Ester Prepared from N-[5-(2-amino-1-{R}-hydroxyethyl)-2-hydroxyphenyl]-methanesulfonamide (0.271 g, 0.1.1 mmol), 1-[(4-{3-ethoxyacetylindol-1yl}-benzene)-sultonyl]-piperidin-4-yl-carboxaldehyde (0.50 g, 1.1 mmol), glacial acetic acid (0.069 g, 1.1 mmol) and sodium cyanoborohydride (0.066 g, 1.1 mmol) according to the procedure used for example 67 (Step B) to give 0.17 g of the title compound as a white solid (isolated as HCl salt).

NMR (DMSO-d$_6$, 400 MHz): δ 1.199 (t, 3H), 1.27 (m, 2H), 1.8 (m, 3H), 2.12 (t, 2H), 2.32 (t, 2H), 2.85 (broad s, 2H), 2.91 (s, 3H), 3.02 (m, 1H), 3.68 (m, 2H), 3.84 (s, 2H), 4.08 (q, 2H), 4.80 (d, 1H), 6.02 (broad, 1H), 6.87 (d, 1H), 7.02 (dd, 1H), 7.2 (m, 2H), 7.26 (dt, 1H), 7.63 (dd, 1H), 7.703 (m, 2H), 7.88 (q, 4H), 8.6 (broad d, 2H), 8.73 (s, 1H), 9.947 (s, 1H). MS (ESI$^+$, m/z): 685 [M+H]$^+$.

EXAMPLE 97

{1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indol-3-yl}-acetic Acid

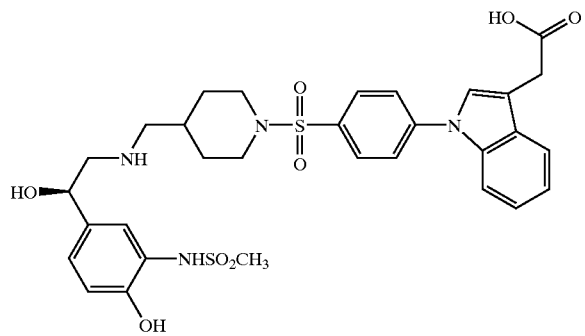

A solution of {1-[4-(4-{[(2R)-2-hydroxy-2-(4-hydroxy-3-methane-sulfonyl-amino-phenyl)-ethylamino]-methyl}-piperidine-1-sulfonyl)-phenyl]-1H-indol-3-yl}-acetic acid ethyl ester (0.154 g, 0.225 mmol) and 0.67 mL of 1N NaOH in 10 mL methanol was heated at reflux overnight. On cooling the reaction was neutralized with 0.67 mL of 1N HCl. The reaction mixture was concentrated in vacuo and triturated with H$_2$O. The solids were filtered and dried (high vacuum) to give 0.070 g of the title compound as an off white solid.

NMR (DMSO-d$_6$, 400 MHz): δ 1.17 (m, 2H), 1.42 (m, 12H), 1.41 (m, 1H), 1.76 (broad d, 2H), 2.290 (t, 2H), 2.62 (m, 1H), 2.898 (s, 3H), 3.67 (broad d, 2H), 3.73 (s, 2H), 4.51 (m, 1H), 6.80 (d, 1H), 6.95 (dd, 1H), 7.18 (m, 2H), 7.25 (t, 1H), 7.67 (m, 3H), 7.86 (q, 4H). MS (APCI$^-$, m/z): 655 [M−H]$^{−n}$.

EXAMPLE 98

1-[4-(4-{[(2R)-2-Hydroxy-2-(4-hydroxy-3-methanesulfonylamino-phenyl)-ethyl-amino]-methyl}-piperidine-1-sulfonyl)-phenyl]-1H-indole-4-carboxylic Acid Methyl Ester

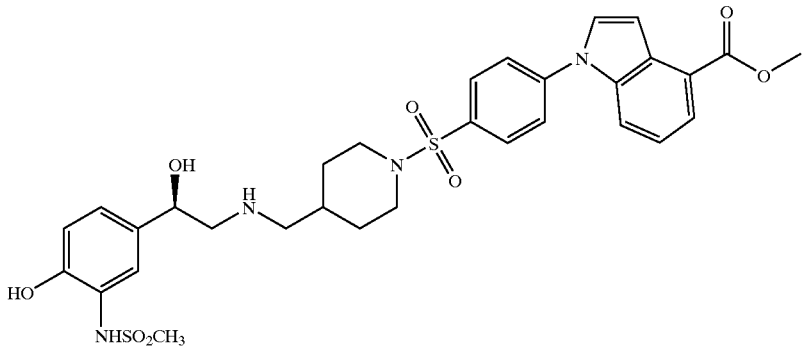

Step A: [1-(4-{4-Ethoxycarbonylindol-1-yl}-benzenesulfonyl)-piperidin-4-yl]-carboxaldehyde Dimethylacetal To a stirred mixture of hexane washed potassium hydride (0.192 g, 4.8 mmol) in 5 mL of DMF was added 4-methoxycarbonylindole (0.82 g, 4.7 mmol) in one portion. Stirring was continued until gas evolution ceased. A solution of [1-(4-fluorobenzenesulfonyl)-piperidin-4-yl]-carboxaldehyde dimethyl acetal (1.5 g, 2 mmol) in 5 mL DMF was added and the solution was heated at 110° C. for 18 hours. The reaction mixture was poured into water and extracted with ethyl acetate. The organic phase was washed with H₂O and dried (Na₂SO₄). Removal of solvent in vacuo provided 1.7 g crude product which was purified by flash chromatography (hexane-ethyl acetate; 2:1) to give 1.25 g of the product as a white solid.

NMR (DMSO-d₆, 400 MHz): δ 1.25 (m, 2H), 1.57 (m, 1H), 1.648 (broad d, 2H), 2.27 (dt, 2H), 3.1958 (s, 6H), 3.70 (broad d, 2H), 3.92 (s, 3H), 4.03 (d, 1H), 7.26 (m, 1H), 7.36 (t, 1H), 7.89 (m, 5H), 7.95 (m, 2H). MS (ESI⁺, m/z): 473 [M+H]⁺.

Step B: [1-(4-{4-Ethoxycarbonylindol-1yl}-benzenesulfonyl)-piperidin-4-yl]-carboxaldehyde The intermediate [1-(4-{4-ethoxycarbonylindol-1-yl}-benzenesulfonyl)-piperidin-4-yl]-carboxaldehyde dimethyl acetal (1.25 g, 2.65 mmol) was dissolved in 10 mL of formic acid and stirred at ambient temperature for 20 minutes. The excess formic acid was removed in vacuo an the product was used as is.

Step C: 1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indole-4-carboxylic Acid Methyl Ester Prepared from N-[5-(2-amino-1-{R}-hydroxyethyl)-2-hydroxyphenyl]-methanesulfonamide (0.570 g, 2.3 mmol), 1-[(4-{4-ethoxycarbonylindol-1-yl}-benzene)-sulfonyl]-piperidin-4-yl-carboxaldehyde (1.0 g, 2.3 mmol), glacial acetic acid (0.138 g, 2.3 mmol) and sodium cyanoborohydride (0.144 g, 2.3 mmol) according to the procedure used for example 67 (Step B) to give 0.258 g of the title compound as a white solid (isolated as the HCl salt).

NMR (DMSO-d₆, 400 MHz): δ 1.259 (m, 2H), 1.8 (m, 3H), 2.331 (t, 2H), 2.87 (m, 2H), 2.9147 (s, 3H), 3.025 (m, 1H), 3.70 (broad d, 2H), 3.9266 (s, 3H), 4.79 (d, 1H), 6.014 (broad s, 1H), 6.87 (d, 1H), 7.01 (dd, 1H), 7.203 (s, 1H), 7.27 (s, 1H), 7.37 (t, 1H), 7.91 (m, 6H), 8.56 (broad, 2H), 8.7308 (s, 1H), 9.9377 (s, 1H). MS (ESI⁺, m/z): 657 [M+H]⁺.

EXAMPLE 99

1-[4-(4-{[(2R)-2-Hydroxy-2-(4-hydroxy-3-methanesulfonylamino-phenyl)-ethylamino]-methyl}-piperidine-1-sulfonyl)-phenyl]-1H-indole-4-carboxylic Acid

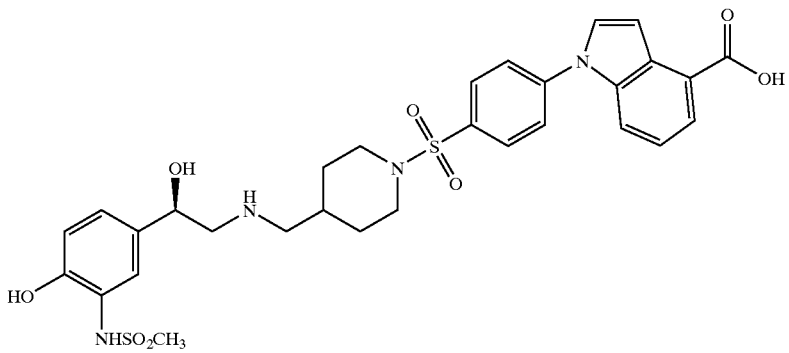

A solution of 1-[4-(4-{[(2R)-2-hydroxy-2-(4-hydroxy-3-methanesulfonyl-amino-phenyl)-ethylamino]-methyl}-piperidine-1-sulfonyl)-phenyl]-1H-indole-4-carboxylic acid methyl ester (0.118 g, 0.18 mmol) and 0.8 mL of 1N NaOH in 10 mL methanol was heated at reflux overnight. On cooling the reaction was neutralized with 0.8 mL of 1N HCl. The reaction mixture was concentrated in vacuo and triturated with H₂O. The solids were filtered and dried (high vac) to give 0.095 g of the title compound as an off white solid.

NMR (DMSO-d₆, 400 MHz): δ 1.22 (m, 2H), 1.59 (broad, 1H), 1.77 (broad t, 2H), 2.31 (t, 2H), 2.69 (m, 3H), 2.9067

(s, 3H), 3.69 (broad d, 2H), 4.65 (broad d, 1H), 6.83 (d, 1H), 6.99 (dd, 1H), 7.18 (s, 1H), 7.29 (m, 2H), 7.90 (s, 7H). MS (ESI⁻, m/z): 641 [M−H]⁻.

EXAMPLE 100

Ethyl 1-{4-[(4-{[((2R)-2-Hydroxy-2-{4-hydroxy-3-[(methylsulfonyl)amino]-phenyl}ethyl)amino]methyl}piperidin-1-yl)sulfonyl]phenyl}-1H-pyrazole-4-carboxylate

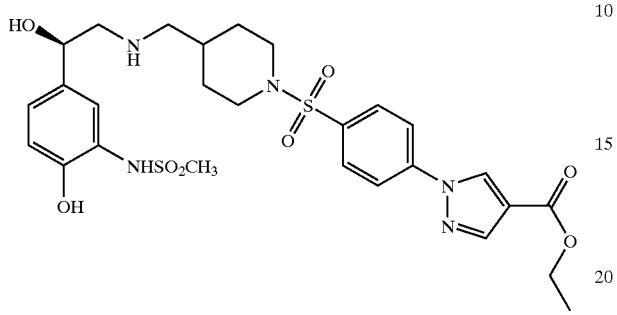

Step A: [1-(4-{4-Ethoxycarbonylpyrazol-1yl}-benzenesulfonyl)-piperidin-4-yl]-carboxaldehyde Dimethylacetal To a stirred mixture of hexane washed potassium hydride (0.284 g, 7.1 mmol) in 10 mL of DMF was added ethyl pyrazole-4-carboxylate (1.0 g, 7.1 mmol) in one portion. Stirring was continued until gas evolution ceased. A solution of [1-(4-fluorobenzene-sulfonyl)-piperidin-4-yl]-carboxaldehyde dimethyl acetal (2.25 g, 7.1 mmol) in 5 mL DMF was added and the solution was heated at 100° C. for 48 hours. The reaction mixture was poured into water and extracted with ethyl acetate. The organic phase was washed with H₂O and dried (Na₂SO₄). Removal of solvent in vacuo provided 2.5 g crude product which was purified by flash chromatography (hexane-ethyl acetate; 2:1) to give 0.48 g of the title compound as a white solid.

NMR (DMSO-d₆, 400 MHz): δ 1.22 (m, 2H), 1.30 (t, 3H), 1.55 (m, 1H), 1.66 (broad d, 2H), 2.208 (dt, 2H), 3.1875 (s, 6H), 3.655 (broad t, 2H), 4.01 (d, 1H), 4.19 (q, 2H), 7.84 (dd, 2H), 8.21 (m, 3H), 9.268 (s, 1H). MS (ESI⁺, m/z): 455 [M+NH₄]⁺.

Step B: [1-(4-{4-Ethoxycarbonylpyrazol-1yl}-benzenesulfonyl)-piperidin-4-yl]-carboxaldehyde The intermediate [1-(4-{4-ethoxycarbonylpyrazol-1yl}-benzenesulfonyl)-piperidin-4-yl]-carboxaldehyde dimethyl acetal (0.4 g, 0.91 mmol) was dissolved in 10 mL of CH₂Cl₂ containing 1 mL of TFA and stirred at ambient temperature for 45 minutes. The reaction mixture was concentrated in vacuo to an oil. The residue was partitioned with CH₂Cl₂ and sat'd NaHCO₃. The organic base was dried (Na₂SO₄) and concentrated in vacuo to give the product (0.26 g) as a clear oil which was used as is.

NMR (DMSO-d₆, 400 MHz): δ 1.25 (m, 2H), 1.303 (t, 3H), 1.53 (m, 2H), 1.90 (m, 2H), 2.36 (m, 1H), 3.55 (m, 2H), 4.28 (q, 2H), 7.86 (d, 2H, J=8.78 Hz), 8.215 (m, 3H), 9.2678 (s, 1H), 9.516 (s, 1H). MS (APCI⁺, m/z): 392 [M+H]⁺.

Step C: Ethyl 1-{4-[(4-{[((2R)-2-Hydroxy-2-{4-hydroxy-3-[(methylsulfonyl)amino]-phenyl}ethyl)amino]methyl}piperidin-1-yl)sulfonyl]phenyl}-1H-pyrazole-4-carboxalate Prepared from N-[5-(2-amino-1-{R}-hydroxyethyl)-2-hydroxyphenyl]-methanesulfonamide (0.22 g, 0.895 mmol), 1-[(4-{4-ethoxycarbonylpyrazol-1yl}-benzene)-sulfonyl]-piperidin-4-yl-carboxaldehyde (0.35 g, 0.895 mmol), glacial acetic acid (0.054 g, 0.9 mmol) and sodium cyanoborohydride (0.055 g, 0.9 mmol) according to the procedure used for example 67 (Step B) to give 0.070 g of the title compound as a white solid (isolated as the HCl salt).

NMR (DMSO-d₆, 400 MHz): δ 1.22 (m, 2H), 1.304 (t, 3H), 1.71 (m, 1H), 1.812 (broad t, 2H), 2.273 (t, 2H), 2.85 (m, 2H), 2.9102 (s, 3H), 3.07 (m, 1H), 3.65 (broad d, 2H), 4.28 (q, 2H), 4.79 (d, 1H), 6.01 (s, 1H), 6.86 (d, 1H), 7.01 (dd, 1H), 7.19 (s, 1H), 7.87 (d, 2H, J=8.78 Hz), 8.22 (m, 3H), 8.57 (broad d, 2H), 8.746 (s, 1H), 9.2799 (s, 1H), 9.9544 (s, 1H). MS (ESI⁺, m/z): 622 [M+H]⁺.

EXAMPLE 101

1-{4-[(4-{[((2R)-2-Hydroxy-2-{4-hydroxy-3-[(methylsulfonyl)amino]-phenyl}ethyl)amino]methyl}piperidin-1-yl)sulfonyl]phenyl}-1H-pyrazole-4-carboxylic Acid

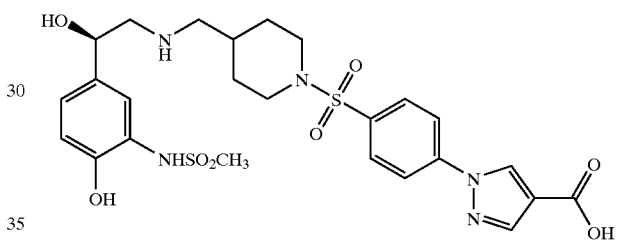

A solution of ethyl 1-{4-[(4-{[((2R)-2-hydroxy-2-{4-hydroxy-3-[(methylsulfonyl)-amino]phenyl}ethyl)amino]methyl}piperidin-1-yl)sulfonyl]-phenyl}-1H-pyrazole-4-carboxylate (0.118 g, 0.18 mmol) and 0.8 mL of 1N NaOH in 10 mL methanol was heated at reflux overnight. On cooling the reaction was neutralized with 0.8 mL of 1N HCl. The reaction mixture was concentrated in vacuo and triturated with H₂O. The solids were filtered and dried (high vacuum) to give 0.095 g of the title compound as an off white solid.

NMR (DMSO-d₆, 400 MHz): δ 1.22 (m, 2H), 1.695 (broad, 1H), 1.792 (broad t, 2H), 2.273 (t, 2H), 2.79 (m, 3H), 2.9103 (s, 3H), 3.648 (m, 2H), 4.72 (d, 1H), 6.84 (d, 1H), 7.01 (dd, 1H), 7.191 (s, 1H), 7.86 (d, 2H, J=8.78 Hz), 8.2 (m, 3H), 9.183 (s, 1H). MS (ESI⁺, m/z): 594 [M+H]⁺.

EXAMPLE 102

4-[(2S)-2-Hydroxy-3-({1-[4-(5-octyl-[1,2,4]oxadiazol-3-yl)-benzenesulfonyl]-piperidin-4-ylmethyl}-amino)-propoxy]-phenol

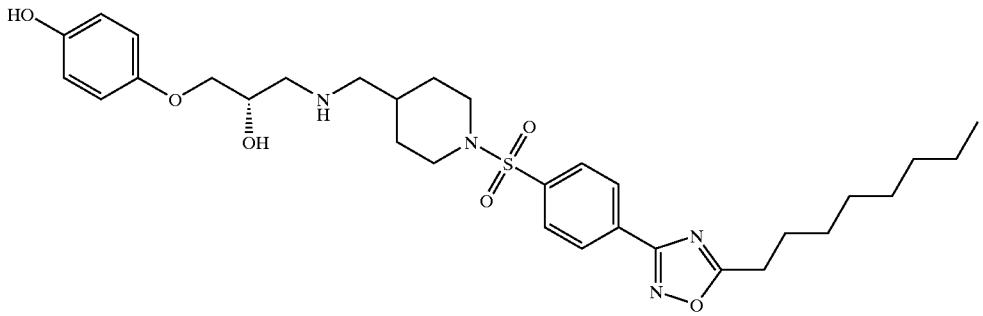

Step A: [1-({4-[Amino(hydroxyimino)methyl]phenyl}sulfonyl)-4-piperidinyl]methyl-carbamic Acid t-Butyl Ester {1-[(4-cyanophenyl)sulfonyl]-4-piperidinyl}methylcarbamic acid t-butyl ester (1 g, 2.6 mmol), potassium carbonate (1.8 g, 13 mmol), and ammonium hydroxide hydrochloride (0.916 g, 13 mmol) were heated in ethanol (5 ml) at reflux for 2.5 days. The reaction was cooled in an ice-water bath, and filtered. The solid was washed with cold ethanol, and evaporated to a white solid (0.870 g, 2.10 mmol).

Step B: (4-{[4-(5-Octyl-1,2,4-oxadiazol-3-yl)phenyl]sulfonyl}-cyclohexyl)-methylcarbamic Acid t-Butyl Ester A solution of [1-({4-[amino(hydroxyimino)methyl]phenyl}sulfonyl)-4-piperidinyl]methylcarbamic acid t-butyl ester (0.850 g, 2.1 mmol) and excess diisopropylethyl amine in DMF (10 mL) was treated with nonanyl chloride (4.12 mmol) [prepared from oxalylchloride (0.770 mL, 8.8 mmol) and nonanoic acid (0.652 g, 4.12 mmol)] After a standard aqueous workup the crude product was carried forward to the next step.

Step C: (4-{[4-(5-Octyl-1,2,4-oxadiazol-3-yl)phenyl]sulfonyl}-4-piperidinyl)-methylamine A solution of (4-{[4-(5-octyl-1,2,4-oxadiazol-3-yl)phenyl]sulfonyl}-4-piperidinyl)-methylcarbamic acid t-butyl ester in formic acid was stirred at ambient temperature for 4 hours. Concentrated in vacuo to give 0.21 g of the product as a formate salt.

Step D: 4-[(2S)-2-Hydroxy-3-({1-[4-(5-octyl-[1,2,4]oxadiazol-3-yl)-benzene-sulfonyl]-piperidin-4-ylmethyl}-amino)-propoxy]-phenol Prepared from t-butyl-[4-(2S)-oxiranylmethoxyphenoxy]-diphenylsilane (0.159 g, 0.39 mmol) and (4-{[4-(5-octyl-1,2,4-oxadiazol-3-yl)phenyl]sulfonyl}-4-piperidinyl)-methylamine (0.210 g, 0.39 mmol) and diisopropylethyl amine (0.1 mL) according to the procedure used for example 37 to give 0.78 g of the title compound as a white solid.

NMR (DMSO-$d_6$, 400 MHz); δ 0.82–0.86 (m, 3H), 1.07–1.37 (m, 13H), ), 1.72–1.82 (m, 4H), 2.22–2.28 (m, 2H), 3.00–3.03 (t, 2H), 3.63–3.79 (m, 5H), 4.85–4.87 (s, 1H), 6.60–6.64 (m, 2H), 6.68–6.72 (m, 2H), 7.88–7.91 (d, 2H), 8.21–8.24 (d, 2H), 8.85 (s, 1H). MS (ESI$^+$, m/z): 601 [M+H]$^+$.

EXAMPLE 103

N-{2-Hydroxy-5-[1-hydroxy-2-({1-[4-(5-octyl-[1,2,4]oxadiazol-3-yl)-benzene-sulfonyl]-piperidin-4-ylmethyl}-amino)-ethyl]-phenyl}-methanesulfonamide

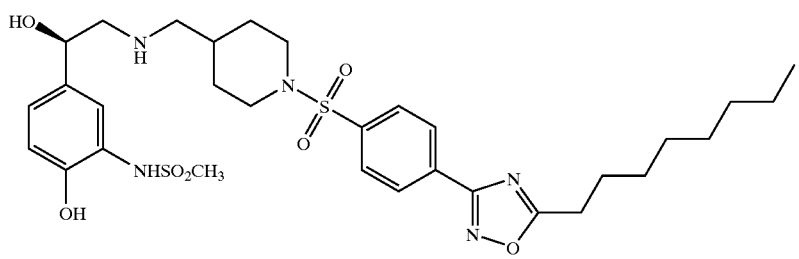

Step A: (1-{[4-(5-Octyl-1,2,4-oxadiazol-3-yl)phenyl]sulfonyl}-4-piperidinyl)methyl Methyl-carboxaldehyde Dimethyl Acetal A solution of 4-{[4-(dimethoxymethyl)-1-piperidinyl]sulfonyl}-N-hydroxybenzene-carboximidamide (0.440 g, 1.2 mmol), and octyl chloride (0.435 g, 2.5 mmol) in pyridine was heated at 100° C. for 7 hours. The pyridine was removed in vacuo, and the crude reaction mixture was partitioned between chloroform and water. The organic layer was washed 1N NaOH, brine, and was dried (Na$_2$SO$_4$). The solvent was evaporated in vacuo to give 0.20 g of the title compound.

Step B: (1-{[4-(5-Octyl-1,2,4-oxadiazol-3-yl)phenyl]sulfonyl}-4-piperidinyl)methyl-carboxaldehyde The intermediate (1-{[4-(5-octyl-1,2,4-oxadiazol-3-yl)phenyl]sulfonyl}-4-piperidinyl)methyl methyl-carboxaldehyde dimethyl acetal (0.4 g, 0.91 mmol) was dissolved in 10 mL of CH$_2$Cl$_2$ containing 1 mL of TFA and stirred at ambient temperature for 45 minutes. The reaction mixture was concentrated in vacuo to an oil. The residue was partitioned with CH$_2$Cl$_2$ and sat'd NaHCO$_3$. The organic base was dried (Na$_2$SO$_4$) and concentrated in vacuo to give the product (0.2 g) as a clear oil which was used as is.

Step C: N-{2-Hydroxy-5-[1-hydroxy-2-({1-[4-(5-octyl-[1,2,4]oxadiazol-3-yl)-benzene-sulfonyl]-piperidin-4-ylmethyl}-amino)-ethyl]-phenyl}-methanesulfonamide Prepared from N-[5-(2-amino-1-{R}-hydroxyethyl)-2-hydroxyphenyl]-methanesulfonamide (0.089 g, 0.039 mmol), (1-{[4-(5-octyl-1,2,4-oxadiazol-3-yl)phenyl]sulfonyl}-4-piperidinyl)methyl-carboxaldehyde (0.2 g, 0.4 mmol), glacial acetic acid (0.020 g, 0.33 mmol) and sodium cyanoborohydride (0.025 g, 0.04 mmol) according to the procedure used for example 67 (Step B) to give 0.123 g of the title compound as a white solid.

NMR (DMSO-$d_6$, 400 MHz): δ 1.11–1.18 (m, 2H), 2.24–2.29 (m, 2H), 3.64–3.66 (m, 2H), 4.48 (m, 1H), 6.78–6.80 (d, 1H), 6.95–6.97 (d, 1H), 7.13–7.14 (s, 1H), 7.89–7.91 (d, 2H), 8.20–8.24 (d, 2H). MS (APCI$^+$, m/z): 664 [M+H]$^+$.

EXAMPLE 104

3-{3-[4-(4-{[(2R)-2-Hydroxy-2-(4-hydroxy-3-methanesulfonylamino-phenyl)-ethylamino]-methyl}-piperidine-1-sulfonyl)-phenyl]-[1,2,4]oxadiazol-5-yl}-propionic Acid Methyl Ester

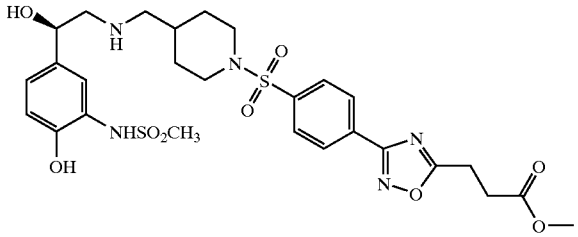

Step A: 3-[3-(4-{[4-(Dimethoxymethyl)-1-piperidinyl]sulfonyl}phenyl)-1,2,4-oxadiazol-5-yl]propanoic Acid Methyl Ester Methyl 4-chloro-4-oxobutanoate (0.391 g, 2.6 mmol), 4-{[4-(dimethoxy-methyl)-1-piperidinyl]sulfonyl}-N-hydroxybenzenecarboximidamide (0.480 g, 1.3 mmol) was dissolved in 4 mL (49.5 mmol) of pyridine and stirred at 85° C. overnight. The solvent was evaporated with toluene, and the reaction mixture was partitioned between chloroform and water. The organic layer was washed with brine and dried with sodium sulfate. The final product was purified my flash chromatography (chloroform-methanol, 50:1) to give 0.130 g (0.22 mmol).

Step B: 3-[3-(4-{[4-Formyl-1-piperidinyl]sulfonyl}phenyl)-1,2,4-oxadiazol-5-yl]propanoic Acid Methyl Ester The intermediate 3-[3-(4-{[4-(dimethoxymethyl)-1-piperidinyl]sulfonyl}-phenyl)-1,2,4-oxadiazol-5-yl]propanoic acid methyl ester(0.13 g, 0.22 mmol) was dissolved in 10 mL of CH$_2$Cl$_2$ containing 1 mL of TFA and stirred at ambient temperature for 45 minutes. The reaction mixture was concentrated in vacuo to an oil. The residue was partitioned with CH$_2$Cl$_2$ and sat'd NaHCO$_3$. The organic base was dried (Na$_2$SO$_4$) and concentrated in vacuo to give the product (0.2 g) as a clear oil which was used as is.

Step C: 3-{3-[4-(4-{[(2R)-2-Hydroxy-2-(4-hydroxy-3-methanesulfonylamino-phenyl)-ethylamino]-methyl}-piperidine-1-sulfonyl)-phenyl]-[1,2,4]oxadiazol-5-yl}-propionic Acid Methyl Ester Prepared from N-[5-(2-amino-1-{R}-hydroxyethyl)-2-hydroxyphenyl]-methane-sulfonamide (0.136 g, 0.55 mmol), 3-[3-(4-{[4-formyl-1-piperidinyl]-sulfonyl}phenyl)-1,2,4-oxadiazol-5-yl]propanoic acid methyl ester (0.55 mmol), glacial acetic acid (0.040 g, 0.66 mmol) and sodium cyanoborohydride (0.0382 g, 0.061 mmol) according to the procedure used for example 67 (Step B) to give 0.180 g of the title compound as a white solid.

NMR (DMSO-$d_6$, 400 MHz): δ 1.09–1.18 (m, 2H), 1.72–1.75 (m, 2H), 2.23–2.29 (m, 2H), 3.63 (m, 2H), 4.48–4.49 (m, 1H), 6.78–6.80 (d, 2H), 6.95–6.97 (d, 2H), 7.13 (s, 1H), 7.89–7.91 (d, 2H), 8.19–8.22 (d, 2H). MS (ESI$^+$, m/z): 638 [M+H]$^+$.

EXAMPLE 105

3-(3-{4-[(4-{[((2S)-2-Hydroxy-2-{4-hydroxy-3-[(methylsulfonyl)amino]-phenyl}ethyl)amino]methyl}-1-piperidinyl)sulfonyl]phenyl}-1,2,4-oxadiazol-5-yl)propanoic Acid

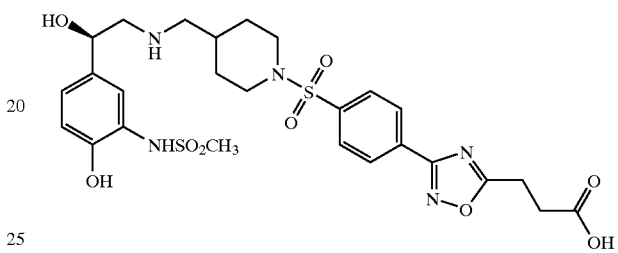

A solution of 3-(3-{4-[(4-{[((2S)-2-hydroxy-2-{4-hydroxy-3-[(methyl-sulfonyl)-amino]-phenyl}ethyl)amino]methyl}-1-piperidinyl)sulfonyl]-phenyl}-1,2,4-oxadiazol-5-yl)propanoic acid methyl ester (0.150 g, 0.24 mmol) in 15 ml of methanol and 0.470 ml of 1N NaOH was heated at reflux for 14 hours. To the reaction mixture was added 0.470 ml of 1N HCl. The solvent was removed in vacuo and the resulting solid was triturated with water, then with ethyl acetate to give the final product (0.088 g) as a white solid.

NMR (DMSO-$d_6$, 400 MHz): δ 1.10–1.14 (m, 2H), 1.70–1.74 (m, 2H), 2.23–2.28 (m, 2H), 3.62–3.65 (m, 2H), 4.47–4.50 (m, 1H), 6.77–6.79 (s, 1H), 6.94–6.96 (d, 1H), 7.12–7.13 (s, 1H), 7.89–7.91 (d, 2H), 8.20–8.23 (d, 2H). MS (ESI$^-$, m/z): 622 [M–H]$^{31}$.

EXAMPLE 106

(R)-N-{2-Hydroxy-5-[1-hydroxy-2-({1-[4-(piperidine-1-sulfonyl)-phenyl]-piperidin-4-ylmethyl}-amino)-ethyl]-phenyl}-methanesulfonamide

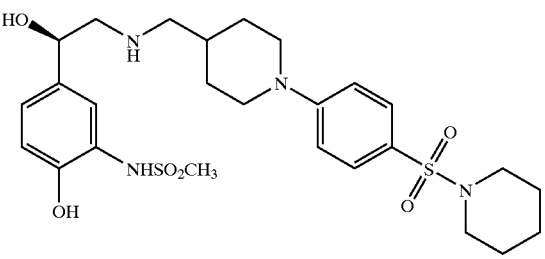

Step A: 1-[(4-Fluorophenyl)sulfonyl]piperidine

A solution of piperidine (5.64 g, 66 mmol), diisopropyl-ethyl amine (1 3.64 mL, 78 mmol), and p-fluorobenzenesulfonyl chloride (13.64 mL, 78 mmol) in THF at 0° C. was stirred for 2 hours at ambient temperature. The solvent was removed in vacuo and the crude reaction mixture was partitioned between ethyl acetate and water.

The organic layer was washed with aqueous HCl, and brine. It was dried over sodium sulfate, and filtered. Removal of the solvent gave near quantitative yield of the title compound.

Step B: {1-[4-(1-Piperidinylsulfonyl)phenyl]-4-piperidinyl}methanol

1-[(4-fluorophenyl)sulfonyl]piperidine (0.437 g, 1.8 mmol), 4-piperidinylmethanol (0.230 g, 2 mmol), and ;potassium carbonate (0.262 g, 2 mmol) were heated to 120° C. for 4 hours. The reaction was cooled, and partitioned between ethyl acetate and water. The organic layer was washed with aqueous HCl, and brine. It was dried with sodium sulfate, filtered, and removal of the solvent gave 0.040 g (0.12 mmol).

Step C: {1-[4-(1-Piperidinylsulfonyl)phenyl]-4-piperidinyl}methylcarboxaldehyde

{1-[4-(1-piperidinylsulfonyl)phenyl]-4-piperidinyl}methanol is oxidized with IBX according to the procedure outlined in intermediate 26 (Step B) to give 0.38 g of title compound.

Step D: (R)-N-{2-Hydroxy-5-[1-hydroxy-2-({1-[4-(piperidine-1-sulfonyl)-phenyl]-piperidin-4-ylmethyl}-amino)-ethyl]-phenyl}-methanesulfonamide A solution of N-[5-(2-amino-1-{R}-hydroxyethyl)-2-hydroxyphenyl]-methane-sulfonamide (0.214 g, 0.87 mmol), {1-[4-(1-piperidinylsulfonyl)phenyl]-4-piperidinyl}methylcarboxaldehyde (0.380 g, 0.87 mmol) and glacial acetic acid (0.053 g, 0.88 mmol) in 5 mL of methanol-THF (4:1, v/v) was stirred for 1 hour over 4A molecular sieves. In one portion sodium cyanoborohydride (0.055 g, 0.88 mmol) was added and the mixture stirred overnight at ambient temperature. The sieves were filtered and the filtrate was preabsorbed on silica gel. The solids were purified by flash chromatography ($CH_2Cl_2$—$CH_3OH$, 20:1). to give the product (0.231 g).

NMR (DMSO-$d_6$, 400 MHz): δ 1.15–1.22 (m, 2H), 1.75–1.80 (m, 2H), 3.88–3.91 (m, 2H), 4.59–4.60 (s, 1H), 6.82–6.85 (d, 1H), 7.00–7.05 (m, 3H), 7.18–7.19 (s, 1H), 7.44–7.47 (d, 2H). MS (ESI$^+$, m/z): 567 [M+H]$^+$.

EXAMPLE 107

Methyl 6-(4-{[((2R)-2-Hydroxy-2-{4-hydroxy-3-[(methylsulfonyl)amino]phenyl}-ethyl)amino]methyl}piperidin-1-yl)-nicotinate

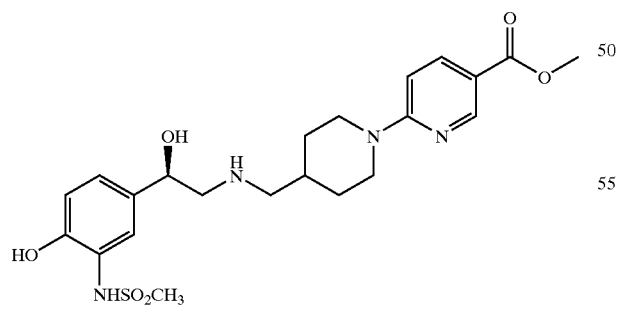

Step A: 1-(3-Methoxycarbonyl-2-pyridyl)-4-formylpiperidine

A solution of 4-formylpiperidine dimethyl acetal (0.636 g, 4 mmol) in 5 mL DMF was added to a slurry of hexane washed potassium hydride (0.16 g, 4 mmol) in 5 mL DMF. Stirred at ambient temperature until gas evolution ceased. Methyl-6-chloronicotinate (0.788 g, 4 mmol) was added in one portion and the reaction was heated at 60° C. overnight. The reaction mixture was partitioned between ethyl acetate and $H_2O$. The organic phase was washed with $H_2O$, brine, and dried ($Na_2SO_4$). Removal of solvent in vacuo afforded a clear oil . The crude product was purified by flash chromatography (hexane-ethyl acetate, 2:1) to give 0.170 g of the intermediate 1-(3-methoxycarbonyl-2-pyridyl)-4-formylpiperidine dimethyl acetal.

NMR (DMSO-$d_6$, 300 MHz): δ 1.18 (m, 2H), 1.67 (broad d, 2H), 1.87 (m, 1H), 2.85 (dt, 2H), 3.12 (s, 6H), 3.35 (s, 1H), 3.77 (s, 3H), 4.05 (d, 1H), 4.42 (broad d, 2H), 6.65 (d, 1H), 6.84 (d, 1H), 7.9 (m, 1H), 8.62 (m, 1H).

The acetal was dissolved in 5 mL $CH_2Cl_2$-TFA (4:1, v/v) and stirred at ambient temperature for 3 hours. The reaction mixture was concentrated in vacuo and the residue partitioned with ethyl acetate and sat'd. $NaHCO_3$. The organic phase was dried ($Na_2SO_4$) and concentrated to give 0.12 g of product as a white solid.

NMR (DMSO-$d_6$, 300 MHz): δ 1.45 (m, 2H), 1.9 (broad d, 2H), 3.18 (dt, 2H), 3.77 (s, 3H), 4.25 (m, 1H), 6.65 (d, 1H), 6.88 (d, 1H), 7.9 (dd 1H), 8.62 (m, 1H), 9.61 (s, 1H).

Step B: Methyl 6-(4-{[((2R)-2-Hydroxy-2-{4-hydroxy-3-[(methylsulfonyl)amino]-phenyl}ethyl)amino]methyl}piperidin-1-yl)-nicotinate Prepared from N-[5-(2-amino-1-{R}-hydroxyethyl)-2-hydroxyphenyl]-methanesulfonamide (0.119 g, 0.48 mmol), 1-(3-methoxycarbonyl-2-pyridyl)-4-formylpiperidine (0.12 g, 0.48 mmol), glacial acetic acid (0.03 g, 0.48 mmol) and sodium cyanoborohydride (0.03 g, 0.48 mmol) according to the procedure used for example 67 (Step B) to give 0.077 g of the title compound as a yellow solid (isolated as the HCl salt).

NMR (DMSO-$d_6$, 400 MHz): δ 1.18 (m, 2H), 1.85 (t, 2H), 2.07 (m, 1H), 1.812 (broad t, 2H), 2.93 (m, 5H), 3.77 (s, 3H), 4.44 (broad d, 2H), 4.86 (d, 1H), 6.91 (m, 2H), 7.05 (dd, 1H), 7.23 (s, 1H), 8.59 (s, 1H), 8.7 (broad d, 2H), 8.759 (s, 1H), 9.99 (broad, 1H). MS (APCI$^+$, m/z): 479 [M+H]$^+$.

EXAMPLE 108

(2S)-2-{[4-(4-{[((2R)-2-Hydroxy-2-{4-hydroxy-3-[(methylsulfonyl)amino]phenyl}-ethyl)amino]methyl}piperidin-1-yl)benzoyl]amino}butanedioic Acid

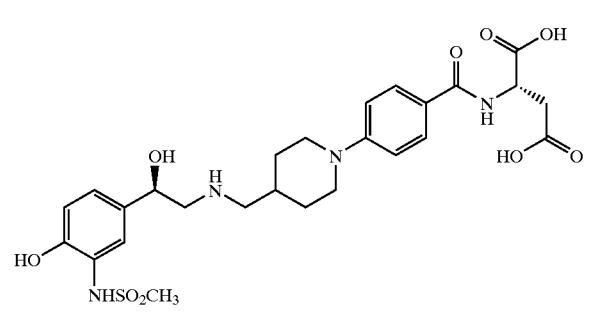

Step A: (2S)-2-{[4-(4-(Dimethoxymethyl)piperidin-1-yl)benzoyl]amino}butanedioic Acid Dibenzyl Ester A solution of 4-(4-(dimethoxymethyl)piperidinyl)benzoic acid (0.45 g, 1.61 mmol), 1-(3-dimethylaminopropyl)-3-ethylcarbodiimide HCl (0.34 g, 1.77 mmol), N-ethyl morpholine (1 mL), hydroxybenzotriazole (0.239 g, 1.77 mmol), and S-aspartic acid dibenzyl ester p-tosylate (0.782 g, 0.0016 mol) in 10 mL of THF was stirred at room temperature overnight. The THF was evaporated under reduced pressure and the residue was dissolved in methylene chloride and washed with 1N HCl, 1N NaOH and brine. The organic layer was dried (Na$_2$SO$_4$), concentrated in vacuo, and purified by flash chromatography (CH$_2$Cl$_2$—CH$_3$OH-methanol, 20:1) to give 0.218 g of the title compound.

NMR (DMSO-d$_6$, 400 MHz): δ 1.22–1.23 (m, 2H), 1.63–1.64 (m, 1H), 1.67 (d, 2H), 2.09–2.10 (t, 2H), 2.96–2.97 (d, 2H), 3.58–3.61 (d, 2H), 4.00–4.01 (d, 1H), 4.74–4.76 (m, 1H), 5.08–5.11 (d, 4H), 6.89–6.91 (d, 1H), 7.29–7.33 (m, 10H), 7.56–7.61 (q, 4H), 9.36 (s, 1H).

Step B: (2S)-2-{[4-(4-(Formyl)Piperidin-1-yl)benzoyl]amino}butanedioic Acid Dibenzyl Ester A solution of (2S)-2-{[4-(4-(dimethoxymethyl)piperidin-1-yl)benzoyl]-amino}-butanedioic acid dibenzyl ester (0.21 g, 0.4 mmol) in methylene chloride (10 mL) containing trifluoroacetic acid (0.2 ml, 2.6 mmol) was stirred at ambient temperature for 1 hour. The reaction was concentrated in vacuo to give the product which was used directly in the next step.

Step C: (2S)-2-{[4-(4-{[((2R)-2-Hydroxy-2-{4-hydroxy-3-[(methylsulfonyl)amino]-phenyl}ethyl)amino]methyl}piperidin-1-yl)benzoyl]amino}butanedioic Acid Dibenzyl Ester A solution of N-[5-(2-amino-1-{R}-hydroxyethyl)-2-hydroxyphenyl]-methanesulfonamide (0.0.093 g, 0.4 mmol), (2S)-2-{[4-(4-(formyl)piperidin-1-yl)benzoyl]amino}butanedioic acid dibenzyl ester (0.4 mmol) and glacial acetic acid (0.022 g, 0.4 mmol) in 5 mL methanol was stirred for 1 hour over 4A molecular sieves. In one portion sodium cyanoborohydride (0.025 g, 0.4 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 19:1). to give the product (0.074 g).

Step D: (2S)-2-{[4-(4-{[((2R)-2-Hydroxy-2-{4-hydroxy-3-[(methylsulfonyl)amino]-phenyl}ethyl)amino]methyl}piperidin-1-yl)benzoyl]amino}butanedioic Acid A mixture of (2S)-2-{[4-(4-{[((2R)-2-hydroxy-2-{4-hydroxy-3-[(methylsulfonyl)-amino]-phenyl}-ethyl)amino]methyl}piperidin-1-yl)benzoyl]-amino}butanedioic acid dibenzyl ester (0.074 g, 0.1 mmol) and 0.08 g of 10% palladium on carbon in 4 mL ethanol-cyclohexene (3:1, v/v) was heated at 78° C. until the reduction was complete. The catalyst was filtered (Celite) and the cake was washed with hot methanol. The solvent was removed in vacuo to give 0.023 g of the title compound.

NMR (DMSO-d$_6$, 400 MHz): δ 1.17–1.18 (m, 2H), 3.85–3.86 (m, 2H), 6.91–6.93 (m, 1H), 6.95–6.99 (m, 2H), 7.03–7.05 (m, 1H), 7.22 (m, 1H), 7.69–7.71 (m, 2H), MS (ESI$^-$, m/z): 577 [M–H]$^-$.

EXAMPLE 109

(2S)-2-{[4-(4-{[((2R)-2-Hydroxy-2-{4-hydroxy-3-[(methylsulfonyl)amino]phenyl}-ethyl)amino]methyl}piperidin-1-yl)benzoyl]amino}-3-phenylpropanoic Acid

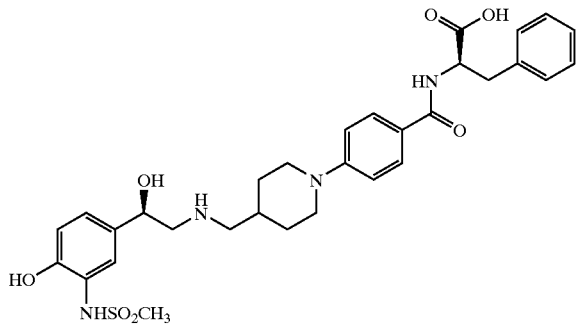

Step A: (2S)-2-{[4-(4-(Dimethoxymethyl)amino]methyl}piperidin-1-yl)benzoyl]amino}-3-phenylpropanoic Methyl Ester A solution of 4-(4-(dimethoxymethyl)piperidinyl)benzoic acid (0.515 g, 1.84 mmol), 1-(3-dimethylaminopropyl)-3-ethylcarbodiimide HCl (0.388 g, 1.84 mmol), N-ethyl morpholine (0.5 mL), hydroxybenzotriazole (0.274 g, 2.02 mmol), and ) L-phenylalanine methyl ester HCl (0.397 g, 1.8 mmol) in 10 mL of THF was stirred at room temperature overnight. The THF was evaporated under reduced pressure and the residue was dissolved in methylene chloride and washed with 1N HCl, 1N NaOH and brine. The organic layer was dried (Na$_2$SO$_4$), concentrated in vacuo, and purified by flash chromatography (CH$_2$Cl$_2$—CH$_3$OH-methanol, 20:1) to give 0.139 g of the product.

Step B: (2S)-2-{[4-(4-(Formyl)amino]methyl}piperidin-1-yl)benzoyl]amino}-3-phenylpropanoic Methyl Ester A solution of (2S)-2-{[4-(4-(dimethoxymethyl)amino]methyl}piperidin-1-yl)benzoyl]amino}-3-phenylpropanoic methyl ester(0.139 g, 0.3 mmol) in methylene chloride (10 mL) containing trifluoroacetic acid (0.165 ml, 2.0 mmol) was stirred at ambient temperature for 1 hour. The reaction was concentrated in vacuo to give the product which was used directly in the next step Step C: (2S)-2-{[4-(4-(Formyl)amino]methyl}piperidin-1-yl)benzoyl]amino}-3-phenylpropanoic Methyl Ester A solution of N-[5-(2-amino-1-{R}-hydroxyethyl)-2-hydroxyphenyl]-methane-sulfonamide (0.0.078 g, 0.316 mmol), (2S)-2-{[4-(4-(dimethoxymethyl)amino]-ethyl}-piperidin-1-yl)benzoyl]amino}-3-phenylpropanoic methyl ester (0.316 mmol) and glacial acetic acid (0.018 g, 0.316 mmol) in 5 mL methanol was stirred for 1 hour over 4A molecular sieves. In one portion sodium cyanoborohydride (0.021 g, 0.316 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 19:1). to give the product (0.060 g).

Step D: (2S)-2-{[4-(4-{[((2R)-2-Hydroxy-2-{4-hydroxy-3-[(methylsulfonyl)amino]-phenyl}ethyl)amino]methyl}piperidin-1-yl)benzoyl]amino}-3-phenylpropanoic Acid A solution of (2S)-2-{[4-(4-(formyl)amino]methyl}piperidin-1-yl)benzoyl]-amino}-3-phenylpropanoic acid methyl ester(0.060 g, 0.1 mmol) in methanol (2 mL) and 1N sodium hydroxide (0.45 mL) was stirred at ambient temperature overnight. When the reaction was complete, 1N HCl (0.45 mL) was added. The methanol and water was evaporated. Additional methanol was added, the reaction was filtered through a 0.5 micron filter, and evaporated in vacuo to give the acid (0.0269).

NMR (DMSO-d$_6$, 400 MHz): δ 1.15–1.80 (m, 2H), 1.73–1.76 (d, 2H), 2.66–2.72 (t, 2H), 3,77–3.80 (d, 2H), 6.43–6.51 (q, 2H), 6.88–6.90 (d, 2H), 7.00–7.01 (d, 1H), 7.04–7.14 (m, 5H), 7.44–7.49 (m, 3H).

EXAMPLE 110

(2R)-2-{[4-(4-{[((2R)-2-Hydroxy-2-{4-hydroxy-3-[(methylsulfonyl)amino]phenyl}-ethyl)amino]methyl}piperidin-1-yl)benzoyl]amino}butanedioic Acid

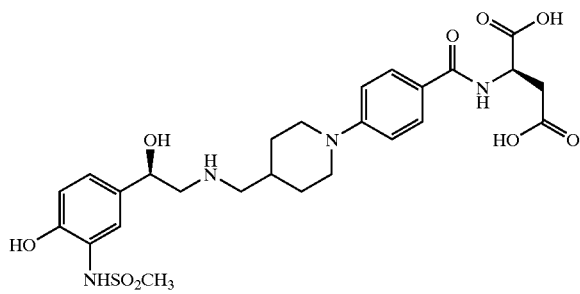

Step A: (2R)-2-{[4-(4-(Dimethoxymethyl)piperidin-1-yl)benzoyl]amino}butanedioic Acid Dibenzyl Ester A solution of 4-(4-(dimethoxymethyl)piperidinyl)benzoic acid (0.45 g, 1.61 mmol), 1-(3-dimethylaminopropyl)-3-ethylcarbodiimide HCl (0.34 g, 1.77 mmol), N-ethyl morpholine (1.0 mL), hydroxybenzotriazole (0.239 g, 1.77 mmol), and R-aspartic acid dibenzyl ester p-tosylate (0.782 g, 1.6 mmol) in 10 mL of THF was stirred at room temperature overnight. The THF was evaporated under reduced pressure and the residue was dissolved in methylene chloride and washed with 1N HCl, 1N NaOH and brine. The organic layer was dried (Na$_2$SO$_4$), concentrated in vacuo, and purified by flash chromatography (CH$_2$Cl$_2$—CH$_3$OH-methanol, 20:1) to give 0.218 g of the product Step B: (2R)-2-{[4-(4-(Formyl)piperidin-1-yl)benzoyl]amino}butanedioic Acid Dibenzyl Ester A solution of (2R)-2-{[4-(4-(dimethoxymethyl)piperidin-1-yl)benzoyl]-amino}-butanedioic acid dibenzyl ester (0.215 g, 0.4 mol) in methylene chloride (10 mL) containing trifluoroacetic acid (0.165 mL, 2.0 mmol) was stirred at ambient temperature for 1 hour. The reaction was concentrated in vacuo to give the product which was used directly in the next step.

Step C: (2R)-2-{[4-(4-{[((2R)-2-Hydroxy-2-{4-hydroxy-3-[(methylsulfonyl)amino]-phenyl}ethyl)amino]methyl}piperidin-1-yl)benzoyl]amino}butanedioic Acid Dibenzyl Ester A solution of N-[5-(2-amino-1-{R}-hydroxyethyl)-2-hydroxyphenyl]-methane-sulfonamide (0.104 g, 0.421 mmol), (2R)-2-{[4-(4-(formyl)piperidin-1-yl)benzoyl]-amino}butanedioic acid dibenzyl ester (0.4 mmol) and glacial acetic acid (0.024 g, 0.421 mmol) in 5 mL methanol was stirred for 1 hour over 4A molecular sieves. In one portion sodium cyanoborohydride (0.028 g, 0.421 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 19:1). to give the product (0.110 g).

Step D: (2R)-2-{[4-(4-{[((2R)-2-Hydroxy-2-{4-hydroxy-3-[(methylsulfonyl)-amino]phenyl}ethyl)amino]methyl}piperidin-1-yl)benzoyl]amino}butanedioic Acid A mixture of (2R)-2-{[4-(4-({[(2R)-2-hydroxy-2-{4-hydroxy-3-[(methylsulfonyl)-amino]-phenyl}ethyl)amino]methyl}piperidin-1-yl)benzoyl]-amino}butanedioic acid dibenzyl ester (0.110 g, 0.14 mmol) and 0.11 g of 10% palladium on carbon in ethanol (3 mL) and cyclohexene (1 mL) was heated at reflux for 3 hours. When complete, the catalyst was filtered (Celite) and the cake was washed with hot methanol. The solvent was removed under reduced pressure, to give the title compound (0.010 g).

NMR (DMSO-d$_6$, 400 MHz): δ 1.20–1.29 (m, 2H), 3.85–3.89 (m, 2H), 4.38–4.37 (m, 2H), 6.81–7.06 (m, 3H), 7.65–7.71 (m, 4H). MS (ESI$^-$, m/z): 577 [M–H]$^-$.

EXAMPLE 111

(2S)-1-({4-[(4-{[((2R)-2-Hydroxy-2-{4-hydroxy-3-[(methylsulfonyl)amino]-phenyl}ethyl)amino]methyl}piperidin-1-yl)sulfonyl]anilino}carbonyl)pyrrolidine-2-carboxylic Acid Methyl Ester

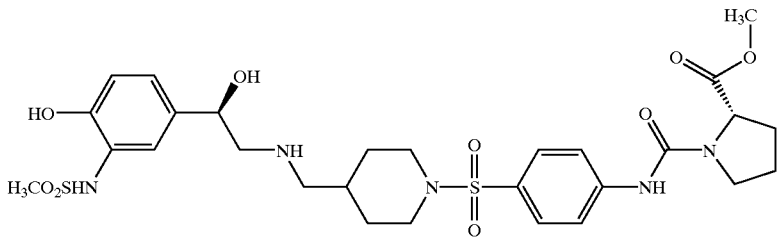

Step A: (2s)-1-[4-(4-Dimethoxymethyl-piperidine-1-sulfonyl)-phenylcarbamoyl]-pyrrolidine-2-carboxylic Acid Methyl Ester A solution of from 1-[(4-amino)benzenesulfonylpiperidin-4ylmethyl]-dimethyl acetal (0.5 g, 1.66 mmol) and diisopropylethyl amine (0.61 mL, 3.5 mmol) in 50 mL THF was added dropwise over 1 hour to a stirred solution of triphosgene (0.184 g, 0.48 mmol) in 10 mL THF. When the addition was complete L-proline methyl ester HCl (0.263 g, 1.6 mmol) and diisopropylethyl amine (0.61 mL, 3.5 mmol) was added and the solution was stirred at ambient temperature overnight. The reaction mixture was partitioned with ethyl acetate and water. The organic phase was washed with brine and dried (Na$_2$SO$_4$). Removal of solvent afforded 0.240 g of a white solid.

NMR (DMSO-d$_6$, 400 MHz): δ 1.21–1.22 (m, 2H), 1.64–1.66 (m, 1H), 2.09–2.10 (m, 2H), 3.18–3.31 (s, 6H), 3.59–3.61 (m, 2H), 4.01 (d, 1H), 7.56–7.58 (d, 2H), 7.73–7.75 (d, 2H), 8.79 (s, 1H). MS (ESI$^-$, m/z): 468 [M–H]$^-$.

Step B: (2s)-1-[4-(4-Formyl-piperidine-1-sulfonyl)-phenylcarbamoyl]-pyrrolidine-2-carboxylic Acid Methyl Ester Under anhydrous conditions, a solution of (2s)-1-[4-(4-dimethoxymethyl-piperidine-1-sulfonyl)-phenylcarbamoyl]-pyrrolidine-2-carboxylic acid methyl ester (0.240 g, 0.5 mmol), sodium iodide (0.192 g, 1.28 mmol), and trichloromethylsilane (0.120 mL, 1.1 mmol) in acetonitrile (2.5 mL) was stirred at ambient temperature for 15 minutes. The reaction mixture was quenched with water and partitioned with methylene chloride. The organic phase was washed with $Na_2S_2O_3$ dilute solution and dried ($Na_2SO_4$). Removal of solvent afforded the crude product which was used directly in the next step without characterization.

Step C: 1-(2S)-1-{4-[(4-{[((2R)-2-Hydroxy-2-{4-hydroxy-3-[(methylsulfonyl)-amino]-phenyl}ethyl)amino]methyl}piperidin-1-yl)sulfonyl]anilino-carbonyl)pyrrolidine-2-carboxylic Acid Methyl Ester A solution of N-[5-(2-amino-1-{R}-hydroxyethyl)-2-hydroxyphenyl]-methane-sultonamide (0.123 g, 0.5 mmol), (2s)-1-[4-(4-formyl-piperidine-1-sulfonyl)-phenylcarbamoyl]-pyrrolidine-2-carboxylic acid methyl ester (0.5 mmol) and glacial acetic acid (0.029 g, 0.5 mmol) in 5 mL methanol was stirred for 1 hour over 4A molecular sieves. In one portion sodium cyanoborohydride (0.033 g, 0.5 mmol) was added and the mixture stirred overnight at ambient temperature. The sieves were filtered and the filtrate was preabsorbed on silica gel. The solids were purified by flash chromatography ($CH_2Cl_2$—$CH_3OH$, 19:1). to give the product (0.111 g).

NMR (DMSO-$d_6$, 400 MHz): δ 6.82–6.84 (m, 1H), 6.99 (m, 1H), 7.17–7.18 (s, 1H), 7.24 (s, 1H), 7.58–7.60 (m, 2H), 7.73–7.76 (m, 2H), 8.79 (broad s, 1H). MS (ESI+, m/z): 654 [M+H]+.

EXAMPLE 112

(2S)-1-({4-[(4-{[((2R)-2-Hydroxy-2-{4-hydroxy-3-[(methylsulfonyl)amino]phenyl}-ethyl)amino]methyl}piperidin-1-yl)sulfonyl]anilino}carbonyl)pyrrolidine-2-carboxylic Acid A solution of 1-(2S)-1-({4-[(4-{[((2R)-2-hydroxy-2-{4-hydroxy-3-[(methylsulfonyl)-amino]-phenyl}ethyl)amino]methyl}piperidin-1-yl)sulfonyl]-anilinocarbonyl)-pyrrolidine-2-carboxylic acid methyl ester (0.098 g, 0.15 mmol) in methanol (2 mL) and 1N sodium hydroxide (0.55 mL) was stirred at ambient temperature overnight. When the reaction was complete, 1N HCl (0.55 mL) was added. The methanol and water was evaporated. Additional methanol was added, the reaction was filtered through a 0.5 micron filter, and evaporated in vacuo to give the acid (0.035 g).

NMR (DMSO-$d_6$, 400 MHz): δ 1.14–1.25 (t, 2H), 1.78–1.82 (t, 2H), 2.66–2.76 (m, 4H), 4.24–4.26 (broad s, 2H), 4.67–4.69 (d, 1H), 6.83–6.85 (d, 1H), 6.99–7.01 (d, 1H), 7.18–7.19 (s, 1H), 7.53–7.75 (m, 5H). MS (ESI+, m/z): 640 [M+H]+.

EXAMPLE 113

(2S)-2-[({4-[(4-{[((2R)-2-Hydroxy-2-{4-hydroxy-3-[(methylsulfonyl)amino]-phenyl}ethyl)amino]methyl}piperidin-1-yl)sulfonyl]anilino}carbonyl)amino]-3-phenylpropanoic Acid

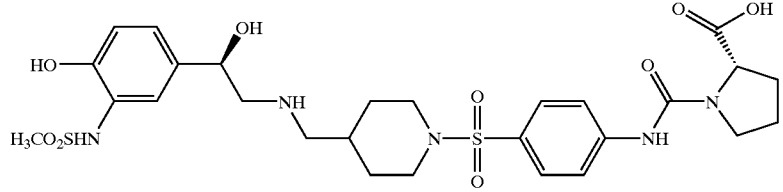

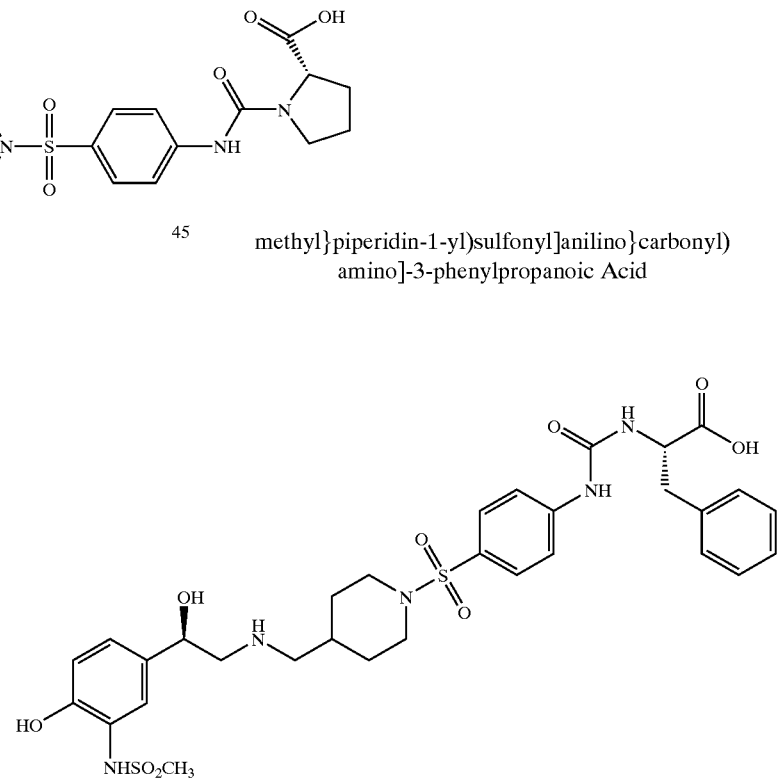

Step A: (2S)-2-{3-[4-(4-Dimethoxymethyl-piperidine-1-sulfonyl)-phenyl]-ureido}-3-phenyl-propionic Acid Benzyl Ester A solution of from 1[(4amino)benzenesulfonylpiperidin-4ylmethyl]-dimethyl acetal (0.5 g, 1.66 mmol) and diisopropylethyl amine (0.61 mL, 3.5 mmol) in 50 mL THF was added dropwise over 1 hour to a stirred solution of triphosgene (0.184 g, 0.48 mmol) in 10 mL THF. When the addition was complete L-phenylalanine benzyl ester HCl (0.464 g, 1.6 mmol) and diisopropylethyl amine (1.21 mL, 7 mmol) was added and the solution was stirred at ambient temperature overnight. The reaction mixture was partitioned with ethyl acetate and water. The organic phase was washed with brine and dried (Na$_2$SO$_4$). Removal of solvent afforded 0.78 g of a white solid.

NMR (DMSO-d$_6$, 400 MHz): δ 1.50–1.51 (m, 1H), 1.62–1.63 (broad d, 2H), 2.04–2.11 (t, 2H), 3.31 (s, 6H), 3.55–3.59 (d, 2H), 3.99–4.00 (d, 1H), 4.49–4.54 (m, 1H), 5.10 (s, 1H), 7.07–7.09 (d, 1H), 7.21–7.34 (m, 10H), 7.54–7.57 (q, 4H), 9.77 (s, 1H).

Step B: (2S)-2-{3-[4-(4-Formyl-piperidine-1-sulfonyl)-phenyl]-ureido}-3-phenyl-propionic Acid Benzyl Ester Under anhydrous conditions, a solution of (2S)-2-{3-[4-(4-dimethoxymethyl-piperidine-1-sulfonyl)-phenyl]-ureido}-3-phenyl-propionic acid benzyl ester (0.78 g, 1.3 mmol), sodium iodide (0.491 g, 3.27 mmol), and trichloromethylsilane (0.308 mL, 2.62 mmol) in acetonitrile (20 mL) was stirred at ambient temperature for 15 minutes. The reaction mixture was quenched with water and partitioned with methylene chloride. The organic phase was washed with Na$_2$S$_2$O$_3$ dilute solution and dried (Na$_2$SO$_4$). Removal of solvent afforded the crude product which was used directly in the next step without characterization.

Step C: (2S)-2-[({4-[(4-{[((2R)-2-Hydroxy-2-{4-hydroxy-3-[(methylsulfonyl)-amino]-phenyl}-ethyl)amino]methyl}piperidin-1-yl)sulfonyl]anilino}carbonyl)-amino]-3-phenylpropanoic Acid A solution of N-[5-(2-amino-1-{R}-hydroxyethyl)-2-hydroxyphenyl]-methane-sulfonamide (0.320 g, 1.3 mmol), (2S)-2-{3-[4-(4-formyl-piperidine-1-sulfonyl)-phenyl]-ureido}-3-phenyl-propionic acid benzyl ester (1.3 mmol) and glacial acetic acid (0.074 g, 1.3 mmol) in 5 mL methanol was stirred for 1 hour over 4A molecular sieves. In one portion sodium cyanoborohydride (0.086 g, 1.3 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 19:1). to give 0.12 g of the product.

NMR (DMSO-d$_6$, 400 MHz): δ 1.46–1.49 (s, 1H), 1.73–1.74 (s, 2H), 2.07–2.12 (t, 2H), 3.54–3.56 (d, 2H), 4.20–4.25 (d, 1H), 4.61–4.64 (d, 1H), 6.51–6.53 (d, 1H), 6.82–6.84 (d, 1H), 6.97–6.99 (d, 1H), 7.12–7.22 (m, 7H), 7.52–7.59 (q, 4H), 9.40–9.42 (broad s, 1H). MS (ESI$^+$, m/z): 690 [M+H]$^+$.

EXAMPLE 114

(2S)-2-{[4-(4-{[((2R)-2-Hydroxy-2-{4-hydroxy-3-[(methylsulfonyl)amino]phenyl}-ethyl)amino]methyl}piperidin-1-yl)benzoyl]amino}-4-methylpentanoic Acid

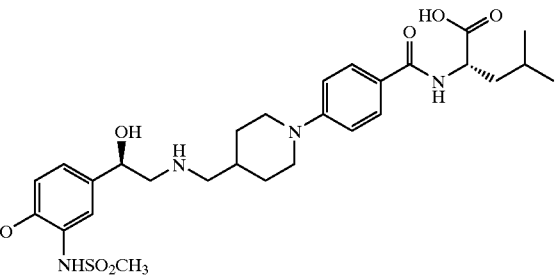

Step A: (2S)-2-{[4-(4-(Dimethoxymethyl)piperidin-1-yl)benzoyl]amino}-4-methylpentanoic Acid Ethyl Ester A solution of 4-(4-(dimethoxymethyl)piperidinyl)benzoic acid (0.450 g, 1.6 mmol), 1-(3-(dimethylamino)propyl)-3-ethylcarbodiimide HCl (0.340 g, 1.77 mmol), N-ethyl morpholine (0.50 mL, 3.9 mmol), hydroxybenzotriazole (0.239 g, 1.77 mmol), and L-leucine ethyl ester HCl (0.322 g, 1.8 mmol) in THF (15 mL) was stirred at ambient temperature overnight. The solvent was evaporated in vacuo and the residue was dissolved in methylene chloride. The organic phase was washed with 1N HCl, 1N NaOH, brine and dried (Na$_2$SO$_4$). The solvent was evaporated in vacuo and the residue purified by flash chromatography (methylene chloride-methanol, 19:1) to give 0.163 g of the title compound.

Step B: (2R)-2-{[4-(4-(Formyl)piperidin-1-yl)benzoyl]amino}4-methylpentanoic Acid Ethyl Ester A solution of (2S)-2-{{[4-(4-(dimethoxymethyl)piperidin-1-yl)benzoyl]-amino}-4-methylpentanoic acid ethyl ester (0.163 g, 0.4 mmol) in methylene chloride (3 mL) and trifluoroacetic acid (0.210 mL) was stirred at ambient temperature for 2 hours. The reaction mixture was diluted with methylene chloride and washed with saturated sodium bicarbonate, brine, and dried (Na$_2$SO$_4$). Removal of solvent in vacuo afforded the crude aldehyde which was used directly in the following step.

Step C: (2S)-2-{[4-(4-{[((2R)-2-Hydroxy-2-{4-hydroxy-3-[(methylsulfonyl)amino]-phenyl}-ethyl)amino]methyl}piperidin-1-yl)benzoyl]amino}-4-methylpentanoic Acid Ethyl Ester A solution of N-[5-(2-amino-1-{R}-hydroxyethyl)-2-hydroxyphenyl]-methane-sulfonamide (0.098 g, 0.4 mmol), (2R)-2-{[4-(4-(formyl)piperidin-1-yl)benzoyl]amino}4-methylpentanoic acid ethyl ester (0.4 mmol) and glacial acetic acid (0.023 g, 0.4 mmol) in 5 mL of methanol-THF (4:1, v/v) was stirred for 1 hour over 4A molecular sieves. In one portion sodium cyanoborohydride (0.026 g, 0.4 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 20:1). to give the product (0.072 g).

Step D: (2S)-2-{[4-(4-{[((2R)-2-hydroxy-2-{4-hydroxy-3-[(methylsulfonyl)amino]-phenyl}-ethyl)amino]methyl}piperidin-1-yl)benzoyl]amino}-4-methylpentanoic Acid A solution of (2S)-2-{[4-(4-{[((2R)-2-hydroxy-2-{4-hydroxy-3-[(methylsulfonyl)amino]-phenyl}-ethyl)amino]methyl}piperidin-1-yl)benzoyl]-amino}-4-methylpentanoic acid (0.072 g, 0.12 mmol) in methanol (2 mL) and 1N sodium hydroxide (0.37 mL) was stirred at ambient temperature overnight. The reaction mixture was neutralized with 1N HCl (0.37 mL) and concentrated in vacuo. The residual solid was washed with water, then ether to give reasonably pure product (0.043 g).

NMR (DMSO-$d_6$, 400 MHz): δ 0.85–0.87 (d, 3H), 0.89–0.90 (d, 3H), 1.15–1.24 (m, 2H), 1.53–1.81 (m, 6H), 4.34–4.40 (m, 1H), 6.83–6.85 (d, 2H), 6.89–6.91 (d, 2H), 7.01–7.04 (d, 1H), 7.20 (d, 1H), 7.73–7.75 (d, 2H), 8.07–8.09 (d, 1H). MS (ESI$^+$, m/z): 577 [M+H]$^+$.

EXAMPLE 115

(2S)-1-[4-(4-{[((2R)-2-Hydroxy-2-{4-hydroxy-3-[(methylsulfonyl)amino]phenyl}-ethyl)amino]methyl}piperidin-1-yl)benzoyl]pyrrolidine-2-carboxylic Acid

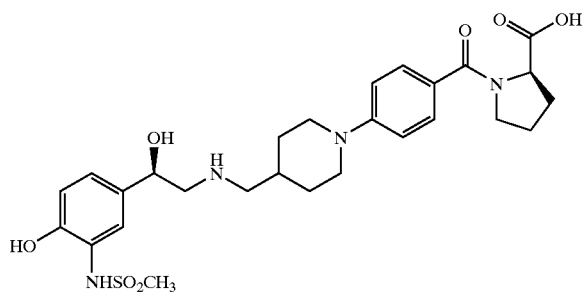

Step A: (2S)-1-[4-(4-(Dimethoxymethyl)amino]methyl}piperidin-1-yl)benzoyl]-pyrrolidine-2-carboxylic Acid Methyl Ester A solution of 4-(4-(dimethoxymethyl)piperidinyl)benzoic acid (0.900 g, 3.2 mmol), 1-(3-(dimethylamino)propyl)-3-ethylcarbodiimide HCl (0.680 g, 3.5 mmol), N-ethyl morpholine (2.0 mL), hydroxybenzotriazole (0.478 g, 3.5 mmol), and L-proline methyl ester HCl (0.534 g, 3.2 mmol) in THF (30 mL) was stirred at ambient temperature overnight. The solvent was evaporated in vacuo and the residue was dissolved in methylene chloride. The organic phase was washed with 1N HCl, 1N NaOH, brine and dried (Na$_2$SO$_4$). The solvent was evaporated in vacuo and the residue purified by flash chromatography (methylene chloride-methanol, 19:1) to give 0.182 g of the title compound.

Step B: (2S)-1-[4-(4-(Formyl)amino]methyl}piperidin-1-yl)benzoyl]pyrrolidine-2-carboxylic Acid Methyl Ester A solution of (2S)-1-[4-(4-(dimethoxymethyl)amino]methyl}piperidin-1-yl)benzoyl]pyrrolidine-2-carboxylic acid methyl ester (0.180 g, 0.5 mmol) in methylene chloride (5 mL) and trifluoroacetic acid (0.240 mL) was stirred at ambient temperature for 2 hours. The reaction mixture was diluted with methylene chloride and washed with saturated sodium bicarbonate, brine, and dried (Na$_2$SO$_4$). Removal of solvent in vacuo afforded the crude aldehyde which was used directly in the following step.

Step C: (2S)-1-[4-(4-{[((2R)-2-Hydroxy-2-{4-hydroxy-3-[(methylsulfonyl)amino]-phenyl}ethyl)amino]methyl}piperidin-1-yl)benzoyl]pyrrolidine-2-carboxylic Acid Methyl Ester A solution of N-[5-(2-amino-1-{R}-hydroxyethyl)-2-hydroxyphenyl]-methane-sulfonamide (0.161 g, 0.466 mmol), (2S)-1-[4-(4-(formyl)amino]methyl}piperidin-1-yl)benzoyl]pyrrolidine-2-carboxylic acid methyl ester (0.466 mmol) and glacial acetic acid (0.027 g, 0.466 mmol) in 5 mL of methanol-THF (4:1, v/v) was stirred for 1 hour over 4A molecular sieves. In one portion sodium cyanoborohydride (0.031 g, 0.466 mmol) was added and the mixture stirred overnight at ambient temperature. The sieves were filtered and the filtrate was preabsorbed on silica gel. The solids were purified by flash chromatography (CH$_2$Cl$_2$—CH$_3$OH, 20:1). to give the product (0.086 g).

Step D: (2S)-1-[4-(4-{[((2R)-2-Hydroxy-2-{4-Hydroxy-3-[(methylsulfonyl)-amino]phenyl}ethyl)amino]methyl}piperidin-1-yl)benzoyl]pyrrolidine-2-carboxylic Acid A solution (2S)-1-[4-(4-{[((2R)-2-hydroxy-2-{4-hydroxy-3-[(methylsulfonyl)-amino]-phenyl}-ethyl)amino]methyl}piperidin-1-yl)benzoyl]-pyrrolidine-2-carboxylic acid methyl ester (0.072 g, 0.12 mmol) in methanol (2 mL) and 1N sodium hydroxide (0.37 mL) was stirred at ambient temperature overnight. The reaction mixture was neutralized with 1N HCl (0.37 mL) and concentrated in vacuo. The residual solid was washed with water, then ether to give reasonably pure product (0.082 g).

NMR (DMSO-$d_6$, 400 MHz): δ 1.22–1.25 (m, 2H), 3.80–3.83 (m, 2H), 4.43–4.45 (m, 1H), 4.77–4.79 (m, 1H), 6.88–7.03 (m, 4H), 7.05 (m, 1H), 7.21 (s, 1H), 7.42 (broad s, 1H). MS (ESI$^+$, m/z): 561 [M+H]$^+$.

EXAMPLES 116–183

To fourteen 20 mL screw cap vials was added 4-methylmorpholinepolystyrene (250 mg/vial, 3.6 mmol/g, 0.90 mmol) and a 0.11 M solution of 4-(hydroxymethyl)piperidine (4 mL, 0.45 mmol). The vials were agitated on an orbital shaker for 2 minutes then to each one was added 0.585 mmol of the corresponding sulfonyl chloride of R$_2$ from Table 2 and capped tightly. After shaking for 1 h aminomethylpolystyrene (94 mg, 2.4 mmol/g, 0.225 mmol) was added to each vial and shaking continued for another 2 h. The mixtures were filtered into separate 20 mL vials, the residual resin was washed with dichloromethane (4×3 mL) and the filtrates were evaporated under a stream of nitrogen. Thin layer chromatography (silica gel, 50% hexane in ethyl acetate) indicated homogeneous products.

To each of the product vials from above was added polymer supported chromium trioxide (1.4 g, 2.5 mmol/g, 3.6 mmol) and 1,2-dichloroethane (5 mL). The vials were capped tightly and the mixtures shaken and heated at 75° C. for 14 h. After cooling to 20° C. the product mixtures were filtered, washed (DCM, 4×2 mL) and evaporated to dryness. To each vial was added aminomethylpolystyrene (0.28 g, 2.39 mmol/g, 0.675 mmol) and trimethylorthoformate (4 mL). After shaking for 1 h the resin was filtered, washed (DCM, 3×3 mL) and dried (hi-vac, 16 h).

Seventy polypropylene filter tubes (15 mL) were fitted with PTFE stopcocks and placed erect in a 5 (column)×14 (row) parallel fashion. Each of the resin supported aldehydes above were divided into five equal batches of 43 mg (68 μMol, approx.) and placed in the individual filter tubes by row so that each sample in each row contained an equal amount of identical resin. To each vessel in a single column of the parallel reaction mixture was added 54 μMol of an amine from table 3 such that a different amine was present in each column. To each reaction mixture was added methanol (0.75 mL) and trimethylorthoformate (0.75 mL). The block of seventy samples was then agitated on an orbital shaker for 1.5 h and stopped. To each vessel was added polymer supported borohydride and orbital shaking continued another 18 h. The mixtures were filtered into 20 mL scintillation vials, the resin was washed (methanol, 1 mL) and the filtrates were evaporated. The crude products were purified by automated reversed phase HPLC and the fractions were evaporated into 8 mL scintillation vials. All products were characterized by reversed phase analytical HPLC (stationary phase: C18, 4.4 mm×5 cm; mobile phase: 2–98% acetonitrile-water containing 0.05% TFA, linear gradient, 1.5 mL/min., 14 mins., 215 nM) and positive electrospray mass spec. See table for structures retention times ($R_t$) and MS data.

Carefully selected examples of compounds previously prepared by non combinatorial methods (examples 31/156, 37/131, 33/132, 39/133, 43/222, and 42/224) were included in the array to demonstrate the validity and utility of the combinatorial approach. The following compounds were prepared.

| Example # | Compound Name |
| --- | --- |
| 116 | (2S)-1-[4-(benzyloxy)phenoxy]-3-({[1-(phenylsulfonyl)piperidin-4-yl]methyl}amino)propan-2-ol |
| 117 | 4-{[(2S)-2-hydroxy-3-({[1-(phenylsulfonyl)piperidin-4-yl]methyl}amino)propyl]oxy}phenol |
| 118 | (2S)-1-(9H-carbazol-4-yloxy)-3-({[1-(phenylsulfonyl)piperidin-4-yl]methyl}amino)propan-2-ol |
| 119 | 4-{[(2S)-2-hydroxy-3-({[1-(phenylsulfonyl)piperidin-4-yl]methyl}amino)propyl)oxy}-1,3-dihydro-2H-benzimidazol-2-one |
| 120 | (2S)-1-[4-(benzyloxy)phenoxy]-3-[({1-[(4-isopropylphenyl)sulfonyl]piperidin-4-yl}methyl)amino]propan-2-ol |
| 121 | 4-({(2S)-2-hydroxy-3-[({1-[(4-isopropylphenyl)sulfonyl]piperidin-4-yl}methyl)amino]propyl}oxy)phenol |
| 122 | (2S)-1-(9H-carbazol-4-yloxy)-3-[({1-[(4-isopropylphenyl)sulfonyl]piperidin-4-yl}methyl)amino]propan-2-ol |
| 123 | 4-({(2S)-2-hydroxy-3-[({1-[(4-isopropylphenyl)sulfonyl]piperidin-4-yl}methyl)amino]propyl}oxy)-1,3-dihydro-2H-benzimidazol-2-one |
| 124 | N-(2-hydroxy-5-{(1R)-1-hydroxy-2-[({1-[(4-isopropylphenyl)-sulfonyl]piperidin-4-yl}methyl)amino]ethyl}phenyl)-methanesulfonamide |
| 125 | (2S)-1-[4-(benzyloxy)phenoxy]-3-[({1-[(4-ethylphenyl)sulfonyl]piperidin-4-yl}methyl)amino]propan-2-ol |
| 126 | 4-({(2S)-3-[({1-[(4-ethylphenyl)sulfonyl]piperidin-4-yl}methyl)amino]-2-hydroxypropyl}oxy)phenol |
| 127 | (2S)-1-(9H-carbazol-4-yloxy)-3-[({1-[(4-ethylphenyl)sulfonyl]piperidin-4-yl}methyl)amino]propan-2-ol |
| 128 | 4-({(2S)-3-[({1-[(4-ethylphenyl)sulfonyl]piperidin-4-yl}methyl)amino]-2-hydroxypropyl}oxy)-1,3-dihydro-2H-benzimidazol-2-one |
| 129 | N-(5-[(1R)-2-[({1-[(4-ethylphenyl)sulfonyl]piperidin-4-yl}methyl)amino]-1-hydroxyethyl}-2-hydroxyphenyl)methanesulfonamide |
| 130 | (2S)-1-[4-(benzyloxy)phenoxy]-3-[({1-[(4-methoxyphenyl)sulfonyl]piperidin-4 yl}methyl)amino]propan-2-ol |
| 131 | 4-((2S)-2-Hydroxy-3-{[1-(4-methoxy-benzenesulfonyl)-piperidin-4-ylmethyl]-amino}-propoxy)-phenol |
| 132 | (2S)-1-(9H-Carbazol-4-yloxy)-3-{[1-(4-methoxy-benzenesulfonyl)-piperidin-4-ylmethyl]-amino}-propan-2-ol |
| 133 | 4-((2S)-2-Hydroxy-3-{[1-(4-methoxy-benzenesulfonyl)-piperidin-4-ylmethyl]-amino}-propoxy)-1,3-dihydro-benzoimidazol-2-one |
| 134 | (2S)-1-[4-(benzyloxy)phenoxy]-3-[({1-[(2,4,6-triisopropylphenyl)sulfonyl]piperidin-4-yl}methyl)amino]propan-2-ol |
| 135 | 4-((2S)-2-hydroxy-3-[({1-[(2,4,6-triisopropylphenyl)sulfonyl]-piperidin-4-yl}methyl)amino]propyl}oxy)phenol |
| 136 | (2S)-1-(9H-carbazol-4-yloxy)-3-[({1-[(2,4,6-triisopropylphenyl)sulfonyl]piperidin-4-yl}methyl)amino]propan-2-ol |
| 137 | 4-{[(2S)-2-hydroxy-3-[({1-[(2,4,6-triisopropylphenyl)sulfonyl]-piperidin-4-yl}methyl)amino]propyl}oxy)-1,3-dihydro-2H-benzimidazol-2-one |
| 138 | N-(2-hydroxy-5-{(1R)-1-hydroxy-2-[({1-[(2,4,6-triisopropyl-phenyl)-sulfonyl]piperidin-4-yl}methyl)amino]ethyl}phenyl)-methanesulfonamide |
| 139 | (2S)-1-[4-(benzyloxy)phenoxy]-3-[({1-[(2,3,4,5,6-pentamethylphenyl)sulfonyl]piperidin-4-yl}methyl)amino]propan-2-ol |
| 140 | 4-({(2S)-2-hydroxy-3-[({1-[(2,3,4,5,6-pentamethylphenyl)-sulfonyl]-piperidin-4-yl}methyl)amino]propyl}oxy)phenol |
| 141 | (2S)-1-(9H-carbazol-4-yloxy)-3-[({1-[(2,3,4,5,6-pentamethylphenyl)sulfonyl]piperidin-4-yl}methyl)amino]propan-2-ol |
| 142 | 4-({(2S)-2-hydroxy-3-[({1-[(2,3,4,5,6-pentamethylphenyl)sulfonyl]piperidin-4-yl}methyl)amino]propyl}oxy)-1,3-dihydro-2H-benzimidazol-2-one |
| 143 | N-(2-hydroxy-5-{(1R)-1-hydroxy-2-[({1-[(2,3,4,5,6-pentamethylphenyl)sulfonyl]piperidin-4-yl}methyl)amino]ethyl}phenyl)methanesulfonamide |
| 144 | (2S)-1-[4-(benzyloxy)phenoxy]-3-{[(1-{[4-(tert-pentyl)phenyl]sulfonyl}piperidin-4-yl)methyl]amino}propan-2-ol |
| 145 | 4-[((2S)-2-hydroxy-3-{[(1-{[4-(tert-pentyl)phenyl]sulfonyl}-piperidin-4-yl)methyl]amino}propyl)oxy]phenol |
| 146 | (2S)-1-(9H-carbazol-4-yloxy)-3-{[(1-{[4-(tert-pentyl)phenyl]sulfonyl}piperidin-4-yl)methyl]amino}propan-2-ol |
| 147 | 4-[((2S)-2-hydroxy-3-{[(1-{[4-(tert-pentyl)phenyl]sulfonyl} piperidin-4-yl)methyl]amino}propyl)oxy]-1,3-dihydro-2H-benzimidazol-2-one |
| 148 | N-[2-hydroxy-5-((1R)-1-hydroxy-2-{[(1-{[4-(tert-pentyl)phenyl]sulfonyl}piperidin-4-yl)methyl)amino}ethyl)phenyl]methanesulfonamide |
| 149 | (2S)-1-[4-(benzyloxy)phenoxy]-3-({[1-(1-naphthylsulfonyl)piperidin-4-yl]methyl}amino)propan-2-ol |
| 150 | 4-{[(2S)-2-hydroxy-3-({[1-(1-naphthylsulfonyl)piperidin-4-yl]methyl}amino)propyl]oxy}phenol |
| 151 | (2S)-1-(9H-carbazol-4-yloxy)-3-({[1-(1-naphthylsulfonyl)piperidin-4-yl]methyl}amino)propan-2-ol |
| 152 | 4-{[(2S)-2-hydroxy-3-({[1-(1-naphthylsulfonyl)piperidin-4-yl]methyl}amino)propyl]oxy}-1,3-dihydro-2H-benzimidazol-2-one |
| 153 | N-{2-hydroxy-5-[(1R)-1-hydroxy-2-({[1-(1-naphthylsulfonyl)piperidin-4-yl]methyl}amino)ethyl]phenyl}methanesulfonamide |
| 154 | (2S)-1-[4-(benzyloxy)phenoxy]-3-({[1-(2-naphthylsulfonyl)piperidin-4-yl]methyl}amino)propan-2-ol |
| 155 | 4-{[(2S)-2-hydroxy-3-({[1-(2-naphthylsulfonyl)piperidin-4-yl]methyl}amino)propyl]oxy}phenol |
| 156 | (2S)-1-(9H-Carbazol-4-yloxy)-3-{[1-(naphthalene-2-sulfonyl)-piperidin-4-ylmethyl]-amino}-propan-2-ol |
| 157 | 4-{[(2S)-2-hydroxy-3-({[1-(2-naphthylsulfonyl)piperidin-4-yl]methyl}amino)propyl]oxy}-1,3-dihydro-2H-benzimidazol-2-one |
| 158 | N-{2-hydroxy-5-[(1R)-1-hydroxy-2-({[1-(2-naphthylsulfonyl)-piperidin-4-yl]methyl}amino)ethyl]phenyl}methanesulfonamide |
| 159 | (2S)-1-[4-(benzyloxy)phenoxy]-3-{[(1-{[4-(tert-butyl)phenyl]sulfonyl}piperidin-4-yl)methyl]amino}propan-2-ol |
| 160 | 4-[((2S)-3-{[(1-{[4-(tert-butyl)phenyl]sulfonyl}piperidin-4-yl)methyl]amino}-2-hydroxypropyl)oxy]phenol |
| 161 | (2S)-1-{[(1-{[4-(tert-butyl)phenyl]sulfonyl}piperidin-4-yl)methyl]amino}-3-(9H-carbazol-4-yloxy)propan-2-ol |
| 162 | 4-[((2S)-3-{[(1-{[4-(tert-butyl)phenyl]sulfonyl}piperidin-4-yl)methyl]-amino}-2-hydroxypropyl)oxy]-1,3-dihydro-2H-benzimidazol-2-one |
| 163 | N-[5-((1R)-2-{[(1-{[4-(tert-butyl)phenyl]sulfonyl}piperidin-4-yl)-methyl]amino}-1-hydroxyethyl)-2-hydroxyphenyl]-methanesulfonamide |
| 164 | (2S)-1-[4-(benzyloxy)phenoxy]-3-[({1-[(4-bromo-2-ethylphenyl)sulfonyl]piperidin-4-yl}methyl)amino]propan-2-ol |
| 165 | 4-({(2S)-3-[({1-[(4-bromo-2-ethylphenyl)sulfonyl]piperidin-4-yl}methyl)amino]-2-hydroxypropyl}oxy)phenol |
| 166 | (2S)-1-[({1-[(4-bromo-2-ethylphenyl)sulfonyl]piperidin-4-yl}methyl)amino]-3-(9H-carbazol-4-yloxy)propan-2-ol |
| 167 | 4-({(2S)-3-[({1-[(4-bromo-2-ethylphenyl)sulfonyl]piperidin-4-yl}methyl)amino]-2-hydroxypropyl}oxy)-1,3-dihydro-2H-benzimidazol-2-one |
| 168 | N-(5-((1R)-2-[({1-[(4-bromo-2-ethylphenyl)sulfonyl]piperidin-4-yl}-methyl)amino]-1-hydroxyethyl}-2-hydroxyphenyl)-methanesulfonamide |
| 169 | (2S)-1-[4-(benzyloxy)phenoxy]-3-[({1-[(4-bromo-2,5-dichlorothien-3-yl)sulfonyl]piperidin-4-yl}methyl)amino]propan-2-ol |
| 170 | 4-({(2S)-3-[({1-[(4-bromo-2,5-dichlorothien-3-yl)sulfonyl]piperidin-4-yl}methyl)amino]-2-hydroxypropyl}oxy)phenol |
| 171 | (2S)-1-[({1-[(4-bromo-2,5-dichlorothien-3-yl)sulfonyl]piperidin-4-yl}methyl)amino]-3-(9H-carbazol-4-yloxy)propan-2-ol |

| Example # | Compound Name |
|---|---|
| 172 | 4-({(2S)-3-[({1-[(4-bromo-2,5-dichlorothien-3-yl)sulfonyl]piperidin-4-yl}methyl)amino]-2-hydroxypropyl}oxy)-1,3-dihydro-2H-benzimidazol-2-one |
| 173 | N-(5-{(1R)-2-[({1-[(4-bromo-2,5-dichlorothien-3-yl)sulfonyl]-piperidin-4-yl}methyl)amino]-1-hydroxyethyl}-2-hydroxyphenyl)-methanesulfonamide |
| 174 | (2S)-1-[4-(benzyloxy)phenoxy]-3-[({1-[(3-bromophenyl)sulfonyl]piperidin-4-yl}methyl)amino]propan-2-ol |
| 175 | 4-({(2S)-3-[({1-[(3-bromophenyl)sulfonyl]piperidin-4-yl}methyl)amino]-2-hydroxypropyl}oxy)phenol |
| 176 | (2S)-1-[({1-[(3-bromophenyl)sulfonyl]piperidin-4-yl}methyl)amino]-3-(9H-carbazol-4-yloxy)propan-2-ol |
| 177 | 4-({(2S)-3-[({-1-[(3-bromophenyl)sulfonyl]piperidin-4-yl}methyl)-amino]-2-hydroxypropyl}oxy)-1,3-dihydro-2H-benzimidazol-2-one |
| 178 | N-(5-{(1R)-2-[({1-[(3-bromophenyl)sulfonyl]piperidin-4-yl}methyl)-amino]-1-hydroxypropyl}oxy)-1,3-dihydro-2H-benzimidazol-2-one |
| 179 | N-{[5-({4-[({(2S)-3-[4-(benzyloxy)phenoxy]-2-hydroxypropyl}amino)methyl]piperidin-1-yl}sulfonyl)thien-2-yl]methyl}benzamide |
| 180 | N-[(5-{[4-({[(2S)-2-hydroxy-3-(4-hydroxyphenoxy)propyl]amino}-methyl)piperidin-1-yl]sulfonyl}thien-2-yl)methyl]benzamide |
| 181 | N-[(5-{[4-({[(2S)-3-(9H-carbazol-4-yloxy)-2-hydroxypropyl]amino}-methyl)piperidin-1-yl]sulfonyl}thien-2-yl)methyl]benzamide |
| 182 | N-{[5-({4-[({(2S)-2-hydroxy-3-[(2-oxo-2,3-dihydro-1H-benzimidazol-4-yl)oxy]propyl}amino)methyl]piperidin-1-yl}sulfonyl)thien-2-yl]methyl}benzamide |
| 183 | N-({5-[4-{[((2R)-2-hydroxy-2-{4-hydroxy-3-[(methylsulfonyl)-amino]-phenyl}ethyl)amino]methyl}piperidin-1-yl)sulfonyl]thien-2-yl}methyl)benzamide |

EXAMPLES 184–240

Sulfonyl chlorides of $R_2$ in Table 2 were used in a procedure identical to the one for examples 116–183. Example Table 2 contains MS and HPLC data expressed as retention times ($R_t$). The following compounds were prepared:

| Example # | Compound Name |
|---|---|
| 184 | (2S)-1-[4-(benzyloxy)phenoxy]-3-[({1-[{(4-butoxyphenyl)sulfonyl]piperidin-4-yl}methyl)amino]propan-2-ol |
| 185 | (2S)-1-[({1-[(4-butoxyphenyl)sulfonyl]piperidin-4-yl}methyl)amino]-3-(9H-carbazol-4-yloxy)propan-2-ol |
| 186 | 4-({(2S)-3-[({1-[(4-butoxyphenyl)sulfonyl]piperidin-4-yl}methyl)amino]-2-hydroxypropyl}oxy)-1,3-dihydro-2H-benzimidazol-2-one |
| 187 | N-(5-{(1R)-2-[({1-[(4-butoxyphenyl)sulfonyl]piperidin-4-yl}methyl)-amino]-1-hydroxyethyl}-2-hydroxyphenyl)methanesulfonamide |
| 188 | (2S)-1-[4-(benzyloxy)phenoxy]-3-[({1-[(4-butylphenyl)sulfonyl]piperidin-4-yl}methyl)amino]propan-2-ol |
| 189 | 4-({(2S)-3-[({1-[(4-butylphenyl)sulfonyl]piperidin-4-yl}methyl)amino]-2-hydroxypropyl}oxy)phenol |
| 190 | (2S)-1-[({1-[(4-butylphenyl)sulfonyl]piperidin-4-yl}methyl)amino]-3-(9H-carbazol-4-yloxy)propan-2-ol |
| 191 | 4-({(2S)-3-[({1-[(4-butylphenyl)sulfonyl]piperidin-4-yl}methyl)amino]-2-hydroxypropyl}oxy)-1,3-dihydro-2H-benzimidazol-2-one |
| 192 | N-(5-[(1R)-2-[({1-[(4-butylphenyl)sulfonyl]piperidin-4-yl}methyl)-amino]-1-hydroxyethyl]-2-hydroxyphenyl)-methanesulfonamide |
| 193 | N-(4-{4-[({(2S)-3-(9H-carbazol-4-yloxy)-2-hydroxypropyl]-amino}methyl)piperidin-1-yl]sulfonyl}phenyl)acetamide |
| 194 | N-[4-({4-[({(2S)-2-hydroxy-3-[(2-oxo-2,3-dihydro-1H-benzimidazol-4-yl)oxy]propyl}amino)methyl]piperidin-1-yl}sulfonyl)phenyl]acetamide |
| 195 | (2S)-1-[4-(benzyloxy)phenoxy]-3-({[1-([1,1'-biphenyl]-4-ylsulfonyl)piperidin-4-yl]methyl}amino)propan-2-ol |
| 196 | 4-{[(2S)-3-({[1-([1,1'-biphenyl]-4-ylsulfonyl)piperidin-4-yl]methyl}amino)-2-hydroxypropyl]oxy}phenol |
| 197 | (2S)-1-({[1-([1,1'-biphenyl]-4-ylsulfonyl)piperidin-4-yl]methyl}amino)-3-(9H-carbazol-4-yloxy)propan-2-ol |
| 198 | 4-{[(2S)-3-({[1-([1,1'-biphenyl]-4-ylsulfonyl)piperidin-4-yl]methyl}amino)-2-hydroxypropyl]oxy}-1,3-dihydro-2H-benzimidazol-2-one |
| 199 | N-{5-[(1R)-2-({[1-([1,1'-biphenyl]-4-ylsulfonyl)piperidin-4-yl]methyl}amino)-1-hydroxyethyl]-2-hydroxyphenyl}-methanesulfonamide |
| 200 | (2S)-1-({[1-(2,1,3-benzothiadiazol-4-ylsulfonyl)piperidin-4-yl]methyl}amino)-3-[4-(benzyloxy)phenoxy]propan-2-ol |
| 201 | 4-{[(2S)-3-({[1-(2,1,3-benzothiadiazol-4-ylsulfonyl)piperidin-4-yl]methyl}amino)-2-hydroxypropyl]oxy}phenol |
| 202 | (2S)-1-({[1-(2,1,3-benzothiadiazol-4-ylsulfonyl)piperidin-4-yl]methyl}amino)-3-(9H-carbazol-4-yloxy)propan-2-ol |
| 203 | 4-{[(2S)-3-({[1-(2,1,3-benzothiadiazol-4-ylsulfonyl)piperidin-4-yl]-methyl}amino)-2-hydroxypropyl]oxy}1,3-dihydro-2H-benzimidazol-2-one |
| 204 | N-{5-[(1R)-2-({[1-(2,1,3-benzothiadiazol-4-ylsulfonyl)piperidin-4-yl]-methyl}amino)-1-hydroxyethyl]-2-hydroxyphenyl}methanesulfonamide |
| 205 | (2S)-1-[4-(benzyloxy)phenoxy]-3-({[1-(benzylsulfonyl)piperidin-4-yl]methyl}amino)propan-2-ol |
| 206 | (2S)-1-({[1-(benzylsulfonyl)piperidin-4-yl]methyl}amino)-3-(9H-carbazol-4-yloxy)propan-2-ol |
| 207 | 4-{[(2S)-3-({[1-(benzylsulfonyl)piperidin-4-yl]methyl}amino)-2-hydroxypropyl]oxy}-1,3-dihydro-2H-benzimidazol-2-one |
| 208 | (2S)-1-[4-(benzyloxy)phenoxy]-3-{[(1-{[4-(methylsulfonyl)phenyl]-sulfonyl}-piperidin-4-yl)methyl]amino}propan-2-ol |
| 209 | 4-[((2S)-2-hydroxy-3-{[(1-{[4-(methylsulfonyl)phenyl]-sulfonyl}piperidin-4-yl)methyl]amino}propyl)oxy]phenol |
| 210 | (2S)-1-(9H-carbazol-4-yloxy)-3-{[(1-{[4-(methylsulfonyl)-phenyl]sulfonyl}piperidin-4-yl)methyl]amino}propan-2-ol |
| 211 | 4-[((2S)-2-hydroxy-3-{[(1-{[4-(methylsulfonyl)phenyl]sulfonyl}piperidin-4-yl)methyl]amino}propyl)oxy]-1,3-dihydro-2H-benzimidazol-2-one |
| 212 | (2S)-1-[4-(benzyloxy)phenoxy]-3-{[(1-{[5-(phenylsulfonyl)thien-2-yl]sulfonyl}piperidin-4-yl)methyl]amino}propan-2-ol |
| 213 | 4-[((2S)-2-hydroxy-3-{[(1-{[5-(phenylsulfonyl)thien-2-yl]sulfonyl}piperidin-4-yl)methyl]amino}propyl)oxy]phenol |
| 214 | (2S)-1-(9H-carbazol-4-yloxy)-3-{[(1-{[5-(phenylsulfonyl)thien-2-yl]sulfonyl}piperidin-4-yl)methyl]amino}propan-2-ol |
| 215 | 4-[((2S)-2-hydroxy-3-{[(1-{[5-(phenylsulfonyl)thien-2-yl]sulfonyl}piperidin-4-yl)methyl]amino}propyl)oxy]-1,3-dihydro-2H-benzimidazol-2-one |
| 216 | (2S)-1-[4-(benzyloxy)phenoxy]-3-[({1-[(4-methylphenyl)sulfonyl]piperidin-4-yl}methyl)amino]propan-2-ol |
| 217 | 4-({(2S)-2-hydroxy-3-[({1-[(4-methylphenyl)sulfonyl]piperidin-4-yl}methyl)amino]propyl}oxy)phenol |
| 218 | (2S)-1-(9H-carbazol-4-yloxy)-3-[({1-[(4-methylphenyl)sulfonyl]piperidin-4-yl}methyl)amino]propan-2-ol |
| 219 | 4-({(2S)-2-hydroxy-3-[({1-[(4-methylphenyl)sulfonyl]piperidin-4-yl}methyl)amino]propyl}oxy)-1,3-dihydro-2H-benzimidazol-2-one |
| 220 | N-(2-hydroxy-5-{(1R)-1-hydroxy-2-[({1-[(4-methylphenyl)sulfonyl]piperidin-4-yl}methyl)amino]ethyl}phenyl)methanesulfonamide |
| 221 | (2S)-1-[4-(benzyloxy)phenoxy]-3-[({1-[(3,4-dimethoxyphenyl)sulfonyl]piperidin-4-yl}methyl)amino]propan-2-ol |
| 222 | 4-({(2S)-3-[({1-[(3,4-dimethoxyphenyl)sulfonyl]piperidin-4-yl}methyl)amino]-2-hydroxypropyl}oxy)phenol |
| 223 | (2S)-1-(9H-carbazol-4-yloxy)-3-[({1-[(3,4-dimethoxyphenyl)sulfonyl]piperidin-4-yl}methyl)amino]propan-2-ol |

-continued

| Example # | Compound Name |
|---|---|
| 224 | 4-({(2S)-3-[({1-[(3,4-dimethoxyphenyl)sulfonyl]piperidin-4-yl}methyl)amino]-2-hydroxypropyl}oxy)-1,3-dihydro-2H-benzimidazol-2-one |
| 225 | N-(5-{(1R)-2-[({1-[(3,4-dimethoxyphenyl)sulfonyl]piperidin-4-yl}methyl)amino]-1-hydroxyethyl}-2-hydroxyphenyl)methanesulfonamide |
| 226 | 4-({(2S)-2-hydroxy-3-[({1-[(5-{[5-(trifluoromethyl)pyridin-2-yl]sulfonyl}thien-2-yl)sulfonyl]piperidin-4-yl}methyl)amino]propyl}oxy)phenol |
| 227 | (2S)-1-(9H-carbazol-4-yloxy)-3-[({1-[(5-{[5-(trifluoromethyl)pyridin-2-yl]sulfonyl}thien-2-yl)sulfonyl]piperidin-4-yl}methyl)amino]propan-2-ol |
| 228 | 4-({(2S)-2-hydroxy-3-[({1-[(5-{[5-(trifluoromethyl)pyridin-2-yl]sulfonyl}thien--yl)sulfonyl]piperidin-4-yl}methyl)amino]propyl}oxy)-1,3-dihydro-2H-benzimidazol-2-one |
| 229 | (2S)-1-[4-(benzyloxy)phenoxy]-3-{[(1-{[5-(dimethylamino)-1-naphthyl]sulfonyl}piperidin-4-yl)methyl]amino}propan-2-ol |
| 230 | 4-[((2S)-3-{[(1-{[5-(dimethylamino)-1-naphthyl]sulfonyl}piperidin-4-yl)methyl]amino}-2-hydroxypropyl)oxy]phenol |
| 231 | (2S)-1-(9H-carbazol-4-yloxy)-3-{[(1-{[5-(dimethylamino)-1-naphthyl]sulfonyl}piperidin-4-yl)methyl]amino}propan-2-ol |
| 232 | 4-[((2S)-3-{[(1-{[5-(dimethylamino)-1-naphthyl]sulfonyl}piperidin-4-yl)methyl]amino}-2-hydroxypropyl)oxy]-1,3-dihydro-2H-benzimidazol-2-one |
| 233 | (2S)-1-[4-(benzyloxy)phenoxy]-3-[({1-[(5-pyridin-2-ylthien-2-yl)sulfonyl]piperidin-4-yl}methyl)amino]propan-2-ol |
| 234 | 4-({(2S)-2-hydroxy-3-[({1-[(5-pyridin-2-ylthien-2-yl)sulfonyl]piperidin-4-yl}methyl)amino]propyl}oxy)phenol |
| 235 | (2S)-1-(9H-carbazol-4-yloxy)-3-[({1-[(5-pyridin-2-ylthien-2-yl)sulfonyl]piperidin-4-yl}methyl)amino]propan-2-ol |
| 236 | 4-({(2S)-2-hydroxy-3-[({1-[(5-pyridin-2-ylthien-2-yl)sulfonyl]piperidin-4-yl}methyl)amino]propyl}oxy)-1,3-dihydro-2H-benzimidazol-2-one |
| 237 | (2S)-1-[4-(benzyloxy)phenoxy]-3-({[1-({5-[2-(methylthio)pyrimidin-4-yl]thien-2-yl}sulfonyl)piperidin-4-yl]methyl}amino)propan-2-ol |
| 238 | (2S)-1-(9H-carbazol-4-yloxy)-3-({[1-({5-[2-(methylthio)pyrimidin-4-yl]thien-2-yl}sulfonyl)piperidin-4-yl]methyl}amino)propan-2-ol |
| 239 | 4-{[(2S)-2-hydroxy-3-({[1-({5-[2-(methylthio)pyrimidin-4-yl]thien-2-yl}sulfonyl)piperidin-4-yl]methyl}amino)propyl]oxy}-1,3-dihydro-2H-benzimidazol-2-one |
| 240 | N-{2-hydroxy-5-[(1R)-1-hydroxy-2-({[1-({5-[2-(methylthio)pyrimidin-4-yl]thien-2-yl}sulfonyl)piperidin-4-yl]methyl}amino)ethyl]phenyl}-methanesulfonamide |

Summary of Structure Evaluation

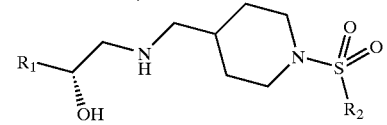

$R_1$

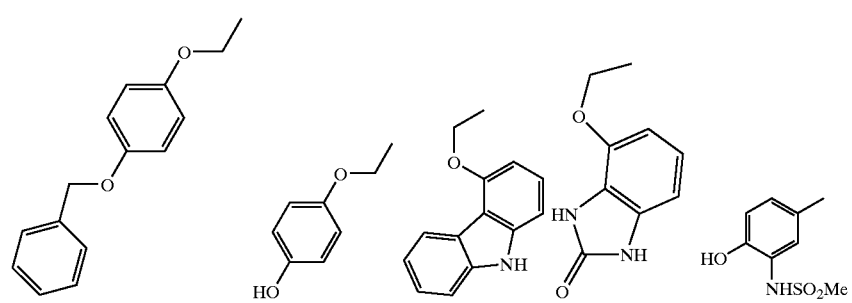

| $R_2$ | | | | |
|---|---|---|---|---|
| 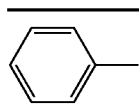 | Example 116<br>$R_t$ = 6.70 +<br>ESMS = 511 | Example 117<br>$R_t$ = 4.53 +<br>ESMS = 421 | Example 118<br>$R_t$ = 6.03 +<br>ESMS = 494 | Example 119<br>$R_t$ = 4.37 +<br>ESMS = 461 | — |

-continued

Summary of Structure Evaluation

| R₂ | R₁: 4-benzyloxyphenyl | R₁: 4-hydroxyphenyl (ethoxy) | R₁: ethoxy-carbazole | R₁: ethoxy-benzimidazolone | R₁: HO-/NHSO₂Me phenyl |
|---|---|---|---|---|---|
| 4-isopropylphenyl | Example 120 R$_t$ = 7.46 + ESMS = 553 | Example 121 R$_t$ = 5.79 + ESMS = 463 | Example 122 R$_t$ = 6.94 + ESMS = 536 | Example 123 R$_t$ = 5.57 + ESMS = 503 | Example 124 R$_t$ = 5.74 + ESMS = 526 |
| 4-ethylphenyl | Example 125 R$_t$ = 7.25 + ESMS = 539 | Example 126 R$_t$ = 5.38 + ESMS = 449 | Example 127 R$_t$ = 6.55 + ESMS = 522 | Example 128 R$_t$ = 5.18 + ESMS = 489 | Example 129 R$_t$ = 5.34 + ESMS = 512 |
| 4-methoxyphenyl | Example 130 R$_t$ = 6.72 + ESMS = 541 | Example 131 R$_t$ = 4.70 + ESMS = 451 | Example 132 R$_t$ = 5.99 + ESMS = 524 | Example 133 R$_t$ = 4.57 + ESMS = 491 | — |
| 2,4,6-triisopropylphenyl | Example 134 R$_t$ = 10.07 + ESMS = 637 | Example 135 R$_t$ = 8.16 + ESMS = 547 | Example 136 R$_t$ = 9.22 + ESMS = 620 | Example 137 R$_t$ = 7.77 + ESMS = 587 | Example 138 R$_t$ = 8.10 + ESMS = 610 |
| 4-tert-amylphenyl | Example 144 R$_t$ = 8.70 + ESMS = 581 | Example 145 R$_t$ = 6.95 + ESMS = 491 | Example 146 R$_t$ = 8.08 + ESMS = 564 | Example 147 R$_t$ = 6.68 + ESMS = 531 | Example 148 R$_t$ = 6.88 + ESMS = 554 |
| 1-naphthyl | Example 149 R$_t$ = 7.79 + ESMS = 561 | Example 150 R$_t$ = 5.83 + ESMS = 471 | Example 151 R$_t$ = 7.07 + ESMS = 544 | Example 152 R$_t$ = 5.60 + ESMS = 511 | Example 153 R$_t$ = 5.77 + ESMS = 534 |
| 2-naphthyl | Example 154 R$_t$ = 7.86 + ESMS = 561 | Example 155 R$_t$ = 5.93 + ESMS = 471 | Example 156 R$_t$ = 7.11 + ESMS = 544 | Example 157 R$_t$ = 5.70 + ESMS = 511 | Example 158 R$_t$ = 5.88 + ESMS = 534 |

-continued

Summary of Structure Evaluation

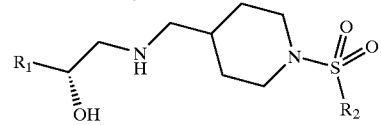

| $R_2$ | $R_1$ | | | | |
|---|---|---|---|---|---|
| | 4-benzyloxyphenyl (OBn-Ph-O) | 4-hydroxyphenyl | 4-ethoxy-carbazole | 4-ethoxy-benzimidazolone | 2-hydroxy-5-methyl-NHSO$_2$Me-phenyl |
| 4-tert-butylphenyl | Example 159 $R_t$ = 8.41 + ESMS = 567 | Example 160 $R_t$ = 6.53 + ESMS = 477 | Example 161 $R_t$ = 7.61 + ESMS = 550 | Example 162 $R_t$ = 6.25 + ESMS = 517 | Example 163 $R_t$ = 6.48 + ESMS = 540 |
| 5-bromo-2-methylphenyl | Example 164 $R_t$ = 8.35 + ESMS = 619 | Example 165 $R_t$ = 6.50 + ESMS = 529 | Example 166 $R_t$ = 7.71 + ESMS = 602 | Example 167 $R_t$ = 6.30 + ESMS = 569 | Example 168 $R_t$ = 6.48 + ESMS = 592 |
| 2,5-dichloro-3-bromo-4-methylthiophene | Example 169 $R_t$ = 8.31 + ESMS = 665 | Example 170 $R_t$ = 6.39 + ESMS = 575 | Example 171 $R_t$ = 7.56 + ESMS = 648 | Example 172 $R_t$ = 6.08 + ESMS = 615 | Example 173 $R_t$ = 6.30 + ESMS = 638 |
| 3-bromophenyl | Example 174 $R_t$ = 7.67 + ESMS = 591 | Example 175 $R_t$ = 5.63 + ESMS = 501 | Example 176 $R_t$ = 6.91 + ESMS = 574 | Example 177 $R_t$ = 5.42 + ESMS = 541 | Example 178 $R_t$ = 5.55 + ESMS = 564 |
| N-(thien-2-ylmethyl)benzamide | Example 179 $R_t$ = 7.33 + ESMS = 650 | Example 180 $R_t$ = 5.35 + ESMS = 560 | Example 181 $R_t$ = 6.56 + ESMS = 633 | Example 182 $R_t$ = 5.17 + ESMS = 600 | Example 183 $R_t$ = 5.24 + ESMS = 623 |
| 4-butoxyphenyl | Example 184 $R_t$ = 5.31 + ESMS = 583 | — | Example 185 $R_t$ = 4.97 + ESMS = 566 | Example 186 $R_t$ = 4.30 + ESMS = 533 | Example 187 |
| 4-butylphenyl | Example 188 $R_t$ = 5.39 + ESMS = 567 | Example 189 $R_t$ = 4.52 + ESMS = 478 | Example 190 $R_t$ = 5.08 + ESMS = 550 | Example 191 $R_t$ = 4.37 + ESMS = 517 | Example 192 $R_t$ = 4.52 + ESMS = 540 |
| N-(4-methylphenyl)acetamide | — | — | Example 193 $R_t$ = 3.93 + ESMS = 551 | Example 194 $R_t$ = 3.21 + ESMS = 518 | — |

-continued

Summary of Structure Evaluation

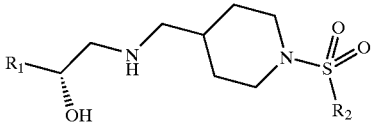

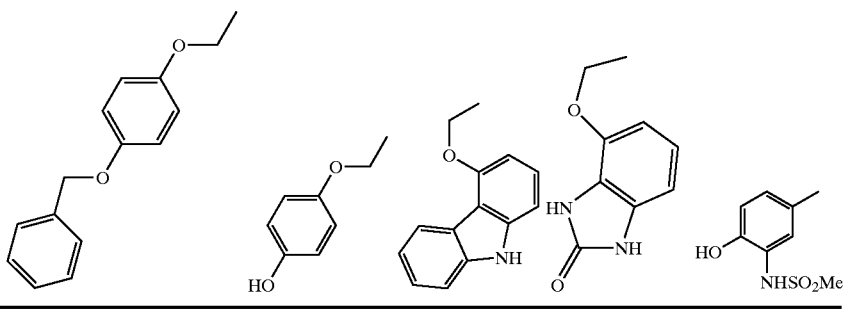

| R₂ | R₁: (4-benzyloxyphenyl) | R₁: (4-hydroxyphenyl, ethoxy) | R₁: (ethoxy carbazole) | R₁: (ethoxy benzimidazolone) | R₁: (HO, NHSO₂Me, methyl) |
|---|---|---|---|---|---|
| 4-methylbiphenyl | Example 195<br>$R_t = 524$ +<br>ESMS = 587 | Example 196<br>$R_t = 4.34$ +<br>ESMS = 497 | Example 197<br>$R_t = 4.92$ +<br>ESMS = 570 | Example 198<br>$R_t = 4.24$ +<br>ESMS = 537 | Example 199<br>$R_t = 4.37$ +<br>ESMS = 560 |
| 4-methylbenzothiadiazole | Example 200<br>$R_t = 4.64$ +<br>ESMS = 569 | Example 201<br>$R_t = 3.47$ +<br>ESMS = 479 | Example 202<br>$R_t = 4.24$ +<br>ESMS = 552 | Example 203<br>$R_t = 3.41$ +<br>ESMS = 519 | Example 204<br>$R_t = 3.43$ +<br>ESMS = 542 |
| ethylbenzene | Example 205<br>$R_t = 4.75$ +<br>ESMS = 525 | — | Example 206<br>$R_t = 4.36$ +<br>ESMS = 508 | Example 207<br>$R_t = 3.52$ +<br>ESMS = 475 | — |
| 4-(methylsulfonyl)toluene | Example 208<br>$R_t = 4.57$ +<br>ESMS = 589 | Example 209<br>$R_t = 3.35$ +<br>ESMS = 499 | Example 210<br>$R_t = 4.11$ +<br>ESMS = 572 | Example 211<br>$R_t = 3.31$ +<br>ESMS = 539 | — |
| 2-(phenylsulfonyl)-5-methylthiophene | Example 212<br>$R_t = 5.10$ +<br>ESMS = 657 | Example 213<br>$R_t = 4.24$ +<br>ESMS = 567 | Example 214<br>$R_t = 4.40$ +<br>ESMS = 640 | Example 215<br>$R_t = 4.12$ +<br>ESMS = 607 | — |
| p-xylene | Example 216<br>$R_t = 4.86$ +<br>ESMS = 525 | Example 217<br>$R_t = 3.71$ +<br>ESMS = 435 | Example 218 | Example 219<br>$R_t = 3.65$ +<br>ESMS = 475 | Example 220<br>$R_t = 3.72$ +<br>ESMS = 498 |
| 3,4-dimethoxytoluene | Example 221<br>$R_t = 4.64$ +<br>ESMS = 571 | Example 222<br>$R_t = 3.45$ +<br>ESMS = 481 | Example 223<br>$R_t = 4.20$ +<br>ESMS = 554 | Example 224<br>$R_t = 3.41$ +<br>ESMS = 521 | Example 225<br>$R_t = 3.66$ +<br>ESMS = 544 |

-continued

Summary of Structure Evaluation

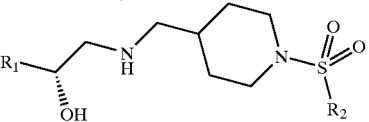

| R2 | R1: (benzyloxy-phenoxy) | R1: (ethoxy-phenol) | R1: (ethoxy-carbazole) | R1: (ethoxy-benzimidazolone) | R1: (HO-tolyl-NHSO2Me) |
|---|---|---|---|---|---|
| (F3C-pyridyl-SO2-methylthiophene) | — | Example 226 $R_t$ = 4.31 + ESMS = 636 | Example 227 $R_t$ = 4.84 + ESMS = 709 | Example 228 $R_t$ = 4.21 + ESMS = 676 | — |
| (dimethylamino-methylnaphthalene) | Example 229 $R_t$ = 4.79 + ESMS = 604 | Example 230 $R_t$ = 3.68 + ESMS = 514 | Example 231 $R_t$ = 3.31 + ESMS = 587 | Example 232 $R_t$ = 3.59 + ESMS = 554 | — |
| (pyridyl-methylthiophene) | Example 233 | Example 234 $R_t$ = 3.88 + ESMS = 504 | Example 235 $R_t$ = 4.50 + ESMS = 577 | Example 236 $R_t$ = 3.80 + ESMS = 544 | — |
| (methylthio-pyrimidyl-methylthiophene) | Example 237 | — | Example 238 | Example 239 $R_t$ = 4.11 + ESMS = 591 | Example 240 |

What is claimed is:

1. A compound of formula I having the structure

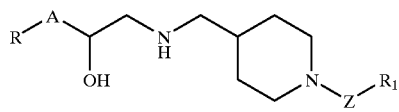

wherein,

A is —OCH$_2$—;

R is
(a) aryl optionally substituted with R$^2$, R$^3$, R$^4$, R$^5$, or R$^6$;

R$^1$ is:
(b) aryl optionally substituted with R$^9$, R$^{10}$, or R$^{11}$;

R$^2$, R$^3$, R$^4$, R$^5$, and R$^6$ are each, independently, alkyl of 1–6 carbon atoms, hydroxy, alkoxy of 1–6 carbon atoms, arylalkoxy having 1–6 carbon atoms in the alkyl moiety, halogen, —NHSO$_2$R$^7$, —CO$_2$R$^8$, or —CONH$_2$;

R$^7$ and R$^8$ are each, independently, hydrogen, alkyl of 1–6 carbon atoms, or arylalkyl having 1–6 carbon atoms in the alkyl moiety;

Z is —SO$_2$—;

R$^9$, R$^{10}$, and R$^{11}$ are each, independently:

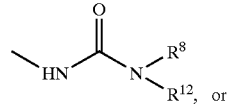

(c)

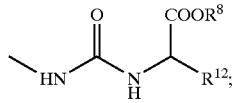

$R^{12}$ is hydrogen, alkyl of 1–6 carbon atoms, or aryl optionally substituted with $R^{15}$, arylalkyl having 1–6 carbon atoms in the alkyl moiety and the aryl moiety optionally substituted with $R^{15}$ $R^{14}$ is hydrogen, alkyl of 1–6 carbon atoms, or aryl optionally substituted by $R^{16}$;

$R^{15}$ is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, $-(CH_2)_n-NHR^{14}$, $-OCH_2(CH_2)_nCO_2R^7$, $-(CH_2)_n-CO_2R^7$, $-COR^7$, $-SO_2R^{13}$, $-(CH_2)_nNHCOR^{14}$, $-CN$, or $NO_2$;

$R^{16}$ is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, $-CO_2R^7$, $-COR^7$, $-CN$, $-NO_2$, or trifluoromethyl;

n=0–6;

or a pharmaceutically acceptable salt thereof.

2. The compound of claim 1, wherein

R is
(a) phenyl, naphthyl, fluorenyl, fluoren-2-one, or fluoren-2-oxime optionally substituted with $R^2$, $R^3$, $R^4$, $R^5$, or $R^6$; or $R^1$ is:
(b) phenyl or naphthyl optionally substituted with $R^9$, $R^{10}$, or $R^{11}$;

or a pharmaceutically acceptable salt thereof.

3. A compound of formula I having the structure

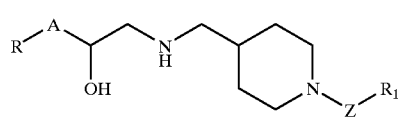

wherein,

A is $-OCH_2-$;

R is
(a) aryl optionally substituted with $R^2$, $R^3$, $R^4$, $R^5$, or $R^6$; or $R^1$ is:
(b) aryl optionally substituted with $R^9$, $R^{10}$, or $R^{11}$;

$R^2$, $R^3$, $R^4$, $R^5$, and $R^6$ are each, independently, alkyl of 1–6 carbon atoms, hydroxy, alkoxy of 1–6 carbon atoms, arylalkoxy having 1–6 carbon atoms in the alkyl moiety, halogen, $-NHSO_2R^7$, $-CO_2R^8$, or $-CONH_2$;

$R^7$ and $R^8$ are each, independently, hydrogen, alkyl of 1–6 carbon atoms, or arylalkyl having 1–6 carbon atoms in the alkyl moiety;

Z is $-SO_2-$;

$R^9$, $R^{10}$, and $R^{11}$ are each, independently:

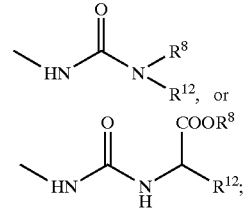

$R^{12}$ is hydrogen, alkyl of 1–6 carbon atoms, aryl optionally substituted with $R^{15}$, or arylalkyl having 1–6 carbon atoms in the alkyl moiety and the aryl moiety optionally substituted with $R^{15}$;

$R^{14}$ is hydrogen, alkyl of 1–6 carbon atoms, aryl optionally substituted by $R^{16}$;

$R^{15}$ is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, aarylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, trifluoromethyl, $-(CH_2)n-NHR^{14}$, $-OCH_2(CH_2)_nCO_2R^7$, $-(CH_2)_n-CO_2R^7$, $-COR^7$, $-SO_2R^{13}$, $-(CH_2)_nNHCOR^{14}$, $-CN$, or $NO_2$;

$R^{16}$ is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, $-CO_2R^7$, $-COR^7$, $-CN$, $-NO_2$, or trifluoromethyl;

n=0–6;

or a pharmaceutically acceptable salt thereof.

4. A compound of formula I having the structure

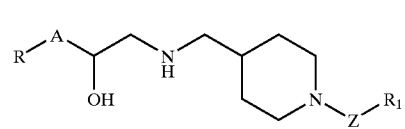

wherein,

A is $-OCH_2-$;

R is
(a) aryl optionally substituted with $R^2$, $R^3$, $R^4$, $R^5$, or $R^6$;

$R^1$ is:
(b) aryl optionally substituted with $R^9$, $R^{10}$, or $R^{11}$;

$R^2$, $R^3$, $R^4$, $R^5$, and $R^6$ are each, independently, alkyl of 1–6 carbon atoms, hydroxy, alkoxy of 1–6 carbon atoms, arylalkoxy having 1–6 carbon atoms in the alkyl moiety, halogen, $-NHSO_2R^7$, $-CO_2R^8$, or $-CONH_2$;

$R^7$ and $R^8$ are each, independently, hydrogen, alkyl of 1–6 carbon atoms, or arylalkyl having 1–6 carbon atoms in the alkyl moiety;

Z is $-SO_2-$;

R⁹, R¹⁰, and R¹¹ are each, independently:

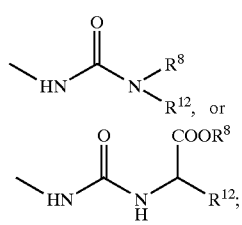

R¹² is hydrogen, alkyl of 1–6 carbon atoms, aryl optionally substituted with R¹⁵, or arylalkyl having 1–6 carbon atoms in the alkyl moiety and the aryl moiety optionally substituted with R¹⁵;

R¹⁴ is hydrogen, alkyl of 1–6 carbon atoms, aryl optionally substituted by R¹⁶;

R¹⁵ is alkyl of 1–6 carbon atoms, cycloalkyl of 3–8 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkytamino of 1–6 carbon atoms per alkyl moiety, arylamino, halogen, alkylthio of 1–6 carbon atoms, trifluoromethyl, —(CH₂)ₙ—NHR¹⁴, —OCH₂(CH₂)ₙCO₂R⁷, —(CH₂)ₙ—CO₂R⁷, —COR⁷, —SO₂R¹³, —(CH₂)ₙNHCOR¹⁴, —CN, or NO₂;

R¹⁶ is alkyl of 1–6 carbon atoms, arylalkyl having 1–6 carbon atoms in the alkyl moiety, alkoxy of 1–6 carbon atoms, aryloxy, arylalkoxy having 1–6 carbon atoms in the alkyl moiety, hydroxy, alkylamino of 1–6 carbon atoms, dialkylamino of 1–6 carbon atoms per alkyl moiety, arylamino, halogen, alkylthio of 1–6 carbon atoms, —CO₂R⁷, —COR⁷, —CN, —NO₂, or trifluoromethyl;

n=0–6;

or a pharmaceutically acceptable salt thereof.

5. The compound of claim 1, which is

| | |
|---|---|
| ggg) | 1-Hexyl-3-[4-(4-{[(2S)-2-hydroxy-3-(4-hydroxy-phenoxy)-propylamino]-methyl}-piperidine-1-sulfonyl)-phenyl]-urea; |
| kkk) | 1-[4-(4-{[(2S)-2-Hydroxy-3-(4-hydroxy-phenoxy)-propylamino]-methyl}-piperidine-1-sulfonyl)-phenyl]-3-phenyl-urea; |
| lll) | 1-Cyclohexyl-3-[4-(4-{[(2S)-2-hydroxy-3-(4-hydroxy-phenoxy)-propylamino]-methyl}-piperidine-1-sulfonyl)-phenyl]-urea; |
| mmm) | 1-[4-(4-{[2-Hydroxy-3-(4-hydroxy-phenoxy)-propylamino]-methyl}-piperidine-1-sulfonyl)-phenyl]-3-isobutyl-urea; |
| qqq) | 1-[4-(4-{[(2S)-2-Hydroxy-3-(4-hydroxy-phenoxy)-propylamino]-methyl}-piperidine-1-sulfonyl)-phenyl]-3-octyl-urea; |
| uuu) | (R)-N-{2-Hydroxy-5-[1-hydroxy-2-({1-[4-(3-octyl-ureido)-benzenesulfonyl]-piperidin-4-ylmethyl}-amino)-ethyl]-phenyl}-methanesulfonamide; |
| yyy) | 1-(2,5-Difluoro-benzyl)-3-[4-(4-{[(2S)-2-hydroxy-3-(4-hydroxy-phenoxy)-propylamino]-methyl}-piperidine-1-sulfonyl)-phenyl]-urea; |
| zzz) | 1-(2,5-Difluoro-benzyl)-3-[4-(4-{[(2S)-3-(3-fluoro-4-hydroxy-phenoxy)-2-hydroxy-propylamino]-methyl}-piperidine-1-sulfonyl)-phenyl]-urea; |
| aaaa) | N-(5-{(2S)-3-[(1-{4-[3-(2,5-Difluoro-benzyl)-ureido]-benzenesulfonyl}-piperidin-4-ylmethyl)-amino]-2-hydroxy-propoxy}-2-hydroxy-phenyl)-methanesulfonamide; |
| bbbb) | 1-[4-(4-{[(2S)-3-(2-Chloro-4-hydroxy-phenoxy)-2-hydroxy-propylamino]-methyl}-piperidine-1-sulfonyl)-phenyl]-3-(2,5-difluoro-benzyl)-urea; |
| cccc) | N-{5-[(1R)-2-({[1-({4-[({[2-(2,5-difluorophenyl)ethyl]amino}carbonyl)amino]-phenyl}sulfonyl)piperidin-4-yl]methyl}amino)-1-hydroxyethyl]-2-hydroxyphenyl}-methanesulfonamide; |
| dddd) | 1-[2-(2,4-Difluoro-phenyl)-ethyl]-3-[4-(4-{[(2S)-2-hydroxy-3-(4-hydroxy-phenoxy)-propylamino]-methyl}-piperidine-1-sulfonyl)-phenyl]-urea; |
| eeee) | 1-(2,6-Difluoro-phenyl)-3-[4-(4-{[(2S)-2-hydroxy-3-(4-hydroxy-phenoxy)-propylamino]-methyl}-piperidine-1-sulfonyl)-phenyl]-urea; |
| lllll) | (2S)-1-[4-(benzyloxy)phenoxy]-3-({[1-(phenylsulfonyl)piperidin-4-yl]methyl}amino)propan-2-ol; |
| mmmmm) | 4-{[(2S)-2-hydroxy-3-({[1-(phenylsulfonyl)piperidin-4-yl]methyl}amino)propyl]oxy}phenol; | or a pharmaceutically acceptable salt thereof.

* * * * *